United States Patent [19]

Hauel et al.

[11] Patent Number: 5,594,003
[45] Date of Patent: Jan. 14, 1997

[54] TETRAHYDROIMIDAZO[1,2-A]PYRIDIN-2-YL-(BENZIMIDAZOL-1-YL)-METHYL-BIPHENYLS USEFUL AS ANGIOTENSIN-II ANTAGONISTS

[75] Inventors: Norbert Hauel, Schemmerhofen; Berthold Narr, deceased, late of Biberach, by Elisabeth Narr, legal representative; Uwe Ries, Biberch; Jacobus C. A. van Meel, Mittelbiberach; Wolfgang Wienen, Biberach/Rissegg; Michael Entzeroth, Warthausen, all of Germany

[73] Assignee: Dr. Karl Thomae GmbH, Biberach an der Riss, Germany

[21] Appl. No.: 456,337

[22] Filed: Jun. 1, 1995

Related U.S. Application Data

[60] Division of Ser. No. 385,936, Feb. 9, 1995, which is a continuation-in-part of Ser. No. 201,139, Feb. 24, 1994, abandoned, which is a continuation of Ser. No. 832,193, Feb. 6, 1992, abandoned, and a continuation of Ser. No. 257,608, Jun. 9, 1994, which is a continuation of Ser. No. 7,315, Jan. 21, 1993, abandoned, and a continuation of Ser. No. 237,477, May 3, 1994, abandoned, which is a continuation of Ser. No. 40,778, Mar. 31, 1993, abandoned, and a continuation of Ser. No. 94,835, Jul. 20, 1993, abandoned.

[30] Foreign Application Priority Data

| Feb. 6, 1991 | [DE] | Germany | 41 03 492.9 |
| May 25, 1991 | [DE] | Germany | 41 17 121.7 |
| Nov. 16, 1991 | [DE] | Germany | 41 37 812.1 |
| Jan. 22, 1992 | [DE] | Germany | 42 01 554.5 |
| Apr. 11, 1992 | [DE] | Germany | 42 12 250.3 |
| Jun. 17, 1992 | [DE] | Germany | 42 19 782.1 |
| Jul. 22, 1992 | [DE] | Germany | 42 24 133.2 |
| Jul. 27, 1992 | [DE] | Germany | 42 24 752.7 |
| Aug. 4, 1992 | [DE] | Germany | 42 25 756.5 |

[51] Int. Cl.⁶ .................... A61K 31/44; C07D 471/02
[52] U.S. Cl. .................... 514/300; 514/397; 514/398; 514/399; 546/121; 548/306.1; 548/306.4
[58] Field of Search .................... 548/181, 252, 548/254, 306.1, 306.4; 514/367, 397, 398, 399, 300; 546/121

[56] References Cited

U.S. PATENT DOCUMENTS

| 3,929,814 | 12/1975 | Narayanan et al. | 514/365 |
| 4,492,708 | 1/1985 | Spitzer | 548/181 |
| 5,171,748 | 12/1992 | Roberts et al. | 514/381 |
| 5,189,048 | 2/1993 | Carini et al. | 514/359 |
| 5,190,942 | 3/1993 | Poss | 548/306.1 |
| 5,194,435 | 3/1993 | Kees | 514/249 |
| 5,200,422 | 4/1993 | Olesen et al. | 514/387 |
| 5,218,125 | 6/1993 | Chen et al. | 514/252 |
| 5,250,554 | 10/1993 | Naka et al. | 514/387 |
| 5,254,546 | 10/1993 | Ardecky et al. | 514/325.4 |

FOREIGN PATENT DOCUMENTS

| 2047496 | 2/1992 | Canada | 548/254 |
| 0426021 | 5/1991 | European Pat. Off. | 548/254 |
| 0468470 | 1/1992 | European Pat. Off. | 548/254 |
| 0495626 | 7/1992 | European Pat. Off. | 548/252 |
| 0512314 | 9/1992 | European Pat. Off. | 548/306.1 |
| 92-04343 | 3/1992 | WIPO | 548/254 |

*Primary Examiner*—Floyd D. Higel
*Attorney, Agent, or Firm*—Robert P. Raymond; Alan R. Stempel; Wendy E. Rieder

[57] ABSTRACT

Angiotensin-II antagonists of the formula

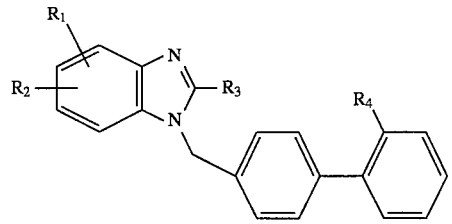

wherein $R_1$ is, other than hydrogen and, inter alia, halogen, lower alkyl or cycloalkyl; $R_2$ is, inter alia, optionally substituted benzimidazol-2-yl, 5,6,7,8-tetrahydro-imidazo[1,2-a]pyridin-2-yl, butanesultam-1-yl, imidazol-4-yl, and tetrahydobenzimidazol-2-yl; $R_3$ is, inter alia, lower alkyl; and, $R_4$ is an acidic group, such as carboxyl or tetrazolyl. An compound is:

4'-[(2-Ethyl-4-methyl-6-(5,6,7,8-tetrahydro-imidazo[1,2-a]pyridin-2-yl)-benzimidazol-1-yl)-methyl]-biphenyl-2-carboxylic acid.

6 Claims, No Drawings

TETRAHYDROIMIDAZO[1,2-A]PYRIDIN-2-YL-(BENZIMIDAZOL-1-YL)-METHYL-BIPHENYLS USEFUL AS ANGIOTENSIN-II ANTAGONISTS

RELATED APPLICATIONS

This application is a division of Ser. No. 08/385,936, filed on Feb. 9, 1995, which is a continuation-in-part of the following four prior applications:

(A) Ser. No. 08/201,139, filed on Feb. 24, 1994, which is a continuation of Ser. No. 07/832,193, filed on Feb. 6, 1992, both now abandoned; and a continuation of (B) Ser. No.08/257,608, filed on Jun. 9, 1994, which is a continuation of Ser. No. 08/007,315, filed on Jan. 21, 1993, both now abandoned; and a continuation of (C) Ser. No. 08/237,477, filed on May 3, 1994, which is a continuation of Ser. No. 08/040,778, filed on Mar. 31. 1993, both now abandoned; and, (D) Ser. No. 08/094,835, filed on Jul. 20, 1993, now abandoned.

FIELD OF THE INVENTION

The invention relates to certain novel benzimidazoles and their use as medicaments.

BACKGROUND AND BRIEF DESCRIPTION OF THE INVENTION

EP-A-0 392 317 has already described benzimidazoles which are valuable angiotensin antagonists.

It has now been found that the new benzimidazoles of formula I described below are even more useful as angiotensin antagonists, particularly angiotensin-II antagonists.

DETAILED DESCRIPTION OF THE INVENTION

A first aspect of the invention comprises compounds of the formula I

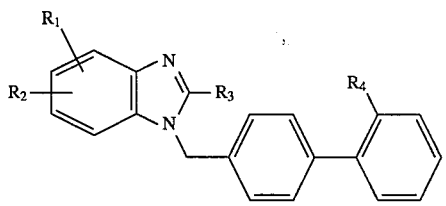

wherein $R_1$, $R_2$, $R_3$ and $R_4$ are defined as set forth in options A, B, C or D, as follows:

Option A $R_1$ in the 4-position represents a fluorine, chlorine or bromine atom, a $C_{1-4}$-alkyl, a cycloalkyl, fluoromethyl, difluoromethyl or trifluoromethyl group and $R_2$ represents a $C_{3-5}$-alkoxy group substituted in the 3-, 4- or 5-position by an imidazolyl group, or $R_2$ may represent a $C_{2-5}$-alkoxy group substituted in the 2-, 3-, 4- or 5-position by a benzimidazolyl or tetrahydrobenzimidazolyl group, or, if $R_4$ represents a 1H-tetrazolyl group, $R_2$ may also represent a 2-(imidazol-1-yl)-ethoxy group, a $C_{1-4}$-alkylsulphonyloxy group, a benzenesulphonyloxy or phenylalkanesulphonyloxy group, an acylamino group optionally substituted at the nitrogen atom by a $C_{1-6}$-alkyl group or by a phenyl, cycloalkyl, phenylalkyl, cycloalkylalkyl, bicyclohexyl or biphenyl group, in which the acyl group is a $C_{1-7}$-alkanoyl group, a $C_{2-4}$(alkoxycarbonyl) group, a $C_{1-6}$-alkylsulphonyl group, a benzoyl, benzenesulphonyl, phenylalkanesulphonyl, naphthalenesulphonyl, cycloalkylcarbonyl, phenylalkanoyl or cycloalkylalkanoyl group, in which the above-mentioned phenyl nuclei may each be mono- or disubstituted by a fluorine, chlorine or bromine atom or by a methyl or methoxy group and the substituents may be identical or different, a phthalimino, homophthalimino, 2-carboxyphenylcarbonyl-amino or 2-carboxyphenylmethylamino group, in which a carbonyl group in a phthalimino group may be replaced by a methylene, alkyl-methylene or dialkylmethylene group, and a methylene group in a homophthalimino group may be substituted by one or two alkyl groups, and additionally the above-mentioned phenyl nuclei may be mono- or disubstituted by alkyl or alkoxy groups, whilst the substituents may be identical or different, and at the same time may be totally or partially hydrogenated, a 5-, 6- or 7-membered alkyleneimino or alkenyleneimino group optionally substituted by one or two alkyl groups or by a tetramethylene or pentamethylene group, in which a methylene group may be replaced by a carbonyl or sulphonyl group, a bicycloalkane-2,3-dicarboxylic acid imino or bicycloalkene-2,3-dicarboxylic acid imino group, wherein the bicycloalkane and bicycloalkene moieties may each contain 9 or 10 carbon atoms, may be substituted by 1, 2 or 3 methyl groups and may have an endomethylene group replaced by an oxygen atom, an amidino group optionally substituted by one or two $C_{1-6}$ alkyl groups, a glutaric acid imino group wherein the n-propylene group may be perfluorinated, or may be substituted by one or two alkyl groups or by a tetramethylene or pentamethylene group, a maleic acid imido group optionally mono- or di-substituted by an alkyl or phenyl group, whilst the substituents may be identical or different, a 5-membered heteroaromatic ring bound via a carbon atom or via an imino group and containing an imino group, an oxygen or sulphur atom, or an imino group and an oxygen, sulphur or nitrogen atom, or $R_2$ may represent a 6-membered heteroaromatic ring bound via a carbon atom and containing 1 or 2 nitrogen atoms, whilst the abovementioned heteroaromatic rings may be substituted in the carbon structure by a $C_{1-6}$ alkyl or by a phenylalkyl group, and an n-propylene, n-butylene or 1,3-butadienyl group may be linked to both the 5-membered and 6-membered heteroaromatic rings via two adjacent carbon atoms or an n-butylene or 1,3-butadienyl group is linked thereto via an imino group and an adjacent carbon atom and, in an anellated pyridine ring thus formed, a methine group may be replaced by a nitrogen atom and a vinylene group in the 3-, 4-position relative to the nitrogen atom of the pyridine ring formed may be replaced by a sulphur atom or in an anellated phenyl ring thus formed, one or two methine groups may be replaced by N-atoms, whilst additionally the above-mentioned fused aromatic or heteroaromatic rings may be monosubstituted in the carbon structure by a fluorine, chlorine or bromine atom or by an alkyl, alkoxy, hydroxy, phenyl, nitro, amino, alkylamino, dialkylamino, alkanoylamino, cyano, carboxy, alkoxycarbonyl, aminocarbonyl, alkylaminocarbonyl, dialkylaminocarbonyl, fluoromethyl, difluoromethyl, trifluoromethyl, alkanoyl, aminosulphonyl, alkylaminosulphonyl or dialkylaminosulphonyl group or may be disubstituted by fluorine or chlorine atoms or by methyl, methoxy or hydroxy groups, and two methyl substituents in the 1,2-position relative to each other may be linked by a methylene or ethylene bridge and an —NH— group optionally present in an imidazole ring may be substituted by a $C_{1-6}$-alkyl group, by a phenylalkyl group or by a cycloalkyl group, or a pyrrolidine, piperidine or pyridine ring bound via a carbon atom, in which a phenyl group may be condensed onto the pyridine ring via two adjacent carbon atoms and a methylene group adjacent to the N-atom in a pyrrolidine or piperidine ring may be replaced by a carbonyl group, an imidazolidinedione group optionally substituted by an alkyl, phenylalkyl, tetramethylene, pentamethylene or hexamethylene group, a pyridazin-3-one or dihydro-pyridazin-3-one group which may be substituted in the 2-position by an optionally phenyl substituted alkyl group and additionally, in the carbon skeleton, by 1 or 2 alkyl groups, an $R_7$—$NR_6$—CO—$NR_5$— group wherein $R_5$ represents a hydrogen atom, a $C_{1-8}$-alkyl group, a $C_{5-7}$ cycloalkyl group or a phenylalkyl group, $R_6$ represents a hydrogen atom, a $C_{1-8}$-alkyl group, a $C_{3-5}$-alkenyl group, a phenyl group, a phenylalkyl group or a $C_{5-7}$-cycloalkyl group, $R_7$ represents a hydrogen atom or a $C_{1-6}$-alkyl group or one of the groups $R_5$, $R_6$ or $R_7$ may also represent a bicyclohexyl or biphenylyl group or $R_6$ and $R_7$ together with the nitrogen atom between them represent an unbranched $C_{4-6}$-alkyleneimino group or a morpholino group or $R_5$ and $R_6$ together represent a $C_{2-4}$-alkylene group, or, $R_2$ may represent a 1H,3H-quinazolin-2,4-dion-3-yl or pentamethylene-oxazolin-2-yl group or $R_1$ represents, in the 5-, 6- or 7-position, a fluorine, chlorine or bromine atom, a $C_{1-4}$-alkyl group, a fluoromethyl, difluoromethyl or trifluoromethyl group and $R_2$ represents a 5-membered heteroaromatic ring bound via a carbon atom or via an imino group and containing an imino group, an oxygen or sulphur atom or, an imino group and an oxygen, sulphur or nitrogen atom, or $R_2$ represents a 6-membered heteroaromatic ring bound via a carbon atom and containing 1 or 2 nitrogen atoms, whilst the abovementioned heteroaromatic rings may be substituted in the carbon skeleton by a $C_{1-6}$ alkyl or by a phenylalkyl group and an n-propylene, n-butylene or 1,3-butadienyl group may be linked via two adjacent carbon atoms to both the 5-membered and 6-membered heteroaromatic rings or an n-butylene or 1,3-butadienyl group may be linked to said 5-membered and 6-membered heteroaromatic rings via an imino group and an adjacent carbon atom and, in an anellated pyridine ring thus formed, a methine group may be replaced by a nitrogen atom and a vinylene group in the 3-, 4-position relative to the nitrogen atom of the pyridine ring formed may be replaced by a sulphur atom or in an anellated phenyl ring thus formed, one or two methine groups may be replaced by N-atoms, whilst additionally the above-mentioned fused aromatic or heteroaromatic rings may be monosubstituted on the carbon skeleton by a fluorine, chlorine or bromine atom or by an alkyl, alkoxy, hydroxy, phenyl, nitro, amino, alkylamino, dialkylamino, alkanoylamino, cyano, carboxy, alkoxycarbonyl, aminocarbonyl, alkylaminocarbonyl, dialkylaminocarbonyl, fluoromethyl, difluoromethyl, trifluoromethyl, alkanoyl, aminosulphonyl, alkylaminosulphonyl or dialkylaminosulphonyl group or may be disubstituted by fluorine or chlorine atoms or by methyl, methoxy or hydroxy groups, and two methyl substituents in the 1,2-position relative to each other may be linked by a methylene or ethylene bridge and an —NH— group optionally present in an imidazole ring may be substituted by a $C_{1-6}$-alkyl group, by a phenylalkyl group or by a cycloalkyl group, or, $R_2$ may represent a pyrrolidine, piperidine or pyridine ring bound via a carbon atom, in which a phenyl group may be condensed onto the pyridine ring via 2 adjacent carbon atoms and a methylene group adjacent to the N-atom in a pyrrolidine or piperidine ring may be replaced by a carbonyl group, $R_3$ represents a hydrogen atom or a $C_{1-5}$-alkyl group in which a methylene group may be replaced by an oxygen or sulphur atom, or $R_3$ may represent a $C_{3-5}$cycloalkyl group, and $R_4$ represents a carboxy, cyano, 1H-tetrazolyl or 1-triphenylmethyltetrazolyl group, a $C_{2-5}$(alkoxycarbonyl) group, an alkanesulphonylaminocarbonyl, arylsulphonylamino-carbonyl or trifluoromethanesulphonylaminocarbonyl group, whilst, unless otherwise specified, an alkanoyl, alkyl or alkoxy moiety mentioned hereinbefore may contain in each case 1 to 3 carbon atoms and a cycloalkyl moiety mentioned hereinbefore may contain 3 to 7 carbon atoms in each case, Option B $R_1$ is in the 4-position and represents a $C_{1-3}$-alkyl group, a fluorine, chlorine or bromine atom, $R_2$ represents an oxazol-4-yl or thiazol-4-yl group optionally substituted in the 2-position by a $C_{1-6}$-alkyl group or by a phenyl group, or an imidazol-4-yl group optionally substituted in the 2-position by a $C_{1-6}$-alkyl group or by a phenyl group, whilst the imidazol-4-yl group is substituted in the 1-position by a $C_{1-7}$-alkyl group which may be substituted in the 1-, 2-, 3-, 4-, 5-, 6- or 7-position by a carboxy, alkoxycarbonyl, aminocarbonyl, alkylaminocarbonyl, dialkylaminocarbonyl, morpholinocarbonyl, thiomorpholinocarbonyl or 1-oxido-thiomorpholinocarbonyl group, by a $C_{2-4}$-alkyl group substituted in the 2-, 3- or 4-position by a hydroxy, alkoxy, alkoxyalkoxy, dialkylamino, pyrrolidino, piperidino, hexamethyleneimino, morpholino, thiomorpholino, 1-oxido-thiomorpholino or imidazol-1-yl group, by an alkyl group which is substituted by a trifluoromethyl group, by a $C_{3-7}$-cycloalkyl group or by a phenyl group optionally mono- or disubstituted by fluorine or chlorine atoms or by trifluoromethyl, methyl or methoxy groups, by an alkyl group substituted by two phenyl groups or by a $C_{3-7}$-cycloalkyl group, where unless otherwise specified the above-mentioned alkyl and alkoxy moieties may each contain 1 to 3 carbon atoms, $R_3$ represents a $C_{2-4}$-alkyl group, an alkoxy or alkylthio group having 2 or 3 carbon atoms in the alkyl moiety, or a cyclopropyl or cyclobutyl group and $R_4$ represents a group which may be converted in vivo into a carboxy group, or a carboxy, cyano, 1H-tetrazolyl, 1-triphenylmethyl-tetrazolyl or 2-triphenylmethyl-tetrazolyl group, Option C $R_1$ denotes a fluorine, chlorine or bromine atom or a fluoromethyl, difluoromethyl, trifluoromethyl or alkyl group, $R_2$ denotes an imidazol-2-yl group optionally substituted in the 1-position by the group $R_a$, wherein
  $R_a$ denotes a phenyl or phenylalkyl group, in which the phenyl nucleus may be mono- or disubstituted by alkyl, hydroxy or alkoxy groups and the substituents may be identical or different, a $C_{3-7}$-cycloalkyl group or a $C_{1-6}$-alkyl group in which the alkyl moiety may additionally be substituted by a group which can be metabolised into a carboxy group in vivo, by a trifluoromethyl, carboxyl, alkoxycarbonyl, aminocarbonyl, alkylaminocarbonyl or dialkylaminocarbonyl group or from position 2 by a hydroxy, alkoxy, amino, alkylamino, dialkylamino, pyrrolidino, piperidino or morpholino group, a 5,5-spiro-cyclopentano-dihydro-imidazol-4-on-2-yl group, an imidazolium-2-yl group which is substituted in the 1- and 3-positions by groups $R_b$, which groups may be identical or different, whilst
  $R_b$ denotes a phenylalkyl group in which the phenyl nucleus may be mono- or disubstituted by alkyl, hydroxy or alkoxy groups and the substituents may be identical or different, or a $C_{1-6}$-alkyl group in which the alkyl moiety may additionally be substituted by a group which can be metabolised into a carboxy group in vivo, or by a trifluoromethyl, carboxyl, alkoxycarbonyl, aminocarbonyl, alkylaminocarbonyl or dialkylamino-carbonyl group, an oxazol-2-yl or thiazol-2-yl group, whilst in the above mentioned imidazol-2-yl, imidazolium-2-yl, oxazol-2-yl or thiazol-2-yl moieties, the 4-, 5-positions may be substituted by a $C_{1-5}$-alkyl group or by a phenyl group, wherein the substituents may be identical or different, or an n-propylene or n-butylene bridge may be added via the 4-, 5-positions, an oxazolin-2-yl or imidazolin-2-yl group substituted in the 4-position by $R_9$ and $R_{10}$ and in the 5-position by $R_8$, whereby an imino group may additionally be substituted by $R_a$, or an $R_8CO—(R_9CR_{10})—NR_a—CO—$ group, wherein
  $R_a$ is defined as hereinbefore,
  $R_8$ to $R_{10}$, which may be identical or different, denote hydrogen atoms, $C_{1-5}$-alkyl groups or phenyl groups, $R_3$ denotes a $C_{1-5}$-alkyl group, a $C_{3-5}$-cycloalkyl group, an alkoxy or alkylthio group each having 1 to 4 carbon atoms and $R_4$ denotes a group which can be metabolised into a carboxy group in vivo, a carboxy, cyano, 2,5-dihydro-5-oxo-1.2.4-oxadiazol-3-yl, 1H-tetrazolyl, 1-triphenylmethyl-tetrazolyl or 2-triphenylmethyl-tetrazolyl group, whilst unless otherwise specified all the above-mentioned alkyl and alkoxy groups may each contain 1 to 3 carbon atoms, Option D $R_1$ denotes a fluorine, chlorine or bromine atom, a $C_{1-3}$-alkyl group, a $C_{3-7}$-cycloalkyl group, a fluoromethyl, difluoromethyl or trifluoromethyl group, $R_2$ denotes a phthalimino or homophthalimino group, whilst a carbonyl group in a phthalimino group may be replaced by a methylene group and a methylene group in a homophthalimino group may be substituted by one or two $C_{1-3}$-alkyl groups, a 5-, 6- or 7-membered alkyleneimino group (optionally substituted by one or two $C_{1-3}$-alkyl groups) in which a methylene group is replaced by a carbonyl or sulphonyl group, a maleic acid imido group optionally mono- or disubstituted by a $C_{1-3}$-alkyl group or by a phenyl group, whilst the substituents may be identical or different, a benzimidazol-2-yl or 4,5,6,7-tetrahydro-benzimidazol-2-yl group optionally substituted in the 1-position by a $C_{1-6}$-alkyl group or by a $C_{3-5}$-cycloalkyl group (whilst the phenyl nucleus of one of the above-mentioned benzimidazole groups may additionally be substituted by a fluorine atom or a methyl or trifluoromethyl group), an imidazo[2,1-b]thiazol-6-yl, imidazo[1,2-a]pyridin-2-yl, 5,6,7,8-tetrahydroimidazo[1,2-a]pyridin-2-yl, 3-chloro-5,6,7,8-tetrahydroimidazo[1,2-a]pyridin-2-yl, imidazo[1,2-a]pyrimidin-2-yl, imidazo[4,5-b]pyridin-2-yl, imidazo[4,5-c]pyridin-2-yl, imidazo[1,2-c]pyrimidin-2-yl, imidazo[1,2-a]pyrazin-2-yl, imidazo[1,2-b]-pyridazin-2-yl, imidazo[4,5-c]pyridin-2-yl, purin-8-yl, imidazo[4,5-b]pyrazin-2-yl, imidazo[4,5-c]pyridazin-2-yl or imidazo[4,5-d]pyridazin-2-yl group, a pyrrolidine, piperidine or pyridine ring bound via a carbon atom, whilst a phenyl group may be condensed on to the pyridine ring via two adjacent carbon atoms and a methylene group adjacent to the N-atom in a pyrrolidine or piperidine ring may be replaced by a carbonyl group, or an $R_7—NR_6—CO—NR_5—$ group wherein
  $R_5$ denotes a hydrogen atom, a $C_{1-5}$-alkyl group, a cyclohexyl or benzyl group,
  $R_6$ denotes a hydrogen atom, a $C_{1-6}$-alkyl group, an allyl, cyclohexyl, benzyl or phenyl group,
  $R_7$ denotes a hydrogen atom or a $C_{1-3}$-alkyl group or
  $R_6$ and $R_7$ together with the nitrogen atom between them denote an unbranched cyclic $C_{4-6}$-alkyleneimino group or a morpholino group or
  $R_5$ and $R_6$ together denote a $C_{2-3}$-alkylene group, $R_3$ denotes a $C_{1-5}$-alkyl group, a $C_{3-5}$-cycloalkyl group or a $C_{1-3}$-alkoxy group and $R_4$ denotes a tetrazolyl group substituted in the 1- or 2-position by an $R_a—CO—O—CH_2—$ group, or an $R_b—CO—O—(R_cCH)—O—CO—$, $R_aO—CO—$ or $R_bO—CO—O—(R_cCH)—O—CO—$ group, wherein
  $R_a$ denotes a straight-chained or branched $C_{1-6}$-alkyl group, a $C_{5-7}$-cycloalkyl group, a benzyl, 1-phenylethyl, 2-phenylethyl, 3-phenylpropyl, methoxymethyl or cinnamyl group,
  $R_b$ denotes a straight-chained or branched $C_{1-6}$-alkyl group, a $C_{5-7}$-cycloalkyl group, a phenyl, benzyl, 1-phenylethyl, 2-phenylethyl or 3-phenylpropyl group and
  $R_c$ denotes a hydrogen atom or a methyl group, or if (i) $R_1$ and $R_2$ are as hereinbefore defined and $R_3$ denotes an alkoxy group, $R_4$ may denote a carboxy, 1H-tetrazolyl or 2H-tetrazolyl group or, if (ii) $R_1$ is as hereinbefore defined, $R_2$ has the meanings given hereinbefore with the exception of the 1-methyl-benzimidazol-2-yl group and $R_3$ denotes a cyclopropyl group, $R_4$ may represent a carboxy group or, if (iii) $R_1$ and $R_3$ are as hereinbefore defined and $R_2$ denotes a butanesultam-1-yl group, $R_4$ may denote a carboxy group or, if (iv) $R_1$ is as hereinbefore defined, $R_2$ denotes a 1-methyl-5-fluoro-benzimidazol-2-yl group and $R_3$ denotes an ethyl group, $R_4$ may represent a carboxy, 1H-tetrazolyl or 2H-tetrazolyl group.

Unless otherwise specified, as used in Options B and C, the term "a group which may be converted in vivo into a carboxy group" denotes, for example, the esters thereof of formulae

—CO—OR',

—CO—O—(HCR")—O—CO—R''' and

—CO—O—(HCR")—O—CO—OR''' wherein

R' denotes a straight-chained or branched $C_{1-6}$-alkyl group, a $C_{5-7}$-cycloalkyl group, a benzyl, 1-phenylethyl, 2-phenylethyl, 3-phenylpropyl, methoxymethyl or cinnamyl group, R" denotes a hydrogen atom or a methyl group and R''' denotes a straight-chained or branched $C_{1-6}$-alkyl group, a $C_{5-7}$-cycloalkyl group, a phenyl, benzyl, 1-phenylethyl, 2-phenylethyl or 3-phenylpropyl group.

The invention also comprises pharmaceutically acceptable acid addition salts of the above-described compounds of formula I, and the 1,3-isomer mixtures.

As examples of the definitions of the groups $R_1$ to $R_4$ mentioned hereinbefore:

In compounds according to Option A $R_1$ may represent a fluorine, chlorine or bromine atom, a methyl, ethyl, n-propyl, isopropyl, isobutyl, n-butyl, 1-methyl-n-propyl, 2-methyl-n-propyl, tert.butyl, cyclopropyl, cyclobutyl, cyclopentyl, cyclohexyl, cycloheptyl, fluoromethyl, difluoromethyl or trifluoromethyl group, $R_2$ may represent a 3-(imidazol-1-yl)propoxy, 4-(imidazol-1-yl)butoxy, 5-(imidazol-1-yl)pentoxy, 2-(benzimidazol-1-yl)ethoxy, 3-(benzimidazol-1-yl)-propoxy, 4-(benzimidazol-1yl)butoxy, 5-(benzimidazol-1-yl)-pentoxy, 2-(tetrahydrobenzimidazol-1-yl) 1)ethoxy, 3-(tetrahydrobenzimidazol-1-yl) 1)propoxy, 4-(tetrahydrobenzimidazol-1-yl)butoxy, 5-(tetrahydrobenzimidazol-1-yl)pentoxy, methanesulphonyloxy, ethanesulphonyloxy, n-propanesulphonyloxy, isopropanesulphonyloxy, n-butanesulphonyloxy, benzenesulphonyloxy, 4-fluorobenzenesulphonyloxy, 4-bromobenzenesulphonyloxy, 4-methylbenzenesulphonyloxy, 4-methoxybenzene-sulphonyloxy, 3,4-dichlorobenzenesulphonyloxy, phenyl-methanesulphonyloxy, 2-phenylethanesulphonyloxy, 3-phenylpropanesulphonyloxy, formylamino, acetylamino, propionylamino, butanoylamino, isobutanoylamino, pentanoylamino, 3-methyl-butanoylamino, hexanoylamino, methoxycarbonylamino, ethoxycarbonylamino, n-propoxycarbonylamino, isopropoxycarbonylamino, methanesulphonylamino, ethanesulphonylamino, n-propanesulphonylamino, isopropanesulphonylamino, n-butanesulphonylamino, n-pentanesulphonylamino, n-hexanesulphonylamino, benzamido, benzenesulphonylamido, 4-fluorobenzenesulphonamido, 4-chlorobenzenesulphonamido, 4-bromobenzenesulphonamido, 4-methylbenzenesulphonamido, 4-methoxybenzenesulphonamido, phenylmethanesulphonyl-amido, 2-phenylethanesulphonylamido, 3-phenylpropane-sulphonylamido, naphthalen-1-yl-sulphonamido, naphthalen-2-yl-sulphonylamido, cyclopentylcarbonyl-amido, cyclohexylcarbonylamido, cycloheptylcarbonyl-amido, phenylacetylamido, 3-phenylpropionylamido, cyclopentylacetylamido, 3-cyclopentylpropionylamido, cyclohexylacetylamido, 3-cyclohexylpropionylamido, cycloheptylacetylamido, 3-cycloheptylpropionylamido, N-methyl-formylamino, N-methyl-acetylamino, N-methyl-propionylamino, N-methyl-butanoylamino, N-methyl-isobutanoylamino, N-methyl-pentanoylamino, N-methyl-3-methyl-butanoylamino, N-methyl-hexanoylamino, N-methyl-methoxycarbonylmino, N-methyl-ethoxycarbonylamino, N-methyl-n-propoxycarbonylamino, N-methyl-isopropoxy-carbonylamino, N-methyl-methanesulphonylamino, N-methyl-ethanesulphonylamino, N-methyl-n-propanesulphonylamino, N-methyl-isopropanesulphonylamino, N-methyl-n-butane-sulphonylamino, N-methyl-n-pentanesulphonylamino, N-methyl-n-hexanesulphonylamino, N-methyl-benzamido, N-methyl-benzenesulphonylamido, N-methyl-4-fluorobenzene-sulphonamido, N-methyl-4-chlorobenzenesulphonamido, N-methyl-4-bromobenzenesulphonamido, N-methyl-4-methylbenzenesulphonamido, N-methyl-4-methoxybenzenesulphonamido, N-methyl-phenylmethanesulphonylamido, N-methyl-2-phenylethanesulphonylamido, N-methyl-3-phenylpropanesulphonylamido, N-methyl-naphthalen-1-ylsulphonamido, N-methyl-naphthalen-2-ylsulphonylamido, N-methyl-cyclopentylcarbonylamido, N-methyl-cyclohexylcarbonylamido, N-methyl-cycloheptylcarbonylamido, N-methyl-phenylacetylamido, N-methyl-3-phenylpropionyl-amido, N-methyl-cyclopentylacetylamido, N-methyl-3-cyclopentylpropionylamido, N-methyl-cyclohexylacetyl-amido, N-methyl-3cyclohexylpropionylamido, N-methyl-cycloheptylacetylamido, N-methyl-3-cycloheptylpropionyl-amido, N-ethyl-formylamino, N-ethyl-acetylamino, N-ethyl-propionylamino, N-ethylbutanoylamino, N-ethyl-isobutanoylamino, N-ethyl-pentanoylamino, N-ethyl-3-methyl-butanoylamino, N-ethyl-hexanoylamino, N-ethyl-methoxycarbonylamino, N-ethyl-ethoxycarbonylamino, N-ethyl-n-propoxycarbonylamino, N-ethyl-isopropoxy-carbonylamino, N-ethyl-methanesulphonylamino, N-ethyl-ethanesulphonylamino, N-ethyl-n-propanesulphonylamino, N-ethyl-isopropanesulphonylamino, N-ethyl-n-butanesulphonylamino, N-ethyl-n-pentanesulphonylamino, N-ethyl-n-hexanesulphonylamino, N-ethyl-benzamido, N-ethyl-benzenesulphonylamido, N-ethyl-4-fluorobenzene-sulphonamido, N-ethyl-4-chlorobenzenesulphonamido, N-ethyl-4-bromobenzenesulphonamido, N-ethyl-4-methylbenzenesulphonamido, N-ethyl-4-methoxybenzenesulphonamido, N-ethyl-phenylmethanesulphonylamido, N-ethyl-2-phenylethanesulphonylamido, N-ethyl-3-phenylpropanesulphonylamido, N-ethyl-naphthalen-1-yl-sulphonamido, N-ethyl-naphthalen-2-yl-sulphonylamido, N-ethyl-cyclopentylcarbonylamido, N-ethyl-cyclohexylcarbonyl-amido, N-ethyl-cycloheptylcarbonylamido, N-ethyl-phenylacetylamido, N-ethyl-3-phenyl-propionylamido, N-ethyl-cyclopentylacetylamido, N-ethyl-3-cyclopentyl-propionylamido, N-ethyl-cyclohexylacetylamido, N-ethyl-3-cyclohexylpropionylamido, N-ethyl-cycloheptylacetylamido, N-ethyl-3-cycloheptylpropionylamido, N-n-propyl-formylamino, N-n-propylacetylamino, N-n-propyl-propionylamino, N-n-propylbutanoylamino, N-n-propyl-isobutanoylamino, N-n-propylpentanoylamino, N-n-propyl-(3-methyl-butanoyl)amino, N-n-propyl-hexanoylamino, N-isopropyl-formylamino, N-isopropylacetylamino, N-isopropyl-propionylamino, N-isopropylbutanoylamino, N-isopropyl-isobutanoylamino, N-isopropylpentanoylamino, N-isopropyl-(3-methyl-butanoyl)amino, N-isopropyl-hexanoylamino, N-n-butyl-formylamino, N-n-butyl-acetylamino, N-n-butyl-propionylamino, N-n-butyl-butanoylamino, N-n-butyl-isobutanoylamino, N-n-butyl-pentanoylamino, N-n-butyl-(3-methyl-butanoyl)amino, N-n-butylhexanoylamino, N-isobutyl-formylamino, N-isobutyl-acetylamino, N-isobutyl-propionylamino, N-isobutyl-butanoylamino, N-isobutyl-isobutanoylamino, N-isobutyl-pentanoylamino, N-n-pentyl-formylamino, N-n-pentyl-acetylamino, N-n-pentyl-propionylamino, N-n-pentyl-butanoylamino, N-n-pentyl-isobutanoylamino, N-n-pentyl-pentanoylamino, N-(1-methyl-butyl)-formylamino, N-(1-methyl-butyl)-acetylamino, N-(1-methyl-butyl)-propionylamino, N-(1-methyl-butyl)-butanoylamino, N-(1-methyl-butyl)-isobutanoylamino, N-(1-methyl-butyl)-pentanoylamino, N-(2-methyl-butyl)-formylamino, N-(2-methyl-butyl)-acetylamino, N-(2-methyl-butyl)propionylamino, N-(2-methyl-butyl)-butanoylamino, N-(2-methyl-butyl)-isobutanoylamino, N-(2-methyl-butyl)-pentanoylamino, N-(3-methyl-butyl)-formylamino, N-(3-methyl-butyl)-acetylamino, N-(3-methyl-butyl)-propionylamino, N-(3-methyl-butyl)-butanoylamino, N-(3-methyl-butyl)-isobutanoylamino, N-(3-methyl-butyl)-pentanoylamino, N-n-hexyl-formylamino, N-n-hexyl-acetylamino, N-n-hexyl-propionylamino, N-n-hexyl-butanoylamino, N-n-hexyl-isobutanoylamino, N-n-hexyl-pentanoylamino, N-n-propyl-cyclohexylcarbonylamino, N-n-propyl-cyclohexylacetylamino, N-n-propyl-3-(cyclohexyl)propionylamino, N-isopropyl-cyclohexylcarbonylamino, N-isopropyl-cyclohexylacetylamino, N-isopropyl-3-(cyclohexyl)-propionylamino, N-n-butyl-cyclohexylcarbonylamino, N-n-butyl-cyclohexylacetylamino, N-n-butyl-3-(cyclohexyl)-propionylamino, N-isobutyl-cyclohexylcarbonylamino, N-isobutyl-cyclohexylacetylamino, N-isobutyl-3-(cyclohexyl)propionylamino, N-n-pentyl-cyclohexylcarbonylamino, N-n-pentyl-3-cyclohexylacetylamino, N-n-pentyl-3-(cyclohexyl)propionylamino, N-n-hexyl-cyclohexylcarbonylamino, N-n-hexyl-cyclohexylacetylamino, N-n-hexyl-3-(cyclohexyl)propionylamino, phthalimino, 5-methoxyphthalimino, 5,6-dimethoxy-phthalimino, 6-methoxyphthalimino, homophthalimino, 4,4-dimethyl-homophthalimino, 7-methoxy-homophthalimino, 6,7-dimethoxy-homophthalimino, 7-methoxy-4,4-dimethyl-homophthalimino, 6,7-dimethoxy-4,4-dimethylhomophthalimino, 1,2,3,6-tetrahydrophthalimino, hexahydrophthalimino, cis-hexahydrophthalimino, transhexahydrophthalimino, 1-oxo-isoindolin-2-yl, 3,4-dimethylphthalimino, 4,5-dimethyl-1,2,3,6-tetrahydrophthalimino, 4,5-dimethylhexahydrophthalimino, 4,5-dimethyl-1-oxo-isoindolin-2-yl, 3,4-dimethoxy-phthalimino, 4,5-dimethoxy-1,2,3,6-tetrahydrophthalimino, 4,5-dimethoxyhexahydrophthalimino, 4,5-dimethoxy-1-oxo-isoindolin-2-yl, 2-carboxyphenylmethylamino, 2-carboxyphenylmethylene-carbonylamino, pyrrolidino, 2-methylpyrrolidino, 3-ethylpyrrolidino, 3-isopropylpyrrolidino, piperidino, 3-methylpiperidino, 4-methylpiperidino, 4-ethylpiperidino, 4-isopropylpiperidino, hexamethyleneimino, 3-methyl-hexamethyleneimino, 4-methylhexamethyleneimino, 3-ethylhexamethyleneimino, 4-isopropylhexamethyleneimino, 3,3-dimethyl-pyrrolidino, 3,4-dimethyl-pyrrolidino, 3,3-dimethyl-piperidino, 3,4-dimethyl-piperidino, 4,4-dimethyl-piperidino, 3,3-dimethyl-hexamethyleneimino, 3,4-dimethyl-hexamethyleneimino, 4,4-dimethyl-hexamethyleneimino, 3,5-dimethylhexamethyleneimino, 3,3-tetramethylene-pyrrolidino, 3,3-pentamethylene-pyrrolidino, 3,3-tetramethylenepiperidino, 3,3-pentamethylene-piperidino, 4,4-tetramethylene-piperidino, 4,4-pentamethylene-piperidino, 3,3-tetramethylene-hexamethyleneimino, 3,3-pentamethylene-hexamethyleneimino, 4,4-tetramethylenehexamethylene-imino, 4,4-pentamethylenehexamethyleneimino, 2-oxo-pyrrolidino, 2-oxo-piperidino, 2-oxo-hexamethyleneimino, propanesultam-1-yl, butanesultam-1-yl, pentanesultam-1-yl, endo-bicyclo[2.2.2]oct-5-ene-2,3-dicarboxylic acid imino, methyl-5-norbornene-2,3-dicarboxylic acid imino, 3,6-endoxo-1,2,3,6-tetrahydrophthalimino, 5-norbornenendo-2,3-dicarboxylic acid imino, glutarimino, 3,3-tetramethylene-glutarimino, 3,3-pentamethyleneglutarimino, 2,2-dimethyl-glutarimino, 3-methylglutarimino, 3,3-dimethyl-glutarimino, 3-ethylglutarimino, 3-ethyl-3-methyl-glutarimino, 1,3-cyclopentanedicarbonylimino, 2,4-dimethylglutarimino, 2,4-di-n-propyl-glutarimino, glutaramino, 3,3-tetramethylene-glutaramino, 3,3-pentamethylene-glutaramino, 2,2-dimethyl-glutaramino, 3-methyl-glutaramino, 3,3-dimethyl-glutaramino, 3-ethyl-glutaramino, 3-ethyl-3-glutaramino, 1,3-cyclopentanedicarbonylamino, 2,4-dimethyl-glutaramino, 2,4-di-n-propyl-glutaramino, maleic acid amido, maleic acid imido, 2-methyl-maleic acid amido, 3-methyl-maleic acid amido, 2-methyl-maleic acid imido, 2-phenyl-maleic acid amido, 3-phenyl-maleic acid amido, 2-phenyl-maleic acid imido, 2,3-dimethyl-maleic acid amido, 3-methyl-2-phenyl-maleic acid amido, 2-methyl-3-phenyl-maleic acid amido, 2-methyl-3-phenyl-maleic acid imido, 2,3-diphenyl-maleic acid amido, 2,3-diphenyl-maleic acid amido, pyrrolidin-2-yl, pyrrolidin-2-on-5-yl, piperidin-2-yl, piperidin-2-on-1-yl, piperidin-2-on-6-yl, quinolin-2-yl, isoquinolin-1-yl, isoquinolin-3-yl, pyridin-2-yl, 4-methylimidazol-2-yl, 1-methylimidazol-4-yl, methylimidazol-5-yl, 1-n-hexylimidazol-4-yl, 1-n-hexylimidazol-5-yl, 1-benzylimidazol-4-yl, 1-benzylimidazol-5-yl, 1,2-dimethylimidazol-4-yl, 1,2-dimethylimidazol-5-yl, 1-n-pentyl-2-methyl-imidazol-4-yl, 1-n-pentyl-2-methyl-imidazol-5-yl, 1-n-butyl-2-methyl-imidazol-4-yl, 1-n-butyl-2-methyl-imidazol-5-yl, 1-benzyl-2-methylimidazol-4-yl, 1-benzyl-2-methyl-imidazol-5-yl, benzimidazol-2-yl, 1-methylbenzimidazol-2-yl, 1-ethylbenzimidazol-2-yl, 1-n-propylbenzimidazol-2-yl, 1-isopropylbenzimidazol-2-yl, 1-n-butylbenzimidazol-2-yl, 1-isobutylbenzimidazol-2-yl, 1-n-pentylbenzimidazol-2-yl, 1-n-hexylbenzimidazol-2-yl, 1-cyclopropyl-benzimidazol-2-yl, 1-cyclobutylbenzimidazol-2-yl, 1-cyclopentylbenzimidazol-2-yl, 1-cyclohexylbenzimidazol-2-yl, 5-nitro-benzimidazol-2-yl, 5-amino-benzimidazol-2-yl, 5-acetamido-benzimidazol-2-yl, 5-methyl-benzimidazol-2-yl, 5-methoxy-benzimidazol-2-yl, 5-ethoxy-benzimidazol-2-yl, 1-methyl-5-methoxy-benzimidazol-2-yl, 1,5-dimethyl-benzimidazol-2-yl, 1,6-dimethyl-benzimidazol-2-yl, 1,4-dimethyl-benzimidazol -2-yl, 5,6-dimethyl-benzimidazol-2-yl, 1,5,6-trimethyl-benzimidazol-2-yl, 5-chloro-benzimidazol-2-yl, 5-chloro-1-methyl-benzimidazol-2-yl, 6-chloro-1-methyl-benzimidazol-2-yl, 5,6-dichloro-1-methyl-benzimidazol-2-yl, 5-dimethylamino-benzimidazol-2-yl, 5-dimethylamino-1-ethyl-benzimidazol-2-yl, 5,6-dimethoxy-1-methyl-benzimidazol-2-yl, 5,6-dimethoxy-1-ethyl-benzimidazol-2-yl, 5-fluoro-1-methyl-benzimidazol-2-yl, 6-fluoro-1-methyl-benzimidazol-2-yl, 5-trifluoromethyl-benzimidazol-2-yl, 5-trifluoromethyl-1-methyl-benzimidazol-2-yl, 4-cyano-1-methyl-benzimidazol-2-yl, 5-carboxy-1-methyl-benzimidazol-2-yl, 5-aminocarbonyl-benzimidazol-2-yl, 5-aminocarbonyl-1-methyl-benzimidazol-2-yl, 5-dimethylaminosulphonyl-1-methyl-benzimidazol-2-yl, 5-methoxycarbonyl-1-methyl-benzimidazol-2-yl, 5-methylaminocarbonyl-1-methyl-benzimidazol-2-yl, 5-dimethylaminocarbonyl-1-methyl-benzimidazol-2-yl, 4,6-difluoro-1-methyl-benzimidazol-2-yl, 5-acetyl-1-methyl-benzimidazol-2-yl, 5,6-dihydroxy-1-methyl-benzimidazol-2-yl, imidazo[1,2-a]pyridin -2-yl, 5-methyl-imidazo[1,2-a]pyridin-2-yl, 6-methyl-imidazo[1,2-a]-pyridin-2-yl, 7-methyl-imidazo[1,2-a]-pyridin-2-yl, 8-methyl-imidazo[1,2-a]pyridin- 2-yl, 5,7-dimethyl-imidazo[1,2-a]pyridin-2-yl, 6-aminocarbonyl-imidazo[1,2-a]pyridin-2-yl, 6-chloro-imidazo[1,2-a]-pyridin-2-yl, 6-bromo-imidazo[1,2-a]-pyridin-2-yl, 5,6,7,8-tetrahydro-imidazo[1,2-a]pyrimidin-2-yl, imidazo[1,2-a]pyrimidin-2-yl, 5,7-dimethyl-imidazo[1,2-a]pyrimidin-2-yl, imidazo[4,5-b]pyridin-2-yl, 1-methyl-imidazo[4,5-b]pyridin-2-yl, 1-n-hexyl-imidazo[4,5-b]pyridin-2-yl, 1-cyclopropylimidazo[4,5-b]pyridin-2-yl, 1-cyclohexyl-imidazo[4,5-b]pyridin-2-yl, 4-methyl-imidazo[4,5-b]pyridin-2-yl, 6-methyl-imidazo[4,5-b]pyridin-2-yl, 1,4-dimethyl-imidazo[4,5-b]pyridin-2-yl, 1,6-dimethyl-imidazo[4,5-b]-pyridin-2-yl, imidazo[4,5-c]pyridin-2-yl, 1-methyl-imidazo[4,5-c]pyridin-2-yl, 1-n-hexyl-imidazo[4,5-c]-pyridin-2-yl, 1-cyclopropyl-imidazo[4,5-c]pyridin-2-yl, 1-cyclohexyl-imidazo[4,5-c]pyridin-2-yl, imidazo[2,1-b]-thiazol-6-yl, 3-methyl-imidazo[2,1-b]thiazol-6-yl, 2-phenyl-imidazo[2,1-b]thiazol-6-yl, 3-phenyl-imidazo[2,1-b]thiazol-6-yl, 2,3-dimethyl-imidazo[2,1-b]-thiazol-6-yl, 2,3-trimethylene-imidazo[2,1-b]thiazol-6-yl, 2,3-tetramethylene-imidazo[2,1-b]thiazol-6-yl, imidazo[1,2-c]pyrimidin-2-yl, imidazo[1,2-a]pyrazin-2-yl, imidazo[1,2-b]pyridazin-2-yl, imidazo[4,5-c]pyridin-2-yl, purin-8-yl, imidazo[4,5-b]pyrazin-2-yl, imidazo[4,5-c]pyridazin-2-yl, imidazo[4,5-d]pyridazin-2-yl, imidazolidin-2,4-dion-3-yl, 5-methyl-imidazolidin-2,4-dion-3-yl, 5-ethyl-imidazolidin-2,4-dion-3-yl, 5-n-propyl-imidazolidin-2,4-dion-3-yl, 5-benzyl-imidazolidin-2,4-dion-3yl, 5-(2-phenylethyl)-imidazolidin-2,4-dion-3-yl, 5-(3-phenylpropyl)-imidazolidin-2,4-dion-3-yl, 5,5-tetramethylene-imidazolidin-2,4-dion-3-yl, 5,5-pentamethylene-imidazolidin-2,4-dion-3-yl, 5,5-hexamethylene-imidazolidin-2,4-dion-3-yl, 1-methyl-imidazolidin-2,4-dion-3-yl, 1-benzyl-imidazolin-2,4-dion-3-yl, 4,5-dihydro-2H-pyridazin-3-on-6-yl, 2-methyl-4,5-dihydro-2H-pyridazin-3-on-6-yl, 2-ethyl-4,5-dihydro-2H-pyridazin-3-on-6-yl, 2-n-propyl-4,5-dihydro-2H-pyridazin-3-on-6-yl, 2-isopropyl-4,5-dihydro-2H-pyridazin-3-on-6-yl, 2-benzyl-4,5-dihydro-2H-pyridazin-3-on-6-yl, 2-(2-phenylethyl)-4,5-dihydro-2H-pyridazin-3-on-6-yl, 2-(3-phenylpropyl)-4,5-dihydro-2H-pyridazin-3-on-6-yl, 4-methyl-4,5-dihydro-2H-pyridazin-3-on-6-yl, 5-methyl-4,5-dihydro-2H-pyridazin-3-on-6-yl, 4,4-dimethyl-4,5-dihydro-2H-pyridazin-3-on-6-yl, 5,5-dimethyl-4,5-dihydro-2H-pyridazin-3-on-6-yl, 4,5-dimethyl-4,5-dihydro-2H-pyridazin-3-on-6-yl, 2,4-dimethyl-4,5-dihydro-2H-pyridazin-3-on-6-yl, 2,5-dimethyl-4,5-dihydro-2H-pyridazin-3-on-6-yl, 2,4,5-trimethyl-4,5-dihydro-2H-pyridazin-3-on-6-yl, 2,4,4-trimethyl-4,5-dihydro-2H-pyridazin-3-on-6-yl, 2,5,5-trimethyl-4,5-dihydro-2H-pyridazin-3-on-6-yl, 2H-pyridazin-3-on-6-yl, 2-methyl-pyridazin-3-on-6-yl, 2-ethyl-pyridazin-3-on-6-yl, 2-n-propyl-pyridazin-3-on-6-yl, 2-isopropyl-pyridazin-3-on-6-yl, 2-benzyl-pyridazin-3-on-6-yl, 2-(2-phenylethyl)-pyridazin-3-on-6-yl, 2-(3-phenylpropyl)-pyridazin-3-on-6-yl, 4-methyl-pyridazin-3-on-6-yl, 5-methyl-pyridazin-3-on-6-yl, 4,5-dimethyl-pyridazin-3-on-6-yl, 2,4-dimethyl-pyridazin-3-on-6-yl, 2,5-dimethyl-pyridazin-3-on-6-yl, 2,4,5-trimethyl-pyridazin-3-on-6-yl, aminocarbonylamino, methylaminocarbonylamino, dimethylaminocarbonylamino, N-methylaminocarbonyl-methylamino, N-(dimethylaminocarbonyl)-methylamino, N-dimethylaminocarbonyl-ethylamino, N-dimethylamino-carbonyl-isopropylamino, N-(dimethylaminocarbonyl)-n-pentylamino, N-methylaminocarbonyl-ethylamino, N-methylaminocarbonyl-n-pentylamino, N-methylaminocarbonyl-n-hexylamino, N-methylaminocarbonyl-n-octylamino, N-methylaminocarbonyl-cyclohexylamino, ethylaminocarbonylamino, N-ethylaminocarbonyl-methylamino, N-ethylaminocarbonyl-ethylamino, N-ethylaminocarbonyl-n-hexylamino, N-ethylaminocarbonyl-n-heptylamino, N-ethylaminocarbonyl-cyclohexylamino, diethylaminocarbonylamino, N-(diethylaminocarbonyl)-methylamino, N-(diethylaminocarbonyl)-ethylamino, N-(diethylaminocarbonyl)-n-butylamino, N-(diethylaminocarbonyl)-n-hexylamino, N-(diethylaminocarbonyl)-n-octylamino, isopropylaminocarbonylamino, N-isopropyl-aminocarbonyl-methylamino, n-butylaminocarbonylamino, N-(n-butylaminocarbonyl)-methylamino, N-(n-butylamino-carbonyl)-ethylamino, N-(n-butylaminocarbonyl)-isopropylamino, N-(n-butylaminocarbonyl)-n-butylamino, N-(n-butylaminocarbonyl)-n-hexylamino, N-(n-butylaminocarbonyl)-cyclohexylamino, N-(di-(n-butyl)-aminocarbonyl)-amino, N-(di-(n-butyl)-aminocarbonyl)-methylamino, N-(di-(n-butyl)-aminocarbonyl)-ethylamino, N-(di-(n-butyl)-aminocarbonyl)-n-butylamino, N-(di-(n-butyl)-aminocarbonyl)-n-hexylamino, N-(n-pentylaminocarbonyl)-methylamino, N-(n-pentylaminocarbonyl)-ethylamino, N-(n-hexylaminocarbonyl)-ethylamino, n-hexylaminocarbonylamino, n-heptylaminocarbonylamino, n-octylaminocarbonylamino, N-(n-hexylaminocarbonyl)-n-butylamino, N-(n-hexylaminocarbonyl)-n-pentylamino, N-(n-hexylaminocarbonyl)-n-hexylamino, N-(n-hexylamino-carbonyl)-cyclohexylamino, di-(n-hexyl)-aminocarbonyl-amino, N-(di-(n-hexyl)-aminocarbonyl)-methylamino, N-((n-hexyl)-methylaminocarbonyl)-amino, cyclohexylamino-carbonylamino, N-cyclohexylaminocarbonyl-methylamino, N-cyclohexylaminocarbonylethylamino, N-cyclohexylamino-carbonyl-n-butylamino, N-cyclohexylaminocarbonylisobutylamino, N-cyclohexylaminocarbonyl-n-pentylamino, cyclohexylaminocarbonyl-n-hexylamino, N-cyclohexylaminocarbonyl-cyclohexylamino, N-(ethyl-cyclohexylaminocarbonyl)-methylamino, N-(propyl-cyclohexylaminocarbonyl)-methylamino, N-(n-butyl-cyclohexylaminocarbonyl)-methylamino, allylaminocarbonylamino, benzylaminocarbonylamino, N-benzylaminocarbonyl-isobutylamino, phenylaminocarbonyl-amino, pyrrolidinocarbonylamino, pyrrolidinocarbonyl-methylamino, piperidinocarbonylamino, hexamethylene-iminocarbonylamino, morpholinocarbonylamino, 3,4,5,6-tetrahydro-2-pyrimidon-1-yl, 3-methyl-3,4,5,6-tetrahydro-2-pyrimidon-1-yl, 3-ethyl-3,4,5,6-tetrahydro-2-pyrimidon-1-yl, 3-n-propyl-3,4,5,6-tetrahydro-2-pyrimidon-1-yl, 3-isopropyl-3,4,5,6-tetrahydro-2-pyrimidon-1-yl, 3-n-butyl-3,4,5,6-tetrahydro-2-pyrimidon-1-yl, 3-isobutyl-3,4,5,6-tetrahydro-2-pyrimidon -1-yl, 3-n-pentyl-3,4,5,6-tetrahydro-2-pyrimidon-1-yl, 3-n-hexyl-3,4,5,6-tetrahydro-2-pyrimidon-1-yl, 3-cyclopentyl-3,4,5,6-tetrahydro-2-pyrimidon-1-yl, 3-cyclohexyl-3,4,5,6-tetrahydro-2-pyrimidon-1-yl, 3-cycloheptyl- 3,4,5,6-tetrahydro-2-pyrimidon-1-yl, 3-benzyl-3,4,5,6-tetrahydro-2-pyrimidon-1-yl, 3,4,5,6-tetrahydro-2(1H) -pyrimidon-1-yl, 3-methyl-3,4,5,6-tetrahydro-2(1H)-pyrimidon-1-yl, 3-ethyl-3,4,5,6-tetrahydro-2(1H)-pyrimidon-1-yl, 3-n-propyl-3,4,5,6-tetrahydro-2(1H)-pyrimidon-1-yl, 3-isopropyl-3,4,5,6-tetrahydro-2(1H)-pyrimidon-1-yl, 3-benzyl-3,4,5,6-tetrahydro-2(1H)-pyrimidon-1-yl, 3-(2-phenylethyl)-3,4,5,6-tetrahydro-2(1H)-pyrimidon-1-yl or 3-(3-phenylpropyl)-3,4,5,6-tetrahydro-2(1H)-pyrimidon-1-yl group, and $R_3$ may represent a hydrogen atom, a methyl, ethyl, n-propyl, isopropyl, n-butyl, isobutyl, tert.butyl, n-pentyl, 1-methyl-butyl, 2-methyl-butyl, 3-methyl-butyl, cyclopropyl, cyclobutyl, cyclopentyl, methoxy, ethoxy, n-propoxy, isopropoxy, n-butoxy, methylmercapto, ethylmercapto, n-propylmercapto, isopropylmercapto or n-butylmercapto group.

In compounds according to Option B $R_1$ may represent a fluorine or chlorine atom, a methyl, ethyl, n-propyl or isopropyl group, $R_2$ may represent an oxazol-4-yl, 2-methyl-oxazol-4-yl, 2-ethyl-oxazol-4-yl, 2-n-propyl-oxazol-4-yl, 2-isopropyl-oxazol-4-yl, 2-n-butyl-oxazol-4-yl, 2-isobutyl-oxazol-4-yl, 2-n-pentyl-oxazol -4-yl, 2-isoamyl-oxazol-4-yl, 2-n-hexyl-oxazol-4-yl, 2-phenyl-oxazol-4-yl, thiazol-4-yl, 2-methyl-thiazol-4-yl, 2-ethyl-thiazol-4-yl, 2-n-propyl-thiazol-4-yl, 2-isopropyl -thiazol-4-yl, 2-n-butyl-thiazol-4-yl, 2-isobutyl-thiazol-4-yl, 2-n-pentyl-thiazol-4-yl, 2-isoamyl-thiazol-4-yl, 2-n-hexyl-thiazol-4-yl, 2-phenyl-thiazol-4-yl, 1-methyl-imidazol-4-yl, 1-ethyl-imidazol-4-yl, 1-n-propyl-imidazol-4-yl, 1-isopropyl -imidazol-4-yl, 1-n-butyl -imidazol-4-yl, 1-isobutyl-imidazol-4-yl, 1-n-pentyl-imidazol-4-yl, 1-isoamyl-imidazol-4-yl, 1-n-hexyl-imidazol-4-yl, 1-n-hexyl-2-methyl-imidazol-4-yl, 1-(1-methyl-n-pentyl)-imidazo 1-4-yl, 1-(1-ethyl-n-butyl)-imidazol-4-yl, 1-(1-methyl-n-hexyl)-imidazol-4-yl, 1-( 1-ethyl-n-pentyl)-imidazol-4-yl, 1-(1-n-propyl-n-butyl)-imidazol-4-yl, 1-n-heptyl-imidazol-4-yl, 1-ethyl-2-methyl-imidazol-4-yl, 1-n-propyl-2-methyl-imidazol-4-yl, 1-isopropyl-2-methyl-imidazol-4-yl, 1-n-butyl-2-methyl-imidazol-4-yl, 1-isobutyl-2-methyl-imidazol-4-yl, 1-n-pentyl-2-methyl-imidazol-4-yl, 1-isoamyl-2-methyl-imidazol-4-yl, 1-n-hexyl-2-methyl-imidazol-4-yl, 1-n-heptyl-2-methyl-imidazol-4-yl, 1-cyclopropylmethyl-imidazol-4-yl, 1-cyclobutylmethyl-imidazol-4-yl, 1-cyclopentylmethyl-imidazol-4-yl, 1-cyclohexylmethyl-imidazol-4-yl, 1-cycloheptylmethyl-imidazol-4-yl, 1-(2-cyclopropylethyl-imidazol-4-yl, 1-(2-cyclobutylethyl)-imidazol-4-yl, 1-(2-cyclopentylethyl)-imidazol-4-yl, 1-(2-cyclohexylethyl)-imidazol-4-yl, 1-(2-cycloheptylethyl)-imidazol-4-yl, 1-(3-cyclopropylpropyl)-imidazol-4-yl, 1-(3-cyclobutylpropyl)-imidazol-4-yl, 1-(3-cyclopentylpropyl)-imidazol-4-yl, 1-(3-cyclohexyl-propyl)-imidazol-4-yl, 1-(3-cycloheptylpropyl)-imidazol-4-yl, 1-(2,2,2-trifluoroethyl)-imidazol-4-yl, 1(3,3,3-trifluoropropyl)-imidazol-4-yl, 1-benzyl-imidazol-4-yl, 1-(2-phenylethyl)-imidazol-4-yl, 1-(3-phenylpropyl)-imidazol-4-yl, 1-(4-fluorobenzyl)-imidazol-4-yl, 1-(4-chlorobenzyl)-imidazol-4-yl, 1-(3-chlorobenzyl)-imidazol-4-yl, 1-(4-trifluoromethyl-benzyl)-imidazol-4-yl, 1-(3-methyl-benzyl)-imidazol-4-yl, 1-(4-methyl-benzyl)-imidazol-4-yl, 1-(3-methoxy-benzyl)-imidazol-4-yl, 1-(4-methoxy-benzyl)-imidazol-4-yl, 1-(3,4-dimethoxy-benzyl)-imidazol-4-yl, 1-(3,5-dimethoxy-benzyl)-imidazol-4-yl, 1-cyclopropylmethyl-2-methyl-imidazol-4-yl, 1-cyclobutylmethyl-2-methyl-imidazol-4-yl, 1-cyclopentylmethyl-2-methyl-imidazol-4-yl, 1-cyclohexylmethyl-2-methyl-imidazol-4-yl, 1-cyclo-heptylmethyl-2-methyl-imidazol-4-yl, 1-(2-cyclopropylethyl)-2-methyl-imidazol-4-yl, 1-(2-cyclobutylethyl)-2-methyl-imidazol-4-yl, 1-(2-cyclopentylethyl)-2-methyl-imidazol-4-yl, 1-(2-cyclohexylethyl)-2-methyl-imidazol-4-yl, 1-(2-cycloheptylethyl)-2-methyl-imidazol-4-yl, 1-(3-cyclopropylpropyl)-2-methyl-imidazol-4-yl, 1-(3-cyclobutylpropyl)-2-methyl-imidazol-4-yl, 1-(3-cyclopentylpropyl)-2-methyl-imidazol-4-yl, 1-(3 -cyclohexylpropyl)-2-methyl-imidazol-4-yl, 1-(3-cycloheptylpropyl)-2-methyl-imidazol-4-yl, 1-(2,2,2-trifluoroethyl)-2-methyl-imidazol-4-yl, 1-(3,3,3-trifluoropropyl)-2-methyl-imidazol-4-yl, 1-benzyl-2-methyl-imidazol-4-yl, 1-(2-phenylethyl)-2-methyl-imidazol-4-yl, 1-(3-phenylpropyl)-2-methyl-imidazol-4-yl, 1-(4-fluorobenzyl)-2-methyl-imidazol-4-yl, 1-(4-chlorobenzyl)-2-methyl-imidazol-4-yl, 1-(3-chlorobenzyl)-2-methyl-imidazol-4-yl, 1-(4-trifluoromethyl-benzyl)-2-methyl-imidazol-4-yl, 1-(3-methyl-benzyl)-2-methyl-imidazol-4-yl, 1-(4-methyl-benzyl)-2-methyl-imidazol-4-yl, 1-(3-methoxy-benzyl)-2-methyl-imidazol-4-yl, 1(4-methoxy-benzyl)-2-methyl-imidazol-4-yl, 1-(3,4-dimethoxy-benzyl)-2-methyl-imidazol-4-yl, 1-(3,5-dimethoxy-benzyl)-2-methyl-imidazol-4-yl, 1-carboxymethyl-imidazol-4-yl, 1-(2-carboxyethyl)-imidazol-4-yl, 1-(3-carboxypropyl)-imidazol-4-yl, 1-(4-carboxybutyl)-imidazol-4-yl, 1-(5-carboxypentyl)-imidazol-4-yl, 1-(6-carboxyhexyl)-imidazo 1-4-yl, 1-(7-carboxyheptyl)-imidazol-4-yl, 1-methoxycarbonylmethyl-imidazol-4-yl, 1-(2-methoxycarbonylethyl)-imidazol-4-yl, 1-(3-methoxycarbonylpropyl)-imidazol-4-yl, 1-(4-methoxycarbonylbutyl)-imidazol-4-yl, 1-(5-methoxycarbonylpentyl)-imidazol-4-yl, 1-(6-methoxycarbonylhexyl)-imidazol-4-yl, 1-(7-methoxy-carbonylheptyl)-imidazol-4-yl, 1-ethoxycarbonylmethyl-imidazol-4-yl, 1-(2-ethoxycarbonylethyl)-imidazol-4-yl, 1-(3-ethoxycarbonylpropyl)-imidazol-4-yl, 1-(4-ethoxycarbonylbutyl)-imidazol-4-yl, 1-(5-ethoxycarbonyl-pentyl)-imidazol-4-yl, 1-(6-ethoxycarbonylhexyl)-imidazol-4-yl, 1-(7-ethoxycarbonylheptyl)-imidazol-4-yl, 1-n-propoxycarbonylmethyl-imidazol-4-yl, 1-(2-n-propoxycarbonylethyl)-imidazol-4-yl, 1-(3-n-propoxycarbonylpropyl)-imidazol-4-yl, 1-(4-n-propoxy-carbonylbutyl)-imidazol-4-yl, 1-(5-n-propoxycarbonyl-pentyl)-imidazol-4-yl, 1-(6-n-propoxycarbonylhexyl)-imidazol-4-yl, 1-(7-n-propoxycarbonylheptyl)-imidazol-4-yl, 1-isopropoxycarbonylmethyl-imidazol-4-yl, 1-(2-isopropoxycarbonylethyl)-imidazol-4-yl, 1-(3-isopropoxycarbonylpropyl)-imidazol-4-yl, 1-(4-isopropoxycarbonylbutyl)-imidazol-4-yl, 1-(5-isopropoxycarbonylpentyl)-imidazol-4-yl, 1-(6-isopropoxycarbonylhexyl)-imidazol-4-yl, 1-(7-isopropoxycarbonylheptyl)-imidazol-4-yl, 1-aminocarbonylmethyl-imidazol-4-yl, 1-(2-aminocarbonyl-ethyl)-imidazol-4-yl, 1-(3-aminocarbonylpropyl)-imidazol-4-yl, 1-(4-aminocarbonylbutyl)-imidazol-4-yl, 1-(5-aminocarbonylpentyl)-imidazol-4-yl, 1-(6-aminocarbonylhexyl)-imidazol-4-yl, 1-(7-aminocarbonyl-heptyl)-imidazol-4-yl, 1-methylaminocarbonylmethyl-imidazol-4-yl, 1-(2-methylaminocarbonylethyl)-imidazol-4-yl, 1-(3-methylaminocarbonylpropyl)-imidazol-4-yl, 1-(4-methylaminocarbonylbutyl)-imidazol-4-yl, 1-(5-methylaminocarbonylpentyl)-imidazol-4-yl, 1-(6-methylaminocarbonylhexyl)-imidazol-4-yl, 1-(7-methylaminocarbonylheptyl)-imidazol-4-yl, 1-ethylaminocarbonylmethyl-imidazol-4-yl, 1-(2-ethylamino-carbonylethyl)-imidazol-4-yl, 1-(3-ethylaminocarbonyl-propyl)-imidazol-4-yl, 1-(4-ethylaminocarbonylbutyl)-imidazol-4-yl, 1(5-ethylaminocarbonylpentyl)-imidazol-4-yl, 1-(6-ethylaminocarbonylhexyl)-imidazol-4-yl, 1-(7-ethylaminocarbonylheptyl)-imidazol-4-yl, 1-n-propylaminocarbonylmethyl-imidazol-4-yl, 1-(2-n-propylaminocarbonylethyl)-imidazol-4-yl, 1-(3-n-propylaminocarbonylpropyl)-imidazol-4-yl, 1-(4-n-propylaminocarbonylbutyl)-imidazol-4-yl, 1-(5-n-propylaminocarbonylpentyl)-imidazol-4-yl, 1-(6-n-propylaminocarbonylhexyl)-imidazol-4-yl, 1-(7-n-propylaminocarbonylheptyl)-imidazol-4-yl, 1-isopropylaminocarbonylmethyl-imidazol-4-yl, 1-(2-isopropylaminocarbonylethyl)-imidazol-4-yl, 1-(3-isopropylaminocarbonylpropyl)-imidazol-4-yl, 1-(4-isopropylaminocarbonylbutyl)-imidazol-4-yl, 1-(5-isopropylaminocarbonylpentyl)-imidazol-4-yl, 1-(6-isopropylaminocarbonylhexyl)-imidazol-4-yl, 1-(7-isopropylaminocarbonylheptyl)-imidazol-4-yl, 1-dimethylaminocarbonylmethyl-imidazol-4-yl, 1-(2-dimethylaminocarbonylethyl)-imidazol-4-yl, 1-(3-dimethylaminocarbonylpropyl)-imidazol-4-yl, 1-(4-dimethylaminocarbonylbutyl)-imidazol-4-yl, 1-(5-dimethylaminocarbonylpentyl)-imidazol-4-yl, 1-(6-dimethylaminocarbonylhexyl)-imidazol-4-yl, 1-(7-dimethylaminocarbonylheptyl)-imidazol-4-yl, 1-diethylaminocarbonylmethyl-imidazol-4-yl, 1-(2-diethylaminocarbonylethyl)-imidazol-4-yl, 1-(3-diethylaminocarbonylpropyl)-imidazol-4-yl, 1-(4-diethylaminocarbonylbutyl)-imidazol-4-yl, 1-(5-diethylaminocarbonylpentyl)-imidazol-4-yl, 1-(6-diethylaminocarbonylhexyl)-imidazol-4-yl, 1-(7-diethylaminocarbonylheptyl)-imidazol-4-yl, 1-di-n-propylaminocarbonylmethyl-imidazol-4-yl, 1-(2-di-n-propylaminocarbonylethyl)-imidazol-4-yl, 1-(3-di-n-propylaminocarbonylpropyl)-imidazol-4-yl, 1-(4-di-n-propylaminocarbonylbutyl)-imidazol-4-yl, 1-(5-di-n-propylaminocarbonylpentyl)-imidazol-4-yl, 1-(6-di-npropylaminocarbonylhexyl)-imidazol-4-yl, 1-(7-di-n-propylaminocarbonylheptyl)-imidazol-4-yl, 1-diisopropylaminocarbonylmethyl-imidazol-4-yl, 1-(2-diisopropylaminocarbonylethyl)-imidazol-4-yl, 1-(3-diisopropylaminocarbonylpropyl)-imidazol-4-yl, 1-(4-diisopropylaminocarbonylbutyl)-imidazol-4-yl, 1-(5-diisopropylaminocarbonylpentyl)-imidazol-4-yl, 1-(6-diisopropylaminocarbonylhexyl)-imidazol-4-yl, 1-(7-diisopropylaminocarbonylheptyl)-imidazol-4-yl, 1-morpholinocarbonylmethyl-imidazol-4-yl, 1-(2-morpholinocarbonylethyl)-imidazol-4-yl, 1-(3-morpholinocarbonylpropyl)-imidazol-4-yl, 1-(4-morpholinocarbonylbutyl)-imidazol-4-yl, 1-(5-morpholinocarbonylmethyl)-imidazol-4-yl, 1-(6-morpholinocarbonylhexyl)-imidazol-4-yl, 1-(7-morpholinocarbonylheptyl)-imidazol-4-yl, 1-thiomorpholinocarbonylmethyl-imidazol-4-yl, 1-(2-thiomorpholinocarbonylethyl)-imidazol-4-yl, 1-(3-thiomorpholinocarbonylpropyl)-imidazol-4-yl, 1-(4-thiomorpholinocarbonylbutyl)-imidazol-4-yl, 1-(5-thiomorpholinocarbonylpentyl)-imidazol-4-yl, 1-(6-thiomorpholinocarbonylhexyl)-imidazol-4-yl, 1-(7-thiomorpholinocarbonylheptyl)-imidazol-4-yl, 1-oxidothiomorpholinocarbonylmethyl-imidazol-4-yl, 1-(2-oxidothiomorpholinocarbonylethyl)-imidazol-4-yl, 1-(3-oxidothiomorpholinocarbonylpropyl)-imidazol-4-yl, 1-(4-oxidothiomorpholinocarbonylbutyl)-imidazol-4-yl, 1-(5-oxidothiomorpholinocarbonylpentyl)-imidazol-4-yl, 1-(6-oxidothiomorpholinocarbonylhexyl)-imidazol-4-yl, 1-(7-oxidothiomorpholinocarbonylheptyl)-imidazol-4-yl, 1-carboxymethyl-2-methyl-imidazol-4-yl, 1-(2-carboxyethyl)-2-methyl-imidazol-4-yl, 1-(3-carboxypropyl)-2-methyl-imidazol-4-yl, 1-(4-carboxybutyl)-2-methyl-imidazol-4-yl, 1-(5-carboxypentyl)-2-methyl-imidazol-4-yl, 1-(6-carboxyhexyl)-2-methyl-imidazol-4-yl, 1-(7-carboxyheptyl)-2-methyl-imidazol-4-yl, 1-methoxycarbonylmethyl-2-methyl-imidazol-4-yl, 1-(2methoxycarbonylethyl)-2-methyl-imidazol-4-yl, 1-(3-methoxycarbonylpropyl)-2-methyl-imidazol-4-yl, 1-(4-methoxycarbonylbutyl)-2-methyl-imidazol-4-yl, 1-(5-methoxycarbonylpentyl)-2-methyl-imidazol-4-yl, 1-(6-methoxycarbonylhexyl)-2-methyl-imidazol-4-yl, 1-(7-methoxycarbonylheptyl)-2-methyl-imidazol-4-yl, 1-ethoxycarbonylmethyl-2-methyl-imidazol-4-yl, 1-(2-ethoxycarbonylethyl)-2-methyl-imidazol-4-yl, 1-(3-ethoxycarbonylpropyl)-2-methyl-imidazol-4-yl, 1-(4-ethoxycarbonylbutyl)-2-methyl-imidazol-4-yl, 1-(5-ethoxycarbonylpentyl)-2-methyl-imidazol-4-yl, 1-(6-ethoxycarbonylhexyl)-2-methyl-imidazol-4-yl, 1-(7-ethoxycarbonylheptyl)-2-methyl-imidazol-4-yl, 1-n-propoxycarbonylmethyl-2-methyl-imidazol-4-yl, 1-(2-n-propoxycarbonylethyl)-2-methyl-imidazol-4-yl, 1-(3-n-propoxycarbonylpropyl)-2-methyl-imidazol-4-yl, 1-(4-n-propoxycarbonylbutyl)-2-methyl-imidazol-4-yl, 1-(5-n-propoxycarbonylpentyl)-2-methyl-imidazol-4-yl, 1-(6-n-propoxycarbonylhexyl)-2-methyl-imidazol-4-yl, 1-(7 -n-propoxycarbonylheptyl)-2-methyl-imidazol-4-yl, 1-isopropoxycarbonylmethyl-2-methyl-imidazol-4-yl, 1-(2-isopropoxycarbonylethyl)-2-methyl-imidazol-4-yl, 1-(3-isopropoxycarbonylpropyl)-2-methyl-imidazol-4-yl, 1-(4-isopropoxycarbonylbutyl)-2-methyl-imidazol-4-yl, 1-(5-isopropoxycarbonylpentyl)-2-methyl-imidazol-4-yl, 1-(6-isopropoxycarbonylhexyl)-2-methyl-imidazol-4-yl, 1-(7-isopropoxycarbonylheptyl)-2-methyl-imidazol-4-yl, 1-aminocarbonylmethyl-2-methyl-imidazol-4-yl, 1-(2-aminocarbonylethyl)-2-methyl-imidazol-4-yl, 1-(3-aminocarbonylpropyl)-2-methyl-imidazol-4-yl, 1-(4-aminocarbonylbutyl)-2-methyl-imidazol-4-yl, 1-(5-aminocarbonylpentyl)-2-methyl-imidazol-4-yl, 1-(6-aminocarbonylhexyl)-2-methyl-imidazol-4-yl, 1-(7-aminocarbonylheptyl)-2-methyl-imidazol-4-yl, 1-methylaminocarbonylmethyl-2-methyl-imidazol-4-yl, 1-(2-methylaminocarbonylethyl)-2-methyl-imidazol-4-yl, 1-(3-methylaminocarbonylpropyl)-2-methyl-imidazol-4-yl, 1-(4-methylaminocarbonylbutyl)-2-methyl-imidazol-4-yl, 1-(5-methylaminocarbonylpentyl)-2-methyl-imidazol-4-yl, 1-(6-methylaminocarbonylhexyl)-2-methyl-imidazol-4-yl, 1-(7-methylaminocarbonylheptyl)-2-methyl-imidazol-4-yl, 1-ethylaminocarbonylmethyl-2-methyl-imidazol-4-yl, 1-(2-ethylaminocarbonylethyl)-2-methyl-imidazol-4-yl, 1-(3-ethylaminocarbonylpropyl)-2-methyl-imidazol-4-yl, 1-(4-ethylaminocarbonylbutyl)-2-methyl-imidazol-4-yl, 1-(5-ethylaminocarbonylpentyl)-2-methyl-imidazol-4-yl, 1-(6-ethylaminocarbonylhexyl)-2-methyl-imidazol-4-yl, 1-(7-ethylaminocarbonylheptyl)-2-methyl-imidazol-4-yl, 1-n-propylaminocarbonylmethyl-2-methyl-imidazol-4-yl, 1-(2-n-propylaminocarbonylethyl)-2-methyl-imidazol-4-yl, 1-(3-n-propylaminocarbonylpropyl)-2-methyl-imidazol-4-yl, 1-(4-n-propylaminocarbonylbutyl)-2-methyl-imidazol-4-yl, 1-(5-n-propylaminocarbonylpentyl)-2-methyl-imidazol-4-yl, 1-(6-n-propylaminocarbonylhexyl)-2-methyl-imidazol-4-yl, 1-(7-n-propylaminocarbonylheptyl)-2-methyl-imidazol-4-yl, 1-isopropylaminocarbonylmethyl-2-methyl-imidazol-4-yl, 1-(2-isopropylaminocarbonylethyl)-2-methyl-imidazol-4-yl, 1-(3-isopropylaminocarbonyl-propyl)-2-methyl-imidazol-4-yl, 1-(4-isopropylamino-carbonylbutyl)-2-methyl-imidazol-4-yl, 1-(5-isopropylaminocarbonylpentyl)-2-methyl-imidazol-4-yl, 1-(6-isopropylaminocarbonylhexyl)-2-methyl-imidazol-4-yl, 1-(7-isopropylaminocarbonylheptyl)-2-methyl-imidazol-4-yl, 1-dimethylaminocarbonylmethyl-2-methyl-imidazol-4-yl, 1-(2-dimethylaminocarbonylethyl)-2-methyl-imidazol-4-yl, 1-(3-dimethylaminocarbonylpropyl)-2-methyl-imidazol-4-yl, 1-(4-dimethylaminocarbonylbutyl)-2-methyl-imidazol-4-yl, 1-(5-dimethylaminocarbonylpentyl)-2-methyl-imidazol-4-yl, 1-(6-dimethylaminocarbonyl-hexyl)-2-methyl-imidazol-4-yl, 1-(7-dimethylamino-carbonylheptyl)-2-methyl-imidazol-4-yl, 1-diethylaminocarbonylmethyl-2-methyl-imidazol-4-yl, 1-(2-diethylaminocarbonylethyl)-2-methyl-imidazol-4-yl, 1-(3-diethylaminocarbonylpropyl)-2-methyl-imidazol-4-yl, 1-(4-diethylaminocarbonylbutyl)-2-methyl-imidazol-4-yl, 1-(5-diethylaminocarbonylpentyl)-2-methyl-imidazol-4-yl, 1-(6-diethylaminocarbonylhexyl)-2-methyl-imidazol-4-yl, 1-(7-diethylaminocarbonylheptyl)-2-methyl-imidazol-4-yl, 1-di-n-propylaminocarbonylmethyl-2-methyl-imidazol-4-yl, 1-(2-di-n-propylaminocarbonylethyl)-2-methyl-imidazol-4-yl, 1-(3-di-n-propylaminocarbonylpropyl)-2-methyl-imidazol-4-yl, 1-(4-di-n-propylaminocarbonylbutyl)-2-methyl-imidazol-4-yl, 1-(5-di-n-propylaminocarbonylpentyl)-2-methyl-imidazol-4-yl, 1-(6-di-n-propylamino-carbonylhexyl)-2-methyl-imidazol-4-yl, 1-(7-di-n-propylaminocarbonylheptyl)-2-methyl-imidazol-4-yl, 1-diisopropylaminocarbonylmethyl-2-methyl-imidazol-4-yl, 1-(2-diisopropylaminocarbonylethyl)-2-methyl-imidazol-4-yl, 1-(3-diisopropylaminocarbonylpropyl)-2-methyl-imidazol-4-yl, 1-(4-diisopropylaminocarbonylbutyl)-2-methyl-imidazol-4-yl, 1-(5-diisopropylaminocarbonyl-pentyl)-2-methyl-imidazol-4-yl, 1-(6-diisopropylaminocarbonylhexyl)-2-methyl-imidazol-4-yl, 1-(7-diisopropyl-aminocarbonylheptyl)-2-methyl-imidazol-4-yl, 1-morpholinocarbonylmethyl-2-methyl-imidazol-4-yl, 1-(2-morpholinocarbonylethyl)-2-methyl-imidazol-4-yl, 1-(3-morpholinocarbonylpropyl)-2-methyl-imidazol-4-yl, 1-(4-morpholinocarbonylbutyl)-2-methyl-imidazol-4-yl, 1-(5-morpholinocarbonylpentyl)-2-methyl-imidazol-4-yl, 1-(6-morpholinocarbonylhexyl)-2-methyl-imidazol-4-yl, 1-(7-morpholinocarbonylheptyl)-2-methyl-imidazol-4-yl, 1-thiomorpholinocarbonylmethyl-2-methyl-imidazol-4-yl, 1-(2-thiomorpholinocarbonylethyl)-2-methyl-imidazol-4-yl, 1-(3-thiomorpholinocarbonylpropyl)-2-methyl-imidazol-4-yl, 1-(4-thiomorpholinocarbonylbutyl)-2-methyl-imidazol-4-yl, 1-(5-thiomorpholinocarbonylpentyl)-2-methyl-imidazol-4-yl, 1-(6-thiomorpholinocarbonyl-hexyl)-2-methyl-imidazol-4-yl, 1-(7-thiomorpholino-carbonylheptyl)-2-methyl-imidazol-4-yl, 1-oxidothio-morpholinocarbonylmethyl-2-methyl-imidazol-4-yl, 1-(2-oxidothiomorpholinocarbonylethyl)-2-methyl-imidazol-4-yl, 1-(3-oxidothiomorpholinocarbonyl-propyl)-2-methyl-imidazol-4-yl, 1-(4-oxidothiomor-pholinocarbonylbutyl)-2-methyl-imidazol-4-yl, 1-(5-oxidothiomorpholinocarbonyl-pentyl)-2-methyl-imidazol-4-yl, 1-(6-oxidothio-morpholinocarbonylhexyl)-2-methyl-imidazol-4-yl, 1-(7-oxidothiomorpholinocarbonylheptyl)-2-methyl-imidazol-4-yl, 1-(2-hydroxyethyl)-imidazol-4-yl, 1-(3-hydroxypropyl)-imidazo-4-yl, 1-(4-hydroxybutyl)-imi-dazol-4-yl, 1-(2-methoxyethyl)-imidazol-4-yl, 1-(3-methoxypropyl)-imidazol-4-yl, 1-(4-methoxybutyl)-imidazol-4-yl, 1-(2-ethoxyethyl)-imidazol-4-yl, 1-(3-ethoxypropyl)-imidazol-4-yl, 1-(4-ethoxybutyl)-imidazol-4-yl, 1-(2-n-propoxyethyl)-imidazol-4-yl, 1-(3-n-propoxypropyl)-imidazol-4-yl, 1-(4-n-propoxy-butyl)-imidazol-4-yl, 1-(2-isopropoxyethyl)-imidazol-4-yl, 1-(3-isopropoxypropyl)-imidazol-4-yl, 1-(4-iso-propoxy-butyl)-imidazol-4-yl, 1-(2-imidazol-1-yl-ethyl)-imidazol-4-yl, 1-(3-imidazol-1-yl-propyl)-imidazol-4-yl, 1-(4-imidazol-1-yl-butyl)-imidazol-4-yl, 1-(2,2-diphenyl-ethyl)-imidazol-4-yl, 1(3,3-diphenyl-propyl)-imidazol-4-yl, 1-(4,4-diphenyl-butyl)-imidazol-4-yl, 1-(2-hydroxyethyl)-2-methyl-imidazol-4-yl, 1(3-hydroxy-propyl)-2-methyl-imidazol-4-yl, 1-(4-hydroxybutyl)-2-methyl-imidazol-4-yl, 1-(2-methoxyethyl)-2-methyl-imidazol-4-yl, 1-(3-methoxypropyl)-2-methyl-imidazol-4-yl, 1-(4-methoxybutyl)-2-methyl-imidazol-4-yl, 1-(2-ethoxy-ethyl)-2-methyl-imidazol-4-yl, 1-(3-ethoxypropyl)-2-methyl-imidazol-4-yl, 1-(4-ethoxybutyl)-2-methyl-imidazol-4-yl, 1-(2-n-propoxyethyl)-2-methyl-imidazol-4-yl, 1-(3-n-propoxypropyl)-2-methyl-imidazol-4-yl, 1-(4-n-propoxybutyl)-2-methyl-imidazol-4-yl, 1-(2-isopropoxyethyl)-2-methyl-imidazol-4-yl, 1-(3-isopropoxypropyl)-2-methylimidazol-4-yl, 1-(4-isopropoxybutyl)-2-methyl-imidazol-4-yl, 1-(2-imidazol-1-yl-ethyl)-2-methyl-imidazol-4-yl, 1-(3-imidazol-1-yl-propyl)-2-methyl-imidazol-4-yl, 1-(4-imidazol-1-yl-butyl)-2-methyl-imidazol-4-yl, 1-(2,2-diphenyl-ethyl)-2-methyl-imidazol-4-yl, 1-(3,3-diphenyl-propyl)-2-methyl-imidazol-4-yl, 1-(4,4-diphenyl-butyl)-2-methyl-imidazol-4-yl, 1-[2-(2-methoxyethoxy)-ethyl]-imidazol-4-yl, 1-[3-(2-methoxyethoxy)propyl]-imidazol-4-yl, 1-[4-(2-methoxyethoxy)-butyl]-imidazol-4-yl, 1-[2-(2-ethoxyethoxy)-ethyl]-imidazol-4-yl, 1-[3-(2-ethoxyethoxy)-propyl]-imidazol-4-yl, 1-[4-(2-ethoxyethoxy)butyl]-imidazol-4-yl, 1-[2-(2-n-propoxyethoxy)-ethyl]-imidazol-4-yl, 1-[3-(2-n-propoxyethoxy)-propyl]-imidazol-4-yl, 1-[4-(2-n-propoxyethoxy)-butyl]-imidazol-4-yl, 1-[2-(2-isopropoxyethoxy)-ethyl]-imidazol-4-yl, 1-[3-(2-isopropoxyethoxy)-propyl]-imidazol-4-yl, 1-[4-(2-isopropoxyethoxy)-butyl]-imidazol-4-yl, 1-(2-dimethylaminoethyl)-imidazol-4-yl, 1-(2-diethylamino-ethyl)-imidazol-4-yl, 1-(2-di-n-propylamino-ethyl)-imidazol-4-yl, 1-(2-diisopropylaminoethyl)-imidazol-4-yl, 1-(3-dimethylaminopropyl)-imidazol-4-yl, 1-(3-diethylaminopropyl)-imidazol-4-yl, 1-(3-di-n-propylamino-propyl)-imidazol-4-yl, 1-(3-di-isopropylamino-propyl)-imidazol-4-yl, 1-(4-dimethylamino-butyl)-imidazol-4-yl, 1-(4-diethylamino-butyl)-imidazol-4-yl, 1-(4-di-n-propylamino-butyl)-imidazol-4-yl, 1(4-diisopropylamino-butyl)-imidazol-4-yl, 1-(2-morpholino-ethyl)-imidazol-4-yl, 1-(3-morpholino-propyl)-imidazol-4-yl, 1-(4-morpholino-butyl)-imidazol-4-yl, 1-(2-pyrrolidino-ethyl)-imidazol-4-yl, 1-(3-pyrrolidino-propyl)-imidazol-4-yl, 1-(4-pyrrolidino-butyl)-imidazol-4-yl, 1-(2-piperidino-ethyl)-imidazol-4-yl, 1-(3-piperidino-propyl)-imidazol-4-yl, 1-(4-piperidino-butyl)-imidazol-4-yl, 1-(2-hexamethyleneimino-ethyl)-imidazol-4-yl, 1-(3-hexamethyleneimino-propyl)-imidazol-4-yl, 1-(4-hexamethyleneimino-butyl)-imidazol-4-yl, 1-(2-thiomorpholino-ethyl)-imidazol-4-yl, 1-(3-thio-morpholino-propyl)-imidazol-4-yl, 1-(4-thiomorpholino-butyl)-imidazol-4-yl, 1-[2-(1-oxido-thiomorpholino)-ethyl]-imidazol-4-yl, 1-[3-(1-oxido-thiomorpholino)-propyl]-imidazol-4yl or 1-[4-(1-oxido-thiomorpholino)-butyl]-imidazol-4-yl group, $R_3$ may represent an ethyl, n-propyl, isopropyl, n-butyl, isobutyl, tert.butyl, cyclopropyl, cyclobutyl, ethoxy, n-propoxy, isopropoxy, ethylthio, n-propylthio or isopropylthio group and $R_4$ may represent a hydroxycarbonyl, methoxycarbonyl, ethoxycarbonyl, n-propyloxycarbonyl, isopropyloxycarbonyl, n-butyloxycarbonyl, isobutyloxycarbonyl, tert.butyloxycarbonyl, n-pentyloxycarbonyl, isoamyloxycarbonyl, n-hexyloxy-carbonyl, cyclopentyloxycarbonyl, cyclohexyloxycarbonyl, benzyloxycarbonyl, 1-phenylethyloxycarbonyl, 2-phenylethyloxycarbonyl, 3-phenylpropyloxycarbonyl, methoxymethoxycarbonyl, cinnamyloxycarbonyl, acetoxymethoxycarbonyl, propionyloxymethoxycarbonyl, n-butyryloxymethoxycarbonyl, isobutyryloxymethoxycarbonyl, n-pentanoyloxymethoxycarbonyl, isopentanoyloxy-methoxycarbonyl, pivaloyloxymethoxycarbonyl, n-hexanoyloxymethoxycarbonyl, cyclopentanoyloxymethoxycarbonyl, cyclohexanoyloxymethoxycarbonyl, phenylacetoxymethoxycarbonyl, 2-phenylpropionyloxy-methoxycarbonyl, 3-phenylpropionyloxymethoxycarbonyl, 4-phenylbutyryloxymethoxycarbonyl, benzoyloxy-methoxycarbonyl, 1-acetoxyethoxycarbonyl, 1-propionyloxyethoxycarbonyl, 1-n-butyryloxy-ethoxycarbonyl, 1-isobutyryloxyethoxycarbonyl, 1-n-pentanoyloxyethoxycarbonyl, 1-isopentanoyloxy-ethoxycarbonyl, 1-pivaloyloxyethoxycarbonyl, 1-n-hexanoyloxyethoxycarbonyl, 1-cyclopentanoyl-oxyethoxycarbonyl, 1-cyclohexanoyloxyethoxycarbonyl, 1-phenylacetoxyethoxycarbonyl, 1-(1-phenylpropionyloxy)-ethoxycarbonyl, 1-(2-phenylpropionyloxy)-ethoxycarbonyl, 1-(3-phenylbutyryloxy)-ethoxycarbonyl, 1-benzoyloxyethoxycarbonyl, methoxycarbonyloxymethoxycarbonyl, ethoxycarbonyloxymethoxycarbonyl, n-propyloxycarbonyloxymethoxycarbonyl, isopropyloxycarbonyloxymethoxycarbonyl, n-butyloxycarbonyloxymethoxycarbonyl, isobutyloxycarbonyloxymethoxy-carbonyl, tert.butyloxycarbonyloxymethoxycarbonyl, n-pentyloxycarbonyloxymethoxycarbonyl, isoamyloxycarbonyloxymethoxycarbonyl, n-hexyloxycarbonyloxymethoxy-carbonyl, cyclopentyloxycarbonyloxymethoxycarbonyl, cyclohexyloxycarbonyloxymethoxycarbonyl, benzyloxycarbonyloxymethoxycarbonyl, 1-phenylethoxycarbonyloxymethoxycarbonyl, 2-phenylethoxycarbonyloxy-methoxycarbonyl, 3-phenylpropyloxycarbonyloxy-methoxycarbonyl, cinnamyloxycarbonyloxymethoxycarbonyl, 1-(methoxycarbonyloxy)ethoxycarbonyl, 1-(ethoxycarbonyloxy)-ethoxycarbonyl, 1-(n-propyloxycarbonyloxy)-ethoxycarbonyl, 1-(isopropyloxycarbonyloxy)-ethoxycarbonyl, 1-(n-butyloxycarbonyloxy)-ethoxycarbonyl, 1-(isobutyloxycarbonyloxy)-ethoxycarbonyl, 1-(tert.butyloxycarbonyloxy)ethoxycarbonyl, 1-(n-pentyloxycarbonyloxy)-ethoxycarbonyl, 1-(isoamyloxycarbonyloxy)-ethoxycarbonyl, 1-(n-hexyloxycarbonyloxy)-ethoxycarbonyl, 1(cyclopentyloxycarbonyloxy)-ethoxy-carbonyl, 1-(cyclohexyloxycarbonyloxy)-ethoxycarbonyl, cyclopentylcarbonyloxymethoxycarbonyl, 1-(benzyloxycarbonyloxy)-ethoxycarbonyl, 1-(1-phenylethoxycarbonyloxy)-ethoxycarbonyl, 1-(2-phenylethoxycarbonyloxy)-ethoxycarbonyl, 1-(3-phenylpropyloxycarbonyloxy)-ethoxycarbonyl, 1-(cinnamyloxycarbonyloxy)-ethoxycarbonyl, cyano, 1H-tetrazolyl, 1-triphenylmethyl-tetrazolyl or 2-triphenylmethyl-tetrazolyl group.

In compounds according to Option C $R_1$ may denote a fluorine, chlorine or bromine atom or a fluoromethyl, difluoromethyl, trifluoromethyl, methyl, ethyl, n-propyl or isopropyl group, $R_2$ may denote the 5,5-spiro-cyclopentano-dihydro-imidazol-4-on-2-yl, 1-methyl-5,5-spiro-cyclopentano-dihydro-imidazol-4-on-2-yl, 1-ethyl-5,5-spiro-cyclopentano-dihydro-imidazol-4-on-2-yl, 1-n-propyl-5,5-spiro-cyclopentano-dihydro-imidazol-4-on-2-yl, 1-isopropyl-5,5-spiro-cyclopentano-dihydro-imidazol-4-on-2-yl, 4,5-dimethyl-oxazol-2-yl, 4-methyl-5-ethyl-oxazol-2-yl, 4-methyl-5-n-propyl-oxazol-2-yl, 4-methyl-5-n-butyl-oxazol-2-yl, 4-methyl-5-n-pentyl-oxazol-2-yl, 4-methyl-5-phenyl-oxazol-2-yl, 4,5-diethyl-oxazol-2-yl, 4-ethyl-5-n-propyl-oxazol-2-yl, 4-ethyl-5-n-butyl-oxazol-2-yl, 4-ethyl-5-n-pentyl-oxazol-2-yl, 4-ethyl-5-phenyl-oxazol-2-yl, 4,5-di-n-propyl-oxazol-2-yl, 4-n-propyl-5-n-butyl-oxazol-2-yl, 4-n-propyl-5-n-pentyl-oxazol-2-yl, 4-n-propyl-5-phenyl-oxazol-2-yl, 5-methyl-4-ethyl-oxazol-2-yl, 5-methyl-4-n-propyl-oxazol-2-yl, 4,5-diphenyl-oxazol-2-yl, 5,6,7,8-tetrahydro-benzoxazol-2-yl, 4,5-dimethyl-thiazol-2-yl, 4-methyl-5-ethyl-thiazol-2-yl, 4-methyl-5-n-propyl-thiazol-2-yl, 4-methyl-5-phenyl-thiazol-2-yl, 4,5-diethyl-thiazol-2-yl, 4-ethyl-5-n-propyl-thiazol-2-yl, 4-ethyl-5-phenyl-thiazol-2-yl, 4,5-di-n-propyl-thiazol-2-yl, 4,5-di-n-isopropyl-thiazol-2-yl, 4-n-propyl-5-phenyl-thiazol-2-yl, 4,5-diphenyl-thiazol-2-yl, 5,6,7,8-tetrahydro-benz-thiazol-2-yl, 4-methyl-oxazolin-2-yl, 4-ethyl-oxazolin-2-yl, 4-n-propyl-oxazolin-2-yl, 4-isopropyl-oxazolin-2-yl, 4-n-butyl-oxazolin-2-yl, 4-isobutyl-oxazolin-2-yl, 4-benzyl-oxazolin-2-yl, 4-phenyl-oxazolin-2-yl, 4,4-dimethyl-oxazolin-2-yl, 4-methyl-5-phenyl-oxazolin-2-yl, 4,4-dimethyl-5-n-propyl-oxazolin-2-yl, 4,5-tetramethylene-oxazolin-2-yl, 4-methyl-imidazolin-2-yl, 4,5-dimethyl-imidazolin-2-yl, 4,5-tetramethylene-imidazolin-2-yl, 4-methyl-imidazol-2-yl, 4,5-dimethyl-imidazol-2-yl, 1,4,5-trimethyl-imidazol-2-yl, 1-ethyl-4,5-dimethyl-imidazol-2-yl, 1-n-propyl-4,5-dimethyl-imidazol-2-yl, 1-isopropyl-4,5-dimethyl-imidazol-2-yl, 1-n-butyl-4,5-dimethyl-imidazol-2-yl, 1-isobutyl-4,5-dimethyl-imidazol-2-yl, 1-cyclopropyl-4,5-dimethyl-imidazol-2-yl, 1-cyclobutyl-4,5-dimethyl-imidazol-2-yl, 1-cyclopentyl-4,5-dimethyl-imidazol-2-yl, 1-cyclohexyl-4,5-dimethyl-imidazol-2-yl, 1-cycloheptyl-4,5-dimethyl-imidazol-2-yl, 1-benzyl-4,5-dimethyl-imidazol-2-yl, 1-(2-phenyl-ethyl)-4,5-dimethyl-imidazol-2-yl, 1-carboxymethyl-4,5-dimethyl-imidazol-2-yl, 3-methoxycarbonylmethyl-4,5-dimethyl-imidazol-2-yl, 1-ethoxycarbonylmethyl-4,5-dimethyl-imidazol-2-yl, 1-n-propoxycarbonylmethyl-4,5-dimethyl-imidazol-2-yl, 1-isopropoxycarbonylmethyl-4,5-dimethyl-imidazol-2-yl, 1-aminocarbonylmethyl-4,5-dimethyl-imidazol-2-yl, 1-methylaminocarbonylmethyl-4,5-dimethyl-imidazol-2-yl, 1-ethylaminocarbonylmethyl-4,5-dimethyl-imidazol-2-yl, 1-n-propoylaminocarbonylmethyl-4,5-dimethyl-imidazol-2-yl, 1-isopropylamino-carbonylmethyl-4,5-dimethyl-imidazol-2-yl, 1-dimethylaminocarbonylmethyl-4,5-dimethyl-imidazol-2-yl, 1-diethylaminocarbonylmethyl-4,5-dimethyl-imidazol-2-yl, 1-di-n-propylaminocarbonylmethyl-4,5-dimethylimidazol-2-yl, 1-diisopropylaminocarbonylmethyl-4,5-dimethyl-imidazol-2-yl, 1-N-methyl-ethylaminocarbonylmethyl-4,5-dimethyl-imidazol-2-yl, 1-(2-carboxy-ethyl)-4,5-dimethyl-imidazol-2-yl, 1-(2-methoxycarbonyl-ethyl)-4,5-dimethyl-imidazol-2-yl, 1-(2-ethoxycarbonyl-ethyl)-4,5-dimethyl-imidazol-2-yl, 1-(2-n-propoxycarbonyl-ethyl)-4,5-dimethyl-imidazol-2-yl, 1-(2-isopropoxycarbonyl-ethyl)-4,5-dimethyl-imidazol-2-yl, 1-(2-aminocarbonyl-ethyl)-4,5-dimethyl-imidazol-2-yl, 1-(2-methylaminocarbonyl-ethyl)-4,5-dimethyl-imidazol-2-yl, 1-(2-ethylaminocarbonyl-ethyl)-4,5-dimethyl-imidazol-2-yl, 1-(2-n-propylaminocarbonyl-ethyl)-4,5-dimethyl-imidazol-2-yl, 1-(2-isopropylaminocarbonylethyl)-4,5-dimethyl-imidazol-2-yl, 1-(2-dimethylaminocarbonyl-ethyl)-4,5-dimethyl-imidazol-2-yl, 1-(2-diethylaminocarbonyl-ethyl)-4,5-dimethyl-imidazol-2-yl, 1-(2-di-n-propylaminocarbonyl-ethyl)-4,5-dimethyl-imidazol-2-yl, 1-(2-diisopropylaminocarbonyl-ethyl)-4,5-dimethyl-imidazol-2-yl, 1-(2-N-methyl-ethylamino-carbonyl-ethyl)-4,5-dimethyl-imidazol-2-yl, 1-(3-carboxy-propyl)-4,5-dimethyl-imidazol-2-yl, 1-(3-methoxycarbonyl-propyl)-4,5-dimethyl-imidazol-2-yl, 1-(3-ethoxycarbonyl-propyl)-4,5-dimethyl-imidazol-2-yl, 1-(3-n-propoxycarbonyl-propyl)-4,5-dimethyl-imidazol-2-yl, 1-(3-isopropoxycarbonyl-propyl)-4,5-dimethyl-imidazol-2-yl, 1-(3-aminocarbonyl-propyl)-4,5-dimethyl-imidazol-2-yl, 1-(3-methylaminocarbonyl-propyl)-4,5-dimethyl-imidazol-2-yl, 1-(3-ethylaminocarbonyl-propyl)-4,5-dimethyl-imidazol-2-yl, 1-(3-n-propylaminocarbonyl-propyl)-4,5-dimethyl-imidazol-2-yl, 1-(3-isopropylaminocarbonylpropyl)-4,5-dimethyl-imidazol-2-yl, 1-(3-dimethylaminocarbonyl-propyl)-4,5-dimethyl-imidazol-2-yl, 1-(3-diethylaminocarbonyl-propyl)-4,5-dimethyl-imidazol-2-yl, 1-(3-di-n-propylaminocarbonyl-propyl)-4,5-dimethyl-imidazol-2-yl, 1-(3-diisopropylaminocarbonyl-propyl)-4,5-dimethyl-imidazol-2-yl, 1-(3-N-methyl-ethylaminocarbonyl-propyl)-4,5-dimethyl-imidazol-2-yl, 1-(2,2,2-trifluoroethyl)-4,5-dimethyl-imidazol-2-yl, 1-(2-hydroxyethyl)-4,5-dimethyl-imidazol-2-yl, 1-(3-hydroxypropyl)-4,5-dimethyl-imidazol-2-yl, 1-(4-hydroxybutyl)-4,5-dimethyl-imidazol-2-yl, 1-(2-methoxyethyl)-4,5-dimethyl-imidazol-2-yl, 1-(3-methoxypropyl)-4,5-dimethyl-imidazol-2-yl, 1-(4-methoxybutyl)-4,5-dimethyl-imidazol-2-yl, 1-(2-ethoxyethyl)-4,5-dimethyl-imidazol-2-yl, 1-(3-ethoxypropyl)-4,5-dimethyl-imidazol-2-yl, 1-(4-ethoxybutyl)-4,5-dimethyl-imidazol-2-yl, 1-(2-isopropoxyethyl)-4,5-dimethyl-imidazol-2-yl, 1-(3-n-propoxypropyl)-4,5-dimethyl-imidazol-2-yl, 1-(4-isopropoxybutyl)-4,5-dimethyl-imidazol-2-yl, 1-(2-pyrrolidinoethyl)-4,5-dimethyl-imidazol-2-yl, 1-(3-pyrrolidinopropyl)-4,5-dimethyl-imidazol-2-yl, 1-(4-pyrrolidinobutyl)-4,5-dimethyl-imidazol-2-yl, 1-(2-piperidinoethyl)-4,5-dimethyl-imidazol-2-yl, 1-(3-piperidinopropyl)-4,5-dimethyl-imidazol-2-yl, 1-(4-piperidinobutyl)-4,5-dimethyl-imidazol-2-yl, 1-(2-morpholinoethyl)-4,5-dimethyl-imidazol-2-yl, 1-(3-morpholinopropyl)-4,5-dimethyl-imidazol-2-yl, 1-(4-morpholinobutyl)-4,5-dimethyl-imidazol-2-yl, 1-phenyl-4,5-dimethyl-imidazol-2-yl, 1-benzyl-4,5-dimethyl-imidazol-2-yl, 1-(1-phenylethyl)-4,5-dimethyl-imidazol-2-yl, 1-(2-phenylethyl)-4,5-dimethyl-imidazol-2-yl, 1-(1-phenylpropyl)-4,5-dimethyl-imidazol-2-yl, 1-(2-phenylpropyl)-4,5-dimethyl-imidazol-2-yl, 1-(3-phenylpropyl)-4,5-dimethyl-imidazol-2-yl, 1-methyl-4,5-diethyl-imidazol-2-yl, 1,4,5-triethyl-imidazol-2-yl, 1-ethyl-4-isopropyl-5-methyl-imidazol-2-yl, 1-ethyl-4-isobutyl-5-methyl-imidazol-2-yl, 1-n-propyl-4-isopropyl-5-methyl-imidazol-2-yl, 1-n-propyl-4-isobutyl-5-methyl-imidazol-2-yl, 1,4-di-isopropyl-5-methyl-imidazol-2-yl, 1-isopropyl-4-isobutyl-5-methyl-imidazol-2-yl, 1-(2-dimethylamino-ethyl)-4-isopropyl-5-methyl-imidazol-2-yl, 1-(2-dimethylamino-ethyl)-4-isobutyl-5-methyl-imidazol-2-yl, 1-(3-dimethylamino-propyl)-4-isopropyl-5-methyl-imidazol-2-yl, 1-(3-dimethylamino-propyl)-4-isobutyl-5-methyl-imidazol-2-yl, 1,5-dimethyl-4-ethyl-imidazol-2-yl, 1,5-dimethyl-4-n-propyl-imidazol-2-yl, 1,5-dimethyl-4-isopropyl-imidazol-2-yl, 1,5-dimethyl-4-isobutyl-imidazol-2-yl, 1,5-dimethyl-4-phenyl-imidazol-2-yl, 1-methyl-4,5-diphenyl-imidazol-2-yl, 1-ethyl-4,5-diphenyl-imidazol-2-yl, 1-n-propyl-4,5-diphenyl-imidazol-2-yl, 1-isopropyl-4,5-diphenyl-imidazol-2-yl, 1-carboxymethyl-4,5- diphenyl-imidazol-2-yl, 1-methoxycarbonylmethyl-4,5-diphenyl-imidazol-2-yl, 1-ethoxycarbonylmethyl-4,5-diphenyl-imidazol-2-yl, 4,5-trimethylene-imidazol-2-yl, 1-methyl-4,5-trimethylene-imidazol-2-yl, 5,6,7,8-tetrahydro-benzimidazol-2-yl, 1-methyl-5,6,7,8-tetrahydro-benzimidazol-2-yl, 1-ethyl-5,6,7,8-tetrahydro-benzimidazol-2-yl, 1-n-propyl-5,6,7,8-tetrahydro-benzimidazol-2-yl, 1-isopropyl-5,6,7,8-tetrahydro-benzimidazol-2-yl, 1-n-butyl-5,6,7,8-tetrahydro-benzimidazol-2-yl, 1-isobutyl-5,6,7,8-tetrahydro-benzimidazol-2-yl, 1-n-pentyl-5,6,7,8-tetrahydro-benzimidazol-2-yl, 1-n-hexyl-5,6,7,8-tetrahydro-benzimidazol-2-yl, 1-cyclopropyl-5,6,7,8-tetrahydro-benzimidazol-2-yl, 1-cyclobutyl-5,6,7,8-tetrahydro-benzimidazol-2-yl, 1-cyclopentyl-5,6,7,8-tetrahydro-benzimidazol-2-yl, 1-cyclohexyl-5,6,7,8-tetrahydro-benzimldazol-2-yl, 1-cycloheptyl-5,6,7,8-tetrahydro-benzimldazol-2-yl, 1-carboxymethyl-5,6,7,8-tetrahydro-benzimidazol-2-yl, 1-methoxycarbonylmethyl-5,6,7,8-tetrahydro-benzimidazol-2-yl, 1-ethoxycarbonylmethyl-5,6,7,8-tetrahydro-benzimidazol- 2-yl, 1-n-propoxycarbonylmethyl-5,6,7,8-tetrahydro-benzimidazol-2-yl, 1-isopropoxycarbonylmethyl-5,6,7,8-tetrahydro-benzimidazol-2-yl, 1-aminocarbonylmethyl-5,6,7,8-tetrahydro-benzimidazol-2-yl, 1-methylaminocarbonylmethyl-5,6,7,8-tetrahydro-benzimidazol-2-yl, 1-ethylaminocarbonylmethyl-5,6,7,8-tetrahydro-benzimidazol-2-yl, 1-n-propylaminocarbonylmethyl-5,6,7,8-tetrahydro-benzimidazol-2-yl, 1-isopropylaminocarbonylmethyl-5,6,7,8-tetrahydro-benzimidazol-2-yl, 1-dimethylaminocarbonylmethyl-5,6,7,8-tetrahydro-benzimidazol-2-yl, 1-diethylaminocarbonylmethyl-5,6,7,8-tetrahydro-benzimidazol-2-yl, 1-di-n-propylaminocarbonylmethyl-5,6,7,8-tetrahydro-benzimidazol-2-yl, 1-diisopropylaminocarbonylmethyl-5,6,7,8-tetrahydro-benzimidazol-2-yl, 1-N-methylethylaminocarbonylmethyl-5,6,7,8-tetrahydro-benzimidazol-2-yl, 1-(2-carboxy-ethyl)-5,6,7,8-tetrahydro-benzimidazol-2-yl, 1-(2-methoxycarbonyl-ethyl)-5,6,7,8-tetrahydro-benzimidazol-2-yl, 1-(2-ethoxycarbonyl-ethyl)-5,6,7,8-tetrahydro-benzimidazol-2-yl, 1(2-n-propoxycarbonyl-ethyl)-5,6,7,8-tetrahydro-benzimidazol-2-yl, 1-(2-isopropoxycarbonyl-ethyl)-5,6,7,8-tetrahydro-benzimidazol-2-yl, 1-(2-aminocarbonyl-ethyl)-5,6,7,8-tetrahydro-benzimidazol-2-yl, 1-(2-methylaminocarbonyl-ethyl)-5,6,7,8-tetrahydro-benzimidazol-2-yl, 1-(2-ethylaminocarbonyl-ethyl)-5,6,7,8-tetrahydro-benzimidazol-2-yl, 1-(2-n-propylaminocarbonyl-ethyl)-5,6,7,8-tetrahydro-benzimidazol-2-yl, 1-(2-isopropylaminocarbonyl-ethyl)-5,6,7,8-tetrahydro-benzimidazol-2-yl, 1-(2-dimethylaminocarbonyl-ethyl)-5,6,7,8-tetrahydro-benzimidazol-2-yl, 1-(2-diethylaminocarbonyl-ethyl)-5,6,7,8-tetrahydro-benzimidazol-2-yl, 1-(2-di-n-propylaminocarbonyl-ethyl)-5,6,7,8-tetrahydro-benzimidazol-2-yl, 1-(2-diisopropylaminocarbonyl-ethyl)-5,6,7,8-tetrahydro-benzimidazol-2-yl, 1-(2-N-methyl-ethylaminocarbonyl-ethyl)-5,6,7,8-tetrahydro-benzimidazol-2-yl, 1-(3-carboxy-propyl)-5,6,7,8-tetrahydro-benzimidazol-2-yl, 1-(3-methoxycarbonylpropyl)-5,6,7,8-tetrahydro-benzimidazol-2-yl, 1-(3-ethoxycarbonyl-propyl)-5,6,7,8-tetrahydro-benzimidazol-2-yl, 1-(3-n-propoxycarbonyl-propyl)-5,6,7,8-tetrahydro-benzimidazol-2-yl, 1-(3-isopropoxycarbonyl-propyl)-5,6,7,8-tetrahydro-benzimidazol-2-yl, 1-(3-aminocarbonyl-propyl)-5,6,7,8-tetrahydro-benzimidazol-2-yl, 1-(3-methylaminocarbonyl-propyl)-5,6,7,8-tetrahydro-benzimidazol-2-yl, 1-(3-ethylaminocarbonyl-propyl)-5,6,7,8-tetrahydro-benzimidazol-2-yl, 1-(3-n-propylaminocarbonyl-propyl)-5,6,7,8-tetrahydro-benzimidazol-2-yl, 1-(3-isopropylaminocarbonyl-propyl)-5,6,7,8-tetrahydro-benzimidazol-2-yl, 1-(3-dimethylaminocarbonyl-propyl)-5,6,7,8-tetrahydro-benzimidazol-2-yl, 1-(3-diethylaminocarbonyl-propyl)-5,6,7,8-tetrahydro-benzimidazol-2-yl, 1-(3-di-n-propylaminocarbonyl-propyl)-5,6,7,8-tetrahydro-benzimidazol-2-yl, 1-(3-diisopropylaminocarbonyl-propyl)-5,6,7,8-tetrahydro-benzimidazol-2-yl, 1-(3-N-methyl-ethylaminocarbonyl-propyl)-5,6,7,8-tetrahydro-benzimidazol-2-yl, 1-(2,2,2-trifluoroethyl)-5,6,7,8-tetrahydro-benzimidazol-2-yl, 1-phenyl-5,6,7,8-tetrahydro-benzimidazol-2-yl, 1-benzyl-5,6,7,8-tetrahydro-benzimidazol -2-yl, 1-(1-phenylethyl)-5,6,7,8-tetrahydro-benzimidazol -2-yl, 1-(2-phenylethyl)-5,6,7,8-tetrahydro-benzimidazol -2-yl, 1-(1-phenylpropyl)-5,6,7,8-tetrahydro-benzimidazol -2-yl, 1-(2-phenylpropyl)-5,6,7,8-tetrahydro-benzimidazol -2-yl, 1-(3-phenylpropyl)-5,6,7,8-tetrahydro-benzimidazol -2-yl, 1,3-dimethyl-5,6,7,8-tetrahydrobenzimidazolium-2-yl, 1,3-d i ethyl -5,6,7,8-tetrahydrobenzimidazolium-2-yl, 1,3-di-n-propyl-5,6,7,8-tetrahydrobenzimidazolium-2-yl or 1,3-dibenzyl-5,6,7,8-tetrahydrobenzimidazolium-2-yl group, $R_3$ may denote a methyl, ethyl, n-propyl, isopropyl, isobutyl, n-butyl, 1-methyl-n-propyl, tert.butyl, n-pentyl, 1-methyl-n-butyl, 2-methyl-n-butyl, cyclopropyl, cyclobutyl, cyclopentyl, methoxy, ethoxy, n-propoxy, isopropoxy, n-butoxy, isobutoxy, methylthio, ethylthio, n-propylthio, isopropylthio, n-butylthio or isobutylthio group and $R_4$ may denote a carboxy, cyano, 1H-tetrazolyl, 1-triphenylmethyl-tetrazolyl, 2-triphenylmethyl-tetrazolyl, methoxycarbonyl, ethoxycarbonyl, n-propyloxycarbonyl, isopropyloxycarbonyl, n-butyloxycarbonyl, isobutyloxycarbonyl, tert.butyloxycarbonyl, n-pentyloxycarbonyl, isoamyloxycarbonyl, n-hexyloxycarbonyl, cyclopentyloxycarbonyl, cyclohexyloxycarbonyl, benzyloxycarbonyl, 1-phenylethyloxycarbonyl, 2-phenylethyloxycarbonyl, 3-phenylpropyloxycarbonyl, methoxymethoxycarbonyl, cinnamyloxycarbonyl, acetoxymethoxycarbonyl, propionyloxymethoxycarbonyl, n-butyryloxymethoxycarbonyl, isobutyryloxymethoxycarbonyl, n-pentanoyloxymethoxycarbonyl, isopentanoyloxy-methoxycarbonyl, pivaloyloxymethoxycarbonyl, n-hexanoyloxymethoxycarbonyl, cyclopentanoyloxy-methoxycarbonyl, cyclohexanoyloxymethoxycarbonyl, phenylacetoxymethoxycarbonyl, 1-phenylpropionyloxymethoxycarbonyl, 2-phenylpropionyloxymethoxycarbonyl, 3-phenylbutyryloxymethoxycarbonyl, benzoyloxymethoxycarbonyl, 1-acetoxyethoxycarbonyl, 1-propionyloxyethoxycarbonyl, 1-n-butyryloxyethoxycarbonyl, 1-isobutyryloxyethoxycarbonyl, 1-n-pentanoyloxyethoxycarbonyl, 1-isopentanoyloxy-ethoxycarbonyl, 1-pivaloyloxyethoxycarbonyl, 1-n-hexanoyloxyethoxycarbonyl, 1-cyclopentanoyloxyethoxycarbonyl, 1-cyclohexanoyloxyethoxycarbonyl, 1-phenylacetoxyethoxycarbony 1, 1-(1-phenylpropionyloxy)ethoxycarbonyl, 1-(2-phenylpropionyloxy)-ethoxycarbonyl, 1-(3-phenylbutyryloxy)-ethoxycarbonyl, 1-benzoyloxyethoxycarbonyl, methoxycarbonyloxy-methoxycarbonyl, ethoxycarbonyloxymethoxycarbonyl, n-propyloxycarbonyloxymethoxycarbonyl, isopropyloxycarbonyloxymethoxycarbonyl, butyloxycarbonyloxymethoxycarbonyl, isobutyloxycarbonyloxymethoxycarbonyl, tert.butyloxycarbonyloxymethoxycarbonyl, n-pentyloxycarbonyloxymethoxycarbonyl, isoamyloxycarbonyloxymethoxycarbonyl, hexyloxycarbonyloxymethoxycarbonyl, cyclopentyloxycarbonyloxymethoxycarbonyl, cyclohexyloxycarbonyloxymethoxycarbonyl, benzyloxycarbonyloxymethoxycarbonyl, 1-phenylethoxycarbonyloxymethoxycarbonyl, 2-phenylethoxycarbonyloxymethoxycarbonyl, 3-phenylpropyloxycarbonyloxymethoxycarbonyl, cinnamyloxycarbonyloxymethoxycarbonyl, 1-(methoxycarbonyloxy)ethoxycarbonyl, 1-(ethoxycarbonyloxy)-ethoxycarbonyl, 1-(n-propyloxycarbonyloxy)-ethoxycarbonyl, 1-(isopropyloxycarbonyloxy)-ethoxycarbonyl, 1-(n-butyloxycarbonyloxy)-ethoxycarbonyl, 1-(isobutyloxycarbonyloxy)-ethoxycarbonyl, 1-(tert.butyloxycarbonyloxy)-ethoxycarbonyl, 1-(n-pentyloxycarbonyloxy)-ethoxycarbonyl, 1-(isoamyloxycarbonyloxy)-ethoxycarbonyl, 1-(n-hexyloxycarbonyloxy)-ethoxycarbonyl, 1-(cyclopentyloxy-carbonyloxy)-ethoxycarbonyl, 1-(cyclohexyloxycarbonyloxy)-ethoxycarbonyl, 1-(benzyloxycarbonyloxy)-ethoxycarbonyl, 1-(1-phenylethoxycarbonyloxy)-ethoxycarbonyl, 1-(2-phenylethoxycarbonyloxy)-ethoxycarbonyl, 1-(3-phenylpropyloxycarbonyloxy)-ethoxycarbonyl, 1-(cinnamyloxycarbonyloxy)-ethoxycarbonyl, aminocarbonyl, methylaminocarbonyl, ethylaminocarbonyl, n-propylaminocarbonyl, isopropylaminocarbonyl, dimethylaminocarbonyl, diethylaminocarbonyl, di-n-propylaminocarbonyl, diisopropylaminocarbonyl, N-methylethylaminocarbonyl, N-ethyl-isopropylaminocarbonyl or 2,5-dihydro-5-oxo-1.2.4-oxadiazol-3-yl group.

In compounds according to Option D $R_1$ may denote, for example, in the 4-position, a fluorine, chlorine or bromine atom, a methyl, ethyl, n-propyl, isopropyl, cyclopropyl, cyclobutyl, cyclopentyl, cyclohexyl, cycloheptyl, difluoromethyl or trifluoromethyl group.

$R_2$ may denote a phthalimino, homophthalimino, 4,4-dimethyl-homophthalimino, 1-oxo-isoindolin-2-yl, 2-oxo-pyrrolidino, 2-oxo-piperidino, 2-oxo-hexamethyleneimino, propanesultam-1-yl, butanesultam-1-yl, pentanesultam-1-yl, maleic acid imido, 2-methyl-maleic acid imido, 2-phenyl-maleic acid imido, 2,3-dimethyl-maleic acid imido, 3-methyl-2-phenyl-maleic acid imido, 2,3-diphenyl-maleic acid imido, piperidin-2-yl, piperidin-2-on-1-yl, quinolin-2-yl, isoquinolin-1-yl, isoquinolin-3-yl, pyridin-2-yl, benzimidazol-2-yl, 1-methyl-benzimidazol-2-yl, 1-ethyl-benzimidazol-2-yl, 1-n-propyl-benzimidazol-2-yl, 1-isopropyl-benzimidazol-2-yl, 1-n-butyl-benzimidazol-2-yl, 1-isobutyl-benzimidazol-2-yl, 1-n-pentyl-benzimidazol-2-yl, 1-n-hexyl-benzimidazol-2-yl, 1-cyclopropyl-benzimidazol-2-yl, 1-cyclobutyl-benzimidazol-2-yl, 1-cyclopentyl-benzimidazol-2-yl, 1-cyclohexyl-benzimidazol-2-yl, 5-fluoro-1-methyl-benzimidazol-2-yl, 6-fluoro-1-methyl-benzimidazol-2-yl, 5-trifluoromethyl-benzimidazol-2-yl, 5-trifluoromethyl-1-methyl-benzimidazol-2-yl, imidazo[1,2-a]pyridin-2-yl, 5,6,7,8-tetrahydro-imidazo[1,2-a]pyridin-2-yl, 3-chloro-5,6,7,8-tetrahydro-imidazo[1,2-a]pyridin-2-yl, imidazo[1,2-a]pyrimidin-2-yl, imidazo[4,5-b]pyridin-2-yl, imidazo[4,5-c]pyridin-2-yl, imidazo[2,1-b]thiazol-6-yl, imidazo[1,2-c]pyrimidin-2-yl, imidazo[1,2-a]pyrazin-2-yl, imidazo[1,2-b]pyridazin-2-yl, imidazo[4,5-c]pyridin-2-yl, purin-8-yl, imidazol-4,5-b]pyrazin-2-yl imidazo[4,5-c]pyridazin-2-yl, imidazo[4,5-d]pyridazin-2-yl, aminocarbonylamino, methylaminocarbonylamino, dimethylaminocarbonylamino, N-methylaminocarbonyl-methylamino, N-(dimethylaminocarbonyl)-methylamino, N-dimethylaminocarbonyl-ethylamino, N-dimethylaminocarbonylisopropylamino, N-(dimethylaminocarbonyl)-n-pentylamino, N-methylaminocarbonylethylamino, N-methylaminocarbonyl-n-pentylamino, N-methylaminocarbonyl-n-hexylamino, N-methylaminocarbonyl-n-octylamino, N-methylaminocarbonyl-cyclohexylamino, ethylamino-carbonylamino, N-ethylaminocarbonyl-methylamino, N-ethylaminocarbonylethylamino, N-ethylaminocarbonyl-n-hexylamino, N-ethylaminocarbonyl-n-heptylamino, N-ethylaminocarbonyl-cyclohexylamino, diethylaminocarbonylamino, N-(diethylaminocarbonyl)-methylamino, N-(diethylaminocarbonyl)-ethylamino, N-(diethylaminocarbonyl)-n-butylamino, N-(diethylaminocarbonyl)-n-hexylamino, N-(diethylaminocarbonyl)-n-octylamino, isopropylaminocarbonylamino, N-isopropylaminocarbonylmethylamino, n-butylaminocarbonylamino, N-(n-butyl-aminocarbonyl)-methylamino, N-(n-butylaminocarbonyl)ethylamino, N-(n-butylaminocarbonyl)-isopropylamino, N-(n-butylaminocarbonyl)-n-butylamino, N-(n-butylaminocarbonyl)-n-hexylamino, N-(n-butylaminocarbonyl)-cyclohexylamino, N-(di-(n-butyl)-aminocarbonyl)-amino, N-(di-(n-butyl)-aminocarbonyl)-methylamino, N-(di-(n-butyl)-aminocarbonyl)-ethylamino, N-(di-(n-butyl)-aminocarbonyl)-n-butylamino, N-(di-(n-butyl)-aminocarbonyl)-n-hexylamino, N-(n-pentylaminocarbonyl)-methylamino, N-(n-pentylaminocarbonyl)ethylamino, N-(n-hexylaminocarbonyl)-ethylamino, n-hexylaminocarbonylamino, n-heptylaminocarbonylamino, n-octylaminocarbonylamino, N-(n-hexylaminocarbonyl)-n-butylamino, N-(n-hexylaminocarbonyl)-n-pentylamino, N-(n-hexylaminocarbonyl)-n-hexylamino, N-(n-hexylaminocarbonyl)cyclohexylamino, di-(n-hexyl)-aminocarbonylamino, N-(di-(n-hexyl)-aminocarbonyl)-methylamino, N-((n-hexyl)-methylaminocarbonyl)-amino, cyclohexylaminocarbonylamino, N-cyclohexylaminocarbonyl-methylamino, N-cyclohexylaminocarbonyl-ethylamino, N-cyclohexylaminocarbonyl-n-butylamino, N-cyclohexylaminocarbonyl-isobutylamino, N-cyclohexylaminocarbonyl-n-pentylamino, N-cyclohexylaminocarbonyl-n-hexylamino, N-cyclohexylaminocarbonyl-cyclohexylamino, N-(ethylcyclohexylaminocarbonyl)-methylamino, N-(propylcyclohexylaminocarbonyl)-methylamino, N-(n-butylcyclohexylaminocarbonyl)-methylamino, allylaminocarbonylamino, benzylaminocarbonylamino, N-benzylaminocarbonyl-isobutylamino, phenylaminocarbonylamino, pyrrolidinocarbonylamino, pyrrolidinocarbonyl-methylamino, piperidinocarbonylamino, hexamethyleneiminocarbonylamino, morpholinocarbonylamino, 3,4,5,6-tetrahydro-2-pyrimidon-1-yl, 3-methyl-3,4,5,6-tetrahydro-2-pyrimidon-1-yl, 3-ethyl-3,4,5,6-tetrahydro-2-pyrimidon-1-yl, 3-n-propyl-3,4,5,6-tetrahydro-2-pyrimidon-1-yl, 3-isopropyl-3,4,5,6-tetrahydro-2-pyrimidon-1-yl, 3-n-butyl-3,4,5,6-tetrahydro-2-pyrimidon-1-yl, 3-isobutyl-3,4,5,6-tetrahydro-2-pyrimidon-1-yl, 3-n-pentyl-3,4,5,6-tetrahydro-2-pyrimidon-1-yl, 3-n-hexyl-3,4,5,6-tetrahydro-2-pyrimidon-1-yl, 3-cyclopentyl-3,4,5,6-tetrahydro-2-pyrimidon-1-yl, 3-cyclohexyl-3,4,5,6-tetrahydro-2-pyrimidon-1-yl, 3-cycloheptyl-3,4,5,6-tetrahydro-2-pyrimidon-1-yl, 3-benzyl-3,4,5,6-tetrahydro-2-pyrimidon-1-yl, 3,4,5,6-tetrahydro-2(1H)-pyrimidon-1-yl, 3-methyl-3,4,5,6-tetrahydro-2(1H)-pyrimidon-1-yl, 3-ethyl-3,4,5,6-tetrahydro-2(1H)-pyrimidon-1-yl, 3-n-propyl-3,4,5,6-tetrahydro-2(1H)-pyrimidon-1-yl, 3-isopropyl-3,4,5,6-tetrahydro-2(1H)-pyrimidon-1-yl, 3-benzyl-3,4,5,6-tetrahydro-2(1H)-pyrimidon-1-yl, 3-(2-phenylethyl)-3,4,5,6-tetrahydro-2(1H)-pyrimidon-1-yl or 3-(3-phenylpropyl)-3,4,5,6-tetrahydro-2(1H)-pyrimidon-1-yl group, $R_3$ may denote a methyl, ethyl, n-propyl, isopropyl, n-butyl, isobutyl, tert.butyl, n-pentyl, 1-methyl-butyl, 2-methyl-butyl, 3-methyl-butyl, cyclopropyl, cyclobutyl, cyclopentyl, methoxy, ethoxy, n-propoxy or isopropoxy group and $R_4$ may denote a hydroxycarbonyl, methoxycarbonyl, ethoxycarbonyl, n-propyloxycarbonyl, isopropyloxycarbonyl, n-butyloxycarbonyl, isobutyloxycarbonyl, tert.butyloxycarbonyl, n-pentyloxycarbonyl, isoamyloxycarbonyl, n-hexyloxycarbonyl, cyclopentyloxycarbonyl, cyclohexyloxycarbonyl, benzyloxycarbonyl, 1-phenylethyloxycarbonyl, 2-phenylethyloxycarbonyl, 3-phenylpropyloxycarbonyl, methoxymethoxycarbonyl, cinnamyloxycarbonyl, acetoxymethoxycarbonyl, propionyloxymethoxycarbonyl, n-butyryloxymethoxycarbonyl, isobutyryloxymethoxycarbonyl, n-pentanoyloxymethoxycarbonyl, isopentanoyloxy-methoxycarbonyl, pivaloyloxymethoxycarbonyl, n-hexanoyloxymethoxycarbonyl, cyclopentanoyloxymethoxycarbonyl, cyclohexanoyloxymethoxycarbonyl, phenylacetoxymethoxycarbonyl, 2-phenylpropionyloxy-methoxycarbonyl, 3-phenylpropionyloxymethoxycarbonyl, 4-phenylbutyryloxymethoxycarbonyl, benzoyloxymethoxycarbonyl, 1-acetoxyethoxycarbonyl, 1-propionyloxyethoxycarbonyl, 1-n-butyryloxyethoxy-carbonyl, 1-isobutyryloxyethoxycarbonyl, 1-n-pentanoyloxyethoxycarbonyl, 1-isopentanoyloxyethoxycarbonyl, 1-pivaloyloxyethoxy-carbonyl, 1-n-hexanoyloxyethoxycarbonyl, 1-cyclopentanoyloxyethoxycarbonyl, 1-cyclohexanoyloxyethoxycarbonyl, 1-phenylacetoxyethoxycarbonyl, 1-(1-phenylpropionyloxy)-ethoxycarbonyl, 1-(2-phenylpropionyloxy)-ethoxycarbonyl, 1-(3-phenylbutyryloxy)ethoxycarbonyl, 1-benzoyloxyethoxycarbonyl, methoxycarbonyloxy-methoxycarbonyl, ethoxycarbonyloxymethoxycarbonyl, n-propyloxycarbonyloxymethoxycarbonyl, isopropyloxycarbonyloxymethoxycarbonyl, n-butyloxycarbonyloxymethoxycarbonyl, isobutyloxycarbonyloxymethoxycarbonyl, tert.butyloxycarbonyloxymethoxycarbonyl, n-pentyloxycarbonyloxymethoxycarbonyl, isoamyloxycarbonyloxymethoxycarbonyl, n-hexyloxycarbonyloxymethoxycarbonyl, cyclopentyloxycarbonyloxymethoxycarbonyl, cyclohexyloxycarbonyloxymethoxycarbonyl, benzyloxycarbonyloxymethoxycarbonyl, 1-phenylethoxycarbonyloxymethoxycarbonyl, 2-phenylethoxycarbonyloxymethoxycarbonyl, 3-phenylpropyloxycarbonyloxymethoxycarbonyl, cinnamyloxycarbonyloxymethoxycarbonyl, 1-(methoxycarbonyloxy)-ethoxycarbonyl, 1-(ethoxycarbonyloxy)-ethoxycarbonyl, 1-(n-propyloxycarbonyloxy)-ethoxycarbonyl, 1-(isopropyloxycarbonyloxy)-ethoxycarbonyl, 1-(n-butyloxycarbonyloxy)-ethoxycarbonyl, 1-(isobutyloxycarbonyloxy)-ethoxycarbonyl, 1-(tert.butyloxycarbonyloxy)-ethoxycarbonyl, 1-(n-pentyloxycarbonyloxy)-ethoxycarbonyl, 1-(isoamyloxycarbonyloxy)-ethoxycarbonyl, 1-(n-hexyloxycarbonyloxy)-ethoxycarbonyl, 1-(cyclopentyloxycarbonyloxy)-ethoxycarbonyl, 1-(cyclohexyloxycarbonyloxy)-ethoxycarbonyl, cyclopentylcarbonyloxymethoxycarbonyl, 1-(benzyloxycarbonyloxy)-ethoxycarbonyl, 1-(1-phenylethoxycarbonyloxy)-ethoxycarbonyl, 1-(2-phenylethoxycarbonyloxy)-ethoxycarbonyl, 1-(3-phenylpropyloxycarbonyloxy)-ethoxycarbonyl, 1-(cinnamyloxycarbonyloxy)-ethoxycarbonyl, cyano, 1H-tetrazolyl, 1-triphenylmethyl-tetrazolyl, 2-triphenylmethyl-tetrazolyl, 1-acetoxymethyl-tetrazolyl, 2-acetoxymethyl-tetrazolyl, 1-propionyloxymethyl-tetrazolyl, 2-propionyloxymethyltetrazolyl, 1-butyryloxymethyl-tetrazolyl, 2-butyryloxymethyl-1-tetrazolyl, 1-isobutyryloxymethyl-tetrazolyl, 2-isobutyryloxymethyl-tetrazolyl, 1-pivaloyloxymethyltetrazolyl, 2-pivaloyloxymethyl-tetrazolyl, 1-ethoxycarbonyloxymethyl-tetrazolyl, 2-ethoxycarbonyloxymethyltetrazolyl, 1-[1-(ethoxycarbonyloxy)-ethyl]-tetrazolyl, 2-[1-(ethoxycarbonyloxy)-ethyl]-tetrazolyl, 1-[1-(cyclohexyloxycarbonyloxy)-ethyl]-tetrazolyl or 2-[1-(cyclohexyloxycarbonyloxy)-ethyl]-tetrazolyl group.

Preferred compounds of general formula I above are those wherein $R_1$, $R_2$, $R_3$ and $R_4$ are as set forth below in options A, B, C or D:

Option A $R_1$ in the 4-position represents a fluorine, chlorine or bromine atom, a $C_{1-3}$-alkyl group, a cycloalkyl, fluoromethyl, difluoromethyl or trifluoromethyl group and $R_2$ represents a $C_{3-5}$-alkoxy group substituted in the 3-, 4- or 5-position by an imidazolyl group, or $R_2$ may represent a $C_{2-5}$-alkoxy group substituted in the 2-, 3-, 4- or 5-position by a benzimidazolyl or tetrahydrobenzimidazolyl group, an acylamino group optionally substituted at the nitrogen atom by a $C_{1-5}$-alkyl group, wherein the acyl group is a $C_{2-7}$-alkanoyl group, a $C_{2-4}$-(alkoxycarbonyl) group, a $C_{1-3}$-alkylsulphonyl group or a benzenesulphonyl group, a phthalimino or homophthalimino group, wherein a carbonyl group in a phthalimino group may be replaced by a methylene group and a methylene in a homophthalimino group may be substituted by one or two alkyl groups, a 5-, 6- or 7-membered alkyleneimino or alkenyleneimino group, optionally substituted by one or two alkyl groups or by a tetramethylene or pentamethylene group, wherein a methylene group may be replaced by a carbonyl or sulphonyl group, a glutaric acid imino group wherein the n-propylene group may be perfluorinated, or may be substituted by one or two alkyl groups or by a tetramethylene or pentamethylene group, a maleic acid imido group optionally mono- or disubstituted by an alkyl or phenyl group, whilst the substituents may be identical or different, an amidino group optionally substituted by one or two $C_{1-4}$ alkyl groups, a benzimidazol-2-yl group optionally substituted in the 1-position by $C_{1-6}$-alkyl or a cycloalkyl group, whilst the phenyl nucleus of one of the abovementioned benzimidazole groups may additionally be substituted by a fluorine atom or by a methyl or trifluoromethyl group, $R_2$ may represent an imidazo[2,1-b]thiazol-6-yl, imidazo[1,2-a]pyridin-2-yl, 5,6,7,8-tetrahydro-imidazo[1,2-a]pyridin-2-yl, imidazo[1,2-a]pyrimidin-2-yl, imidazo[4,5-b]pyridin-2-yl, imidazo[4,5-c]pyridin-2-yl, imidazo[1,2-c]pyrimidin-2-yl, imidazo[1,2-a]pyrazin-2-yl, imidazo[1,2-b]-pyridazin-2-yl, imidazo[4,5-c]pyridin-2-yl, purin-8-yl, imidazo[4,5-b]pyrazin-2-yl, imidazo[4, 5-c]pyridazin-2-yl or imidazo[4,5-d]pyridazin-2-yl group, or a carbon attached pyrrolidine, piperidine or pyridine ring in which a phenyl group may be condensed onto the pyridine ring via two adjacent carbon atoms and a methylene group adjacent to the N-atom in a pyrrolidine or piperidine ring may be replaced by a carbonyl group, a carbon attached imidazolyl group optionally substituted in the 1-position by a $C_{1-3}$-alkyl group or by a benzyl group, and which may also be substituted in the carbon skeleton by a $C_{1-3}$-alkyl group, an imidazolidindione group optionally substituted by an alkyl, phenylalkyl, tetramethylene, pentamethylene or hexamethylene group, a pyridazin-3-one or dihydro-pyridazin-3-one group which may be substituted in the 2-position by a methyl or benzyl group, an $R_7$—$NR_6$—CO—$NR_5$— group wherein $R_5$ represents a hydrogen atom, a $C_{1-5}$-alkyl group, a cyclohexyl or benzyl group, $R_6$ represents a hydrogen atom, a $C_{1-6}$-alkyl group, an allyl, cyclohexyl, benzyl or phenyl group, $R_7$ represents a hydrogen atom or a $C_{1-3}$-alkyl group or $R_6$ and $R_7$ together with the nitrogen atom between them represent an unbranched $C_{4-6}$-alkyleneimino group or a morpholino group or $R_5$ and $R_6$ together represent a $C_{2-3}$-alkylene group, or $R_1$, in the 5-, 6- or 7-position, represents a fluorine, chlorine or bromine atom, a $C_{1-4}$-alkyl or a trifluoromethyl group and $R_2$ represents a benzimidazol-2-yl group optionally substituted in the 1-position by a $C_{1-6}$-alkyl group or by a cycloalkyl group, whilst the phenyl nucleus of one of the abovementioned benzimidazole groups may additionally be substituted by a fluorine atom or by a methyl or trifluoromethyl group, or $R_2$ may represent an imidazo[2,1-b]thiazol-6-yl, imidazo[1,2-a]pyridin-2-yl, 5,6,7,8-tetrahydroimidazo[1,2-a]pyridin-2-yl, imidazo[1,2-a]pyrimidin-2-yl, imidazo[4,5-b]pyridin-2-yl, imidazo[4,5-c]pyridin-2-yl, imidazo[1,2-c]pyrimidin-2-yl, imidazo[1,2-a]pyrazin-2-yl, imidazo[1,2-b]-pyridazin-2-yl, imidazo[4,5-c]-pyridin-2-yl, purin-8-yl, imidazo[4,5-b]pyrazin-2-yl, imidazo[4,5-c]pyridazin-2-yl or imidazo[4,5-d]-pyridazin-2-yl group, or a carbon attached pyrrolidine, piperidine or pyridine ring in which a phenyl group may be condensed onto the pyridine ring via 2 adjacent carbon atoms and a methylene group adjacent to the N-atom in a pyrrolidine or piperidine ring may be replaced by a carbonyl group, or a carbon attached imidazolyl group optionally substituted in the 1-position by a $C_{1-3}$ alkyl group or by a benzyl group which may also be substituted in the carbon skeleton by a $C_{1-3}$ alkyl group, $R_3$ represents a $C_{1-5}$-alkyl group or a $C_{3-5}$-cycloalkyl group and $R_4$ represents a carboxy or 1H-tetrazolyl group, whilst, unless otherwise specified, an alkanoyl, alkyl or alkoxy moiety as mentioned hereinbefore may in each case contain 1 to 3 carbon atoms and a cycloalkyl moiety mentioned above may contain from 3 to 7 carbon atoms, Option B $R_1$ to $R_4$ are defined as in Option B, above, and $R_2$ is in the 6-position of the benzimidazole ring, Option C $R_1$ denotes a fluorine, chlorine or bromine atom, a trifluoromethyl group or a $C_{1-3}$-alkyl group, $R_2$ denotes an imidazol-2-yl group optionally substituted in the 1-position by the group $R_a$, wherein $R_a$ denotes a phenyl group, a phenylalkyl group having 1 to 3 carbon atoms in the alkyl moiety, a C5-7-cycloalkyl group or a $C_{1-5}$-alkyl group in which the alkyl moiety may additionally be substituted by a group which can be metabolised into a carboxy group in vivo, a trifluoromethyl, carboxyl, methoxycarbonyl, ethoxycarbonyl, aminocarbonyl, methylaminocarbonyl or dimethylaminocarbonyl group or from position 2 by a hydroxy, methoxy, ethoxy, amino, methylamino, dimethylamino, pyrrolidino, piperidino or morpholino group, a 5,5-spiro-cyclopentano-dihydroimidazol-4-on-2-yl group, an imidazolium-2-yl group substituted in the 1- and 3-positions by groups $R_b$, which may be identical or different, whilst $R_b$ denotes an alkyl or phenylalkyl group each having 1 to 3 carbon atoms in the alkyl moiety, an oxazol-2-yl or thiazol-2-yl group, whilst in the abovementioned imidazol-2-yl, imidazolium-2-yl, oxazol-2-yl or thiazol-2-yl moieties the 4-, 5-positions may be substituted by a $C_{1-4}$-alkyl group or by a phenyl group, wherein the substituents may be identical or different, or an n-butylene bridge may be added via the 4-, 5-positions, an oxazolin-2-yl or imidazolin-2-yl group substituted by $R_8$ to $R_{10}$, wherein an imino group may be additionally substituted by $R_a$, whereby $R_8$ to $R_{10}$ and $R_a$ each represent a hydrogen atom or an alkyl group with 1 to 4 carbon atoms, $R_3$ denotes a $C_{2-5}$-alkyl group, a $C_{3-5}$-cycloalkyl group, an alkoxy or alkylthio group each having 2 to 4 carbon atoms and $R_4$ denotes a group which can be metabolised into a carboxy group in vivo, a carboxy, cyano, 1H-tetrazolyl, 1-triphenylmethyl-tetrazolyl or 2-triphenylmethyl-tetrazolyl group, whilst the expression "a group which can be metabolised into a carboxy group in vivo" which appears above denotes the esters thereof of the formulae

—CO—OR',

—CO—O—(HCR")—O—CO—R''' and

—CO—O—(HCR")—O—CO—OR''' wherein

R' denotes a straight-chained or branched $C_{1-4}$-alkyl group or a $C_{5-7}$-cycloalkyl group, R" denotes a hydrogen atom or a methyl group and R''' denotes a straight-chained or branched $C_{1-4}$alkyl group or a $C_{5-7}$-cycloalkyl group, Option D $R_1$ denotes, in the 4-position, a chlorine atom, a $C_{1-3}$-alkyl group or a trifluoromethyl group, $R_2$ denotes a phthalimino or homophthalimino group, whilst a carbonyl group in a phthalimino group may be replaced by a methylene group, a 5-, 6- or 7-membered alkyleneimino group in which a methylene group is replaced by a carbonyl or sulphonyl group, a maleic acid imido group optionally mono- or disubstituted by a methyl or phenyl group, whilst the substituents may be identical or different, a benzimidazol-2-yl o r 4,5,6,7-tetrahydro-benzimidazol-2-yl group optionally substituted in the 1-position by a $C_{1-6}$-alkyl group or by a cycloalkyl group (whilst the phenyl nucleus of one of the above-mentioned benzimidazole groups may additionally be substituted by a fluorine atom or a methyl or trifluoromethyl group ), an imidazo[2,1-b]thiazol-6-yl, imidazo[1,2-a]pyridin-2-yl, 5,6,7,8-tetrahydro-imidazo[1,2-a]pyridin-2-yl, 3-chloro-5,6,7,8-tetrahydro-imidazo[1,2-a]pyridin-2-yl imidazo[1,2-a]pyrimidin-2-yl, imidazo[4,5-b]pyridin-2-yl, imidazo[4,5-c]pyridin-2-yl, imidazo[1,2-c]pyrimidin-2-yl, imidazo[1,2-a]pyrazin-2-yl, imidazo[1,2-b]pyridazin-2-yl, imidazo[4,5-c]pyridin-2-yl, purin-8-yl, imidazo[4,5-b ]pyrazin-2-yl, imidazo[4,5-c]pyridazin-2-yl or imidazo[4,5-d]pyridazin-2-yl group or an $R_7$—$NR_6$—CO—$NR_5$— group wherein $R_5$ denotes a hydrogen atom, a $C_{1-5}$-alkyl group, a cyclohexyl or benzyl group, $R_6$ denotes a hydrogen atom, a $C_{1-6}$-alkyl group, an allyl, cyclohexyl, benzyl or phenyl group, $R_7$ denotes a hydrogen atom or a $C_{1-3}$-alkyl group or $R_6$ and $R_7$ together with the nitrogen atom between them denote a straight-chained $C_{4-6}$-alkyleneimino group or a morpholino group or $R_5$ and $R_6$ together denote a $C_{2-3}$-alkylene group, $R_3$ denotes a $C_{1-5}$-alkyl group, a $C_{3-5}$-cycloalkyl group or a $C_{2-3}$-alkoxy group and $R_4$ denotes a tetrazolyl group substituted in the 1- or 2-position by an $R_a$—CO—O—$CH_2$— group, or an $R_b$—CO—O—($R_c$CH)—O—CO—, $R_a$O—CO— or $R_b$O—CO—O—($R_c$CH)—O—CO— group, wherein $R_a$ denotes a straight-chained or branched $C_{1-6}$-alkyl group, a $C_{5-7}$-cycloalkyl group, a benzyl, 1-phenylethyl, 2-phenylethyl, 3-phenylpropyl, methoxymethyl or cinnamyl group, $R_b$ denotes a straight-chained or branched $C_{1-6}$-alkyl group, a $C_{5-7}$-cycloalkyl group, a phenyl, benzyl, 1-phenylethyl, 2-phenylethyl or 3-phenylpropyl group and $R_c$ denotes a hydrogen atom or a methyl group, or, if (i) $R_1$ and $R_2$ are as hereinbefore defined and $R_3$ denotes an alkoxy group, $R_4$ may denote a carboxy, 1H-tetrazolyl or 2H-tetrazolyl group or, if (ii) $R_1$ is as hereinbefore defined, $R_2$ has the meanings given hereinbefore with the exception of the 1-methyl-benzimidazol-2-yl group and $R_3$ denotes a cyclopropyl group, $R_4$ may represent a carboxy group or, if (iii) $R_1$ and $R_3$ are as hereinbefore defined and $R_2$ denotes a butanesultam-1-yl group, $R_4$ may denote a carboxy group or, if (iv) $R_1$ is as hereinbefore defined, $R_2$ denotes a 1-methyl-5-fluoro-benzimidazol-2-yl group and $R_3$ denotes an ethyl group, $R_4$ may represent a carboxy, 1H-tetrazolyl or 2H-tetrazolyl group.

Particularly preferred compounds of general formula I above are those wherein $R_1$, $R_2$, $R_3$ and $R_4$ are as set forth below in options A, B, C or D:

Option A $R_1$ in the 4-position represents a chlorine atom, or a $C_{1-3}$-alkyl or a trifluoromethyl group and $R_2$ represents a $C_{3-5}$-alkoxy substituted in the 3-, 4- or 5-position by an imidazolyl group, or $R_2$ may represent a $C_{2-5}$-alkoxy group substituted in the 2-, 3-, 4- or 5-position by a benzimidazolyl or tetrahydrobenzimidazolyl group, a $C_{2-5}$(alkanoyl)amino group or an N-benzenesulphonylmethylamino group, a phthalimino or homophthalimino group, wherein a carbonyl group in a phthalimino group may be replaced by a methylene group, a 5-, 6- or 7-membered alkyleneimino group wherein a methylene group is replaced by a carbonyl or sulphonyl, group, a glutaric acid imino group wherein the n-propylene group may be substituted by one or two alkyl groups or by a tetramethylene or pentamethylene group, a maleic acid imido group optionally mono- or disubstituted by an alkyl or phenyl group, whilst the substituents may be identical or different, a benzimidazol-2-yl group optionally substituted in the 1-position by a $C_{1-6}$-alkyl or by a cycloalkyl group, whilst the phenyl nucleus of one of the abovementioned benzimidazole groups may additionally be substituted by a fluorine atom or by a methyl or trifluoromethyl group, or $R_2$ may represent an imidazo[2,1-b]thiazol-6-yl, imidazo[1,2-a]pyridin-2-yl, 5,6,7,8-tetrahydro-imidazo[1,2-a]pyridin-2-yl, imidazo[1,2-a]pyrimidin-2-yl, imidazo[4,5-b]pyridin-2-yl, imidazo[4,5-c]pyridin-2-yl, imidazo[1,2-c]pyrimidin-2-yl, imidazo[1,2-a]pyrazin-2-yl, imidazo[1,2-b]-pyridazin-2-yl, imidazo[4,5-c]pyridin-2-yl, purin-8-yl, imidazo[4,5-b]pyrazin-2-yl, imidazo[4,5-c]pyridazin-2-yl or imidazo[4,5-d]pyridazin-2-yl group, or a carbon attached pyrrolidine, piperidine or pyridine ring in which a phenyl group may be condensed onto the pyridine ring via two adjacent carbon atoms and a methylene group adjacent to the N-atom in a pyrrolidine or piperidine ring may be replaced by a carbonyl group, or an imidazol-4-yl group substituted in the 1-position by a $C_{1-3}$ alkyl group or by a benzyl group which may also be substituted in the carbon skeleton by a $C_{1-3}$ alkyl group, a pyridazin-3-one or dihydro-pyridazin-3-one group which may be substituted in the 2-position by a methyl or benzyl group, an $R_7$—$NR_6$—CO—$NR_5$— group wherein $R_5$ represents a hydrogen atom, a $C_{1-5}$-alkyl group, a cyclohexyl or benzyl group, $R_6$ represents a hydrogen atom, a $C_{1-6}$-alkyl group, an allyl, cyclohexyl, benzyl or phenyl group, $R_7$ represents a hydrogen atom or a $C_{1-3}$-alkyl group or $R_6$ and $R_7$ together with the nitrogen atom between them represent an unbranched $C_{4-6}$-alkyleneimino group or a morpholino group or $R_5$ and $R_6$ together represent a $C_{2-3}$-alkylene group, or $R_1$, in the 5-, 6- or 7-position, represents a $C_{1-4}$-alkyl group or a trifluoromethyl group and $R_2$ represents a benzimidazol-2-yl group optionally substituted in the 1-position by a $C_{1-6}$-alkyl group or by a cycloalkyl group, whilst the phenyl nucleus of one of the abovementioned benzimidazole groups may additionally be substituted by a fluorine atom or by a methyl or trifluoromethyl group, or $R_2$ may represent an imidazo[2,1-b]thiazol-6-yl, imidazo[1,2-a]pyridin-2-yl, 5,6,7,8-tetrahydroimidazo[1,2-a]pyridin-2-yl, imidazo[1,2-a]pyrimidin-2-yl, imidazo[4,5-b]pyridin-2-yl, imidazo[4,5-c]pyridin-2-yl, imidazo[1,2-c]pyrimidin-2-yl, imidazo[1,2-a]pyrazin-2-yl, imidazo[1,2-b]-pyridazin-2-yl, imidazo[4,5-c]-pyridin-2-yl, purin-8-yl, imidazo[4,5-b]pyrazin-2-yl, imidazo[4,5-c]pyridazin-2-yl or imidazo[4,5-d]pyridazin-2-yl group, or a carbon attached pyrrolidine, piperidine or pyridine ring in which a phenyl group may be condensed onto the pyridine ring via two adjacent carbon atoms and a methylene group adjacent to the N-atom in a pyrrolidine or piperidine ring may be replaced by a carbonyl group, or an imidazol-4-yl group substituted in the 1-position by a $C_{1-3}$ alkyl group or by a benzyl group which may also be substituted in the carbon skeleton by a $C_{1-3}$ alkyl group, $R_3$ represents a $C_{1-5}$-alkyl group or a $C_{3-5}$-cycloalkyl group and $R_4$ represents a carboxy or 1H-tetrazolyl group, Option B $R_1$ represents a chlorine atom or a methyl group, $R_2$ represents an oxazol-4-yl or thiazol-4-yl group optionally substituted in the 2-position by a methyl or phenyl group, or an imidazol-4-yl group optionally substituted in the 2-position by a methyl group and which is substituted in the 1-position by a $C_{1-7}$-alkyl group which itself may be substituted in the 1-, 2-, 3-, 4-, 5-, 6- or 7-position by a carboxy, methoxycarbonyl, aminocarbonyl, methylaminocarbonyl, ethylaminocarbonyl, n-propylaminocarbonyl, dimethylaminocarbonyl, morpholinocarbonyl, thiomorpholinocarbonyl or 1-oxido-thiomorpholino-carbonyl group, by a $C_{1-3}$-alkyl group which is substituted in the 2-, 3- or 4-position by a hydroxy, methoxy, 2-methoxyethoxy, dimethylamino, diethylamino, pyrrolidino, piperidino, morpholino or imidazol-1-yl group, or by a 2,2,2-trifluoroethyl, 3,3,3-trifluoropropyl, cyclopropylmethyl, cyclobutylmethyl, cyclopentylmethyl, cyclohexylmethyl, benzyl, 2-phenylethyl, 4-fluorobenzyl, 3-chlorobenzyl, 4-methyl-benzyl, 4-trifluoromethyl-benzyl, 3,5-dimethoxybenzyl or 2,2-diphenylethyl group, $R_3$ represents a $C_{2-4}$-alkyl group, an alkoxy or alkylthio group each having 2 or 3 carbon atoms in the alkyl moiety, a cyclopropyl or cyclobutyl group and $R_4$ represents a group which may be converted in vivo into a carboxy group, or a carboxy or 1H-tetrazolyl group, Option C $R_1$ in the 4-position denotes a fluorine, chlorine or bromine atom, a trifluoromethyl group or a $C_{1-3}$-alkyl group, $R_2$ is in the 6-position and has the meanings given above with respect to the preferred compounds, and $R_3$ and $R_4$ are defined as above with respect to the preferred compounds, Option D $R_1$ denotes, in the 4-position, a methyl group, $R_2$ denotes an imidazo[1,2-a]pyridin-2-yl, 5,6,7,8-tetrahydroimidazo[1,2-a]pyridin-2-yl, 3-chloro-5,6,7,8-tetrahydroimidazo[1,2-a]pyridin-2-yl, 1-methyl-benzimidazol-2-yl, 1-methyl-5-fluoro-benzimidazol-2-yl or butanesultam-1-yl group, $R_3$ denotes a $C_{2-4}$-alkyl group, a cyclopropyl group or a $C_{2-3}$-alkoxy group and $R_4$ denotes a tetrazolyl group substituted in the 1- or 2-position by an $R_a$—CO—O—CH$_2$— group, or an $R_b$—CO—O—(R$_c$CH)—O—CO—, $R_a$O—CO— or $R_b$O—CO—O—(R$_c$CH)—O—CO— group, whilst $R_a$ denotes a straight-chained or branched $C_{1-6}$-alkyl group, a $C_{5-7}$-cycloalkyl group, a benzyl, 1-phenylethyl, 2-phenylethyl, 3-phenylpropyl, methoxymethyl or cinnamyl group, $R_b$ denotes a straight-chained or branched $C_{1-6}$-alkyl group, a $C_{5-7}$-cycloalkyl group, a phenyl, benzyl, 1-phenylethyl, 2-phenylethyl or 3-phenylpropyl group and $R_c$ denotes a hydrogen atom or a methyl group.

Even more preferred are those compounds of general formula I above wherein $R_1$, $R_2$, $R_3$ and $R_4$ are as set forth below in options A, B or C:

Option A $R_1$ in the 4-position represents a methyl group or a chlorine atom and $R_2$ represents a $C_{3-5}$-alkoxy group substituted in the 3-, 4- or 5-position by an imidazolyl group, or $R_2$ may represent a $C_{2-5}$-alkoxy group substituted in the 2-, 3-, 4- or 5-position by a benzimidazolyl or tetrahydrobenzimidazolyl group, a $C_{2-5}$(alkanoyl)amino group or an N-benzenesulphonylmethylamino group, a phthalimino or homophthalimino group, wherein a carbonyl group in a phthalimino group may be replaced by a methylene group, a 5-, 6- or 7-membered alkyleneimino group, wherein a methylene group is replaced by a carbonyl or sulphonyl group, a maleic acid imido group optionally mono- or disubstituted by an alkyl or phenyl group, whilst the substituents may be identical or different, a benzimidazol-2-yl group optionally substituted in the 1-position by a $C_{1-3}$-alkyl group, whilst the phenyl nucleus of one of the abovementioned benzimidazole groups may additionally be substituted by a fluorine atom, or $R_2$ may represent an imidazo[1,2-a]-pyridin-2-yl group, 5,6,7,8-tetrahydro-imidazo[1,2-a]-pyridin-2-yl, imidazo[1,2-a]pyrimidin-2-yl or imidazo[2,1-b]thiazol-6-yl group, an imidazol-4-yl group substituted in the 1-position by a $C_{1-3}$-alkyl group, a pyridazin-3-one or dihydro-pyridazin-3-one group which may be substituted in the 2-position by a methyl or benzyl group, or $R_1$, in the 5-, 6- or 7-position, may represent a methyl group and $R_2$ represents a benzimidazol-2-yl group optionally substituted in the 1-position by a $C_{1-3}$-alkyl group, whilst the phenyl nucleus may additionally be substituted by a fluorine atom, or $R_2$ may represent an imidazo[1,2-a]pyridin-2-yl group, an imidazol-4-yl group substituted in the 1-position by a $C_{1-3}$-alkyl group, $R_3$ represents a $C_{1-5}$-alkyl group or a $C_{3-5}$-cycloalkyl group and $R_4$ represents a carboxy or 1H-tetrazolyl group, Option B $R_1$, $R_2$ and $R_3$ are as defined above and $R_4$ denotes a carboxy group or a group of formulae

—CO—OR′,

—CO—O—(HCR″)—O—CO—R‴ and

—CO—O—(HCR″)—O—CO—OR‴ wherein

R′ denotes a straight-chained or branched $C_{1-6}$-alkyl group, a $C_{5-7}$-cycloalkyl group, a benzyl, 1-phenylethyl, 2-phenylethyl, 3-phenylpropyl, methoxymethyl or cinnamyl group, R″ denotes a hydrogen atom or a methyl group and R‴ denotes a straight-chained or branched $C_{1-6}$-alkyl group, a $C_{5-7}$-cycloalkyl group, a phenyl, benzyl, 1-phenylethyl, 2-phenylethyl or 3-phenylpropyl group, or Option C $R_1$ to $R_4$ are defined as above and $R_2$ is in the 6-position and denotes one of the imidazolyl groups mentioned above.

Specifically preferred compounds are:

(a) 4′-[[2-n-propyl-4-methyl-6-(1-methyl-benzimidazole-2-yl)-benzimidazol-1-yl]-methyl]-biphenyl-2-carboxylic acid.

(b) 4′-[[2-n-Propyl-4-methyl-6-(1-methyl-benzimidazol-2-yl)-benzimidazol-1-yl]-methyl]-2-(1H-tetrazol-5-yl)-biphenyl.

(c) 4′-[(2-Ethyl-4-methyl-6-(5,6,7,8-tetrahydro-imidazo[1,2-a]pyridin-2-yl)-benzimidazol-1-yl)-methyl]-biphenyl-2-carboxylic acid.

(d) 4′-[(2-n-Propyl-4-methyl-6-(butanesultam-1-yl)-benzimidazol-1-yl)-methyl]-biphenyl-2-carboxylic acid, (e) 4′-[(2-n-Propyl-4-methyl-6-(1-(2-N-morpholinoethyl)-imidazol-4-yl)-benzimidazol-1-yl)-methyl]-biphenyl-2-carboxylic acid, (f) 4′-[(2-Cyclopropyl-4-methyl-6-(1-methylbenzimidazol-2-yl)-benzimidazol-1-yl)-methyl]-biphenyl-2-carboxylic acid, (g) 4′-[(2-Cyclopropyl-4-methyl-6-(1-methylbenzimidazol-2-yl)-benzimidazol-1-yl)-methyl]-2-(1H-tetrazol-5-yl)-biphenyl, (h) 4′-[[2-n-Propyl-4-methyl-6-(1-methyl-5,6,7,8-tetrahydrobenzimidazol-2-yl)-1H-benzimidazol-1-yl]-methyl]-biphenyl-2-carboxylic acid-hydrate, (i) 4′-[[2-n-Propyl-4-methyl-6-(5,6,7,8-tetrahydro-benzimidazol-2-yl)-1H-benzimidazol-1-yl]-methyl]-2-(1H-tetrazol-5-yl)biphenyl-semihydrate, and (j) 4′-[[2-Ethyl-4-methyl-6-(1-methyl-5,6,7,8-tetrahydro-benzimidazol-2-yl)-1H-benzimidazol-1-yl]-methyl]-2-(1H-tetrazol-5-yl)-biphenyl-hydrate.

According to the invention, the compounds are obtained by the following processes:

a) Cyclising a compound of general formula

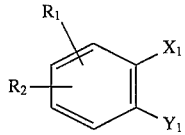
(II)

wherein $R_1$ and $R_2$ are defined as hereinbefore, one of the groups $X_1$ or $Y_1$ represents a group of general formula

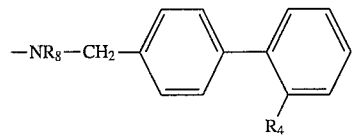

and the other group $X_1$ or $Y_1$ represents a group of the general formula

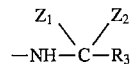

wherein $R_2$ and $R_4$ are defined as hereinbefore, $R_8$ represents a hydrogen atom or an $R_3CO$— group, wherein $R_3$ is defined as hereinbefore, $Z_1$ and $Z_2$, which may be identical or different, represent optionally substituted amino groups or hydroxy or mercapto groups optionally substituted by lower alkyl groups or $Z_1$ and $Z_2$ together represent an oxygen or sulphur atom, an optionally $C_{1-3}$-alkyl substituted imino group, or a $C_{2-3}$-alkylenedioxy or $C_{2-3}$-alkylenedithio group, but one of the groups $X_1$ or $Y_1$ must represent a group of general formula

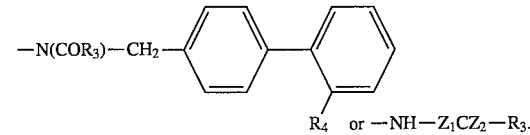

The cyclisation is conveniently carried out in a solvent or mixture of solvents such as ethanol, isopropanol, glacial acetic acid, benzene, chlorobenzene, toluene, xylene, glycol, glycolmonomethylether, diethyleneglycol-dimethylether, sulpholane, dimethylformamide, tetraline or in an excess of the acylating agent used to prepare the compound of general formula II, e.g. in the corresponding nitrile, anhydride, acid halide, ester or amide, e.g. at temperatures between 0° and 250° C., but preferably at the boiling temperature of the reaction mixture, optionally in the presence of a condensing agent such as phosphorusoxychloride, thionylchloride, sulphurylchloride, sulphuric acid, p-toluenesulphonic acid, methanesulphonic acid, hydrochloric acid, phosphoric acid, polyphosphoric acid, acetic anhydride or optionally in the presence of a base such as potassium ethoxide or potassium tert.-butoxide. However, cyclisation may also be carried out without a solvent and/or condensing agent.

However, it is particularly advantageous to carry out the reaction by preparing a compound of general formula II in the reaction mixture by reducing a corresponding o-nitroamino compound, optionally in the presence of a carboxylic acid of general formula R₃COOH, or by acylation of a corresponding o-diamino compound. When the reduction of the nitro group is broken off at the hydroxylamine stage, the N-oxide of a compound of general formula I is obtained in the subsequent cyclisation. The resulting N-oxide is then converted by reduction into a corresponding compound of general formula I.

The subsequent reduction of the N-oxide of formula I obtained is preferably carried out in a solvent such as water, water/ethanol, methanol, glacial acetic acid, ethyl acetate or dimethylformamide with hydrogen in the presence of a hydrogenation catalyst such as Raney nickel, platinum or palladium/charcoal, with metals such as iron, tin or zinc in the presence of an acid such as acetic, hydrochloric or sulphuric acid, with salts such as iron(II)sulphate, tin(I-I)chloride or sodium dithionite, or with hydrazine in the presence of Raney nickel at temperatures between 0° and 50° C., but preferably at ambient temperature.

b) Reaction of a benzimidazole of general formula

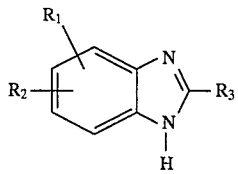

wherein

R₁ to R₃ are defined as hereinbefore, with a biphenyl compound of general formula

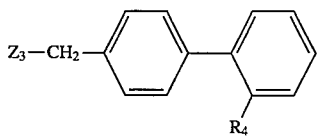

wherein

R₄ is defined as hereinbefore and

Z₃ represents a nucleophilic leaving group such as a halogen atom, e.g. a chlorine, bromine or iodine atom, or a substituted sulphonyloxy group, e.g. a methanesulphonyloxy, phenylsulphonyloxy or p-toluenesulphonyloxy group.

The reaction is conveniently carried out in a solvent or mixture of solvents such as methylene chloride, diethylether, tetrahydrofuran, dioxane, dimethyl-sulphoxide, dimethylformamide or benzene, optionally in the presence of an acid binding agent such as sodium carbonate, potassium carbonate, sodium hydroxide, potassium tert.-butoxide, triethylamine or pyridine, whilst the latter two may simultaneously also be used as solvent, preferably at temperatures between 0° and 100° C., e.g. at temperatures between ambient temperature and 50° C.

In the reaction, a mixture of the 1- and 3-isomers is preferably obtained which can if desired subsequently be resolved into the corresponding 1- and 3-isomers, preferably by chromatography using a substrate such as silica gel or aluminium oxide.

c) In order to prepare a compound of general formula I wherein R₄ represents a carboxy group:

Converting a compound of general formula

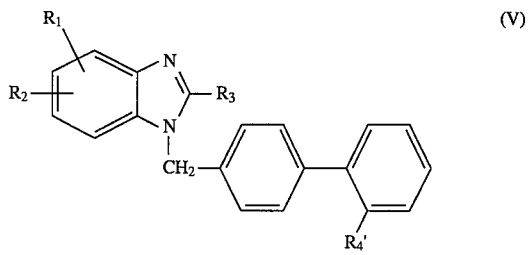

wherein

R₁ to R₃ are defined as hereinbefore and

R₄' represents a group which may be converted into a carboxy group by hydrolysis, thermolysis or hydrogenolysis.

For example, functional derivatives of the carboxy group such as unsubstituted or substituted amides, esters, thiolesters, orthoesters, iminoethers, amidines or anhydrides, a nitrile group or a tetrazolyl group may be converted into a carboxy group by hydrolysis, esters with tertiary alcohols, e.g. tert.butylester, may be converted into a carboxy group by thermolysis and esters with aralkanols, e.g. benzylester, may be converted into a carboxy group by hydrogenolysis.

The hydrolysis is conveniently carried out in the presence of an acid such as hydrochloric, sulphuric, phosphoric, trichloroacetic or trifluoroacetic acid in the presence of a base such as sodium hydroxide or potassium hydroxide in a suitable solvent such as water, water/methanol, ethanol, water/ethanol, water/isopropanol or water/dioxane at temperatures between −10° C. and 120° C., e.g. at temperatures between ambient temperature and the boiling temperature of the reaction mixture. When hydrolysis is carried out in the presence of an organic acid such as trichloroacetic or trifluoroacetic acid, any alcoholic hydroxy groups present may optionally be simultaneously converted into a corresponding acyloxy group such as a trifluoroacetoxy group.

If R₄' in a compound of general formula V represents a cyano or aminocarbonyl group, these groups may also be converted into a carboxy group with a nitrite, e.g. sodium nitrite, in the presence of an acid such as sulphuric acid, which may also be simultaneously used as solvent, at temperatures between 0° and 50° C.

If R₄' in a compound of general formula V represents, for example, a tert.-butyloxycarbonyl group, the tert.-butyl group may also be thermally cleaved, optionally in an inert solvent such as methylene chloride, chloroform, benzene, toluene, tetrahydrofuran or dioxane and preferably in the presence of a catalytic amount of an acid such as p-toluenesulphonic acid, sulphuric, phosphoric or polyphosphoric acid, preferably at the boiling temperature of the solvent used, e.g. at temperatures between 40° C. and 100° C.

If R₄' in a compound of general formula V represents, for example, a benzyloxycarbonyl group, the benzyl group may also be hydrogenolytically cleaved in the presence of a hydrogenation catalyst such as palladium/charcoal in a suitable solvent such as methanol, ethanol, ethanol/water, glacial acetic acid, ethyl acetate, dioxane or dimethylformamide, preferably at temperatures between 0° and 50° C., e.g. at ambient temperature, under a hydrogen pressure of 1 to 5 bar. During hydrogenolysis, other groups may be reduced at the same time, e.g. a nitro group may be reduced to an amino group, a benzyloxy group to a hydroxy group, a vinylidene group to the corresponding alkylidene group or a cinnamic acid group to the corresponding phenyl-propionic acid group, or they may be replaced by hydrogen atoms, e.g. a halogen may be replaced by a hydrogen atom.

d) In order to prepare a compound of general formula I wherein $R_4$ represents a 1H-tetrazolyl group:

Cleaving of a protective group from a compound of general formula

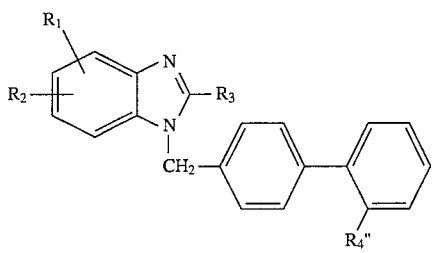

(VI)

wherein $R_1$, $R_2$ and $R_3$ are defined as hereinbefore and $R_4''$ represents a 1H-tetrazolyl group protected in the 1- or 3-position by a protecting group.

Suitable protecting groups include, for example, triphenylmethyl, tributyl tin or triphenyl tin groups.

The cleaving of a protective group used is preferably carried out in the presence of a hydrohalic acid, preferably in the presence of hydrochloric acid, in the presence of a base such as sodium hydroxide or alcoholic ammonia, in a suitable solvent such as methylene chloride, methanol, methanol/ammonia, ethanol or isopropanol at temperatures between 0° and 100° C., but preferably at ambient temperature or, if the reaction is carried out in the presence of alcoholic ammonia, at elevated temperatures, e.g. at temperatures between 100° and 150° C., preferably at temperatures between 120° and 140° C.

e) In order to prepare a compound of general formula I wherein $R_4$ represents a 1H-tetrazolyl group:

Reaction of a compound of general formula

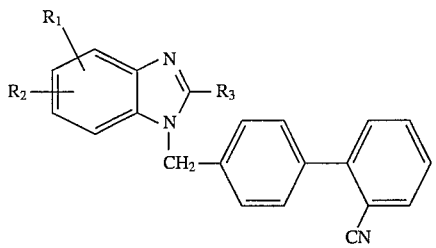

(VII)

wherein $R_1$ to $R_3$ are defined as hereinbefore, with hydrazoic acid or the salts thereof.

The reaction is preferably carried out in a solvent such as benzene, toluene or dimethylformamide at temperatures between 80° and 150° C., preferably at 125° C. Conveniently, either the hydrazoic acid is liberated during the reaction from an alkali metal azide, e.g. sodium azide, in the presence of a weak acid such as ammonium chloride or a tetrazolide salt obtained in the reaction mixture during the reaction with a salt of hydrazoic acid, preferably with aluminium azide or tributyl tin azide, which is also preferably produced in the reaction mixture by reacting aluminium chloride or tributyl tin chloride with an alkali metal azide such as sodium azide, is subsequently liberated by acidification with a dilute acid such as 2N hydrochloric or 2N sulphuric acid.

f) In order to prepare compounds of general formula I wherein $R_2$ represents one of the above-mentioned imidazo [1,2-a]pyridin-2-yl, imidazo[1,2-a]pyrimidin-2-yl, imidazo [1,2-c]pyrimidin-2-yl, imidazo[1,2-a]pyrazin-2-yl, imidazo [1,2-b]pyridazin-2-yl or imidazo[2,1-b]-thiazol-6-yl groups:

Reaction of a compound of general formula

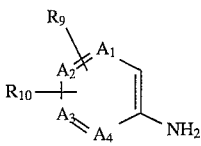

(VIII)

wherein one of the groups $A_1$, $A_2$, $A_3$ or $A_4$ represents a methine group or a nitrogen atom and the remaining groups $A_1$, $A_2$, $A_3$ or $A_4$ represent methine groups or $A_1$ and $A_2$ each represent a methine group and the —$A_3$=$A_4$— group represents a sulphur atom, $R_9$ represents a hydrogen, fluorine, chlorine or bromine atom, an alkyl, alkoxy, hydroxy, phenyl, nitro, amino, alkylamino, dialkylamino, alkanoylamino, cyano, carboxy, alkoxycarbonyl, aminocarbonyl, alkylaminocarbonyl, dialkylaminocarbonyl, trifluoromethyl, alkanoyl, aminosulphonyl, alkylaminosulphonyl or dialkylamino-sulphonyl group and $R_{10}$ represents a hydrogen, fluorine or chlorine atom, or a methyl, methoxy or hydroxy group, whilst if $R_9$ and $R_{10}$ represent adjacent methyl groups these may be linked together by a methylene or ethylene group, with a compound of general formula

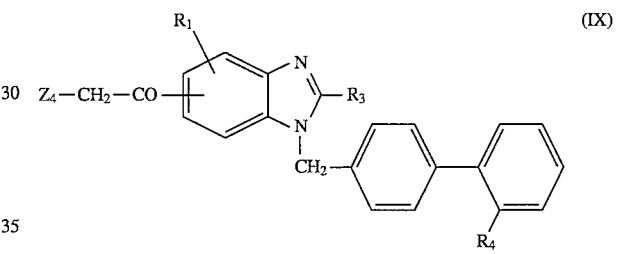

(IX)

wherein $R_1$, $R_3$ and $R_4$ are defined as hereinbefore and $Z_4$ represents a nucleophilic leaving group such as a halogen atom, e.g. a chlorine or bromine atom.

The reaction is expediently carried out in a solvent or mixture of solvents such as ethanol, isopropanol, benzene, glycol, glycolmonomethylether, dimethyl-formamide or dioxane, e.g. at temperatures between 0° and 150° C., preferably, at temperatures between 20° and 100° C. However, the reaction may also be carried out without solvents.

g) In order to prepare compounds of general formula I wherein $R_2$ represents one of the above-mentioned benzimidazol-2-yl, imidazo[4,5-b]pyridin-2-yl, imidazo[4,5-c] pyridin-2-yl, imidazo[4,5-b]pyrazin-2-yl, imidazo[4,5-c]pyridazin-2-yl, imidazo[4,5-d]pyridazin-2-yl or purin-8-yl groups:

Cyclisation of a compound of general formula

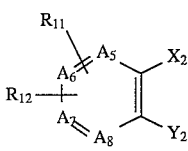

(X)

wherein none, one or two of the groups $A_5$, $A_6$, $A_7$ or $A_8$ represent a nitrogen atom and the remaining groups $A_5$, $A_6$, $A_7$ or $A_8$ represent methine groups, $R_{11}$ represents a hydrogen, fluorine, chlorine or bromine atom or an alkyl, alkoxy, hydroxy, phenyl, nitro, amino, alkylamino, dialkylamino, alkanoylamino, cyano, carboxy, alkoxycarbonyl, aminocarbonyl, alkylaminocarbonyl, dialkylaminocarbonyl, trifluoromethyl, alkanoyl, aminosulphonyl, alkylaminosulphonyl or dialkylamino-sulphonyl group and $R_{12}$ represents a hydrogen, fluorine or chlorine atom or a methyl, methoxy or hydroxy group, one of the groups $X_2$ or $Y_2$ represents an $R_{13}$—NH— group and the other $X_2$ or $Y_2$ group represents a group of general formula

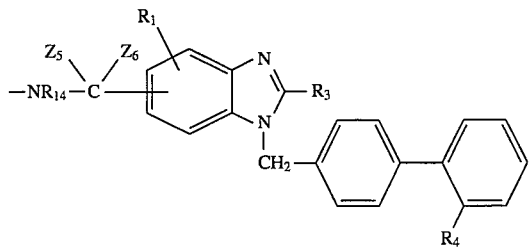

wherein $R_1$, $R_3$ and $R_4$ are defined as hereinbefore, one of the groups $R_{13}$ or $R_{14}$ represents a hydrogen atom and the other $R_{13}$ or $R_{14}$ group represents a hydrogen atom, a $C_{1-6}$-alkyl group or a cycloalkyl group, $Z_5$ and $Z_6$, which may be identical or different, represent optionally substituted amino groups or hydroxy or mercapto groups optionally substituted by lower alkyl groups or $Z_5$ and $Z_6$ together represent an oxygen or sulphur atom, an optionally $C_{1-3}$-alkyl substituted imino group, or an alkylenedioxy or alkylenedithio group each having 2 or 3 carbon atoms, optionally with subsequent hydrolysis.

The cyclisation is conveniently carried out in a solvent or mixture of solvents such as ethanol, isopropanol, glacial acetic acid, benzene, chlorobenzene, toluene, xylene, glycol, glycolmonomethylether, diethyleneglycol-dimethylether, sulpholan, dimethylformamide, tetralin or in an excess of the acylating agent used to prepare the compound of general formula X, e.g. in the corresponding nitrile, anhydride, acid halide, ester or amide, e.g. at temperatures between 0° and 250° C., but preferably at the boiling temperature of the reaction mixture, optionally in the presence of a condensing agent such as phosphorus oxychloride, thionylchloride, sulphurylchloride, sulphuric acid, p-tuluenesulphonic acid, methanesulphonic acid, hydrochloric acid, phosphoric acid, polyphosphoric acid, acetic acid anhydride or optionally in the presence of a base such as potassium ethoxide or potassium tert.-butoxide. However, the cyclisation may also be carried out without a solvent and/or condensing agent.

However, it is particularly advantageous to perform the reaction by preparing a compound of general formula X in the reaction mixture by reducing a corresponding o-nitroamino compound, optionally in the presence of a carboxylic acid of general formula

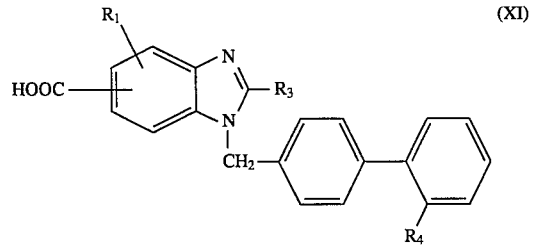

wherein $R_1$, $R_3$ and $R_4$ are defined as hereinbefore, or by acylating a corresponding o-diamino compound with a carboxylic acid of general formula XI.

When the reduction of the nitro group is broken off at the hydroxylamine stage, subsequent cyclisation produces the N-oxide of a compound of general formula I. The N-oxide thus obtained is then converted by reduction into a corresponding compound of general formula I.

The subsequent reduction of an N-oxide thus obtained is preferably carried out in a solvent such as water, water/ethanol, methanol, glacial acetic acid, ethyl acetate or dimethylformamide with hydrogen in the presence of a hydrogenation catalyst such as Raney nickel, platinum or palladium/charcoal, with metals such as iron, tin or zinc in the presence of an acid such as acetic, hydrochloric or sulphuric acid, with salts such as iron(II)sulphate, tin(II)chloride or sodium dithionite, or with hydrazine in the presence of Raney nickel at temperatures between 0° and 50° C., but preferably at ambient temperature.

The subsequent hydrolysis is conveniently carried out either in the presence of an acid such as hydrochloric, sulphuric, phosphoric, trichloroacetic or trifluoroacetic acid in the presence of a base such as sodium hydroxide or potassium hydroxide in a suitable solvent such as water, water/methanol, ethanol, water/ethanol, water/isopropanol or water/dioxane at temperatures between −10° C. and 120° C., e.g. at temperatures between ambient temperature and the boiling temperature of the reaction mixture. When hydrolysis is carried out in the presence of an organic acid such as trichloroacetic or trifluoroacetic acid, any alcoholic hydroxy groups present may simultaneously be converted into a corresponding acyloxy group such as the trifluoroacetoxy group.

h) In order to prepare compounds of general formula I wherein $R_2$ represents a dihydro-pyridazin-3-one or pyridazin-3-one group which may be substituted in the 2-position by an optionally phenyl-substituted $C_{1-3}$-alkyl group or in the carbon structure by one or two $C_{1-3}$-alkyl groups:

Reaction of a carboxylic acid of general formula

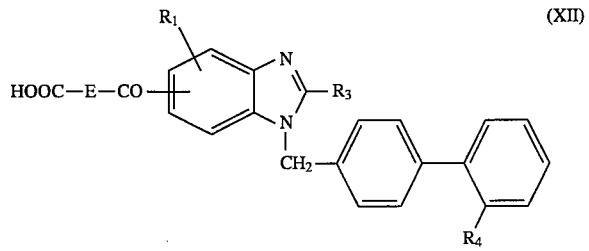

wherein $R_1$, $R_3$ and $R_4$ are defined as hereinbefore and E represents an ethylene or ethenylene group optionally substituted by one or two $C_{1-3}$-alkyl groups, or the reactive acid derivatives thereof such as the esters, amides or halides thereof, with a hydrazine of general formula $$H_2N-NHR_{15} \qquad (XIII)$$

wherein $R_{15}$ represents a hydrogen atom or an optionally phenyl-substituted $C_{1-3}$-alkyl group.

The reaction is conveniently carried out in a solvent such as methanol, ethanol, isopropanol, glacial acetic acid or propionic acid and/or in an excess of the hydrazine or hydrazine hydrate used at temperatures between 0° and 200° C., e.g. at temperatures between 20° and 150° C., but preferably at the boiling temperature of the reaction mixture, and optionally in the presence of an acid such as sulphuric or p-toluenesulphonic acid as condensing agent. The reaction may, however, also be carried out without a solvent.

i) In order to prepare compounds of general formula I wherein $R_2$ denotes an oxazol-2-yl, thiazol-2-yl or imidazol-2-yl group, in which an n-butylene bridge is added via the 4,5-positions and additionally the imino group in the imidazole ring may be substituted by a $C_{1-6}$-alkyl group, by a phenylalkyl group having 1 to 3 carbon atoms in the alkyl moiety or by a phenyl group:

Reaction of a compound of general formula

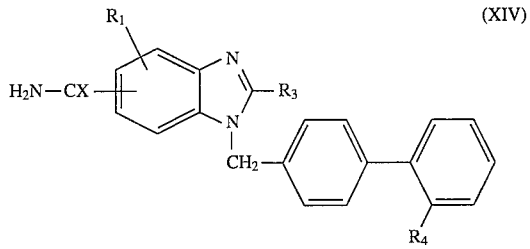

(XIV)

wherein $R_1$, $R_3$ and $R_4$ are as hereinbefore defined and X denotes an oxygen or sulphur atom or an imino group optionally substituted by a $C_{1-6}$-alkyl group, by a phenylalkyl group having 1 to 3 carbon atoms in the alkyl moiety or by a phenyl group, with an α-haloketone of general formula

(XV)

wherein $Z_7$ denotes a halogen atom such as a chlorine atom.

The reaction is preferably carried out in the presence of a suitable solvent such as dimethylformamide, diethyleneglycoldimethylether, triethyleneglycoldimethyl-ether or sulpholane, optionally in the presence of a base such as potassium carbonate, pyridine, triethylamine, N-ethyl-diisopropylamine or N-ethyl-dicyclohexylamine, at temperatures between 0° and 250° C.

If X denotes an oxygen or sulphur atom, the reaction is preferably carried out in a solvent having a boiling point above 150° C. or in a melt at temperatures between 150° and 250° C., preferably at temperatures between 175° and 225° C.

If X denotes an optionally alkyl-substituted imino group the reaction is preferably carried out in the presence of a corresponding amine as solvent, e.g. in the presence of liquid ammonia, methylamine, ethylamine, n-propylamine or isopropylamine, at temperatures between 0° and 100° C., preferably at temperatures between 20° and 75° C.

j) In order to prepare compounds of general formula I wherein $R_2$ denotes one of the imidazol-2-yl groups mentioned hereinbefore:

Reaction of a compound of general formula

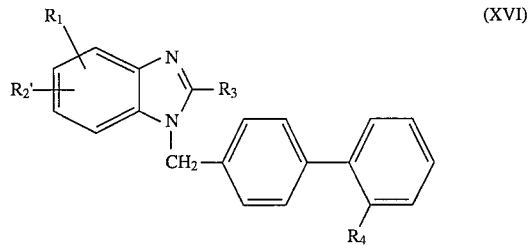

(XVI)

wherein $R_1$, $R_3$ and $R_4$ are as hereinbefore defined and
$R_2'$ denotes one of the above-mentioned oxazol-2-yl groups, with an amine of general formula

(XVII)

wherein $R_{16}$ has the meanings given for $R_a$ hereinbefore or denotes a hydrogen atom.

The reaction is expediently carried out in an excess of the amine used and preferably in the presence of a corresponding formamide of formula $HCONHR_{16}$ as solvent, optionally in a pressurised vessel at elevated temperatures, e.g. at temperatures between 100° and 250° C., preferably at temperatures between 175° and 225° C.

During the reaction, any substituted carboxy group present in the group $R_4$ is simultaneously converted into the carboxy group or any substituted tetrazolyl group present is converted into the 1H-tetrazol-5-yl group.

k) In order to prepare compounds of general formula I wherein $R_2$ denotes a 5,5-spiro-cyclopentano-dihydro-imidazol-4-on-2-yl group:

Treating a benzimidazole of general formula

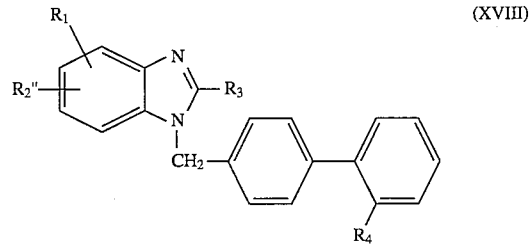

(XVIII)

wherein $R_1$, $R_3$ and $R_4$ are as hereinbefore defined and $R_2''$ denotes an imidazol-2-yl group in which an n-butylene group is attached via the 4,5-positions, with a base in the presence of air and light.

The reaction is carried out in the presence of a base such as sodium hydroxide or potassium hydroxide, in a suitable solvent such as water, water/methanol, ethanol, water/ethanol, water/isopropanol or water/dioxane, at temperatures between −10° C. and 120° C., e.g. at temperatures between ambient temperature and the boiling temperature of the reaction mixture.

During the reaction any ester group present in the group $R_4$ is simultaneously converted into a carboxy group.

l) In order to prepare compounds of general formula I wherein $R_2$ denotes one of the above-mentioned imidazol-2-yl groups which may be substituted in the 1-position by a phenylalkyl group (whilst the phenyl nucleus may be mono- or disubstituted by alkyl, hydroxy or alkoxy groups and the substituents may be identical or different), or by a $C_{1-6}$-alkyl group, whilst the alkyl group may additionally be substituted by a group which can be metabolised into a carboxy group in vivo, or by a trifluoromethyl, carboxyl, alkoxycarbonyl, aminocarbonyl, alkylaminocarbonyl or dialkylaminocarbonyl group, or $R_2$ denotes one of the imidazolium-2-yl groups mentioned hereinbefore:

Reacting a compound of general formula

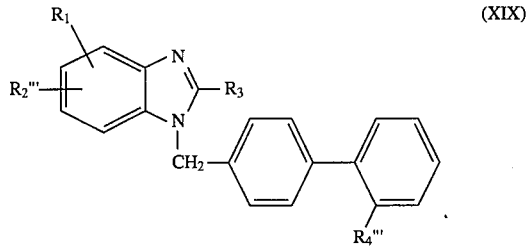

wherein $R_1$ and $R_3$ are as hereinbefore defined, $R_2'''$ represents one of the imidazol-2-yl groups unsubstituted in the 1-position mentioned hereinbefore and $R_4'''$ denotes a carboxy group or a group which can be converted into a carboxy group by hydrolysis, thermolysis or hydrogenolysis, or a 1H-tetrazolyl or 2H-tetrazolyl group protected by a protecting group, with a compound of general formula $$Z_8-R_{17} \quad (XX)$$

wherein $R_{17}$ denotes a phenylalkyl group, whilst the phenyl nucleus may be mono- or disubstituted by alkyl, hydroxy or alkoxy groups and the substituents may be identical or different, or a $C_{1-6}$-alkyl group, whilst the alkyl group may additionally be substituted by a group which can be metabolised in vivo into a carboxy group, or by a trifluoromethyl, carboxyl, alkoxycarbonyl, aminocarbonyl, alkylaminocarbonyl or dialkylaminocarbonyl group, and $Z_8$ denotes a nucleophilic leaving group such as a halogen atom, e.g. a chlorine, bromine or iodine atom, and subsequently, if necessary, cleaving the protecting groups used.

The reaction is conveniently carried out in a solvent or mixture of solvents such as methylene chloride, diethylether, tetrahydrofuran, dioxane, dimethylsulphoxide, dimethylformamide or benzene optionally in the presence of an acid binding agent, such as sodium carbonate, potassium carbonate, sodium hydroxide, sodium hydride, potassium tert.butoxide, triethylamine or pyridine, whilst the latter two may simultaneously be used as solvents, preferably at temperatures between 0° and 100° C., e.g. at temperatures between ambient temperature and 50° C.

If the reaction is carried out in the presence of an excess of the compound of formula XX used, a corresponding imidazolium-2-yl compound of general formula I is obtained at the same time.

The subsequent cleaving of a protecting group is preferably carried out by hydrolysis, thermolysis or hydrogenolysis.

The hydrolyric cleaving of a protecting group used is preferably carried out in the presence of an acid such as hydrochloric acid, hydrobromic acid, sulphuric acid, phosphoric acid, trichloroacetic acid or trifluoroacetic acid, optionally in the presence of a reaction accelerator such as hexadecyltributyl-phosphonium bromide in a suitable solvent such as water, water/methanol, ethanol, water/ethanol, water/isopropanol or water/dioxane at temperatures between −10° C. and 120° C., e.g. at temperatures between ambient temperature and the boiling temperature of the reaction mixture.

The thermolytic cleaving of a protecting group such as the tert.butyloxycarbonyl group is preferably effected in an inert solvent such as methylene chloride, chloroform, benzene, toluene, tetrahydrofuran or dioxane and preferably in the presence of a catalytic amount of an acid such as p-toluenesulphonic acid, sulphuric acid, phosphoric acid or polyphosphoric acid, preferably at the boiling temperature of the solvent used, e.g. at temperatures between 40° C. and 100° C.

The hydrogenolytic cleaving of a protecting group such as the benzyloxycarbonyl group is effected in the presence of a hydrogenation catalyst such as palladium/charcoal in a suitable solvent such as methanol, ethanol, ethanol/water, glacial acetic acid, ethyl acetate, dioxane or dimethylformamide, preferably at temperatures between 0° and 50° C., e.g. at ambient temperature, and a hydrogen pressure of 1 to 5 bar.

m) In order to prepare compounds of general formula I wherein $R_2$ represents one of the imidazol-2-yl groups mentioned hereinbefore substituted by the groups $R_{18}$ to $R_{20}$, but $R_{19}$ or $R_{20}$ must denote a hydrogen atom:

Reacting an aminoketone of general formula

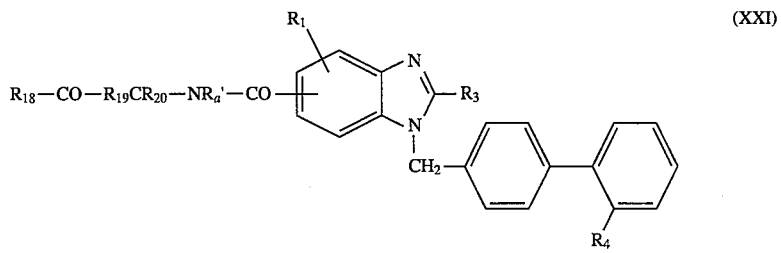

wherein $R_1$, $R_3$, $R_4$ and $R_{18}$ to $R_{20}$ are as hereinbefore defined, but $R_{19}$ or $R_{20}$ must denote a hydrogen atom, and $R_a'$ has the meanings given for $R_a$ hereinbefore or denotes a hydrogen atom, with an ammonium salt of a lower aliphatic carboxylic acid.

The reaction is carried out with an ammonium salt of a lower aliphatic carboxylic acid such as ammonium acetate or ammonium propionate, preferably in the presence of a solvent such as glacial acetic acid or propionic acid at elevated temperatures, but preferably at the boiling temperature of the reaction mixture, e.g. at temperatures between 100° and 150° C.

n) In order to prepare compounds of general formula I wherein $R_2$ denotes one of the oxazolin-2-yl or imidazolin-2-yl groups as hereinbefore defined:

Dehydrating a compound of general formula

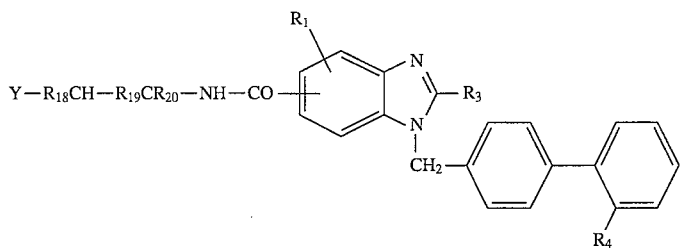

(XXII)

wherein

R₁, R₃, R₄ and R₁₈ to R₂₀ are as hereinbefore defined and Y denotes a hydroxy or NHR_a group, wherein R_a is as hereinbefore defined.

The dehydration is carried out in the presence of a dehydrating agent such as phosphorusoxychloride, sulphuric acid, polyphosphoric acid or thionyl chloride, the latter preferably being used as solvent at the same time, at elevated temperatures, e.g. at the boiling temperature of the dehydrating agent used, e.g. at temperatures between 105° and 150° C.

o) In order to prepare compounds of general formula I wherein $R_2$ denotes one of the imidazolin-2-yl groups as hereinbefore defined:

Reacting a compound of general formula

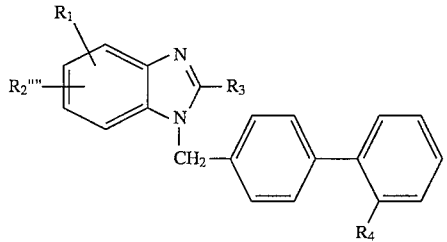

(XXIII)

wherein $R_1$, $R_3$ and $R_4$ are as hereinbefore defined and $R_2''''$ denotes one of the oxazolin-2-yl groups mentioned for $R_2$ hereinbefore, substituted by groups $R_8$ to $R_{10}$, with an amine of general formula

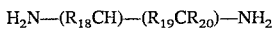

H₂N—(R₁₈CH)—(R₁₉CR₂₀)—NH₂    (XXIV)

wherein $R_{18}$ to $R_{20}$ are as hereinbefore defined.

The reaction is conveniently carried out in a solvent such as toluene, dimethylformamide or dimethylsulphoxide, but preferably in an excess of the amine of general formula XXIV used, at elevated temperatures, e.g. at temperatures between 100° and 150° C. However, the reaction is preferably carried out without a solvent.

p) In order to prepare compounds of general formula I wherein $R_2$ denotes one of the oxazol-2-yl groups mentioned hereinbefore substituted by groups $R_{18}$ to $R_{20}$:

Dehydrating an aminoketone of general formula

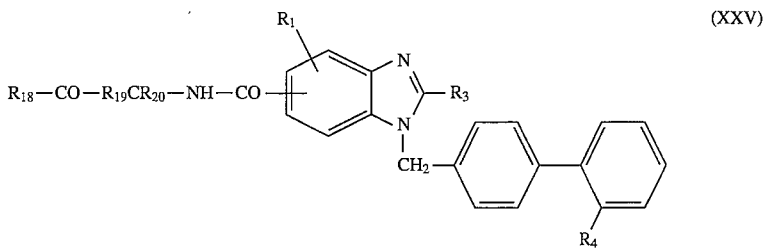

(XXV)

wherein $R_1$, $R_3$, $R_4$ and $R_{18}$ to $R_{20}$ are as hereinbefore defined, but $R_{19}$ or $R_{20}$ must denote a hydrogen atom, with an ammonium salt of a lower aliphatic carboxylic acid.

The dehydration is carried out in the presence of a dehydrating agent such as phosphorusoxychloride, phosphoric acid or sulphuric acid, which is preferably used as solvent at the same time, at elevated temperatures, e.g. at the boiling temperature of the dehydrating agent used, e.g. at temperatures between 105° and 150° C. During the reaction with phosphorusoxychloride any tert.butylester present at the same time can be cleaved.

q) In order to prepare compounds of general formula I wherein $R_2$ denotes one of the imidazol-2-yl groups mentioned hereinbefore, substituted by the groups $R_{18}$ to $R_{20}$:

Dehydrogenating a compound of general formula

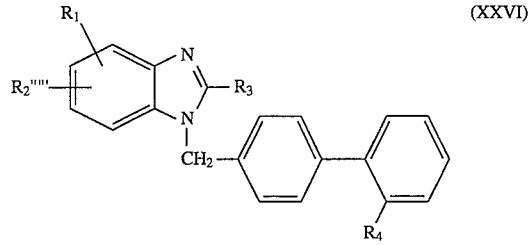

(XXVI)

wherein $R_1$, $R_3$ and $R_4$ are as hereinbefore defined and $R_2''''$ denotes one of the imidazolin-2-yl groups mentioned for $R_2$ hereinbefore, substituted by the groups $R_{18}$ to $R_{20}$, but $R_{19}$ or $R_{20}$ must denote a hydrogen atom.

The dehydrogenation is carried out in the presence of a dehydrogenating agent such as palladium/charcoal, barium manganate or selenium dioxide, in a suitable solvent such as toluene or methylene chloride at elevated temperatures, e.g.

at the boiling temperature of the solvent used, e.g. at temperatures between 110° and 150° C.

r) In order to prepare compounds of general formula I wherein $R_4$ denotes a 2,5-dihydro-5-oxo-1,2,4-oxadiazol-3-yl group:

Reacting an optionally in the reaction mixture prepared amidoxime of general formula

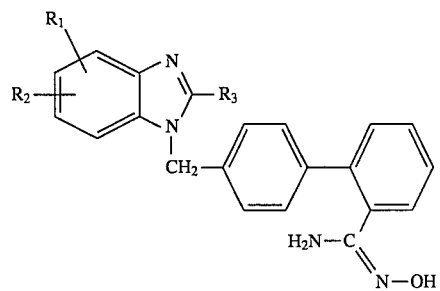

(XXVII)

wherein $R_1$ to $R_3$ are as hereinbefore defined, with a compound of general formula $$Z_9\text{—CO—OR}_{21} \quad \text{(XXVIII)}$$

wherein $Z_9$ denotes a nucleophilic leaving group such as a halogen atom, e.g. a chlorine, bromine or iodine atom, and $R_{21}$ denotes an alkyl, aryl or aralkyl group, preferably a lower alkyl group such as the methyl, ethyl, n-propyl or isopropyl group, and subsequently cyclisizing a thus obtained acylated amidoxime.

The reaction is conveniently carried out in a solvent such as methylene chloride, chloroform, tetrahydrofuran, dioxane or acetonitrile preferably in the presence of an inorganic base such as sodium or potassium carbonate or of an organic base such as triethylamine or pyridine whilst the latter two may simultaneously also be used as solvent at temperatures between 0° and 20° C.

The subsequent cyclization of a thus obtained acylated amidoxime is conveniently carried out in an organic solvent such as benzene, toluene, xylene, tetrahydrofuran or dioxane at elevated temperatures, e.g. at temperatures between 50° and 100° C., preferably at the boiling temperature of the solvent used.

The necessary starting amidoxime is prepared conveniently by reaction of a corresponding nitrile with hydroxylamine in the presence of a solvent such as methanol, ethanol, methylene chloride, chloroform, dimethylformamide, tetrahydrofuran or dioxane in the presence of a suitable base such as sodium carbonate, potassium carbonate, sodium hydroxide, triethylamine, sodium methoxide, sodium ethoxide or sodium hydride at temperatures between 50° and 100° C.

s) In order to prepare a compound of general formula I wherein $R_4$ denotes a tetrazolyl group substituted in the 1- or 2-position by an $R_a$—CO—O—CH$_2$— group, or it denotes an $R_a$O—CO—, $R_b$—CO—O—($R_c$CH)—O—CO— or $R_b$O—CO—O—($R_c$CH)—O—CO— group:

Reacting a compound of general formula

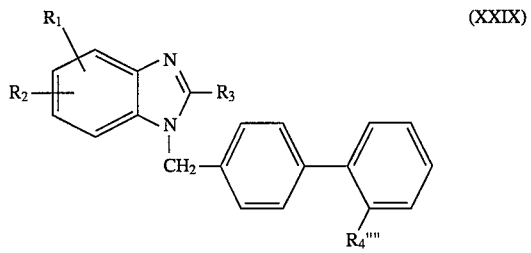

(XXIX)

wherein $R_1$ to $R_3$ are as hereinbefore defined and $R_4''''$ denotes a carboxy, 1H-tetrazolyl or 2H-tetrazolyl group, with a compound of general formula $$Z_{10}\text{—}Y_3 \quad \text{(XXX)}$$

wherein $Y_3$ denotes an $R_a$—CO—O—CH$_2$—, $R_b$—CO—O—($R_c$CH)—, $R_b$O—CO—O—($R_c$CH)— or $R_a$— group, wherein $R_a$ to $R_c$ are as hereinbefore defined and $Z_{10}$ denotes a nucleophilic leaving group such as a halogen atom, e.g. a chlorine or bromine atom, or, if Y denotes an $R_a$— group, $Z_{10}$ may also represent a hydroxy group.

The reaction is conveniently carried out by esterification with a corresponding alcohol or with a corresponding reactive derivative such as the halide, conveniently in a solvent or mixture of solvents such as water, methylene chloride, chloroform, ether, tetrahydrofuran, dioxane or dimethylformamide or in an excess of the acylating agent as solvent, optionally in the presence of an acid activating or dehydrating agent such as thionylchloride, with the anhydrides, esters or halides thereof optionally in the presence of an inorganic or tertiary organic base such as sodium hydroxide, potassium carbonate, triethylamine or pyridine, whilst the latter two may simultaneously be used as solvent, at temperatures between −25° and 100° C., but preferably at temperatures between −10° and 80° C.

In the reactions described hereinbefore, any reactive groups present such as hydroxy, amino or alkylamino groups may be protected during the reaction by conventional protecting groups which are split off again after the reaction.

Examples of protecting groups for a hydroxy group are trimethylsilyl, acetyl, benzoyl, methyl, ethyl, tert.-butyl, benzyl and tetrahydropyranyl groups and protecting groups for an amino, alkylamino or imino group include the acetyl, benzoyl, ethoxycarbonyl and benzyl groups.

The optional subsequent cleaving of a protecting group is preferably carried out by hydrolysis in an aqueous solvent, e.g. in water, isopropanol/water, tetrahydrofuran/water or dioxane/water, in the presence of an acid such as hydrochloric or sulphuric acid or in the presence of an alkali metal base such as sodium hydroxide or potassium hydroxide at temperatures between 0° and 100° C., preferably at the boiling temperature of the reaction mixture. However, a benzyl group is preferably split off by hydrogenolysis, e.g. with hydrogen in the presence of a catalyst such as palladium/charcoal in a solvent such as methanol, ethanol, ethyl acetate or glacial acetic acid, optionally with the addition of an acid such as hydrochloric acid at temperatures between 0° and 50° C., but preferably at ambient temperature, under a hydrogen pressure of 1 to 7 bar, preferably 3 to 5 bar.

An isomer mixture of a compound of general formula I thus obtained may if desired be resolved by chromatography using a substrate such as silica gel or aluminium oxide.

Moreover, the compounds of general formula I obtained may be converted into the acid addition salts thereof, more particularly for pharmaceutical use the physiologically acceptable salts thereof with inorganic or organic acids. Suitable acids for this purpose include hydrochloric, hydrobromic, sulphuric, phosphoric, fumaric, succinic, lactic, citric, tartaric or maleic acid.

Furthermore, the new compounds of general formula I thus obtained, if they contain a carboxy or 1H-tetrazolyl group, may if desired subsequently be converted into the salts thereof with inorganic or organic bases, more particularly for pharmaceutical use into the physiologically acceptable addition salts thereof. Suitable bases include for example sodium hydroxide, potassium hydroxide, cyclohexylamine, ethanolamine, diethanolamine and triethanolamine.

The compounds of general formulae II to XXX used as starting materials are, in some cases, known from the literature, or may be obtained by methods known from the literature.

Thus, for example, a compound of general formula II is obtained by alkylation of a corresponding o-amino-nitro compound with a compound of general formula IV and subsequent reduction of the nitro group.

A compound of general formula III, V, VI, VII, IX, X, XII, XIV, XVI, XVIII, XIX or XXIX used as starting material is obtained by acylation of a corresponding o-phenylenediamine or a corresponding o-amino-nitro compound, followed by reduction of the nitro group and subsequent cyclisation of an o-diaminophenyl compound thus obtained, optionally followed by the cleaving of any protecting group used or by cyclisation of a correspondingly substituted benzimidazole with a corresponding amine or by NH-alkylation of a corresponding 1H-benzimidazole, whilst the isomer mixture thus obtained may subsequently be resolved by conventional methods, e.g. chromatography. Some of the starting compounds mentioned above are described in EP-A-0 392 317. Before the reduction of the nitro group an oxazol-4-yl compound thus obtained may be converted into the corresponding imidazol-4-yl compound by means of a corresponding amine, preferably with ammonia, under pressure, or an imidazol-4-yl compound unsubstituted in the 1-position obtained in this way may be converted by alkylation into a corresponding imidazol-4-yl compound alkylated in the 1-position.

The conversions of oxazol-2-yl compounds into imidazol-2-yl compounds substituted in the 1-position, as described in this application, are carried out analogously to the synthesis of 1H-imidazole described in Angew. Chem. 71, 761 (1959) (conversion of oxazoles into 1H-imidazoles using formamide/ammonia), whereby the oxazoles can be prepared by acylation of a corresponding α-aminoketone with a corresponding carboxylic acid chloride or carboxylic acid anhydride followed by cyclisation analogously to J. Chem. Soc. 95, 2167 (1909) and Synthesis 1.970, 648, using as condensation agents strong acids such as sulphuric acid, phosphoric acid, hydrofluoric acid or $POCl_{13}$.

For example, 2-n-propyl-5-(imidazo[1,2-a]pyridin-2-yl)-3H-benzimidazole is obtained by reacting p-amino-acetophenone with butyric acid chloride, followed by nitration, bromination, cyclisation with 2-aminopyridine to form the 6-n-butanoylamido-3-(imidazo[1,2-a]pyridin-2-yl)-nitrobenzene, which is subsequently converted into the desired compound by cyclisation, after reduction of the nitro group, or 2-n-propyl-4-methyl-6-(1-methylbenzimidazol-2-yl)-1H-benzimidazole may be obtained by nitration of methyl 3-methyl-4-n-butanoylamido-benzoate, subsequent reduction of the nitro group and cyclisation to yield 2-n-propyl-4-methyl-6-methoxycarbonyl-1H-benzimidazole, which is then converted into the desired compound using 2-methylamino-aniline with cyclisation.

A benzimidazole in which the alkoxy group is substituted in the 2-, 3-, 4- or 5-position by an imidazole group may be obtained for example by reaction of a corresponding 7-hydroxybenzimidazole, as described in EP-A-0 392 317, by reaction with a corresponding α, ω-dihaloalkane and subsequent reaction with a corresponding imidazole.

A starting compound of general formula XXI or XXV is obtained by acylating a corresponding α-amino-acetone with a corresponding activated benzimidazole carboxylic acid, to obtain the desired α-amino-acetone from the corresponding α-amino acids according to Dakin/West (see Chem. Soc. Rev., 17, 91 (1988)).

A starting compound of general formula XXII is obtained by acylation of a corresponding β-amino-alcohol and a compound of general formula XXIII is obtained by cyclisation of a compound of general formula XXII thus obtained.

The acylated α-aminoketones mentioned above can also be converted directly into the corresponding substituted imidazoles by treatment with ammonium acetate in glacial acetic acid analogously to Chem. Bet. 106, 2415 (1973).

A starting compound of general formula XXVI is obtained by acylating a corresponding β-amino-alcohol with a corresponding activated benzimidazole carboxylic acid, the resulting compound subsequently being cyclised and then reacted with a corresponding ethylenediamine.

The new compounds of general formula I and the physiologically acceptable salts thereof have valuable pharmacological properties. They are angiotensin antagonists, particularly angiotensin-II-antagonists.

By way of example, the following compounds were tested for their biological effects as described hereinafter:

A=4'-[[2-n-butyl-7-[3-(imidazol-1-yl)-propyloxy]-4-methyl-benzimidazol-1-yl]-methyl]-biphenyl-2-carboxylic acid, B=4'-[[2-n-butyl-7-[3-(benzimidazol-1-yl)-propyloxy]-4-methyl-benzimidazol-1-yl]-methyl]-biphenyl-2-carboxylic acid trifluoroacetate, C=4'-[[2-n-butyl-4-methyl-7-[4-(tetrahydro-benzimidazol-1-yl)-butoxy]-benzimidazol-1-yl]-methyl]-biphenyl-2-carboxylic acid, D=4'-[[2-n-propyl-4-methyl-6-(1-methylbenzimidazol-2-yl)-benzimidazol-1-yl]-methyl]-biphenyl-2-carboxylic acid, E=4'-[[2-n-propyl-4-methyl-6-(1-methylbenzimidazol-2-yl)-benzimidazol-1-yl]-methyl]-2-(1H-tetrazol-5-yl)-biphenyl, F=4'-[[2-n-propyl-4-methyl-6-(1-oxo-isoindolin-2-yl)-benzimidazol-1-yl]-methyl]-2-(1H-tetrazol-5-yl)-biphenyl, G=4'-[[2-n-propyl-4-methyl-6-(butanesultam-1-yl)-benzimidazol-1-yl]-methyl]-2-(1H-tetrazol-5-yl)-biphenyl, H=4'-[[2-n-butyl-6-(2,3-dimethylmaleic acid imino)-4-methyl-benzimidazol-1-yl]-methyl]-biphenyl-2-carboxylic acid semihydrate, I=4'-[[2-n-butyl-6-(isopropylcarbonylamino)-4-methyl-benzimidazol-1-yl]-methyl]-biphenyl-2-carboxylic acid, J=4'-[[2-n-butyl-4-methyl-6-(morpholinocarbonylamino)-benzimidazol-1-yl]-methyl]-biphenyl-2-carboxylic acid, K=4'-[[2-n-butyl-6-(cyclohexylaminocarbonylamino)-4-methyl-benzimidazol-1-yl]-methyl]-biphenyl-2-carboxylic acid semitrifluoroacetate, L=4'-[[2-n-butyl-7-[3-(imidazol-1-yl)-propyloxy]-4-methyl-benzimidazol-1-yl]-methyl]-2-(1H-tetrazol-5-yl)-biphenyl, M=4'-[(2-cyclopropyl-4-methyl-6-(1-methylbenzimidazol-2-yl)-benzimidazol-1-yl)-methyl]-biphenyl-2-carboxylic acid, N=4'-[(2-n-propyl-4-methyl-6-(1-methyl-5-fluoro-benzimidazol-2-yl)-benzimidazol-1-yl)-methyl]-biphenyl-2-carboxylic acid, O=4'-[(2-n-propyl-4-methyl-6-(imidazo[1,2-a]pyrimidin-2-yl)-benzimidazol-1-yl)-methyl]-2-(1H-tetrazol-5-yl)-biphenyl, P=4'-[(2-n-propyl-4-methyl-6-(5,6,7,8-tetrahydro-imidazo[1,2-a]pyridin-2-yl)-benzimidazol-1-yl)-methyl]-biphenyl-2-carboxylic acid, Q=4'-[(2-n-propyl-4-methyl-6-(5,6,7,8-tetrahydro-imidazo[1,2-a]pyridin-2-yl)-benzimidazol-1-yl)-methyl]-2-(1H-tetrazol-5-yl)-biphenyl, R=4'-[(2-n-propyl-4-chloro-6-(1-methylbenzimidazol-2-yl)-benzimidazol-1-yl)-methyl]-2-(1H-tetrazol-5-yl)-biphenyl-hydrochloride, S=4'-[[2-n-propyl-4-methyl-6-(imidazo[2,1-b]thiazol-6-yl)-benzimidazol-1-yl]-methyl]-biphenyl-2-carboxylic acid, T=4'-[[2-n-butyl-4-methyl-6-(1-methylbenzimidazol-2-yl)-benzimidazol-1-yl]-methyl-2-(1H-tetrazol-5-yl)-biphenyl, U=4'-[[2-n-propyl-4-methyl-6-(imidazo[1,2-a]pyridin-2-yl)-benzimidazol-1-yl]-methyl-2-(1H-tetrazol-5-yl)-biphenyl, V=4'-[(2-n-propyl-4-methyl-6-(1-methyl-imidazol-4-yl)-benzimidazol-1-yl)-methyl]-biphenyl-2-carboxylic acid, W=4'-[(2-n-propyl-4-methyl-6-(1-isopropyl-imidazol-4-yl)-benzimidazol-1-yl)-methyl]-2-(1H-tetrazol-5-yl)-biphenyl, X=4'-[(2-n-propyl-4-methyl-6-(2-methyl-oxazol-4-yl)-benzimidazol-1-yl)-methyl]-biphenyl-2-carboxylic acid, Y=4'-[(2-ethoxy-6-(1-isopropyl-imidazol-4-yl)-benzimidazol-1-yl)-methyl]-biphenyl-2-carboxylic acid, Z=4'-[(2-n-propyl-4-methyl-6-(1-cycloheptyl-imidazol-4-yl)-benzimidazol-1-yl)-methyl]-biphenyl-2-carboxylic acid, AA=4'-[(2-n-propyl-4-methyl-6-(1-aminocarbonylmethyl-imidazol-4-yl)-benzimidazol-1-yl)-methyl]-biphenyl-2-carboxylic acid, BB=4'-[(2-n-propyl-4-methyl-6-(1-(3-dimethylaminopropyl)- imidazol-4-yl)-benzimidazol-1-yl)-methyl]-biphenyl-2-carboxylic acid-dihydrochloride-pentahydrate, CC=4'-[[2-n-propyl-4-methyl-6-(5,6,7,8-tetrahydro-benzimidazol-2-yl)-1H-benzimidazol-1-yl]-methyl]-biphenyl-2-carboxylic acid, DD=4'-[[2-n-propyl-4-methyl-6-(1-methyl-5,6,7,8-tetrahydro-benzimidazol-2-yl)-1H-benzimidazol-1-yl]-methyl]-biphenyl-2-carboxylic acid, EE=4'-[[2-n-propyl-4-methyl-6-(1-methyl-5,6,7,8-tetrahydro-benzimidazol-2-yl)-1H-benzimidazol-1-yl]-methyl]-2-(1H-tetrazol-5-yl)biphenyl, FF=4'-[[2-n-propyl-4-methyl-6-(1-benzyl-5,6,7,8-tetrahydro-benzimidazol-2-yl)-1H-benzimidazol-1-yl]-methyl]-biphenyl-2-carboxylic acid, GG=4'-[[2-ethyl-4-methyl-6-(1-phenyl-5,6,7,8-tetrahydro-benzimidazol-2-yl)-1H-benzimidazol-1-yl]-methyl]-biphenyl-2-carboxylic acid-hydrate, HH=4'-[[2-n-propyl-4-methyl-6-(1-carboxymethyl-5,6,7,8-tetrahydrobenzimidazol-2-yl)-1H-benzimidazol-1-yl]-methyl]-biphenyl-2-carboxylic acid-semihydrate, II=4'-[[2-ethyl-4-methyl-6-(1-ethyl-5,6,7,8-tetrahydrobenzimidazol-2-yl)-1H-benzimidazol-1-yl]-methyl]-2-(1H-tetrazol-5-yl)-biphenyl-hydrate, JJ=4'-[[2-n-propyl-4-methyl-6-(4,4-dimethyl-oxazolin-2-yl)-1H-benzimidazol-1-yl]-methyl]-biphenyl-2-carboxylic acid-di-trifluoroacetate, KK=4'-[[2-n-propyl-4-methyl-6-(1,5-dimethyl-4-phenyl-imidazol-2-yl)-1H-benzimidazol-1-yl]-methyl]-biphenyl-2-carboxylicacid-hydrate, LL=4'-[[2-n-propyl-4-methyl-6-(4-isopropyl-1,5-dimethyl-imidazol-2-yl)-1H-benzimidazol-1-yl]-methyl]-biphenyl-2-carboxylic acid x 1.25 water, MM=4'-[(2-ethyl-4-methyl-6-(1-methyl-5-fluoro-benzimidazol-2-yl)-benzimidazol-1-yl)-methyl]-biphenyl-2-carboxylic acid, NN=4'-[(2-n-propyl-4-methyl-6-(butanesultam-1-yl)-benzimidazol-1-yl)-methyl]-biphenyl-2-carboxylic acid, OO=4'-[(2-cyclopropyl-4-methyl-6-(imidazo[1,2-a]-pyridin-2-yl)-benzimidazol-1-yl)-methyl]-biphenyl-2-carboxylic acid, PP=4'-[(2-cyclopropyl-4-methyl-6-(5,6,7,8-tetrahydro-imidazo[1,2-a]pyridin-2-yl)-benzimidazol-1-yl)-methyl]-biphenyl-2-carboxylic acid and QQ=4'-[(2-ethoxy-4-methyl-6-(1-methyl-benzimidazol-2-yl)-benzimidazol-1-yl)-methyl]-2-(1H-tetrazol-5-yl)-biphenyl, Description of method: Anaiotensin II-receptor bonding The tissue (rats lung) is homogenised in Tris-buffer (50 mMol Tris, 150 mMol NaCl, 5 mMol EDTA, pH 7.40) and centrifuged twice for 20 minutes at 20,000×g. The finished pellets are resuspended in incubating buffer (50 mMol Tris, 5 mMol $MgCl_2$, 0.2% BSA, pH 7.40) 1:75, based on the moist weight of the tissue. Each 0.1 ml of homogenate is incubated for 60 minutes at 37° C. with 50 pM [$^{125}$I]-antiotensin II (NEN, Dreieich, FRG) with increasing concentrations of the test substance in a total volume of 0.25 ml. Incubation is ended by rapid filtration through glass fibre filter mats. The filters are each washed with 4 ml of ice cold buffer (25 mMol Tris, 2.5 mMol $MgCl_2$, 0.1% BSA, pH 7.40). The bound radioactivity is measured using a gamma-counter. The corresponding $IC_{50}$ value is obtained from the dose-activity curve.

In the test described, substances A to AM show the following $IC_{50}$ values:

| Substance | $IC_{50}$ [nM] |
| --- | --- |
| A | 510.0 |
| B | 52.0 |
| C | 130.0 |
| D | 3.7 |
| E | 14.0 |
| F | 5.0 |
| G | 1.2 |
| H | 20.0 |

-continued

| Substance | IC$_{50}$ [nM] |
| --- | --- |
| I | 6.6 |
| J | 3.5 |
| K | 17.0 |
| L | 240.0 |
| M | 12.0 |
| N | 26.0 |
| O | 3.4 |
| P | 1.2 |
| Q | 1.7 |
| R | 20.0 |
| S | 7.8 |
| V | 1.2 |
| W | 1.5 |
| X | 40.0 |
| Y | 10.0 |
| Z | 15.0 |
| AA | 3.4 |
| BB | 1.3 |
| CC | 12.0 |
| DD | 3.8 |
| EE | 2.6 |
| FF | 6.0 |
| GG | 46.0 |
| HH | 38.0 |
| II | 1.6 |
| JJ | 37.0 |
| KK | 3.2 |
| LL | 19.5 |
| MM | 7.4 |
| NN | 0.9 |
| OO | 1.7 |
| PP | 1.3 |
| QQ | 3.3 |

Selected compounds were also investigated for their ability to lower blood pressure using the following test protocol. Description of method: Renovascular Hypertension Blood pressure lowering effects of angiotensin-II antagonists were investigated in a rat model of renovascular hypertension. This model, the 2-kidney 1-clip rat, is characterized by an elevated renin activity (see J. Exper. Med. 59, 347–378 (1934), J. Applied Physiol. 31(1), 142–144 (1971) and Gross D. R. in "Animal Models in Cardiovascular Research: Animal Models of hypertension" Martinus Nijhoff Publishers (1985)). The compounds are given two times daily by oral administration to conscious freely moving rats which have been implanted with a chronic-use pressure transmitter to monitor blood pressure and heart rate continuously (PhysioTel® telemetry device).

Male rats (140–150 g) are anaesthetized with pentobarbitone-sodium (50 mg/kg i.p.). The abdominal cavity is opened by a midline incision. A solid silver clip with an internal diameter of 0.20 mm is applied to the left renal artery as close as possible to the aorta. The contralateral kidney is not disturbed. The catheter of a pressure transmitter (TA11PA-C40) is inserted in the abdominal aorta and the transmitter fixed to abdominal musculature. The abdomen is closed with sutures. The animals are allowed to recover for several weeks and housed individually in cages.

After the implantation of the chronic-use device, blood pressure and heart rate are transmitted by telemetry and the signals are received by a RA 1010 General Purpose Receiver (Data Science Int.). Data are acquired with the Dataquest® IV 1.11 System on a Hewlett Packard Vectra ES/12 386 computer.

Compounds are dissolved in 1M HCl or 1M NaOH. To stabilize the solution β-cyclodextrin (1.8 g/v%) is added. The solutions (0.3 and 1 mg/kg/2 ml) are orally given by gavage at 10.00 a.m. and 4.00 p.m.

In the test described, substances D, E, T and U show the following values:

| Substance | Dosage* mg/kg | Blood pressure lowering activity in mmHg |
| --- | --- | --- |
| D | 0.3 | −37 |
| D | 1.0 | −68 |
| E | 0.3 | −55 |
| E | 1.0 | −78 |
| T | 0.3 | −24 |
| U | 1.0 | −43 |

*two times daily

In addition, compounds D, E, F, G, H, M and O were tested on conscious renally hypertensive rats for their effect after oral administration using methods known from the literature. At a dosage of 10 mg/kg these compounds exhibited a hypotensive effect.

Moreover, when the above-mentioned compounds described by options A and C were administered in a dose of 30 mg/kg i.v. no toxic side effects, e.g. negative inotropic effects or disorders in heart rhythm, were observed. The compounds are therefore well tolerated.

In view of their pharmacological properties, the new compounds and the physiologically acceptable addition salts thereof are suitable for the treatment of hypertension and cardiac insufficiency and also for treating ischaemic peripheral circulatory disorders, myocardial ischaemia (angina), for the prevention of the progression of cardiac insufficiency after myocardial infarction and for treating diabetic nephropathy, glaucoma, gastrointestinal diseases and bladder diseases.

The new compounds and the physiologically acceptable addition salts thereof are also suitable for treating pulmonary diseases, e.g. lung oedema and chronic bronchitis, for preventing arterial re-stenosis after angioplasty, for preventing thickening of blood vessel walls after vascular operations, and for preventing arteriosclerosis and diabetic angiopathy. In view of the effects of angiotensin on the release of acetyl-choline and dopamine in the brain, the new angiotensin antagonists are also suitable for alleviating central nervous system disorders, e.g. depression, Alzheimer's disease, Parkinson syndrome, bulimia and disorders of cognitive function.

The dosage required for the compounds described by option A to achieve these effects in adults is appropriately, when administered intravenously, 20 to 100 mg, preferably 30 to 70 mg, and, when administered orally, 50 to 200 mg, preferably 75 to 150 mg, 1 to 3 times a day, and the dosage required for the compounds described by options B to D to achieve these effects in adults is appropriately, when administered intravenously, 0.5 to 100 mg, preferably 1 to 70 mg, and, when administered orally, 0.1 to 200 mg, preferably 1 to 100 mg, 1 to 3 times a day.

For this purpose, the compounds of general formula I prepared according to the invention, optionally in conjunction with other active substances, such as hypotensives, diuretics and/or calcium antagonists, may be incorporated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene-glycol, propyleneglycol, cetylstearyl alcohol, carboxymethylcellulose or fatty substances such as hard fat or suitable mixtures thereof, in conventional galenic preparations such as plain or coated tablets, capsules, powders, suspensions or suppositories.

Additional active substances which may be included in the combinations mentioned above might be, for example, bendroflumethiazide, chlorothiazide, hydrochloro-thiazide, spironolactone, benzothiazide, cyclothiazide, ethacrinic acid, furosemide, metoprolol, prazosine, atenolol, propranolol, (di)hydralazinehydrochloride, diltiazem, felodipin, nicardipin, nifedipin, nisoldipin and nitrendipin. The dosage for these active substances is appropriately one fifth of the lowest recommended dose up to 1/1 of the normally recommended dose, i.e., for example, 15 to 200 mg of hydrochlorothiazide, 125 to 2000 mg of chlorothiazide, 15 to 200 mg of ethacrinic acid, 5 to 80 mg of furosemide, 20 to 480 mg of propranolol, 5 to 60 mg of felodipine, 5 to 60 mg of nifedipin or 5 to 60 mg of nitrendipin.

The Examples which follow are intended to illustrate the invention:

EXAMPLE 1

4'-[[2-n-Butyl-7-[5-(imidazol-1-yl)-pentyloxy]-4-methyl-benzimidazol-1-yl]-methyl]-biphenyl-2-carboxylic acid hydrate 0.7 g (1.15 mMol) of tert.-butyl 4'-[[2-n-butyl-7-[5-(imidazol-1-yl)-pentyloxy]-4-methyl-benzimidazol-1-yl]-methyl]-biphenyl-2-carboxylate are dissolved in 35 ml of methylene chloride, 5 ml of trifluoroacetic acid are added and the mixture is stirred for 12 hours at ambient temperature. It is diluted with methylene chloride and extracted with water and with saturated sodium bicarbonate solution. The organic phase is dried over sodium sulphate and evaporated down in vacuo. The crude product thus obtained is purified over a silica gel column (particle size: 0.063–0.02 mm, ethyl acetate/ethanol/ammonia—90:10:0.1) and crystallised from acetone.

Yield: 0.19 g (29.9% of theory),
Melting point: 185°–187° C.
$C_{34}H_{38}N_4O_3 \times H_2O$ (550.70) Calculated: C 71.81 H 7.09 N 9.85 Found: 72.03 7.19 9.71
Mass spectrum: m/e =M$^+$550

The following compounds are obtained analogously to Example 1:

4'-[[2-n-butyl-4-methyl-6-(4,5-dihydro-2H-pyridazin-3-on-6-yl)-benzimidazol-1-yl]-methyl]-biphenyl-2-carboxylic acid 4'-[[2-n-propyl-4-methyl-6-(4,5-dihydro-2H-pyridazin-3-on-6-yl)-benzimidazol-1-yl]-methyl]-biphenyl-2-carboxylic acid 4'-[[2-ethyl-4-methyl-6-(4,5-dihydro-2H-pyridazin-3-on-6-yl)-benzimidazol-1-yl]-methyl]-biphenyl-2-carboxylic acid 4'-[[2-n-butyl-4-methyl-6-(phenylaminocarbonylamino)-benzimidazol-1-yl]-methyl]-biphenyl-2-carboxylic acid 4'-[[2-ethyl-4-methyl-6-(cyclohexylaminocarbonylamino)-benzimidazol-1-yl]-methyl]-biphenyl-2-carboxylic acid 4'-[[2-n-propyl-4-methyl-6-(cyclohexylaminocarbonylamino)-benzimidazol-1-yl]-methyl]-biphenyl-2-carboxylic acid 4'-[[2-n-butyl-4-methyl-6-(cyclohexylaminocarbonylamino)-benzimidazol-1-yl]-methyl]-biphenyl-2-carboxylic acid 4'-[[2-n-propyl-4-methyl-6-(methylaminocarbonyl-methylamino)-benzimidazol-1-yl]-methyl]-biphenyl-2-carboxylic acid 4'-[[2-n-propyl-4-methyl-6-(n-pentylaminocarbonyl-methylamino)-benzimidazol-1-yl]-methyl]-biphenyl-2-carboxylic acid 4'-[[2-n-propyl-4-methyl-6-(n-pentylaminocarbonylamino)-benzimidazol-1-yl]-methyl]-biphenyl-2-carboxylic acid 4'-[[2-n-propyl-4-methyl-6-(n-butylaminocarbonyl-methylamino)-benzimidazol-1-yl]-methyl]-biphenyl-2-carboxylic acid 4'-[[2-n-propyl-4-methyl-6-(benzylaminocarbonylamino)-benzimidazol-1-yl]-methyl]-biphenyl-2-carboxylic acid 4'-[[2-n-propyl-4-methyl-6-(allylaminocarbonylamino)-benzimidazol-1-yl]-methyl]-biphenyl-2-carboxylic acid 4'-[[2-n-propyl-4-methyl-6-(cyclohexylaminocarbonyl-methylamino)-benzimidazol-1-yl]-methyl]-biphenyl-2-carboxylic acid 4'-[[2-n-propyl-4-methyl-6-(dimethylaminocarbonyl-methylamino)-benzimidazol-1-yl]-methyl]-biphenyl-2-carboxylic acid 4'-[[2-n-propyl-4-methyl-6-(dimethylaminocarbonylamino)-benzimidazol-1-yl]-methyl]-biphenyl-2-carboxylic acid 4'-[[2-n-propyl-4-methyl-6-(cyclohexylaminocarbonyl-n-butylamino)-benzimidazol-1-yl]-methyl]-biphenyl-2-carboxylic acid 4'-[[2-n-propyl-4-methyl-6-(methylaminocarbonyl-cyclohexyl-amino)-benzimidazol-1-yl]-methyl]-biphenyl-2-carboxylic acid 4'-[[2-n-propyl-4-methyl-6-(methylaminocarbonyl-benzylamino)-benzimidazol-1-yl]-methyl]-biphenyl-2-carboxylic acid 4'-[[2-n-propyl-4-methyl-6-(n-hexylaminocarbonyl-cyclohexylamino)-benzimidazol-1-yl]-methyl]-biphenyl-2-carboxylic acid 4'-[[2-n-propyl-4-methyl-6-(cyclohexylaminocarbonyl-ethylamino)-benzimidazol-1-yl]-methyl]-biphenyl-2-carboxylic acid 4'-[[2-n-propyl-4-methyl-6-(dimethylaminocarbonyl-n-pentylamino)-benzimidazol-1-yl]-methyl]-biphenyl-2-carboxylic acid 4'-[[2-n-propyl-4-methyl-6-(morpholinocarbonylamino)-benzimidazol-1-yl]-methyl]-biphenyl-2-carboxylic acid 4'-[[2-n-propyl-4-methyl-6-(pyrrolidinocarbonylamino)-benzimidazol-1-yl]-methyl]-biphenyl-2-carboxylic acid 4'-[[2-n-propyl-4-methyl-6-(pyrrolidinocarbonyl-methylamino)-benzimidazol-1-yl]-methyl]-biphenyl-2-carboxylic acid 4'-[[2-n-propyl-4-methyl-6-(piperidinocarbonylamino)-benzimidazol-1-yl]-methyl]-biphenyl-2-carboxylic acid 4'-[[2-n-propyl-4-methyl-6-(3-benzyl-3,4,5,6-tetrahydro-2(1H)-pyrimidinon-1-yl)-benzimidazol-1-yl]-methyl]-biphenyl-2-carboxylic acid

EXAMPLE 2

4'-[[2-n-Butyl-7-[3-(imidazol-1-yl)-propyloxy]-4-methyl-benzimidazol-1-yl]-methyl]-biphenyl-2-carboxylic acid Prepared analogously to Example 1 from tert.-butyl 4'-[[2-n-butyl-7-[3-(imidazol-1-yl)-propyloxy]-4-methyl-benzimidazol-1-yl]-methyl]-biphenyl-2-carboxylate and trifluoroacetic acid in methylene chloride.

Yield: 69.4% of theory,
Melting point: 208°–210° C.
$C_{32}H_{34}N_4O_3$ (522.64) Calculated: C 73.54 H 6.56 N 10.72 Found: 73.45 6.62 10.60
$R_f$ value: 0.50 (silica gel; ethyl acetate/ethanol/ammonia =50:45:5)

EXAMPLE 3

4'-[[2-n-Butyl-7-[3-(benzimidazol-1-yl)-propyloxy]-4-methyl-benzimidazol-1-yl]-methyl]-biphenyl-2-carboxylic acid trifluoroacetate Prepared analogously to Example 1 from tert.-butyl 4'-[[2-n-butyl-7-[3-(benzimidazol-1-yl)-propyloxy]-4-methyl-benzimidazol-1-yl]-methyl]-biphenyl-2-carboxylate and trifluoroacetic acid in methylene chloride.

Yield: 87.8% of theory,
Melting point: 221°–223° C.
$C_{36}H_{36}N_4O_3 \times CF_3COOH$ (686.72) Calculated: C 66.46 H 5.43 N 8.15 Found: 66.58 5.62 8.31
$R_f$ value: 0.45 (silica gel; ethyl acetate/ethanol/ammonia =50:45:5

EXAMPLE 4

4'-[[2-n-Butyl-7-[4-(imidazol-1-yl)-butyloxy]-4-methyl-benzimidazol-1-yl]-methyl]-biphenyl-2-carboxylic acid hydrate Prepared analogously to Example 1 from tert.-butyl 4'-[[2-n-butyl-7-[4-(imidazol-1-yl)-butyloxy]-4-methyl-benzimidazol-1-yl]-methyl]-biphenyl-2-carboxylate and trifluoroacetic acid in methylene chloride.
Yield: 68.5% of theory,
Melting point: 126°–128° C.
$C_{33}H_{36}N_4O_3 \times H_2O$ (554.68) Calculated: C 71.46 H 6.91 N 10.10 Found: 71.63 7.02 9.98 Mass spectrum: m/e=536

EXAMPLE 5

4'-[[2-n-Butyl-7-[2-(benzimidazol-1-yl)-ethoxy]-4-methyl-benzimidazol-1-yl]-methyl]-biphenyl-2-carboxylic acid Prepared analogously to Example 1 from tert.-butyl 4'-[[2-n-butyl-7-[2-(benzimidazol-1-yl)-ethoxy]-4-methyl-benzimidazol-1-yl]-methyl]-biphenyl-2-carboxylate and trifluoroacetic acid in methylene chloride.
Yield: 78.1% of theory,
Melting point: 167°–169° C.
$C_{35}H_{34}N_4O_3$ (558.68) Calculated: C 75.25 H 6.13 N 10.03 Found: 75.03 6.17 9.95

EXAMPLE 6

4'-[[2-n-Butyl-7-[5-(benzimidazol-1-yl)-pentyloxy]-4-methyl-benzimidazol-1-yl]-methyl]-biphenyl-2-carboxylic acid Prepared analogously to Example 1 from tert.-butyl 4'-[[2-n-butyl-7-[5-(benzimidazol-1-yl)-pentyloxy]-4-methyl-benzimidazol-1-yl]-methyl]-biphenyl-2-carboxylate and trifluoroacetic acid in methylene chloride.

EXAMPLE 7

4'-[[2-n-Butyl-7-[4-(benzimidazol-1-yl)-butyloxy]-4-methyl-benzimidazol-1-yl]-methyl]-biphenyl-2-carboxylic acid Prepared analogously to Example 1 from tert.-butyl 4'-[[2-n-butyl-7-[4-(benzimidazol-1-yl)-butyloxy]-4-methyl-benzimidazol-1-yl]-methyl]-biphenyl-2-carboxylate and trifluoroacetic acid in methylene chloride.

EXAMPLE 8

4'-[[2-n-Butyl-4-methyl-7-[4-(tetrahydrobenzimidazol-1-yl)-butyloxy]-benzimidazol-1-yl]-methyl]-biphenyl-2-carboxylic acid Prepared analogously to Example 1 from tert.-butyl 4'-[[2-n-butyl-4-methyl-7-[4-(tetrahydrobenzimidazol-1-yl)-butyloxy]-benzimidazol-1-yl]-methyl]-biphenyl-2-carboxylate and trifluoroacetic acid in methylene chloride.
Yield: 86% of theory,
Melting point: 229°–231° C.
$C_{37}H_{42}N_4O_3$ (590.76) Calculated: C 75.23 H 7.17 N 9.48 Found: 75. 34 7.06 9.38

EXAMPLE 9

4'-[[2-n-Propyl-4-methyl-6-(1-methylbenzimidazol-2-yl)-benzimidazol-1-yl]-methyl]-biphenyl-2-carboxylic acid Prepared analogously to Example 1 from tert.-butyl 4'-[[2-n-propyl-4-methyl-6-(1-methylbenzimidazol-2-yl)-benzimidazol-1-yl]-methyl]-biphenyl-2-carboxylate and trifluoroacetic acid in dimethylformamide.
Yield: 63.9% of theory,
Melting point: 261°–263° C. $C_{33}H_{30}N_4O_2$ (514.60) Calculated: C 77.02 H 5.87 N 10.89 Found: 76.90 5.85 10.99

The following compounds are obtained analogously to Example 9:

4'-[[2-n-propyl-4-methyl-6-(1-n-propylbenzimidazol-2-yl)-benzimidazol-1-yl]-methyl]-biphenyl-2-carboxylic acid 4'-[[2-n-propyl-4-methyl-6-(1-n-hexylbenzimidazol-2-yl)-benzimidazol-1-yl]-methyl]-biphenyl-2-carboxylic acid 4'-[[2-n-propyl-4-methyl-6-(1-cyclopropylbenzimidazol-2-yl)-benzimidazol-1-yl]-methyl]-biphenyl-2-carboxylic acid 4'-[[2-n-propyl-4-methyl-6-(1-cyclohexylbenzimidazol-2-yl)-benzimidazol-1-yl]-methyl]-biphenyl-2-carboxylic acid

EXAMPLE 10

4'-[[2-n-Propyl-4-methyl-6-(1-methylbenzimidazol-2-yl)-benzimidazol-1-yl]-methyl]-2-(1H-tetrazol-5-yl)-biphenyl 4.3 g (66 mMol) of sodium azide and 3.5 g (66 mMol) of ammonium chloride are added to a solution of 1.60 g (3.3 mMol) of 4'-[[2-n-propyl-4-methyl-6-(1-methylbenzimidazol-2-yl)-benzimidazol-1-yl]-methyl]-2-cyano-biphenyl in 50 ml of dimethylformamide and the mixture is stirred for 24 hours at 140° C. Then water is added and the precipitate is removed by suction filtering. The crude product thus obtained is purified by chromatography over silica gel (300 g of silica gel, methylene chloride +6% ethanol).
Yield: 900 mg (51% of theory),
Melting point: 228°–230° C. $C_{33}H_{30}N_8$ (538.70) Calculated: C 73.58 H 5.61 N 20.80 Found: 73.48 5.55 20.70

The following compounds are obtained analogously to Example 10:

4'-[[2-n-propyl-4-methyl-6-(1-n-hexylbenzimidazol-2-yl)-benzimidazol-1-yl]-methyl]-2-(1H-tetrazol-5-yl)-biphenyl 4'-[[2-n-propyl-4-methyl-6-(1-cyclobutylbenzimidazol-2-yl)-benzimidazol-1-yl]-methyl]-2-(1H-tetrazol-5-yl)-biphenyl 4'-[[2-n-propyl-4-methyl-6-(1-cyclohexylbenzimidazol-2-yl)-benzimidazol-1-yl]-methyl]-2-(1H-tetrazol-5-yl)-biphenyl 4'-[[2-n-butyl-4-methyl-7-[2-(imidazol-1-yl)-ethoxy]-benzimidazol-1-yl]-methyl]-2-(1H-tetrazol-5-yl)-biphenyl 4'-[[2-n-butyl-7-[3-(imidazol-1-yl)-propyloxy]-4-methyl-benzimidazol-1-yl]-methyl]-2-(1H-tetrazol-5-yl)-biphenyl 4'-[[2-n-butyl-7-[4-(imidazol-1-yl)-butyloxy]-4-methyl-benzimidazol-1-yl]-methyl]-2-(1H-tetrazol-5-yl)-biphenyl 4'-[[2-n-butyl-4-methyl-7-[5-(imidazol-1-yl)-pentyloxy]-benzimidazol-1-yl]-methyl]-2-(1H-tetrazol-5-yl)-biphenyl 4'-[[2-n-butyl-7-[2-(benzimidazol-1-yl)-ethoxy]-4-methyl-benzimidazol-1-yl]-methyl]-2-(1H-tetrazol-5-yl)-biphenyl 4'-[[2-n-butyl-4-methyl-7-[3-(benzimidazol-1-yl)-propyloxy]-benzimidazol-1-yl]-methyl]-2-(1H-tetrazol-5-yl)-biphenyl 4'-[[2-n-butyl-7-[4-(benzimidazol-1-yl)-butyloxy]-4-methyl-benzimidazol-1-yl]-methyl]-2-(1H-tetrazol-5-yl)-biphenyl 4'-[[2-n-butyl-4-methyl-7-[5-(benzimidazol-1-yl)-pentyloxy]-benzimidazol-1-yl]-methyl]-2-(1H-tetrazol-5-yl)-biphenyl 4'-[[2-n-butyl-7-[2-(4,5,6,7-tetrahydrobenzimidazol-1-yl)-ethoxy]-4-methyl-benzimidazol-1-yl]-methyl]-2-(1H-tetrazol-5-yl)-biphenyl 4'-[[2-n-butyl-4-methyl-7-[3-(tetrahydrobenzimidazol-1-yl)-propyloxy]-benzimidazol-1-yl]-methyl]-2-(1H-tetrazol-5-yl)-biphenyl 4'-[[2-n-butyl-7-[4-(tetrahydrobenzimidazol-1-yl)-butyloxy]-4-methyl-benzimidazol-1-yl]-methyl]-2-(1H-tetrazol-5-yl)-biphenyl 4'-[[2-n-butyl-4-methyl-7-[5-(tetrahydrobenzimidazol-1-yl)-pentyloxy]-benzimidazol-1-yl]-methyl]-2-(1H-tetrazol-5-yl)-biphenyl 4'-[[2-n-butyl-4-methyl-6-(phenylaminocarbonylamino)-benzimidazol-1-yl]-methyl]-2-(1H-tetrazol-5-yl)-biphenyl 4'-[[2-ethyl-4-methyl-6-(cyclohexylaminocarbonylamino)-benzimidazol-1-yl]-methyl]-2-(1H-tetrazol-5-yl)-biphenyl 4'-[[2-propyl-4-methyl-6-(cyclohexylaminocarbonylamino)-benzimidazol-1-yl]-methyl]-2-(1H-tetrazol-5-yl)-biphenyl 4'-[[2-n-butyl-4-methyl-6-(cyclohexylaminocarbonylamino)-benzimidazol-1-yl]-methyl]-2-(1H-tetrazol-5-yl)-biphenyl 4'-[[2-n-propyl-4-methyl-6-(methylaminocarbonyl-methylamino)-benzimidazol-1-yl]-methyl]-2-(1H-tetrazol-5-yl)-biphenyl 4'-[[2-n-propyl-4-methyl-6-(n-pentylaminocarbonyl-methylamino)-benzimidazol-1-yl]-methyl]-2-(1H-tetrazol-5-yl)-biphenyl 4'-[[2-n-propyl-4-methyl-6-(n-pentylaminocarbonylamino)-benzimidazol-1-yl]-methyl]-2-(1H-tetrazol-5-yl)-biphenyl 4'-[[2-n-propyl-4-methyl-6-(n-butylaminocarbonyl-methylamino)-benzimidazol-1-yl]-methyl]-2-(1H-tetrazol-5-yl)-biphenyl 4'-[[2-n-propyl-4-methyl-6-(benzylaminocarbonylamino)-benzimidazol-1-yl]-methyl]-2-(1H-tetrazol-5-yl)-biphenyl 4'-[[2-n-propyl-4-methyl-6-(allylaminocarbonylamino)-benzimidazol-1-yl]-methyl]-2-(1H-tetrazol-5-yl)-biphenyl 4'-[[2-n-propyl-4-methyl-6-(cyclohexylaminocarbonyl-methylamino)-benzimidazol-1-yl]-methyl]-2-(1H-tetrazol-5-yl)-biphenyl 4'-[[2-n-propyl-4-methyl-6-(dimethylaminocarbonylmethylamino)-benzimidazol-1-yl]-methyl]-2-(1H-tetrazol-5-yl)-biphenyl 4'-[[2-n-propyl-4-methyl-6-(dimethylaminocarbonylamino)-benzimidazol-1-yl]-methyl]-2-(1H-tetrazol-5-yl)-biphenyl 4'-[[2-n-propyl-4-methyl-6-(cyclohexylaminocarbonyl-n-butylamino)-benzimidazol-1-yl]-methyl]-2-(1H-tetrazol-5-yl)-biphenyl 4'-[[2-n-propyl-4-methyl-6-(methylaminocarbonyl-cyclohexylamino)-benzimidazol-1-yl]-methyl]-2-(1H-tetrazol-5-yl)-biphenyl 4'-[[2-n-propyl-4-methyl-6-(methylaminocarbonyl-benzylamino)-benzimidazol-1-yl]-methyl]-2-(1H-tetrazol-5-yl)-biphenyl 4'-[[2-n-propyl-4-methyl-6-(n-hexylaminocarbonyl-cyclohexylamino)-benzimidazol-1-yl]-methyl]-2-(1H-tetrazol-5-yl)-biphenyl 4'-[[2-n-propyl-4-methyl-6-(cyclohexylaminocarbonyl-ethylamino)-benzimidazol-1-yl]-methyl]-2-(1H-tetrazol-5-yl)-biphenyl 4'-[[2-n-propyl-4-methyl-6-(dimethylaminocarbonyl-n-pentylamino)-benzimidazol-1-yl]-methyl]-2-(1H-tetrazol-5-yl)-biphenyl 4'-[[2-n-propyl-4-methyl-6-(morpholinocarbonylamino)-benzimidazol-1-yl]-methyl]-2-(1H-tetrazol-5-yl)-biphenyl 4'-[[2-n-propyl-4-methyl-6-(pyrrolidinocarbonylamino)-benzimidazol-1-yl]-methyl]-2-(1H-tetrazol-5-yl)-biphenyl 4'-[[2-n-propyl-4-methyl-6-(pyrrolidinocarbonyl-methylamino)-benzimidazol-1-yl]-methyl]-2-(1H-tetrazol-5-yl)-biphenyl 4'-[[2-n-propyl-4-methyl-6-(piperidinocarbonyl-methylamino)-benzimidazol-1-yl]-methyl]-2-(1H-tetrazol-5-yl)-biphenyl 4'-[[2-n-propyl-4-methyl-6-(3-benzyl-3,4,5,6-tetrahydro-2(1H)-pyrimidinon-1-yl)-benzimidazol-1-yl]-methyl]-2-(1H-tetrazol-5-yl)-biphenyl

EXAMPLE 11

4'-[(2-n-Propyl-4-methyl-6-phthalimino-benzimidazol-1-yl)-methyl]-2-(1H-tetrazol-5-yl)-biphenyl Prepared analogously to Example 10 from 4'-[(2-n-propyl-4-methyl-6-phthalimino-benzimidazol-1-yl)-methyl]-2-cyanobiphenyl and sodium azide in dimethylformamide.

Yield: 6.8% of theory,

Melting point: sintering from 160° C.

$C_{33}H_{27}N_7O_2$ (553.60) Calculated: C 71.59 H 4.92 N 17.71 Found: 71.39 4.88 17.54

EXAMPLE 12

4'-[(2-n-Butyl-4-methyl-6-phthalimino-benzimidazol-1-yl)-methyl]-2-(1H-tetrazol-5-yl)-biphenyl Prepared analogously to Example 10 from 4'-[(2-n-butyl-4-methyl-6-phthalimino-benzimidazol-1-yl)-methyl]-2-cyanobiphenyl and sodium azide in dimethylformamide.

Yield: 7.1% of theory,

Melting point: sintering from 150° C.

$C_{34}H_{29}N_7O_2$ (567.70) Calculated: C 71.94 H 5.15 N 17.27 Found: 71.75 5.19 17.22

EXAMPLE 13

4'-[[2-n-Propyl-4-methyl-6-(1-oxo-isoindolin-2-yl)-benzimidazol-1-yl]-methyl]-2-(1H-tetrazol-5-yl)-biphenyl Prepared analogously to Example 10 from 4'-[[2-n-propyl-4-methyl-6-(1-oxo-isoindolin-2-yl)-benzimidazol-1-yl]-methyl]-2-cyano-biphenyl and sodium azide in dimethylformamide.

Yield: 25.0% of theory,

Melting point: sintering from 170° C.

$C_{33}H_{29}N_7O$ (539.60) Calculated: C 73.45 H 5.42 N 18.17 Found: 73.20 5.41 18.33

EXAMPLE 14

4'-[[2-n-Butyl-4-methyl-6-(1-oxo-isoindolin-2-yl)-benzimidazol-1-yl]-methyl]-2-(1H-tetrazol-5-yl)-biphenyl Prepared analogously to Example 10 from 4'-[[2-n-butyl-4-methyl-6-(1-oxo-isoindolin-2-yl)-benzimidazol-1-yl]-methyl]-2-cyano-biphenyl and sodium azide in dimethylformamide.

Yield: 21.0% of theory,
Melting point: sintering from 165° C.
$C_{34}H_{31}N_7O$ (553.70) Calculated: C 73.76 H 5.64 N 17.71
Found: 73.58 5.33 17.4

EXAMPLE 15

4'-[[2-n-Propyl-4-methyl-6-(butanesultam-1-yl)-benzimidazol-1-yl]-methyl]-2-(1H-tetrazol-5-yl)-biphenyl Prepared analogously to Example 10 from 4'-[[2-n-propyl-4-methyl-6-(butanesultam-1-yl)-benzimidazol-1-yl]-methyl]-2-cyano-biphenyl and sodium azide in dimethylformamide.
Yield: 49.0% of theory,
Melting point: Sintering from 186° C.
$C_{29}H_{31}N_7O_2S$ (541.70) Calculated: C 64.30 H 5.77 N 18.10 S 5.92 Found: 64.10 5.39 18.01 5.98

EXAMPLE 16

4'-[[2-Ethyl-4-methyl-6-(butanesultam-1-yl)-benzimidazol-1-yl]-methyl]-2-(1H-tetrazol-5-yl)-biphenyl Prepared analogously to Example 10 from 4'-[[2-ethyl-4-methyl-6-(butanesultam-1-yl)-benzimidazol-1-yl]-methyl]-2-cyano-biphenyl and sodium azide in dimethylformamide.
Yield: 60.0% of theory,
Melting point: amorphous, sintering from 194° C.
$C_{28}H_{29}N_7O_2S$ (527.70) Calculated: C 63.74 H 5.54 N 18.58 S 6.08 Found: 63.83 5.66 18.41 5.82

EXAMPLE 17

4'-[[2-n-Butyl-4-methyl-6-(butanesultam-1-yl)-benzimidazol-1-yl]-methyl]-2-(1H-tetrazol-5-yl)-biphenyl Prepared analogously to Example 10 from 4'-[[2-n-butyl-4-methyl-6-(butanesultam-1-yl)-benzimidazol-1-yl]-methyl]-2-cyano-biphenyl and sodium azide in dimethyl-formamide.
Yield: 48.0% of theory,
Melting point: amorphous, sintering from 183° C.
$C_{30}H_{33}N_7O_2S$ (555.70) Calculated: C 64.84 H 5.99 N 17.64 S 5.77 Found: 64.53 5.66 17.63 5.55

EXAMPLE 18

4'-[[2-n-Propyl-4-ethyl-6-(butanesultam-1-yl)-benzimidazol-1-yl]-methyl]-2-(1H-tetrazol-5-yl)-biphenyl Prepared analogously to Example 10 from 4'-[[2-n-propyl-4-ethyl-6-(butanesultam-1-yl)-benzimidazol-1-yl]-methyl]-2-cyano-biphenyl and sodium azide in dimethylformamide.
Yield: 27.0% of theory,
Melting point: amorphous, sintering from 189° C.
$C_{30}H_{33}N_7O_2S$ (555.70) Calculated: C 64.84 H 5.99 N 17.64 S 5.77 Found: 64.81 5.68 17.87 5.31

EXAMPLE 19

4'-[[2-Ethyl-4-ethyl-6-(butanesultam-1-yl)-benzimidazol-1-yl]-methyl]-2-(1H-tetrazol-5-yl)-biphenyl Prepared analogously to Example 10 from 4'-[[2-ethyl-4-ethyl-6-(butanesultam-1-yl)-benzimidazol-1-yl]-methyl]-2-cyano-biphenyl and sodium azide in dimethylformamide.
Yield: 39.0% of theory,
Melting point: amorphous, sintering from 212° C.
$C_{29}H_{31}N_7O_2S$ (541.70) Calculated: C 64.30 H 5.77 N 18.10 S 5.92 Found: 64.30 5.51 17.99 5.59

EXAMPLE 20

4'-[[2-n-Propyl-4-isopropyl-6-(butanesultam-1-yl)-benzimidazol-1-yl]-methyl]-2-(1H-tetrazol-5-yl)-biphenyl Prepared analogously to Example 10 from 4'-[[2-n-propyl-4-isopropyl-6-(butanesultam-1-yl)-benzimidazol-1-yl]-methyl]-2-cyano-biphenyl and sodium azide in dimethylformamide.
Yield: 22.0% of theory,
Melting point: amorphous
$C_{31}H_{35}N_7O_2S$ (569.70) Calculated: C 65.35 H 6.19 N 17.21 S 5.63 Found: 65.13 6.10 17.54 5.40

EXAMPLE 21

4'-[[2-Ethyl-4-isopropyl-6-(butanesultam-1-yl)-benzimidazol-1-yl]-methyl]-2-(1H-tetrazol-5-yl)-biphenyl Prepared analogously to Example 10 from 4'-[[2-ethyl-4-isopropyl-6-(butanesultam-1-yl)-benzimidazol-1-yl]-methyl]-2-cyano-biphenyl and sodium azide in dimethyl-formamide.
Yield: 24.0% of theory,
Melting point : amorphous, sintering from 209° C.
$C_{30}H_{33}N_7O_2S$ (555.70) Calculated: C 64.84 H 5.99 N 17.64 S 5.77 Found: 64.99 5.71 17.43 5.71

EXAMPLE 22

4'-[[2-n-Propyl-4-trifluoromethyl-6-(butanesultam-1-yl)-benzimidazol-1-yl]-methyl]-2-(1H-tetrazol-5-yl)-biphenyl Prepared analogously to Example 10 from 4'-[[2-n-propyl-4-trifluoromethyl-6-(butanesultam-1-yl)-benzimidazol-1-yl]-methyl]-2-cyano-biphenyl and sodium azide in dimethylformamide.
Yield: 17.0% of theory,
Melting point: 199°–203° C.
$C_{29}H_{28}F_3N_7O_2S$ (595.70) Calculated: C 58.48 H 4.74 N 16.46 Found: 58.28 4.43 16.22

EXAMPLE 23

4'-[[2-n-Propyl-4-methyl-6-(N-benzenesulphonyl-methylamino)-benzimidazol-1-yl]-methyl]-2-(1H-tetrazol-5-yl)-biphenyl Prepared analogously to Example 10 from 4'-[[2-n-propyl-4-methyl-6-(N-benzenesulphonyl-methylamino)-benzimidazol-1-yl]-methyl]-2-cyano-biphenyl and sodium azide in dimethylformamide.
Yield: 42.0% of theory,
Melting point: 161°–163° C. $C_{32}H_{31}N_7O_2S$ (577.70) Calculated: C 66.53 H 5.41 N 16.97 S 5.55 Found: 66.32 5.36 16.70 5.31

EXAMPLE 24

4'-[[2-n-Butyl-4-methyl-6-(N-benzenesulphonyl-methylamino)-benzimidazol-1-yl]-methyl]-2-(1H-tetrazol-5-yl)-biphenyl Prepared analogously to Example 10 from 4'-[[2-n-butyl-4-methyl-6-(N-benzenesulphonyl-methylamino)-benzimidazol-1-yl]-methyl]-2-cyano-biphenyl and sodium azide in dimethylformamide.
Yield: 37.0% of theory,
Melting point: 150°–153° C.
$C_{33}H_{33}N_7O_2S$ (591.70) Calculated: C 66.98 H 5.62 N 16.57 Found: 66.71 5.38 16.39

The following compounds are obtained analogously to Example 24:

4'-[[2-ethyl-4-methyl-6-(4,5-dihydro-2H-pyridazin-3-on-6-yl)-benzimidazol-1-yl]-methyl]-2-(1H-tetrazol-5-yl)-biphenyl 4'-[[2-n-propyl-4-methyl-6-(4,5-dihydro-2H-pyridazin-3-on-6-yl)-benzimidazol-1-yl]-methyl]-2-(1H-tetrazol-5-yl)-biphenyl 4'-[[2-n-butyl-4-methyl-6-(4,5-dihydro-2H-pyridazin-3-on-6-yl)-benzimidazol-1-yl]-methyl]-2-(1H-tetrazol-5-yl)-biphenyl 4'-[[2-n-propyl-4-methyl-6-(3-benzyl-3,4,5,6-tetrahydro-2(1H)-pyrimidinon-1-yl)-benzimidazol-1-yl]-methyl]-2-(1H-tetrazol-5-yl)-biphenyl 4'-[[2-ethyl-4-methyl-6-(3-benzyl-3,4,5,6-tetrahydro-2(1H)-pyrimidinon-1-yl)-benzimidazol-1-yl]-methyl]-2-(1H-tetrazol-5-yl)-biphenyl

EXAMPLE 25

4'-[[2-n-Butyl-4-methyl-6-(1-methylbenzimidazol-2-yl)-benzimidazol-1-yl]-methyl]-biphenyl-2-carboxylic acid Prepared analogously to Example 1 from tert.-butyl 4'-[[2-n-butyl-4-methyl-6-(1-methylbenzimidazol-2-yl)-benzimidazol-1-yl]-methyl]-biphenyl-2-carboxylate and trifluoroacetic acid in methylene chloride.

Yield: 48.0% of theory,

Melting point: 233°–235° C.

$C_{34}H_{32}N_4O_2$ (528.70) Calculated: C 77.25 H 6.10 N 10.60 Found: 77.10 5.98 10.46

EXAMPLE 26

4'-[[2-n-Butyl-4-methyl-6-(1-methylbenzimidazol-2-yl)-benzimidazol-1-yl]-methyl]-2-(1H-tetrazol-5-yl)-biphenyl Prepared analogously to Example 10 from 4'-[[2-n-butyl-4-methyl-6-(1-methylbenzimidazol-2-yl)-benzimidazol-1-yl]-methyl]-2-cyano-biphenyl and sodium azide in dimethylformamide.

Yield: 41.0% of theory,

Melting point: 235°–237° C.

$C_{34}H_{32}N_8$ (552.70) Calculated: C 73.89 H 5.84 N 20.28 Found: 73.67 5.81 19.93

The following compounds are obtained analogously to Example 26:

4'-[[2-n-butyl-4-methyl-6-(1-ethylbenzimidazol-2-yl)-benzimidazol-1-yl]-methyl]-2-(1H-tetrazol-5-yl)-biphenyl 4'-[[2-n-butyl-4-methyl-6-(1-cyclopropylbenzimidazol-2-yl)-benzimidazol-1-yl]-methyl]-2-(1H-tetrazol-5-yl)-biphenyl 4'-[[2-n-butyl-4-methyl-6-(1-n-pentylbenzimidazol-2-yl)-benzimidazol-1-yl]-methyl]-2-(1H-tetrazol-5-yl)-biphenyl 4'-[[2-n-butyl-4-methyl-6-(1-cyclopentylbenzimidazol-2-yl)-benzimidazol-1-yl]-methyl]-2-(1H-tetrazol-5-yl)-biphenyl

EXAMPLE 27

4'-[[2-n-Propyl-4-methyl-6-(2-oxo-piperidin-1-yl)-benzimidazol-1-yl]-methyl]-2-(1H-tetrazol-5-yl)-biphenyl Prepared analogously to Example 10 from 4'-[[2-n-propyl-4-methyl-6-(2-oxo-piperidin-1-yl)-benzimidazol-1-yl]-methyl]-2-cyano-biphenyl and sodium azide in dimethylformamide.

Yield: 51.0% of theory,

Melting point: amorphous, from 140° C. (sintering)

$C_{30}H_{31}N_7O$ (505.60) Calculated: C 71.26 H 6.18 N 19.39 Found: 71.08 6.22 19.47

Example 28

4'-[[2-n-Butyl-4-methyl-6-(2-oxo-piperidin-1-yl)-benzimidazol-1-yl]-methyl]-2-(1H-tetrazol-5-yl)-biphenyl Prepared analogously to Example 10 from 4'-[[2-n-butyl-4-methyl-6-(2-oxo-piperidin-1-yl)-benzimidazol-1-yl]-methyl]-2-cyano-biphenyl and sodium azide in dimethyl-formamide.

Yield: 39.0% of theory,

Melting point: amorphous, from 128° C. (sintering)

$C_{31}H_{33}N_7O$ (519.70) Calculated: C 71.65 H 6.40 N 18.87 Found: 71.44 6.23 18.59

EXAMPLE 29

4'-[[2-n-Propyl-4-methyl-6-(2-oxo-piperidin-1-yl)-benzimidazol-1-yl]-methyl]-2-(1H-tetrazol-5-yl)-biphenyl Prepared from 4'-[[2-n-propyl-4-methyl-6-(2-oxo-piperidin-1-yl)-benzimidazol-1-yl]-methyl]-2-(2-triphenylmethyl-tetrazol-5-yl)biphenyl by cleaving the triphenylmethyl group with methanolic hydrochloric acid.

Yield: 51.0% of theory,

Melting point: amorphous, sintering from 115° C.

$C_{30}H_{31}N_7O$ (505.60) Calculated: C 71.26 H 6.18 N 19.39 Found: 71.51 6.39 19.09

EXAMPLE 30

4'-[[2-n-Propyl-6-(imidazo[1,2-a]pyridin-2-yl)-benzimidazol-1-yl]-methyl]-biphenyl-2-carboxylic acid Prepared analogously to Example 1 from tert.-butyl 4'-[[2-n-propyl-6-(imidazo[1,2-a]pyridin-2-yl)-benzimidazol-1-yl]-methyl]-biphenyl-2-carboxylate and trifluoroacetic acid in methylene chloride.

Yield: 54.0% of theory,

Melting point: 202°–204° C.

$C_{31}H_{26}N_4O_2$ (486.60) Calculated: C 76.52 H 5.39 N 11.52 Found: 76.33 5.32 11.30

The following compounds may be prepared analogously to Example 30:

4'-[[2-n-propyl-6-(8-methyl-imidazo[1,2-a]pyridin-2-yl)-benzimidazol-1-yl]-methyl]-biphenyl-2-carboxylic acid 4'-[[2-n-butyl-6-(6-methyl-imidazo[1,2-a]pyridin-2-yl)-benzimidazol-1-yl]-methyl]-biphenyl-2-carboxylic acid 4'-[[2-n-propyl-6-(5,7-dimethyl-imidazo[1,2-a]pyridin-2-yl)-benzimidazol-1-yl]-methyl]-biphenyl-2-carboxylic acid 4'-[[2-n-propyl-6-(6-aminocarbonyl-imidazo[1,2-a]-pyridin-2-yl)-benzimidazol-1-yl]-methyl]-biphenyl-2-carboxylic acid 4'-[[2-n-butyl-6-(6-chloro-imidazo[1,2-a]pyridin-2-yl)-benzimidazol-1-yl]-methyl]-biphenyl-2-carboxylic acid 4'-[[2-n-propyl-6-(imidazo[1,2-a]pyridin-2-yl)-benzimidazol-1-yl]-methyl]-biphenyl-2-carboxylic acid 4'-[[2-n-propyl-6-(imidazo[2,1-b]thiazol-6-yl)-benzimidazol-1-yl]-methyl]-biphenyl-2-carboxylic acid 4'-[[2-n-butyl-6-(2,3-dimethyl-imidazo[2,1-b]thiazol-6-yl)-benzimidazol-1-yl]-methyl]-biphenyl-2-carboxylic acid

EXAMPLE 31

4'-[[2-n-Butyl-6-(imidazo[1,2-a]pyridin-2-yl)-benzimidazol-1-yl]-methyl]-biphenyl-2-carboxylic acid Prepared analogously to Example 1 from tert.-butyl 4'-[[2-n-butyl-6-(imidazo[1,2-a]pyridin-2-yl)-benzimidazol-1-yl]-methyl]-biphenyl-2-carboxylate and trifluoroacetic acid in methylene chloride.

Yield: 41.0% of theory,
Melting point: 193°–195° C.
$C_{32}H_{28}N_4O_2$ (500.60) Calculated: C 76.78 H 5.64 N 11.19 Found: 76.73 5.48 11.00

EXAMPLE 32

4'-[[2-n-Propyl-6-(imidazo[1,2-a]pyridin-2-yl)-benzimidazol-1-yl]-methyl]-2-(1H-tetrazol-5-yl)-biphenyl Prepared analogously to Example 10 from 4'-[[2-n-propyl-6-(imidazo[1,2-a]pyridin-2-yl)-benzimidazol-1-yl]-methyl]-2-cyano-biphenyl and sodium azide in dimethylformamide.

Yield: 28.0% of theory,
Melting point: 187°–189° C.
$C_{31}H_{26}N_8$ (510.60) Calculated: C 72.92 H 5.13 N 21.95 Found: 72.80 4.97 21.74

The following compounds may be prepared analogously to Example 32:

4'-[[2-n-propyl-6-(7-methyl-imidazo[1,2-a]pyridin-2-yl)-benzimidazol-1-yl ]-methyl ]-2-(1H-tetrazol-5-yl)-biphenyl 4'-[[2-n-propyl-6-(5-methyl-imidazo[1,2-a]pyridin-2-yl)-benzimidazol-1-yl]-methyl]-2-(1H-tetrazol-5-yl)-biphenyl 4'-[[2-n-butyl-6-(6-bromo-imidazo[1,2-a]pyridin-2-yl)-benzimidazol-1-yl]-methyl]-2-(1H-tetrazol-5-yl)-biphenyl 4'-[[2-n-propyl-6-(5,7-dimethyl-imidazo[1,2-a]pyrimidin-2-yl)-benzimidazol-1-yl]-methyl]-2-(1H-tetrazol-5-yl)-biphenyl 4'-[[2-n-butyl-6-(3-methyl-imidazo[2,1-b]thiazol-6-yl)-benzimidazol-1-yl]-methyl]-2-(1H-tetrazol-5-yl)-biphenyl 4'-[[2-n-propyl-6-(2-phenyl-imidazo[2,1-b]thiazol-6-yl)-benzimidazol-1-yl]-methyl]-2-(1H-tetrazol-5-yl)-biphenyl

EXAMPLE 33

4'-[[2-n-Butyl-6-(imidazo[1,2-a]pyridin-2-yl)-benzimidazol-1-yl]-methyl]-2-(1H-tetrazol-5-yl)-biphenyl Prepared analogously to Example 10 from 4'-[[2-n-butyl-6-(imidazo[1,2-a]pyridin-2-yl)-benzimidazol-1-yl]-methyl]-2-cyano-biphenyl and sodium azide in dimethylformamide.

Yield: 23.0% of theory,
Melting point: 170°–173° C.
$C_{32}H_{28}N_8$ (524.60) Calculated: C 73.26 H 5.38 N 21.36 Found: 73.09 5.32 21.20

EXAMPLE 34

4'-[[2-n-Propyl-4-methyl-6-(imidazo[1,2-a]pyridin-2-yl)-benzimidazol-1-yl]-methyl]-biphenyl-2-carboxylic acid Prepared analogously to Example 1 from tert.-butyl 4'-[[2-n-propyl-4-methyl-6-(imidazo[1,2-a]pyridin-2-yl)-benzimidazol-1-yl]-methyl]-biphenyl-2-carboxylate and trifluoroacetic acid in methylene chloride.

Yield: 38.0% of theory,
Melting point: 195°–197° C. (after evaporation and without recrystallisation)
Melting point: 299°–303° C. (methylene chloride/ethanol=20:1)
$C_{32}H_{28}N_4O_2$ (500.60) Calculated: C 76.78 H 5.64 N 11.19 Found: 76.55 5.61 10.87

The following compounds may be prepared analogously to Example 34:

4'-[[2-n-propyl-4-methyl-6-(8-methyl-imidazo[1,2-a]-pyridin-2-yl)-benzimidazol-1-yl]-methyl]-biphenyl-2-carboxylic acid 4'-[[2-n-butyl-4-methyl-6-(7-methyl-imidazo[1,2-a]-pyridin-2-yl)-benzimidazol-1-yl]-methyl]-biphenyl-2-carboxylic acid 4'-[[2-n-butyl-4-methyl-6-(6-methyl-imidazo[1,2-a]-pyridin-2-yl)-benzimidazol-1-yl]-methyl]-biphenyl-2-carboxylic acid 4'-[[2-n-propyl-4-methyl-6-(5-methyl-imidazo[1,2-a]-pyridin-2-yl)-benzimidazol-1-yl]-methyl]-biphenyl-2-carboxylic acid 4'-[[2-n-propyl-4-methyl-6-(5,7-dimethyl-imidazo-[1,2-a]pyridin-2-yl)-benzimidazol-1-yl]-methyl]-biphenyl-2-carboxylic acid 4'-[[2-ethyl-4-methyl-6-(6-aminocarbonyl-imidazo-[1,2-a]pyridin-2-yl)-benzimidazol-1-yl]-methyl]-biphenyl-2-carboxylic acid 4'-[[2-ethyl-4-methyl-6-(6-chloro-imidazo[1,2-a]pyridin-2-yl)-benzimidazol-1-yl]-methyl]-biphenyl-2-carboxylic acid

EXAMPLE 35

4'-[[2-n-Propyl-4-methyl-6-(imidazo[1,2-a]pyridin-2-yl)-benzimidazol-1-yl]-methyl]-2-(1H-tetrazol-5-yl)-biphenyl Prepared analogously to Example 10 from 4'-[[2-n-propyl-4-methyl-6-(imidazo[1,2-a]pyridin-2-yl)-benzimidazol-1-yl]-methyl]-2-cyano-biphenyl and sodium azide in dimethylformamide.

Yield: 21.0% of theory,
Melting point: sintering from 181° C.
$C_{32}H_{28}N_8$ (524.60) Calculated: C 73.26 H 5.38 N 21.36 Found: 73.10 5.24 21.13

The following compounds may be prepared analogously to Example 35:

4'-[[2-n-propyl-4-methyl-6-(5-methyl-imidazo[1,2-a]-pyridin-2-yl)-benzimidazol-1-yl]-methyl]-2-(1H-tetrazol-5-yl)-biphenyl 4'-[[2-n-propyl-4-methyl-6-(imidazo[1,2-a]pyrimidin-2-yl)-benzimidazol-1-yl]-methyl]-2-(1H-tetrazol-5-yl)-biphenyl

EXAMPLE 36

4'-[[2-n-Butyl-4-methyl-6-(imidazo[1,2-a]pyridin-2-yl)-benzimidazol-1-yl]-methyl]-biphenyl-2-carboxylic acid Prepared analogously to Example 1 from tert.-butyl 4'-[[2-n-butyl-4-methyl-6-(imidazo[1,2-a]pyridin-2-yl)-benzimidazol 1-yl]-methyl]-biphenyl-2-carboxylate and trifluoroacetic acid in methylene chloride.

Yield: 51.0% of theory,
Melting point: 194°–197° C.
$C_{33}H_{30}N_4O_2$ (514.60) Calculated: C 77.02 H 5.88 N 10.89 Found: 76.81 5.78 10.64

The following compounds are obtained analogously to Example 36:

4'-[[2-n-propyl-6-(pyrrolidin-2-on-5-yl)-benzimidazol-1-yl]-methyl]-biphenyl-2-carboxylic acid 4'-[[2-n-propyl-6-(pyrrolidin-2-yl)-benzimidazol-1-yl]-methyl]-biphenyl-2-carboxylic acid 4'-[[2-n-propyl-6-(quinolin-2-yl)-benzimidazol-1-yl]-methyl]-biphenyl-2-carboxylic acid 4'-[[2-n-butyl-6-(quinolin-2-yl)-benzimidazol-1-yl]-methyl]-biphenyl-2-carboxylic acid 4'-[[2-n-propyl-6-(isoquinolin-3-yl)-benzimidazol-1-yl]-methyl]-biphenyl-2-carboxylic acid 4'-[[2-ethyl-6-(isoquinolin-3-yl)-benzimidazol-1-yl]-methyl]-biphenyl-2-carboxylic acid

EXAMPLE 37

4'-[[2-n-Butyl-4-methyl-6-(imidazo[1,2-a]pyridin-2-yl)-benzimidazol-1-yl]-methyl]-2-(1H-tetrazol-5-yl)-biphenyl Prepared analogously to Example 10 from 4'-[[2-n-butyl-4-methyl-6-(imidazo[1,2-a]pyridin-2-yl)-benzimidazol-1-yl]-methyl]-2-cyano-biphenyl and sodium azide in dimethylformamide.

Yield: 26.0% of theory, $C_{33}H_{30}N_8$ (538.60) Calculated: C 73.58 H 5.61 N 20.80 Found: 73.39 5.40 20.92

The following compounds are obtained analogously to Example 37:

4'-[[2-n-propyl-6-(pyrrolidin-2-on-5-yl)-benzimidazol-1-yl]-methyl]-2-(1H-tetrazol-5-yl)-biphenyl 4'-[[2-n-propyl-6-(pyrrolidin-2-yl)-benzimidazol-1-yl]-methyl]-2-(1H-tetrazol-5-yl)-biphenyl 4'-[[2-n-propyl-6-(piperidin-2-on-6-yl)-benzimidazol-1-yl]-methyl]-2-(1H-tetrazol-5-yl)-biphenyl 4'-[[2-n-butyl-6-(piperidin-2-on-6-yl)-benzimidazol-1-yl]-methyl]-2-(1H-tetrazol-5-yl)-biphenyl 4'-[[2-n-propyl-6-(piperidin-2-yl)-benzimidazol-1-yl]-methyl]-2-(1H-tetrazol-5-yl)-biphenyl 4'-[[2-n-butyl-6-(piperidin-2-yl)-benzimidazol-1-yl]-methyl]-2-(1H-tetrazol-5-yl)-biphenyl 4'-[[2-ethyl-6-(pyridin-2-yl)-benzimidazol-1-yl]-methyl]-2-(1H-tetrazol-5-yl)-biphenyl 4'-[[2-n-propyl-6-(pyridin-2-yl)-benzimidazol-1-yl]-methyl]-2-(1H-tetrazol-5-yl)-biphenyl 4'-[[2-n-butyl-6-(pyridin-2-yl)-benzimidazol-1-yl]-methyl]-2-(1H-tetrazol-5-yl)-biphenyl 4'-[[2-n-propyl-6-(quinolin-2-yl)-benzimidazol-1-yl]-methyl]-2-(1H-tetrazol-5-yl)-biphenyl 4'-[[2-n-butyl-6-(quinolin-2-yl)-benzimidazol-1-yl]-methyl]-2-(1H-tetrazol-5-yl)-biphenyl 4'-[[2-n-propyl-6-(isoquinolin-3-yl)-benzimidazol-1-yl]-methyl]-2-(1H-tetrazol-5-yl)-biphenyl 4'-[[2-ethyl-6-(isoquinolin-3-yl)-benzimidazol-1-yl]-methyl]-2-(1H-tetrazol-5-yl)-biphenyl

EXAMPLE 38

4'-[[2-n-Butyl-4-methyl-6-(2,2-dimethylpropionylamino)-benzimidazol-1-yl]-methyl]-biphenyl-2-carboxylic acid Prepared analogously to Example 1 from tert.-butyl 4'-[[2-n-butyl-4-methyl-6-(2,2-dimethylpropionylamino)-benzimidazol-1-yl]-methyl]-biphenyl-2-carboxylate and trifluoroacetic acid in methylene chloride.

EXAMPLE 39

4'-[[2-n-Butyl-7-[2-(tetrahydrobenzimidazol-1-yl)-ethoxy]-4-methyl-benzimidazol-1-yl]-methyl]-biphenyl-2-carboxylic acid Prepared analogously to Example 1 from tert.-butyl 4'-[[2-n-butyl-7-[2-(tetrahydrobenzimidazol-1-yl)-ethoxy]-4-methyl-benzimidazol-1-yl]-methyl]-biphenyl-2-carboxylate and trifluoroacetic acid in methylene chloride.

Yield: 81% of theory,

Melting point: 236°–237° C.

$C_{35}H_{38}N_4O_3$ (562.71) Calculated: C 74.71 H 6.81 N 9.96 Found: 74.51 6.79 9.98

EXAMPLE 40

4'-[[2-n-Butyl-4-methyl-7-[5-(tetrahydrobenzimidazol-1-yl)-pentyloxy]-benzimidazol-1-yl]-methyl]-biphenyl-2-carboxylic acid Prepared analogously to Example 1 from tert.-butyl 4'-[[2-n-butyl-4-methyl-7-[5-(tetrahydrobenzimidazol-1-yl)-pentyloxy]-benzimidazol-1-yl]-methyl]-biphenyl-2-carboxylate and trifluoroacetic acid in methylene chloride.

EXAMPLE 41

4'-[[2-n-Butyl-7-[3-(tetrahydrobenzimidazol-1-yl)-propyloxy]-4-methyl-benzimidazol-1-yl]-methyl]-biphenyl-2-carboxylic acid Prepared analogously to Example 1 from tert.-butyl 4'-[[2-n-butyl-7-[3-(tetrahydrobenzimidazol-1-yl)-propyloxy]-4-methyl-benzimidazol-1-yl]-methyl]-biphenyl-2-carboxylate and trifluoroacetic acid in methylene chloride.

EXAMPLE 42

4'-[[2-n-Propyl-4-methyl-6-(imidazo[1,2-a]pyrimidin-2-yl)-benzimidazol-1-yl]-methyl]-biphenyl-2-carboxylic acid Prepared analogously to Example 1 from tert.-butyl 4'-[[2-n-propyl-4-methyl-6-(imidazo[1,2-a]pyrimidin-2-yl)-benzimidazol-1-yl]-methyl]-biphenyl-2-carboxylate and trifluoroacetic acid in methylene chloride.

Yield: 47% of theory,

Melting point: 224°–226° C. (after evaporation and without recrystallisation)

Melting point: 294°–297° C. (methylene chloride/ethanol=20:1)

$C_{31}H_{27}N_5O_2$ (501.60) Calculated: C 74.23 H 5.43 N 13.96 Found: 74.10 5.31 13.66

EXAMPLE 43

4'-[[2-n-Propyl-4-methyl-6-(imidazo[2,1-b]thiazol-6-yl)-benzimidazol-1-yl]-methyl]-biphenyl-2-carboxylic acid Prepared analogously to Example 1 from tert.-butyl 4'-[[2-n-propyl-4-methyl-6-(imidazo[2,1-b]thiazol-6-yl)-benzimidazol-1-yl]-methyl]-biphenyl-2-carboxylate and trifluoroacetic acid in methylene chloride.

Yield: 43% of theory,

Melting point: 192°–195° C. (after evaporation and without recrystallisation)

Melting point: >300° C. (methylene chloride/ethanol—20:1)

$C_{30}H_{26}N_4O_2S$ (506.64) Calculated: C 71.12 H 5.17 N 11.06 S 6.33 Found: 70.97 5.19 10.88 6.09

The following compounds may be prepared analogously to Example 43:

4'-[[2-n-propyl-4-methyl-6-(3-methyl-imidazo[2,1-b]-thiazol-6-yl)-benzimidazol-1-yl]-methyl]-biphenyl-2-carboxylic acid 4'-[[2-n-propyl-4-methyl-6-(2,3-dimethyl-imidazo[2,1-b]thiazol-6-yl)-benzimidazol-1-yl]-methyl]-biphenyl-2-carboxylic acid 4'-[[2-n-butyl-4-methyl-6-(2,3-trimethylene-imidazo[2,1-b]-thiazol-6-yl)-benzimidazol-1-yl]-methyl]-biphenyl-2-carboxylic acid 4'-[[2-n-propyl-4-methyl-6-(2,3-tetramethylene-imidazo[2,1-b]-thiazol-6-yl)-benzimidazol-1-yl]-methyl]-biphenyl-2-carboxylic acid 4'-[[2-ethyl-4-methyl-6-(2-phenyl-imidazo[2,1-b]-thiazol-6-yl)-benzimidazol-1-yl]-methyl]-biphenyl-2-carboxylic acid

EXAMPLE 44

4'-[[2-n-Propyl-4-methyl-6-(imidazo[2,1-b]thiazol-6-yl)-benzimidazol-1-yl]-methyl]-2-(1H-tetrazol-5-yl)-biphenyl Prepared analogously to Example 10 from 4'-[[2-n-propyl-4-methyl-6-(imidazo[2,1-b]thiazol-6-yl)-benzimidazol-1-yl]-methyl]-2-cyano-biphenyl and sodium azide in dimethylformamide.

Yield: 21% of theory,
Melting point: amorphous, sintering from 196° C.
$C_{30}H_{26}N_8S$ (530.67) Calculated: C 67.90 H 4.94 N 21.12 S 6.04 Found: 67.77 4.84 21.00 5.87

The following compounds may be prepared analogously to Example 44:

4'-[[2-n-propyl-4-methyl-6-(3-methyl-imidazo[2,1-b]-thiazol-6-yl)-benzimidazol-1-yl]-methyl]-2-(1H-tetrazol-5-yl)-biphenyl 4'-[[2-n-butyl-4-methyl-6-(2,3-dimethyl-imidazo[2,1-b] thiazol-6-yl)-benzimidazol-1-yl]-methyl]-2-(1H-tetrazol-5-yl)-biphenyl 4'-[[2-n-butyl-4-methyl-6-(2,3-trimethylene-imidazo[2,1-b]-thiazol-6-yl)-benzimidazol-1-yl]-methyl]-2-(1H-tetrazol-5-yl)biphenyl 4'-[[2-ethyl-4-methyl-6-(2,3-tetramethylene-imidazo[2,1-b]-thiazol-6-yl)-benzimidazol-1-yl]-methyl]-2-(1H-tetrazol-5-yl)biphenyl 4'-[[2-n-propyl-4-methyl-6-(2-phenyl-imidazo[2,1-b]-thiazol-6-yl)-benzimidazol-1-yl]-methyl]-2-(1H-tetrazol-5-yl)-biphenyl

EXAMPLE 45

4'-[[2-n-Propyl-4-methyl-6-(benzimidazol-2-yl)-benzimidazol-1-yl]-methyl]-2-(1H-tetrazol-5-yl)-biphenyl Prepared analogously to Example 10 from 4'-[[2-n-propyl-4-methyl-6-(benzimidazol-2-yl)-benzimidazol-1-yl]-methyl]-2-cyanobiphenyl and sodium azide in dimethylformamide.

Yield: 28% of theory,
Melting point: 202°–205° C.
$C_{32}H_{28}N_8$ (524.64) Calculated: C 73.26 H 5.38 N 21.36 Found: 73.01 5.22 21.56

The following compounds are obtained analogously to Example 45:

4'-[[2-ethyl-4-methyl-6-(benzimidazol-2-yl)-benzimidazol-1-yl]-methyl]-2-(1H-tetrazol-5-yl)-biphenyl 4'-[[2-n-butyl-4-methyl-6-(benzimidazol-2-yl)-benzimidazol-1-yl]-methyl]-2-(1H-tetrazol-5-yl)-biphenyl 4'-[[2-n-propyl-4-methyl-6-(1-n-hexyl-benzimidazol-2-yl)-benzimidazol-1-yl]-methyl]-2-(1H-tetrazol-5-yl)-biphenyl 4'-[[2-n-propyl-4-methyl-6-(1-cyclopropyl-benzimidazol-2-yl)-benzimidazol-1-yl]-methyl]-2-(1H-tetrazol-5-yl)-biphenyl 4'-[[2-n-propyl-4-methyl-6-(1-cyclohexyl-benzimidazol-2-yl)-benzimidazol-1-yl]-methyl]-2-(1H-tetrazol-5-yl)-biphenyl

EXAMPLE 46

4'-[[2-n-Propyl-4-methyl-6-(benzimidazol-2-yl)-benzimidazol-1-yl]-methyl]-biphenyl-2-carboxylic acid Prepared analogously to Example 1 from tert.-butyl 4'-[[2-n-propyl-4-methyl-6-(benzimidazol-2-yl)-benzimidazol-1-yl]-methyl]-biphenyl-2-carboxylate and trifluoroacetic acid in methylene chloride.

Yield: 43% of theory,
Melting point: 239°–242° C.
$C_{32}H_{28}N_4O_2$ (500.61) Calculated: C 76.78 H 5.64 N 11.19 Found: 76.55 5.60 11.41

The following compounds are obtained analogously to Example 46:

4'-[[2-ethyl-4-methyl-6-(benzimidazol-2-yl)-benzimidazol-1-yl]-methyl]-biphenyl-2-carboxylic acid 4'-[[2-n-butyl-4-methyl-6-(benzimidazol-2-yl)-benzimidazol-1-yl]-methyl]-biphenyl-2-carboxylic acid 4'-[[2-n-propyl-4-methyl-6-(1-n-hexyl-benzimidazol-2-yl)-benzimidazol-1-yl]-methyl]-biphenyl-2-carboxylic acid 4'-[[2-n-propyl-4-methyl-6-(1-cyclopropyl-benzimidazol-2-yl)-benzimidazol-1-yl]-methyl]-biphenyl-2-carboxylic acid 4'-[[2-n-propyl-4-methyl-6-(1-cyclohexyl-benzimidazol-2-yl)-benzimidazol-1-yl]-methyl]-biphenyl-2-carboxylic acid

EXAMPLE 47

4'-[[2-n-Butyl-7-[3-(imidazol-1-yl)-propyloxy]-4-methyl-benzimidazol-1-yl]-methyl]-2-(1H-tetrazol-5-yl)-biphenyl Prepared from 4'-[[2-n-butyl-7-[3-(imidazol-1-yl)-propyloxy]-4-methyl-benzimidazol-1-yl]-methyl]-2-(1-triphenylmethyl-tetrazol-5-yl)-biphenyl by cleaving the 1-triphenylmethyl group by means of ethanol/hydro-chloric acid.

Yield: 89.8% of theory,
Melting point: 83°–87° C.
$C_{32}H_{34}N_8O \times 1.5\ H_2O$ (573.69) Calculated: C 66.99 H 6.50 N 19.53 Found: 66.83 6.52 19.43

EXAMPLE 48

4'-[[6-(N-Benzenesulphonyl-methylamino)-2-n-butyl-4-methyl-benzimidazol-1-yl]-methyl]-biphenyl-2-carboxylic acid Prepared analogously to Example 1 from tert.butyl 4'-[[6-(N-benzenesulphonylmethylamino)-2-n-butyl-4-methyl benzimidazol-1-yl]-methyl]-biphenyl-2-carboxylate and trifluoroacetic acid in methylene chloride.

Yield: 95.6% of theory,
Melting point: 211°–212° C.
$C_{33}H_{33}N_3O_4S$ (567.70) Calculated: C 69.80 H 5.86 N 7.40 S 5.65 Found: 69.52 5.92 7.33 5.84

EXAMPLE 49

4'-[[6-(N-Benzenesulphonyl-n-pentylamino)-2-n-butyl-4-methyl-benzimidazol-1-yl]-methyl]-biphenyl-2-carboxylic acid Prepared analogously to Example 1 from tert.butyl 4'-[[6-(N-benzenesulphonyl-n-pentylamino)-2-n-butyl-4-methyl-benzimidazol-1-yl]-methyl]-biphenyl-2-carboxylate and trifluoroacetic acid in methylene chloride.

Yield: 81.8% of theory,
Melting point: 232°–233° C.
$C_{37}H_{41}N_3O_4S$ (623.81) Calculated: C 71.24 H 6.62 N 6.74 S 5.14 Found: 71.30 6.77 6.68 5.33

EXAMPLE 50

4'-[[2-n-Butyl-6-(isopropylcarbonylamino)-4-methyl-benzimidazol-1-yl]-methyl]-biphenyl-2-carboxylic acid Prepared analogously to Example 1 from tert.butyl 4'-[[2-n-butyl-6-(isopropyl carbonylamino)-4-methyl-benzimidazol-1-yl]-methyl]-biphenyl-2-carboxylate and trifluoroacetic acid in methylene chloride.

Yield: 86.3% of theory,
Melting point: 313°–315° C.
$C_{30}H_{33}N_3O_3$ (483.6 1) Calculated: C 74.51 H 6.88 N 8.69 Found: 74.37 7.10 8.74

EXAMPLE 51

4'-[[2-n-Butyl-6-(2,3-dimethylmaleic acid imino)-4-methyl-benzimidazol-1-yl]-methyl]-biphenyl-2-carboxylic acid-semihydrate Prepared analogously to Example 1 from tert.butyl 4'-[[2-n-butyl-6-(2,3-dimethylmaleic acid imino)-4-methyl-benzimidazol-1-yl]-methyl]-biphenyl-2-carboxylate and trifluoroacetic acid in methylene chloride.

Yield: 88.9% of theory,
Melting point: 321°–322° C.
$C_{32}H_{31}N_3O_4 \times 0.5\ H_2O$ (530.62) Calculated: C 72.43 H 6.08 N 7.92 Found: 72.89 6.16 7.89

EXAMPLE 52

4'-[[6-(2,3-Dimethylmaleic acid imino)-2-n-propyl-4-methyl-benzimidazol-1-yl]-methyl]-biphenyl-2-carboxylic acid semihydrate Prepared analogously to Example 1 from tert.butyl 4'-[[6-(2,3-dimethylmaleic acid imino)-2-n-propyl-4-methyl-benzimidazol-1-yl]-methyl]-biphenyl-2-carboxylate and trifluoroacetic acid in methylene chloride.

Yield: 75.4% of theory,
Melting point: 329°–331° C.
$C_{31}H_{29}N_3O_4 \times 0.5\ H_2O$ (516.60) Calculated: C 72.08 H 5.85 N 8.13 Found: 72.04 5.84 7.96

EXAMPLE 53

4'-[(6-Acetamino-2-n-butyl-4-methyl-benzimidazol-1-yl)-methyl]-biphenyl-2-carboxylic acid trifluoroacetate semihydrate Prepared analogously to Example 1 from tert.butyl 4'-[(6-acetamino-2-n-butyl-4-methyl-benzimidazol-1-yl)-methyl]-biphenyl-2-carboxylate and trifluoroacetic acid in methylene chloride.

Yield: 95.7% of theory,
Melting point: 112°–114° C. (amorphous)
$C_{28}H_{29}N_3O_3 \times CF_3COOH \times 0.5\ H_2O$ (578.59) Calculated: C 62.28 H 5.40 N 7.26 Found: 62.57 5.46 7.21

EXAMPLE 54

4'-[[2-n-Butyl-4-methyl-6-(morpholinocarbonylamino)-benzimidazol-1-yl]-methyl]-biphenyl-2-carboxylic acid Prepared analogously to Example 1 from tert.butyl 4'-[[2-n-butyl-4-methyl-6-(morpholinocarbonylamino)-benzimidazol-1-yl]-methyl]-biphenyl-2-carboxylate and trifluoroacetic acid in methylene chloride.

Yield: 80.9% of theory,
Melting point: 279°–28° C.
$C_{31}H_{34}N_4O_4$ (526.64) Calculated: C 70.70 H 6.51 N 10.64 Found: 70.48 6.50 10.51

EXAMPLE 55

4'-[[2-n-Butyl-6-(cyclohexylaminocarbonylamino)-4-methyl-benzimidazol-1-yl]-methyl]-biphenyl-2-carboxylic acid semitrifluoroacetate Prepared analogously to Example 1 from tert.butyl 4'-[[2-n-butyl-6-(cyclohexylaminocarbonylamino)-4-methyl-benzimidazol-1-yl]-methyl]-biphenyl-2-carboxylate and trifluoroacetic acid in methylene chloride.

Yield: 76.9% of theory,
Melting point: 288°–289° C.
$C_{33}H_{38}N_4O_3 \times 0.5\ CF_3COOH$ (595.70) Calculated: C 68.55 H 6.51 N 9.41 Found: 69.08 7.02 9.65

EXAMPLE 56

4'-[[2-n-Propyl-4-isopropyl-6-(1-oxo-isoindolin-2-yl)-benzimidazol-1-yl]-methyl]-2-(1H-tetrazol-5-yl)-biphenyl Prepared analogously to Example 10 from 4'-[[2-n-propyl-4-isopropyl-6-(1-oxo-isoindolin-2-yl)-benzimidazol-1-yl]-methyl]-2-cyano-biphenyl and sodium azide in dimethylformamide.

Yield: 14% of theory,
Melting point: amorphous
$C_{35}H_{33}N_7O$ (567.71) Calculated: C 74.05 H 5.86 N 17.27 Found: 73.97 5.82 17.26
Mass spectrum: $M^+=567$

EXAMPLE 57

4'-[[2-n-Propyl-5-(imidazo[1,2-a]pyridin-2-yl)-benzimidazol-1-yl]-methyl]-biphenyl-2-carboxylic acid Prepared analogously to Example 1 from tert.butyl 4'-[[2-n-propyl-5-(imidazo[1,2-a]pyridin-2-yl)-benzimidazol-1-yl]-methyl]-biphenyl-2-carboxylate and trifluoroacetic acid in methylene chloride.

Yield: 32% of theory,
Melting point: 250°–253° C.
$C_{31}H_{26}N_4O_2$ (486.60) Calculated: C 76.52 H 5.39 N 11.52 Found: 76.28 5.47 11.27

EXAMPLE 58

4'-[(2-n-Propyl-4-ethyl-6-(1-methylbenzimidazol-2-yl)-benzimidazol-1-yl)-methyl]-biphenyl-2-carboxylic acid Prepared analogously to Example 1 from tert.butyl 4'-[(2-n-propyl-4-ethyl-6-(1-methylbenzimidazol-2-yl)-benzimidazol-1-yl)-methyl]-biphenyl-2-carboxylate and trifluoroacetic acid in methylene chloride.

Yield: 64% of theory,
Melting point: 217°–219° C.
$C_{34}H_{32}N_4O_2$ (528.70) Calculated: C 77.24 H 6.10 N 10.60 Found: 77.12 6.09 10.75

EXAMPLE 59

4'-[(2-n-Propyl-4-ethyl-6-(1-methylbenzimidazol-2-yl)-benzimidazol-1-yl)-methyl]-2-(1H-tetrazol-5-yl)-biphenyl Prepared analogously to Example 10 from 4'-[(2-n-propyl-4-ethyl-6-(1-methylbenzimidazol-2-yl)-benzimidazol-1-yl)-methyl]-2-cyano-biphenyl and sodium azide in dimethylformamide.

Yield: 15% of theory,
Melting point: 215°–217° C.
$C_{34}H_{32}N_8$ (552.70) Calculated: C 73.89 H 5.84 N 20.28 Found: 73.66 6.02 20.56

EXAMPLE 60

4'-[(2-Cyclopropyl-4-methyl-6-(1-methylbenzimidazol-2-yl)-benzimidazol-1-yl)-methyl]-biphenyl-2-carboxylic acid Prepared analogously to Example 1 from tert.butyl 4'-[(2-cyclopropyl-4-methyl-6-(1-methylbenzimidazol-2-yl)-benzimidazol-1-yl)-methyl]-biphenyl-2-carboxylate and trifluoroacetic acid in methylene chloride.

Yield: 52% of theory,
Melting point: 244°–246° C.

EXAMPLE 61

4'-[(2-Cyclopropyl-4-methyl-6-(1-methylbenzimidazol-2-yl)-benzimidazol-1-yl)-methyl]-2-(1H-tetrazol-5-yl)-biphenyl Prepared analogously to Example 10 from 4'-[(2-cyclopropyl-4-methyl-6-(1-methylbenzimidazol-2-yl)-benzimidazol-1-yl)-methyl]-2-cyano-biphenyl and sodium azide in dimethylformamide.

Yield: 59% of theory,
Melting point: 245°–247° C.
$C_{33}H_{28}N_8$ (536.65) Calculated: C 73.86 H 5.26 N 20.88 Found: 73.95 5.42 20.90

EXAMPLE 62

4'-[(2-Cyclobutyl-4-methyl-6-(1-methylbenzimidazol-2-yl)-benzimidazol-1-yl)-methyl]-biphenyl-2-carboxylic acid Prepared analogously to Example 1 from tert.butyl 4'-[(2-cyclobutyl-4-methyl-6-(1-methylbenzimidazol-2-yl)-benzimidazol-1-yl)-methyl]-biphenyl-2-carboxylate and trifluoroacetic acid in methylene chloride.

Yield: 63% of theory,
Melting point: 189°–191° C.
$C_{34}H_{30}N_4O_2$ (526.60) Calculated: C 77.55 H 5.74 N 10.64 Found: 77.35 5.92 10.40

EXAMPLE 63

4'-[(2-Cyclobutyl-4-methyl-6-(1-methylbenzimidazol-2-yl)-benzimidazol-1-yl)-methyl]-2-(1H-tetrazol-5-yl)-biphenyl Prepared analogously to Example 10 from 4'-[(2-cyclobutyl-4-methyl-6-(1-methylbenzimidazol-2-yl)-benzimidazol-1-yl)-methyl]-2-cyano-biphenyl and sodium azide in dimethylformamide.

Yield: 61% of theory,
Melting point: 197°–199° C.
$C_{34}H_{30}N_8$ (550.70) Calculated: C 74.16 H 5.49 N 20.35 Found: 74.12 5.74 20.67

EXAMPLE 64

4'-[(2-n-Propyl-4-methyl-6-(1-methyl-5-fluoro-benzimidazol-2-yl)-benzimidazol-1-yl)-methyl]-biphenyl-2-carboxylic acid Prepared analogously to Example 1 from tert.butyl 4'-[(2-n-propyl-4-methyl-6-(1-methyl-5-fluoro-benzimidazol-2-yl)-benzimidazol-1-y)-methyl]-biphenyl-2-carboxylate and trifluoroacetic acid in methylene chloride.

Yield: 34% of theory,
Melting point: 250°–252° C.
$C_{33}H_{29}FN_4O_2$ (532.60) Calculated: C 74.42 H 5.49 N 10.52 Found: 74.14 5.64 10.54

The following compounds are obtained analogously to Example 64:

4'-[(2-n-propyl-4-methyl-6-(pyridin-2-yl)-benzimidazol-1-yl)-methyl]-biphenyl-2-carboxylic acid
4'-[(2-n-propyl-4-methyl-6-(quinolin-2-yl)-benzimidazol-1-yl)-methyl]-biphenyl-2-carboxylic acid
4'-[(2-n-propyl-4-methyl-6-(isoquinolin-3-yl)-benzimidazol-1-yl)-methyl]-biphenyl-2-carboxylic acid
4'-[(2-n-propyl-4-methyl-6-(isoquinolin-1-yl)-benzimidazol-1-yl)-methyl]-biphenyl-2-carboxylic acid

EXAMPLE 65

4'-[(2-n-Propyl-4-methyl-6-(imidazo[1,2-a]pyrimidin-2-yl)-benzimidazol-1-yl)-methyl]-2-(1H-tetrazol-5-yl)-biphenyl Prepared analogously to Example 10 from 4'-[(2-n-propyl-4-methyl-6-(imidazo[1,2-a]pyrimidin-2-yl)-benzimidazol-1-yl)-methyl]-2-cyano-biphenyl and sodium azide in dimethylformamide.

Yield: 16.5% of theory,
Melting point: from 275° C. (decomp.)
$C_{31}H_{27}N_9 \times H_2O$ (543.65) Calculated: C 68.49 H 5.38 N 23.19 Found: 68.25 5.50 23.37

The following compounds are obtained analogously to Example 65:

4'-[(2-n-propyl-4-methyl-6-(pyridin-2-yl)-benzimidazol-1-yl)-methyl]-2-(1H-tetrazol-5-yl)-biphenyl
4'-[(2-n-propyl-4-methyl-6-(quinolin-2-yl)-benzimidazol-1-yl)-methyl]-2-(1H-tetrazol-5-yl)-biphenyl
4'-[(2-n-propyl-4-methyl-6-(isoquinolin-3-yl)-benzimidazol-1-yl)-methyl]-2-(1H-tetrazol-5-yl)-biphenyl
4'-[(2-n-propyl-4-methyl-6-(isoquinolin-1-yl)-benzimidazol-1-yl)-methyl]-2-(1H-tetrazol-5-yl)-biphenyl

EXAMPLE 66

4'-[(2-n-Propyl-4-methyl-6-(5,6,7,8-tetrahydro-imidazo[1,2-a]-pyridin-2-yl)-benzimidazol-1-yl)-methyl]-biphenyl-2-carboxylic acid Prepared analogously to Example 1 from tert.butyl 4'-[(2-n-propyl-4-methyl-6-(5,6,7,8-tetrahydro-imidazo-[1,2-a]pyridin-2-yl)-benzimidazol-1-yl)-methyl]-biphenyl-2-carboxylate and trifluoroacetic acid in methylene chloride.

Yield: 67% of theory,
Melting point: from 240° C. (sinters)
$C_{32}H_{32}N_4O_2$ (504.64) Calculated: C 76.16 H 6.39 N 11.10 Found: 75.94 6.46 11.20

The following compounds are obtained analogously to Example 66:

4'-[(2-n-butyl-4-methyl-6-(5,6,7,8-tetrahydro-imidazo[1,2-a]-pyridin-2-yl)-benzimidazol-1-yl)-methyl]-biphenyl-2-carboxylic acid
4'-[(2-ethyl-4-methyl-6-(5,6,7,8-tetrahydro-imidazo[1,2-a]pyridin-2-yl)-benzimidazol-1-yl)-methyl]-biphenyl-2-carboxylic acid

EXAMPLE 67

4'-[(2-n-Propyl-4-methyl-6-(5,6,7,8-tetrahydro-imidazo-[1,2-a]pyridin-2-yl)-benzimidazol-1-yl)-methyl]-2-(1H-tetrazol-5-yl)-biphenyl Prepared analogously to Example 10 from 4'-[(2-n-propyl-4-methyl-6-(5,6,7,8-tetrahydro-imidazo[1,2-a]pyridin-2-yl)-benzimidazol- 1-yl)-methyl]-2-cyano-biphenyl and sodium azide in dimethylformamide.

Yield: 73.5% of theory,
Melting point: from 275° C. (decomp.)
$C_{32}H_{32}N_8$ (528.67) Calculated: C 72.70 H 6.10 N 21.20 Found: 72.40 6.07 21.48

The following compounds are obtained analogously to Example 67:

4'-[(2-n-butyl-4-methyl-6-(5,6,7,8-tetrahydro-imidazo[1,2-a]-pyridin-2-yl)-benzimidazol-1-yl)-methyl]-2-(1H-tetrazol-5-yl)-biphenyl
4'-[(2-ethyl-4-methyl-6-(5,6,7,8-tetrahydro-imidazo[1,2-a]-pyridin-2-yl)-benzimidazol-1-yl)-methyl]-2-(1H-tetrazol-5-yl)-biphenyl

---

$C_{33}H_{28}N_4O_2$ (512.60) Calculated: C 77.32 H 5.51 N 10.93 Found: 77.75 5.71 10.94

EXAMPLE 68

4'-[(2-n-Propyl-4-methyl-6-(1-methyl-6-fluoro-benzimidazol-2-yl)-benzimidazol-1-yl)-methyl]-biphenyl-2-carboxylic acid Prepared analogously to Example 1 from tert.butyl 4'-[(2-n-propyl-4-methyl-6-(1-methyl-6-fluoro-benzimidazol-2-yl)-benzimidazol-1-yl)-methyl]-biphenyl-2-carboxylate and trifluoroacetic acid in methylene chloride.

Yield: 76% of theory,
Melting point: 243°–245° C.
$C_{33}H_{29}FN_4O_2$ (532.60) Calculated: 74.42 H 5.49 N 10.52 Found: 74.74 5.52 10.77
Mass spectrum: m/e=532

EXAMPLE 69

4'-[(2-n-Propyl-4-chloro-6-(1-oxo-isoindolin-2-yl)-benzimidazol-1-yl)-methyl]-biphenyl-2-carboxylic acid Prepared analogously to Example 1 from tert.butyl 4'-[(2-n-propyl-4-chloro-6-(1-oxo-isoindolin-2-yl)-benzimidazol-1-yl)-methyl]-biphenyl-2-carboxylate and trifluoroacetic acid in methylene chloride.

Yield: 7.5% of theory,
Melting point: 209°–210° C.
$C_{32}H_{26}ClN_3O_3$ (536.04)
Mass spectrum: m/e=535/537
$R_f$ value: 0.25 (silica gel; methylene chloride/ethanol=9:1)

EXAMPLE 70

4'-[(2-n-Propyl-4-chloro-6-(1-methylbenzimidazol-2-yl)-benzimidazol-1-yl)-methyl]-biphenyl-2-carboxylic acid Prepared analogously to Example 1 from tert.butyl 4'-[(2-n-propyl-4-chloro-6-(1-methylbenzimidazol-2-yl)-benzimidazol-1-yl)-methyl]-biphenyl-2-carboxylate and trifluoroacetic acid in methylene chloride.

Yield: 52.7% of theory,
Melting point: 292°–295° C.
$C_{32}H_{27}ClN_4O_2$ (535.06)
$R_f$ value: 0.30 (silica gel; methylene chloride/ethanol=19:1) Calculated: C 71.90 H 5.08 N 10.45 Cl 6.63 Found: 71.29 5.21 10.40 6.76

EXAMPLE 71

4'-[(2-n-Propyl-4-chloro-6-(1-methylbenzimidazol-2-yl)-benzimidazol-1-yl)-methyl]-2-(1H-tetrazol-5-yl)-biphenyl hydrochloride Prepared analogously to Example 10 from 4'-[(2-n-propyl-4-chloro-6-(1-methylbenzimidazol-2-yl)-benzimidazol-1-yl)-methyl]-2-cyano-biphenyl and sodium azide in dimethylformamide.

Yield: 54.8% of theory,
Melting point: sintering from 204° C.
$C_{32}H_{27}ClN_8 \times HCl$ (595.55)
$R_f$ value: 0.20 (silica gel; petroleum ether/ethyl acetate=1:1 and 1% glacial acetic acid) Calculated: C 62.55 H 4.71 N 18.85 Cl 11.85 Found: 62.34 4.97 18.84 11.57

EXAMPLE 72

4'-[(2-n-Propyl-4-chloro-6-(1-oxo-isoindolin-2-yl)-benzimidazol-1-yl)-methyl]-2-(1H-tetrazol-5-yl)-biphenyl Prepared analogously to Example 10 from 4'-[(2-n-propyl-4-chloro-6-(1-oxo-isoindolin-2-yl)-benzimidazol-1-yl)-methyl]-2-cyano-biphenyl and sodium azide in dimethylformamide.

Yield: 24.6% of theory,
Melting point: 246°–248° C.
$C_{32}H_{26}ClN_7O$ (560.08)
$R_f$ value: 0.15 (silica gel; methylene chloride/ethanol=9:1) Calculated: C 69.00 H 4.67 N 17.55 Cl 6.40 Found: 68.26 4.75 17.73 6.97

The following compound is obtained analogously to Example 72:

4'-[(2-n-propyl-4-methyl-6-(4-methyl-imidazol-2-yl)-benzimidazol-1-yl)-methyl]-2-(1H-tetrazol-5-yl)-biphenyl

EXAMPLE 73

4'-[(2-n-Propyl-4-chloro-6-(cyclohexylaminocarbonyl-amino)-benzimidazol-1-yl)-methyl]-biphenyl-2-carboxylic acid Prepared analogously to Example 1 from tert.butyl 4'-[(2-n-propyl-4-chloro-6-(cyclohexylaminocarbonylamino)-benzimidazol-1-yl)-methyl]-biphenyl-2-carboxylate and trifluoroacetic acid in methylene chloride.

Yield: 75% of theory,
Melting point: 222°–224° C.
$C_{31}H_{33}ClN_4O_3$ (545.09)
$R_f$ value: 0.15 (silica gel; methylene chloride/ethanol=19:1) Calculated: C 68.50 H 6.10 N 10.30 Cl 6.48 Found: 68.89 5.98 10.02 7.04

EXAMPLE 74

4'-[(2-n-Propyl-4-methyl-6-amidino-benzimidazol-1-yl)-methyl]-biphenyl-2-carboxylic acid hydrate a) Methyl 4'-[(2-n-propyl-4-methyl-6-amidino-benzimidazol-1-yl)-methyl]-biphenyl-2-carboxylate 2.1 g (5 mMol) of methyl 4'-[(2-n-propyl-4-methyl-6-cyano-benzimidazol-1-yl)-methyl]-biphenyl-2-carboxylate are dissolved in 250 ml of methanol at ambient temperature with stirring. Hydrogen chloride is introduced at 10°–20° C. for 3 hours whilst cooling with ice. The mixture is then stirred for a further 3 hours at ambient temperature. The solvent is distilled off in vacuo, the residue is twice mixed with ether and concentrated by evaporation. The iminoether formed is taken up in 250 ml of methanol and mixed with 10.0 g of ammonium carbonate. The reaction mixture is stirred for 12 hours at ambient temperature. After the solvent has been removed in vacuo the residue is purified over a silica gel column (particle size 0.063–0.032 mm), using as eluant mixtures of methylene chloride and methanol of increasing polarity (9:1 and 8:2). The uniform fractions are evaporated down in vacuo.

Yield: 1.5 g (58% of theory)
$R_f$ value: 0.15 (silica gel; eluant: methylene chloride/methanol=9:1)

b) 4'-[(2-n-Propyl-4-methyl-6-amidino-benzimidazol-1-yl)-methyl]-biphenyl-2-carboxylic acid 0.51 g (1.0 mMol) of methyl 4'-[(2-n-propyl-4-methyl-6-amidino-benzimidazol-1-yl)-methyl]-biphenyl-2-carboxylate are dissolved in 6 ml of tetrahydrofuran, 2.8 ml of 1.4M aqueous lithium hydroxide solution and 3 ml of water are added and the mixture is stirred for 2 days at ambient temperature. Then a solution of 300 mg of ammonium chloride in 4 ml of water is added. The mixture is stirred for 5 minutes, the precipitate formed is suction filtered, washed with acetone and dried over potassium hydroxide.

Yield: 0.25 g (59% of theory),
Melting point: 270°–271° C. (decomp.)
$C_{26}H_{26}N_4O_2 \times H_2O$ (426.53) Calculated: C 70.25 H 6.35 N 12.60 Found: 70.04 6.23 12.50
$R_f$ value: 0.55 (silica gel; eluant: methylene chloride/methanol/ammonia=2:1:0.25)

The following compound is obtained analogously to Example 74:

4'-[(2-n-propyl-4-methyl-6-(3-methyl-imidazol-2-yl)-benzimidazol-1-yl)-methyl]-biphenyl-2-carboxylic acid

EXAMPLE 75

4'-[(2-n-Propyl-4-methyl-6-(1-methyl-imidazol-4-yl)-benzimidazol-1-yl)-methyl]-biphenyl-2-carboxylic acid a) 3-Methyl-4-butyrylamino-5-nitro-acetophenone 32.6 g (148 mmol) of 3-methyl-4-butyrylamino-acetophenone are added in batches at −15° C. to 300 ml of fuming nitric acid with stirring, and stirred for a further 30 minutes. at −15° C. The reaction mixture is then poured onto 3 liters of ice, with stirring, the crude product precipitated is suction filtered, washed with 400 ml of water, dried and purified by recrystallisation from ethanol/diethylether (1:1).

Yield: 23.8 g (61.0% of theory),
$R_f$ value: 0.32 (silica gel; methylene chloride),
$R_f$ value: 0.48 (silica gel; methylene chloride/methanol=50:1).

b) 3-Methyl-4-butyrylamino-5-nitro-1-bromoacetophenone

A solution of 16.0 g (200 mmol) of bromine in 140 ml of dioxane is added dropwise to a solution of 23.8 g (90 mmol) of 3-methyl-4-butyrylamino-5-nitro-acetophenone in 900 ml of dichloromethane at ambient temperature, with stirring, so slowly that total decolorisation of the reaction mixture occurs constantly. The mixture is then stirred for a further two hours, then the reaction mixture is evaporated to dryness in vacuo, the residue obtained is triturated with about 20 ml of dichloromethane/diethylether (1:1), suction filtered and then dried. 23 g (74% of theory) of 3-methyl-4-butyrylamino-5-nitro-ω-bromoacetophenone are thus obtained, still containing about 10% starting material. The product is further reacted without any more purification.

$R_f$ value: 0.69 (silica gel; methylene chloride/methanol=50:1)
$R_f$ value: 0.84 (silica gel; methylene chloride/methanol=9:1).

c) 2-Butyrylamino-3-nitro-5-(imidazo-4-yl)-toluene

A solution of 6.8 g (20 mmol) of 3-methyl-4-butyrylamino-5-nitro-ω-bromoacetophenone in 20 ml of formamide is heated to 140° C. for two hours. The cooled solution is then poured into about 50 ml of 1N ammonia and stirred for about 15 minutes. The crude product precipitated is suction filtered, washed with about 50 ml of water and dried. In this way, 4.4 g (75% of theory) of the product are obtained, which is further reacted without any more purification.

$R_f$ value: 0.29 (silica gel; methylene chloride/methanol=9:1)

d) 2-Butyrylamino-3-nitro-5-(1-methyl-imidazol-4-yl)-toluene 1.3 g (9.5 mmol) of methyliodide are added dropwise at ambient temperature to a solution of 2.5 g (8.7 mmol) of 2-butyrylamino-3-nitro-5-(imidazol-4-yl)-toluene and 5.2 g (30 mmol) of potassium carbonate dihydrate in 30 ml of dimethylsulfoxide and the mixture is then stirred for two hours. The reaction mixture is then stirred into about 150 ml of water and extracted four times with 25 ml of ethylacetate. The organic extracts are washed with about 30 ml of water, dried and evaporated down. The crude product thus obtained is purified by column chromatography (300 g of silica gel, eluant: methylene chloride/methanol=30:1).

Yield: 640 mg (24% of theory),
$R_f$ value: 0.54 (silica gel; methylene chloride/methanol=9:1)

e) 2-Butyrylamino-3-amino-5-(1-methyl-imidazol-4-yl)-toluene 640 mg (2.1 mmol) of 2-butyrylamino-3-nitro-5-(1-methyl-imidazol-4-yl)-toluene are hydrogenated in 30 ml of methanol after the addition of about 200 mg of palladium/charcoal (20%) at ambient temperature under a hydrogen pressure of 5 bar. After all the hydrogen has been absorbed the catalyst is removed by filtering and the filtrate is evaporated down. The crude product obtained is further reacted without any more purification.

Yield: 600 mg (100% of theory),
$R_f$ value: 0.23 (silica gel; methylene chloride/methanol=9:1)

f) 2-n-Propyl-4-methyl-6-(1-methyl-imidazol-4-yl)-benzimidazole 600 mg (2.1 mmol) of 2-butyrylamino-3-amino-5-(1-methyl-imidazol-4-yl)-toluene are refluxed for one hour in 10 ml of glacial acetic acid. Then the mixture is evaporated to dryness in vacuo, the residue is mixed with about 15 ml of water, made alkaline with ammonia and extracted four times with about 10 ml of ethylacetate. The organic extracts are washed with about 15 ml of water, dried and finally evaporated down. The crude product thus obtained is further reacted without any more purification.

Yield: 420 mg (79% of theory),
$R_f$ value: 0.37 (silica gel; methylene chloride/methanol=9:1)

g) Tert.butyl-4'-[(2-n-propyl-4-methyl-6-(1-methyl-imidazol-4-yl)-benzimidazol-1-yl)methyl]-biphenyl-2-carboxylate 280 mg (0.8 mmol) of tert.butyl-4'-bromomethyl-biphenyl-2-carboxylate are added to a solution of 200 mg (0.79 mmol) of 2-n-propyl-4-methyl-6-(1-methyl-imidazol-4-yl)-benzimidazole and 90 mg (0.8 mmol) of potassium tert.butoxide in 5 ml of dimethylsulfoxide and the mixture is stirred for 90 minutes at ambient temperature, then stirred into about 40 ml of water, extracted four times with about 10 ml of ethylacetate, then the organic extracts are washed with 10 ml of water, dried and evaporated to dryness. The crude product thus obtained is purified by column chromatography (100 g silica gel, eluant: dichloromethane/methanol=30:1).

Yield: 230 mg (56% of theory),
$R_f$ value: 0.61 (silica gel; methylene chloride/methanol=9:1)

h) 4'-[2-n-Propyl-4-methyl-6-(1-methyl-imidazol-4-yl)-benzimidazol-1-yl)-methyl]-biphenyl-2-carboxylic acid A solution of 230 mg (0.44 mmol) of tert.butyl-4'-[(2-n-propyl-4-methyl-6-(1-methyl-imidazol-4-yl)-benzimidazol-1-yl)-methyl]-biphenyl-2-carboxylate and 2 ml of trifluoroacetic acid in 10 ml of dichloromethane was stirred overnight at ambient temperature and then evaporated to dryness. The residue was dissolved in about 5 ml of dilute sodium hydroxide solution, the solution was neutralised with acetic acid, the precipitate was suction filtered, washed with water and dried.

Yield: 120 mg (59% of theory);
Melting point: 293°–295° C.
$R_f$ value: 0.39 (silica gel; methylene chloride/methanol=9:1)

The following compounds are obtained analogously to Example 75:

4'-[(2-n-propyl-4-methyl-6-(1-ethyl-imidazol-4-yl)-benzimidazol-1-yl)-methyl]-biphenyl-2-carboxylic acid 4'-[(2-n-propyl-4-methyl-6-(1-n-hexyl-imidazol-4-yl)-benzimidazol-1-yl)-methyl]-biphenyl-2-carboxylic acid 4'-[(2-n-propyl-4-methyl-6-(1-benzyl-imidazol-4-yl)-benzimidazol-1-yl)-methyl]-biphenyl-2-carboxylic acid 4'-[(2-n-propyl-4-methyl-6-(1-isopropyl-imidazol-4-yl)-benzimidazol-1-yl)-methyl]-biphenyl-2-carboxylic acid 4'-[(2-n-propyl-4-methyl -6-(1-cyclohexyl-imidazol-4-yl)-benzimidazol-1-yl)-methyl]-biphenyl-2-carboxylic acid

EXAMPLE 76

4'-[(2-n-Propyl-4-methyl-6-(1-methyl-imidazol-4-yl)-benzimidazol-1-yl)-methyl]-2-(1H-tetrazol-5-yl)-biphenyl Prepared analogously to Example 10 from 4'-[(2-n-propyl-4-methyl-6-(1-methyl-imidazol-4-yl)-benzimidazol-1-yl)-methyl]-2-cyano-biphenyl and sodium azide in dimethylformamide.

Yield: 24% of theory
Melting point: 255°–257° C.
$R_f$-value: 0.24 (silica gel; methylene chloride/methanol= 9:1)
$C_{29}H_{28}N_8 \times H_2O$ (506.62) calculated: C 68.75 H 5.97 N 22.12 found: 68.90 5.97 22.03

The following compounds are obtained analogously to Example 76:

4'-[(2-n-propyl-4-methyl-6-(1-ethyl-imidazol-4-yl)-benzimidazol-1-yl)-methyl]-2-(1H-tetrazol-5-yl)-biphenyl 4'-[(2-n-propyl-4-methyl-6-(1-n-hexyl-imidazol-4-yl)-benzimidazol-1-yl)-methyl]-biphenyl -2-carboxylic acid 4'-[(2-n-propyl-4-methyl-6-(1-benzyl-imidazol-4-yl)-benzimidazol-1-yl)-methyl]-biphenyl-2-carboxylic acid 4'-[(2-n-propyl-4-methyl-6-(1-isopropyl-imidazol-4-yl)-benzimidazol-1-yl)-methyl]-2-(1H-tetrazol-5-yl)-biphenyl 4'-[(2-n-propyl-4-methyl-6-(1-cyclohexyl-imidazol-4-yl)-benzimidazol-1-yl)-methyl]-2-(1H-tetrazol-5-yl)-biphenyl

EXAMPLE 77

4'-[2-Ethyl-4-methyl-6-(5,6,7,8-tetrahydro-imidazo[1,2-a]pyridin-2-yl)-benzimidazol-1-yl)-methyl]-2-(1H-tetrazol-5-yl)-biphenyl Prepared analogously to Example 10 from 4'-[(2-ethyl-4-methyl-6-(5,6,7,8-tetrahydro-imidazo[1,2-a]pyridin-2-yl)-benzimidazol-1-yl)methyl]-2-cyano-biphenyl and sodium azide in dimethylformamide.

Yield: 21% of theory
Melting point: amorph.
$R_f$-value: 0.27 (silica gel; methylene chloride/ethanol= 9:1)
$C_{31}H_{30}N_8$ (514.64) calculated: C 72.35 H 5.88 N 21.78 found: 72.01 5.82 21.44

EXAMPLE 78

4'-[(2-n-Propyl-4-methyl-6-(8-methyl-imidazo-[1,2-a]-pyridin-2-yl)-benzimidazol-1-yl)-methyl]-biphenyl-2-carboxylic acid Prepared analogously to Example 1 from tert.butyl 4'-[(2-n-propyl-4-methyl-6-(8-methyl-imidazo-[1,2-a]-pyridin-2-yl)-benzimidazol-1-yl)-methyl]-biphenyl-2-carboxylate and trifluoroacetic acid in methylene chloride.

Yield: 87% of theory
Melting point: 295°–297° C.
$R_f$-value: 0.34 (silica gel; methylene chloride/ethanol= 9:1)
$C_{33}H_{30}N_4O_2 \times H_2O$ (532.65) calculated: C 74.41 H 6.06 N 10.52 found: 74.81 6.05 10.43

EXAMPLE 79

4'-[(2-n-Propyl-4-methyl-6-(2-pyridyl)-benzimidazol-1-yl)-methyl]-2-(1H-tetrazol-5-yl)-biphenyl Prepared analogously to Example 10 from 4'-[(2-n-propyl-4-methyl-6-(2-pyridyl)-benzimidazol-1-yl)-methyl]-2-cyano-biphenyl and sodium azide in dimethylformamide.

Yield: 56% of theory,
Melting point: from 136° C. (decomp.)
$C_{30}H_{27}N_7 \times 0.5 H_2O$ (494.60) Calculated: C 72.85 H 5.71 N 19.83 Found: 72.45 6.01 19.83

EXAMPLE 80

4'-[(2-n-Propyl-4-methyl-6-(8-methyl-imidazo[1,2-a]pyridin-2-yl)-benzimidazol-1-yl)-methyl]-2-(1H-tetrazol-5-yl)-biphenyl Prepared analogously to Example 10 from 4'-[(2-n-propyl-4-methyl-6-(8-methyl-imidazo[1,2-a]pyridin-2-yl)-benzimidazol-1-yl)-methyl]-2-cyano-biphenyl and sodium azide in dimethylformamide.

Yield: 19% of theory
Melting point: amorph.
$R_f$-value: 0.36 (silica gel; methylene chloride/ethanol= 9:1)
$C_{29}H_{28}N_8 \times H_2O$ (538.61)
mass spectrum: m/e=538

EXAMPLE 81

4'-[(2-Ethyl-4-methyl-6-(5,6,7,8-tetrahydro-imidazo[1,2-a]pyridin-2-yl)-benzimidazol-1-yl)-methyl]-biphenyl-2-carboxylic acid Prepared analogously to Example 1 from tert.butyl 4'-[2-ethyl-4-methyl-6-(5,6,7,8-tetrahydro-imidazo[1,2-a]pyridin-2-yl)-benzimidazol- 1-yl)-methyl]-biphenyl-2-carboxylate and trifluoroacetic acid in methylene chloride.

Yield: 50% of theory
Melting point: >300° C.
$R_f$-value: 0.16 (silica gel; methylene chloride/ethanol= 9:1)

EXAMPLE 82

4'-[(2-n-Propyl-4-methyl-6-(1-isopropyl-imidazol-4-yl)-benzimidazol-1-yl)-methyl]-biphenyl-2-carboxylic acid Prepared analogously to Example 1 from tert.butyl 4'-[(2-n-propyl-4-methyl-6-(1-isopropyl-imidazol-4-yl)-benzimidazol-1-yl)-methyl]-biphenyl-2-carboxylate and trifluoroacetic acid in methylene chloride.

Yield: 84% of theory
Melting point: 285°–286° C.
$R_f$-value: 0.55 (silica gel; methylene chloride/methanol= 9:1)

EXAMPLE 83

4'-[(2-n-Propyl-4-methyl-6-(1-isopropyl-imidazol-4-yl)-benzimidazol-1-yl)-methyl]-2-(1H-tetrazol-5-yl)-biphenyl Prepared analogously to Example 10 from 4'-[(2-n-propyl-4-methyl-6-(1-isopropyl-imidazol-4-yl)-benzimidazol-1-yl)-methyl]-2-cyano-biphenyl and sodium azide in dimethylformamide.

Yield: 18% o f theory
Melting point: amorph.
$R_f$-value: 0.29 (silica gel; methylene chloride/methanol= 9:1)
$C_{31}H_{32}N_8$ (51 6.66)
mass spectrum: m/e=516

EXAMPLE 84

4'-[(2-n-Propyl-4-methyl-6-(1-n-hexyl-imidazol-4-yl)-benzimidazol-1-yl)-methyl]-biphenyl-2-carboxylic acid Prepared analogously to Example 1 from tert.butyl 4'-[(2-n-propyl-4-methyl-6-(1-n-hexyl-imidazol-4-yl)-benzimidazol-1-yl)-methyl]-biphenyl and trifluoroacetic acid in methylene chloride.

EXAMPLE 85

4'-[(2-n-Propyl-4-methyl-6-(1-benzyl-imidazol-4-yl)-benzimidazol-1-yl)-methyl]-biphenyl-2-carboxylic acid Prepared analogously to Example 1 from tert.butyl 4'-[(2-n-propyl-4-methyl-6-(1-benzyl-imidazol-4-yl)-benzimidazol-1-yl)-methyl]-biphenyl and trifluoroacetic acid in methylene chloride.

EXAMPLE 86

4'-[(2-n-Propyl-4-methyl-6-(1-n-hexyl-imidazol-4-yl)-benzimidazol-1-yl)-methyl]-2-(1H-tetrazol-5-yl)-biphenyl Prepared analogously to Example 10 from 4'-[(2-n-propyl-4-methyl-6-(1-n-hexyl-imidazol-4-yl)-benzimidazol-1-yl)-methyl]-2-cyano-biphenyl and sodium azide in dimethylformamide.

EXAMPLE 87

4'-[(2-n-Propyl-4-methyl-6-(1-benzyl-imidazol-4-yl)-benzimidazol-1-yl)-methyl]-2-(1H-tetrazol-5-yl)-biphenyl Prepared analogously to Example 10 from 4'-[(2-n-propyl-4-methyl-6-(1-benzyl-imidazol-4-yl)-benzimidazol-1-yl)-methyl]-2-cyano-biphenyl and sodium azide in dimethylformamide.

EXAMPLE 88

4'-[(2-n-Propyl-4-methyl-6-(1-methyl-imidazol-4-yl)-benzimidazol-1-yl)-methyl]-biphenyl-2-carboxylic acid a) 3-Methyl-4-butyrylamino-5-nitro-acetophenone 32.6 g (148 mMol) of 3-methyl-4-butyrylamino-acetophenone are added in batches to 300 ml of fuming nitric acid, with stirring, at −15° C. and stirred for a further 30 minutes at −15° C. The reaction mixture is then poured onto 3 liters of ice with stirring, the crude product precipitated is suction filtered, washed with 400 ml of water, dried and purified by recrystallisation from ethanol/diethylether (1:1).

Yield: 23.8 g (61.0% of theory),
$R_f$ value: 0.32 (silica gel; methylene chloride)
$R_f$ value: 0.48 (silica gel; methylene chloride/methanol= 50:1)

b) 3-Methyl-4-butyrylamino-5-nitro-ω-bromoacetophenone

At ambient temperature, with stirring, a solution of 16.0 g (200 mMol) of bromine in 140 ml of dioxane is slowly added dropwise to a solution of 23.8 g (90 mMol) of 3-methyl -4-butyrylamino-5-nitro-acetophenone in 900 ml of dichloromethane so that the reaction mixture is constantly completely decolorised. It is then stirred for a further two hours, then the reaction mixture is evaporated to dryness in vacuo, the residue thus obtained is triturated with about 20 ml of dichloromethane/diethylether (1:1), suction filtered and then dried. 23 g (74% of theory) of 3-methyl-4-butyrylamino-5-nitro-ω-bromoacetophenone are thus obtained, containing about 10% of starting material. The product is further reacted without any more purification.

$R_f$ value: 0.69 (silica gel; methylene chloride/methanol= 50:1)
$R_f$ value: 0.84 (silica gel; methylene chloride/methanol= 9:1)

c) 2-Butyrylamino-3-nitro-5-(imidazol-4-yl)-toluene

A solution of 6.8 g (20 mMol) of 3-methyl-4-butyrylamino-5-nitro-ω-bromoacetophenone in 20 ml of formamide is heated to 140 ° C. for 2 hours. The cooled solution is then poured into about 50 ml of 1N ammonia and stirred for about 15 minutes. The crude product precipitated is suction filtered, washed with about 50 ml of water and dried. In this way, 4.4 g (75% of theory) of the product are obtained, which is further reacted without any more purification.

$R_f$ value: 0.29 (silica gel; methylene chloride/methanol= 9:1)

d) 2-Butyrylamino-3-nitro-5-(1-methyl-imidazol-4-yl)-toluene 1.3 g (9.5 mMol) of methyl iodide are added dropwise at ambient temperature to a solution of 2.5 g (8.7 mMol) of 2-butyrylamino-3-nitro-5-(imidazol-4-yl)-toluene and 5.2 g (30 mMol) of potassium carbonate dihydrate in 30 ml of dimethylsulphoxide at ambient temperature and then stirred for 2 hours. The reaction mixture is then stirred into about 150 ml of water and then extracted four times with 25 ml of ethyl acetate. The organic extracts are washed with about 30 ml of water, dried and concentrated by evaporation. The crude product thus obtained is purified by column chromatography (300 g silica gel, eluant: methylene chloride/methanol=30:1).

Yield: 640 mg (24% of theory),
$R_f$ value: 0.54 (silica gel; methylene chloride/methanol= 9:1)

e) 2-Butyrylamino-3-amino-5-(1-methyl-imidazol-4-yl)-toluene 640 mg (2.1 mMol) of 2-butyrylamino-3-nitro-5-(1-methyl-imidazol-4-yl)-toluene are hydrogenated at ambient temperature under a hydrogen pressure of 5 bar in 30 ml of methanol after the addition of about 200 mg of 20% palladium/charcoal. After all the water has been absorbed the catalyst is filtered off and the filtrate is evaporated down. The crude product thus obtained is further reacted without any more purification.

Yield: 600 mg (100% of theory),
$R_f$ value: 0.23 (silica gel; methylene chloride/methanol= 9:1)

f) 2-n-Propyl -4-methyl-6-(1-methyl-imidazol-4-yl)-benzimidazole 600 mg (2.1 mMol) of 2-butyrylamino-3-amino-5-(1-methyl-imidazol-4-yl)-toluene are refluxed in 10 ml of glacial acetic acid for one hour. Then the mixture is evaporated to dryness in vacuo, the residue is mixed with about 15 ml of water, made alkaline with ammonia and extracted four times with about 10 ml of ethyl acetate. The organic extracts are washed with about 15 ml of water, dried and finally evaporated down. The crude product thus obtained is further reacted without any more purification.

Yield: 420 mg (79% of theory), $R_f$ value: 0.37 (silica gel; methylene chloride/methanol= 9:1)

g) Tert.butyl 4'-[(2-n-propyl-4-methyl-6-(1-methyl-imidazol-4-yl)-benzimidazol-1-yl)-methyl]-biphenyl-2-carboxylate 280 mg (0.8 mMol) of tert.butyl 4'-bromomethyl-biphenyl -2-carboxylate are added to a solution of 200 mg (0.79 mMol) of 2-n-propyl-4-methyl-6-(1-methyl-imidazol-4-yl)-benzimidazole and 90 mg (0.8 mMol) of potassium tert.butoxide in 5 ml of dimethylsulphoxide and the mixture is stirred for 90 minutes at ambient temperature, then stirred into about 40 ml of water, extracted four times with about 10 ml of ethyl acetate, then the organic extracts are washed with 10 ml of water, dried and evaporated to dryness. The crude product thus obtained is purified by column chromatography (100 g silica gel; eluant; dichloromethane/methanol=30:1).

Yield: 230 mg (56% of theory), $R_f$ value: 0.61 (silica gel; methylene chloride/methanol= 9:1)

h) 4'-[(2-n-Propyl-4-methyl-6-(1-methyl-imidazol-4-yl)-benzimidazol-1-yl)-methyl]-biphenyl-2-carboxylic acid A solution of 230 mg (0.44 mMol) of tert.butyl 4'-[(2-n-propyl-4-methyl-6-(1-methyl-imidazol-4-yl)-benzimidazol-1-yl)-methyl]-biphenyl-2-carboxylate and 2 ml of trifluoroacetic acid in 10 ml of dichloromethane is stirred overnight at ambient temperature and then evaporated to dryness. The residue is dissolved in about 5 ml of dilute sodium hydroxide solution, the solution is neutralised with acetic acid, the precipitate formed is suction filtered, washed with water and dried.

Yield: 120 mg (59% of theory),

Melting point: 293°–295° C.

$R_f$ value: 0.39 (silica gel; methylene chloride/methanol= 9:1)

EXAMPLE 89

4'-[(2-n-Propyl-4-methyl-6-(1-methyl-imidazol-4-yl)-benzimidazol-1-yl)-methyl]-2-(1H-tetrazol-5-yl)-biphenyl-hydrate a) 4'-[(2-n-Propyl-4-methyl-6-(1-methylimidazol-4-yl)-benzimidazol-1-yl)-methyl]-2-cyano-biphenyl 218 mg (0.8 mMol) of 4'-bromomethyl-2-cyano-biphenyl are added to a solution of 200 mg (0.79 mMol) of 2-n-propyl-4-methyl-6-(1-methyl-imidazol-4-yl)-benzimidazole and 90 mg (0.8 mMol) of potassium tert.butoxide in 6 ml of dimethylsulphoxide and the mixture is stirred for 14 hours at ambient temperature. Then it is stirred into about 40 ml of water, extracted four times with about 10 ml of ethyl acetate, the organic extracts are washed with about 10 ml of water, dried and evaporated to dryness. The crude product thus obtained is purified by column chromatography (100 g silica gel; eluant: dichloromethane/ethanol=50:1).

Yield: 240 mg (67% of theory), $R_f$ value: 0.38 (silica gel; methylene chloride/ethanol= 19:1)

b) 4'-[(2-n-Propyl-4-methyl-6-(1-methyl-imidazol-4-yl)-benzimidazol-1-yl)-methyl]-2-(1H-tetrazol-5-yl)-biphenyl-hydrate A solution of 222 mg (0.5 mMol) of 4'-[(2-n-propyl-4-methyl-6-(1-methyl-imidazol-4-yl)-benzimidazol-1-yl)-methyl]-2-cyanobiphenyl, 660 mg (10 mMol) of sodium azide and 540 mg (10 mMol) of ammonium chloride in 12 ml of pure dimethylformamide is heated to 140° C. for 18 hours. The solution is then evaporated substantially to dryness and the product is isolated by column chromatography (60 g of silica gel, eluant: dichloromethane with 10% ethanol). The product thus obtained is taken up in about 10 ml of dilute ammonia solution and the solution is then adjusted to pH 6 with acetic acid. A greasy residue is formed which becomes crystalline after the addition of a little ethyl acetate and several hours stirring. The crystalline product is suction filtered, washed with about 5 ml of water and dried.

Yield: 61.0 mg (24.0% of theory),

Melting point: 255°–257° C.

$C_{29}H_{28}N_8 \times H_2O$ (506.62) Calculated: C 68.75 H 5.97 N 22.12 Found: 68.90 5.97 22.03

$R_f$ value: 0.24 (silica gel; methylene chloride/methanol= 9:1)

EXAMPLE 90

4'-[(2-n-Propyl-4-methyl-6-(1-isopropyl-imidazol-4-yl)-benzimidazol-1-yl)-methyl]-biphenyl-2-carboxylic acid Prepared analogously to Example 88 from tert.butyl 4'-[(2-n-propyl-4-methyl-6-(1-isopropyl-imidazol-4-yl)-benzimidazol-1-yl)-methyl]-biphenyl-2-carboxylate and trifluoroacetic acid in methylene chloride.

Yield: 84.0% of theory,

Melting point: 285°–286° C.

$R_f$ value: 0.55 (silica gel; methylene chloride/methanol= 9:1)

EXAMPLE 91

4'-[(2-n-Propyl-4-methyl-6-(1-n-hexyl-imidazol-4-yl)-benzimidazol-1-yl)-methyl]-biphenyl-2-carboxylic acid Prepared analogously to Example 88 from tert.butyl 4'-[(2-n-propyl-4-methyl-6-(1-n-hexyl-imidazol-4-yl)-benzimidazol- 1-yl)-methyl]-biphenyl-2-carboxylate and trifluoroacetic acid in methylene chloride.

Yield: 74.0% of theory,

Melting point: 258°–259° C.

$C_{34}H_{38}N_4O_2$ (534.71)

$R_f$ value: 0.48 (silica gel; methylene chloride/methanol= 9:1)

Mass spectrum: m/e=534

EXAMPLE 92

4'-[(2-n-Propyl-4-methyl-6-(1-cyclopentylmethyl-imidazol-4-yl)-benzimidazol-1-yl)-methyl]-biphenyl-2-carboxylic acid Prepared analogously to Example 88 from tert.butyl 4'-[(2-n-propyl-4-methyl-6-(1-cyclopentylmethyl-imidazol-4-yl)-benzimidazol-1-yl)-methyl]-biphenyl-2-carboxylate and trifluoroacetic acid in methylene chloride.

EXAMPLE 93

4'-[(2-n-Propyl-4-methyl-6-(1-cyclohexylmethyl-imidazol-4-yl)-benzimidazol-1-yl)-methyl]-biphenyl-2-carboxylic acid Prepared analogously to Example 88 from tert.butyl 4'-[(2-n-propyl-4-methyl-6-(1-cyclohexylmethyl-imidazol-4-yl)-benzimidazol-1-yl)-methyl]-biphenyl-2-carboxylate and trifluoroacetic acid in methylene chloride.

EXAMPLE 94

4'-[(2-n-Propyl-4-methyl -6-(1-benzyl-imidazol-4-yl)-benzimidazol-1-yl)-methyl]-biphenyl-2-carboxylic acid Prepared analogously to Example 88 from tert.butyl 4'-[(2-n-propyl-4-methyl-6-(1-benzyl-imidazol-4-yl)-benzimidazol -1-yl)-methyl]-biphenyl-2-carboxylate and trifluoroacetic acid in methylene chloride.

Yield: 44.0% of theory,
Melting point: 226°–227° C.
$C_{35}H_{32}N_4O_2$ (540.68)
$R_f$ value: 0.51 (silica gel; methylene chloride/methanol= 9:1)
Mass spectrum: m/e=540

EXAMPLE 95

4'-[(2-n-Propyl-4-methyl-6-(1-(4-fluorobenzyl)-imidazol-4-yl)-benzimidazol-1-yl)-methyl]-biphenyl-2-carboxylic acid Prepared analogously to Example 88 from tert.butyl 4'-[(2-n-propyl-4-methyl-6-(1-(4-fluorobenzyl)-imidazol-4-yl)-benzimidazol-1-yl)-methyl]-biphenyl-2-carboxylate and trifluoroacetic acid in methylene chloride.

The following compounds may be obtained analogously to Example 95:

4'-[(2-n-propyl-4-methyl -6-(1-(3-chlorobenzyl)-imidazol-4-yl)-benzimidazol-1-yl)-methyl]-biphenyl-2-carboxylic acid 4'-[(2-n-propyl-4-methyl-6-(1-(3,5-dimethoxybenzyl)-imidazol-4-yl)-benzimidazol-1-yl)-methyl]-biphenyl-2-carboxylic acid 4'-[(2-n-propyl-4-methyl -6-(1-(4-methylbenzyl)-imidazol-4-yl)-benzimidazol-1-yl)-methyl]-biphenyl-2-carboxylic acid 4'-[(2-n-propyl-4-methyl -6-(1-(4-trifluoromethyl-benzyl)-imidazol-4-yl)-benzimidazol-1-yl)-methyl]-biphenyl-2-carboxylic acid

EXAMPLE 96

4'-[(2-n-Propyl-4-methyl-6-(1-(2-phenylethyl)-imidazol-4-yl)-benzimidazol-1-yl)-methyl]-biphenyl-2-carboxylic acid Prepared analogously to Example 88 from tert.butyl 4'-[(2-n-propyl-4-methyl-6-(1-(2-phenylethyl)-imidazol-4-yl)-benzimidazol-1-yl)-methyl]-biphenyl-2-carboxylate and trifluoroacetic acid in methylene chloride.

EXAMPLE 97

4'-[(2-n-Propyl-4-methyl-6-(1-(2,2,2-trifluoroethyl)-imidazol-4-yl)-benzimidazol-1-yl)-methyl]-biphenyl-2-carboxylic acid Prepared analogously to Example 88 from tert.butyl 4'-[(2-n-propyl-4-methyl-6-(1-(2,2,2-trifluoroethyl)-imidazol-4-yl)-benzimidazol-1-yl)-methyl]-biphenyl-2-carboxylate and trifluoroacetic acid in methylene chloride.

EXAMPLE 98

4'-[(2-n-Propyl-4-methyl-6-(1-(3,3,3-trifluoropropyl)-imidazol-4-yl)-benzimidazol-1-yl)-methyl]-biphenyl-2-carboxylic acid Prepared analogously to Example 88 from tert.butyl 4'-[(2-n-propyl-4-methyl-6-(1-(3,3,3-trifluoropropyl)-imidazol -4-yl)-benzimidazol-1-yl)-methyl]-biphenyl-2-carboxylate and trifluoroacetic acid in methylene chloride.

EXAMPLE 99

4'-[(2-n-Propyl-4-methyl-6-(1-aminocarbonylmethyl-imidazol-4-yl)-benzimidazol-1-yl)-methyl]-biphenyl-2-carboxylic acid Prepared analogously to Example 88 from tert.butyl 4'-[(2-n-propyl-4-methyl-6-(1-aminocarbonylmethyl-imidazol-4-yl)-benzimidazol-1-yl)-methyl]-biphenyl-2-carboxylate and trifluoroacetic acid in methylene chloride.

EXAMPLE 100

4'-[(2-n-Propyl-4-methyl-6-(1-cyclobutylmethyl-imidazol-4-yl)-benzimidazol-1-yl)-methyl]-biphenyl-2-carboxylic acid Prepared analogously to Example 88 from tert.butyl 4'-[(2-n-propyl-4-methyl-6-(1-cyclobutylmethyl-imidazol-4-yl)-benzimidazol-1-yl)-methyl]-biphenyl-2-carboxylate and trifluoroacetic acid in methylene chloride.

EXAMPLE 101

4'-[(2-n-Propyl-4-methyl-6-(1-cyclopropylmethyl-imidazol-4-yl)-benzimidazol-1-yl)-methyl]-biphenyl-2-carboxylic acid Prepared analogously to Example 88 from tert.butyl 4'-[(2-n-propyl-4-methyl-6-(1-cyclopropylmethyl-imidazol-4-yl)-benzimidazol-1-yl)-methyl]-biphenyl-2-carboxylate and trifluoroacetic acid in methylene chloride.

Yield: 59.0% of theory,
Melting point: 279°–280° C.
$C_{32}H_{32}N_4O_2$ (504.64) Calculated: C 76.16 H 6.39 N 11.10 Found: 76.41 6.37 11.20
$R_f$ value: 0.44 (silica gel; methylene chloride/methanol= 9:1)
Mass spectrum: m/e=504

EXAMPLE 102

4'-[(2-n-Propyl-4-methyl-6-(1-isopropyl-imidazol-4-yl)-benzimidazol-1-yl)-methyl]-2-(1H-tetrazol-5-yl)-biphenyl Prepared analogously to Example 89 from 4'-[(2-n-propyl-4-methyl-6-(1-isopropyl-imidazol-4-yl)-benzimidazol-1-yl)-methyl]-2-cyano-biphenyl and sodium azide in dimethylformamide.

Yield: 18.0% of theory,
Melting point: amorphous
$C_{31}H_{32}N_8$ (516.66)
$R_f$ value: 0.29 (silica gel; methylene chloride/methanol= 9:1)
Mass spectrum: m/e=516

EXAMPLE 103

4'-[(2-n-Propyl-4-methyl-6-(1-cyclopropylmethyl-imidazol-4-yl)-benzimidazol-1-yl)-methyl]-2-(1H-tetrazol-5-yl)-biphenyl a) 4'-[(2-n-Propyl-4-methyl-6-(1-cyclopropylmethyl-imidazol-4-yl)-benzimidazol-1-yl)-methyl]-2-(2-triphenylmethyl-tetrazol-5-yl)-biphenyl To a solution of 300 mg (1.0 mMol) of 2-n-propyl-4-methyl-6-(1-cyclopropylmethyl-imidazol-4-yl)-benzimidazole and 110 mg (1.0 mMol) potassium tert.butoxide in 20 ml of dimethyl sulphoxide are added 560 mg (1.0 mMol) of 4'-bromomethyl-2-(2-triphenylmethyl-tetrazol-5-yl)-biphenyl and the mixture is stirred for 16 hours at ambient temperature, then stirred into about 120 ml of water and extracted four times with 15 ml of ethyl acetate. The organic extracts are washed with about 30 ml of water, dried and then evaporated to dryness. The crude product thus obtained is purified by column chromatography (100 g silica gel, eluant: methylene chloride/methanol=30:1).

Yield: 460 mg (60% of theory),
$R_f$ value: 0.78 (silica gel; methylene chloride/methanol= 9:1)

b) 4'-[(2-n-Propyl-4-methyl-6-(1-cyclopropylmethyl-imidazol-4-yl)-benzimidazol-1-yl)-methyl]-2-(1H-tetrazol-5-yl)-biphenyl A mixture of 460 mg (0.6 mMol) of 4'-[(2-n-propyl-4-methyl-6-(1-cyclopropylmethyl-imidazol-4-yl)-benzimidazol-1-yl)-methyl]-2-(2-triphenylmethyl-tetrazol-5-yl)-biphenyl and 10 ml of saturated methanolic hydrochloric acid is stirred for one hour at ambient temperature. The mixture is then evaporated to dryness, the residue is dissolved in dilute ammonia solution and washed with ether. The aqueous phase is adjusted to pH 5 to 6 with acetic acid and subsequently the solid precipitate is suction filtered. The crude product thus obtained is purified by column chromatography (100 g silica gel, eluant: methylene chloride/methanol=15:1)

Yield: 130 mg (41% of theory),
Melting point: amorphous
$C_{32}H_{32}N_8$ (528.67)
$R_f$ value: 0.32 (silica gel; methylene chloride/methanol=9:1)
Mass spectrum: m/e=528

EXAMPLE 104

4'-[(2-n-Propyl-4-methyl-6-(1-cyclobutylmethyl-imidazol-4-yl)-benzimidazol-1-yl)-methyl ]-2-(1H-tetrazol-5-yl)-biphenyl Prepared analogously to Example 103 from 4'-[(2-n-propyl-4-methyl-6-(1-cyclobutylmethyl-imidazol-4-yl)-benzimidazol-1-yl)-methyl]-2-(2-triphenylmethyl-tetrazol-5-yl)-biphenyl and sodium azide in dimethylformamide.

EXAMPLE 105

4'-[(2-n-Propyl-4-methyl-6-(2-methyl-oxazol4-yl)-benzimidazol-1-yl)-methyl]-biphenyl-2-carboxylic acid Prepared analogously to Example 88 from tert.butyl 4'-[(2-n-propyl-4-methyl-6-(2-methyl-oxazol-4-yl)-benzimidazol-1-yl)-methyl]-biphenyl-2-carboxylate and trifluoroacetic acid in methylene chloride.

Yield: 67.0% of theory,
Melting point: 241°–243° C.
$C_{29}H_{27}N_3O_3$ (465.56) Calculated: C 74.82 H 5.85 N 9.03 Found: 74.65 5.98 8.85
$R_f$ value: 0.27 (silica gel; methylene chloride/ethanol=19:1)

EXAMPLE 106

4'-[(2-n-Propyl-4-methyl-6-(2-methyl-oxazol-4-yl)-benzimidazol-1-yl)-methyl]-2-(1H-tetrazol-5-yl)-biphenyl Prepared analogously to Example 103 from 4'-[(2-n-propyl-4-methyl-6-(2-methyl-oxazol-4-yl)-benzimidazol-1-yl)-methyl ]-2-(2-triphenylmethyl-tetrazol -5-yl)-biphenyl and sodium azide in dimethylformamide.

EXAMPLE 107

4'-[(2-n-Propyl-4-methyl-6-(2-phenyl-oxazol-4-yl)-benzimidazol-1-yl)-methyl]-biphenyl -2-carboxylic acid Prepared analogously to Example 88 from tert.butyl 4'-[(2-n-propyl-4-methyl-6-(2-phenyl-oxazol-4-yl)-benzimidazol-1-yl)-methyl]-biphenyl-2-carboxylate and trifluoroacetic acid in methylene chloride.

Yield: 87.0% of theory,
Melting point: 281°–283° C.
$C_{34}H_{29}N_3O_3$ (527.63) Calculated: C 77.40 H 5.54 N 7.96 Found: 77.09 5.71 7.76
$R_f$ value: 0.18 (silica gel; methylene chloride/ethanol=19:1)

EXAMPLE 108

4'-[(2-n-Propyl-4-methyl-6-(2-phenyl-oxazol-4-yl)-benzimidazol-1-yl)-methyl]-2-(1H-tetrazol-5-yl)-biphenyl Prepared analogously to Example 103 from 4'-[(2-n-propyl-4-methyl-6-(2-phenyl-oxazol-4-yl)-benzimidazol-1-yl)-methyl]-2-(2-triphenylmethyl-tetrazol-5-yl)-biphenyl and sodium azide in dimethylformamide.

EXAMPLE 109

4'-[(2-n-Propyl-4-methyl-6-(1-benzyl-imidazol-4-yl)-benzimidazol-1-yl)-methyl]-2-(1H-tetrazol-5-yl)-biphenyl Prepared analogously to Example 103 from 4'-[(2-n-propyl-4-methyl-6-(1-benzyl-imidazol-4-yl)-benzimidazol-1-yl)-methyl]-2-(2-triphenylmethyl-tetrazol-5-yl)-biphenyl.

Yield: 45.0% of theory,
Melting point: 168°–170° C.
$C_{35}H_{32}N_8$ (564.70)
$R_f$ value: 0.37 (silica gel; methylene chloride/methanol=9:1)
Mass spectrum: m/e=564

EXAMPLE 110

4'-[(2-n-Propyl-4-methyl-6-(1-n-hexyl-imidazol-4-yl)-benzimidazol-1-yl)-methyl]-2-(1H-tetrazol-5-yl)-biphenyl Prepared analogously to Example 103 from 4'-[(2-n-Propyl-4-methyl-6-(1-n-hexyl-imidazol-4-yl)-benzimidazol-1-yl)-methyl]-2-(2-triphenylmethyl-tetrazol-5-yl)-biphenyl.

Yield: 61.0% of theory,
Melting point: 126°–128° C.
$C_{34}H_{38}N_8$ (558.74)
$R_f$ value: 0.31 (silica gel; methylene chloride/methanol=9:1)
Mass spectrum: m/e=558

EXAMPLE 111

4'-[(2-Ethoxy-6-(1-isopropyl-imidazol-4-yl)-benzimidazol-1-yl)-methyl]-2-(1H-tetrazol-5-yl)-biphenyl Prepared analogously to Example 103 from 4'-[(2-ethoxy-6-(1-isopropyl-imidazol-4-yl)-benzimidazol-1-yl)-methyl]-2-(2-triphenylmethyl-tetrazol-5-yl)-biphenyl.

Yield: 69.0% of theory,
Melting point: 175°–178° C.
$C_{29}H_{28}N_8O$ (504.61) Calculated: C 69.03 H 5.59 N 22.21 Found: 68.85 5.58 21.97
$R_f$ value: 0.27 (silica gel; methylene chloride/ethanol=9:1)
Mass spectrum: m/e=504

EXAMPLE 112

4'-[(2-Ethoxy-6-(1-isopropyl-imidazol-4-yl)-benzimidazol-1-yl)-methyl]-biphenyl-2-carboxylic acid Prepared analogously to Example 88 from tert.butyl 4'-[(2-ethoxy-6-(1-isopropyl-imidazol-4-yl)-benzimidazol-1-yl)-methyl]-biphenyl-2-carboxylate and trifluoroacetic acid in methylene chloride.

Yield: 38.0% of theory,
Melting point: 220°–223° C.
$C_{29}H_{28}N_4O_3$ (480.58) Calculated: C 72.48 H 5.87 N 11.66 Found: 72.36 6.05 11.41
$R_f$ value: 0.26 (silica gel; methylene chloride/methanol=9:1)
Mass spectrum: m/e=480

EXAMPLE 113

4'-[(2-Ethoxy-5-(1-isopropyl-imidazol-4-yl)-benzimidazol-1-yl)-methyl]-2-(1H-tetrazol-5-yl)-biphenyl Prepared analogously to Example 103 from 4'-[(2-ethoxy-5-(1-isopropyl-imidazol-4-yl)-benzimidazol-1-yl)-methyl]-2-(2-triphenylmethyl-tetrazol-5-yl)-biphenyl.

Yield: 44.0% of theory,
Melting point: amorphous
$C_{29}H_{28}N_8O$ (504.61)
$R_f$ value: 0.24 (silica gel; methylene chloride/ethanol= 9:1)
Mass spectrum: m/e=504

EXAMPLE 114

4'-[(2-n-Propyl-4-methyl-6-(1-cycloheptyl-imidazol-4-yl)-benzimidazol-1-yl)-methyl]-biphenyl-2-carboxylic acid Prepared analogously to Example 88 from tert.butyl 4'-[(2-n-propyl-4-methyl-6-(1-cycloheptyl-imidazol-4-yl)-benzimidazol-1-yl)-methyl]-biphenyl-2-carboxylate and trifluoroacetic acid in methylene chloride.

Yield: 79.0% of theory,
Melting point: from 190° C. (decomp.)
$C_{35}H_{38}N_4O_2$ (546.71)
$R_f$ value: 0.36 (silica gel; methylene chloride/methanol= 9:1)
Mass spectrum: m/e=546

EXAMPLE 115

4'-[(2-n-Propyl-4-methyl-6-(1-cycloheptyl-imidazol-4-yl)-benzimidazol-1-yl)-methyl]-2-(1H-tetrazol-5-yl)-biphenyl Prepared analogously to Example 103 from 4'-[(2-n-propyl-4-methyl-6-(1-cycloheptyl-imidazol-4-yl)-benzimidazol-1-yl)-methyl]-2-(2-triphenylmethyl-tetrazol-5-yl)-biphenyl.

Yield: 27.0% of theory,
Melting point: 198°–201° C.
$C_{35}H_{38}N_8$ (570.75)
$R_f$ value: 0.48 (silica gel; methylene chloride/methanol= 9:1)
Mass spectrum: m/e=570

EXAMPLE 116

4'-[(2-n-Propyl-4-methyl-6-(1-(1-n-propyl-n-butyl)-imidazol-4-yl)-benzimidazol-1-yl)-methyl]-biphenyl-2-carboxylic acid Prepared analogously to Example 88 from tert.butyl 4'-[(2-n-propyl-4-methyl-6-(1-(1-n-propyl-n-butyl)-imidazol-4-yl)-benzimidazol-1-yl)-methyl]-biphenyl-2-carboxylate and trifluoroacetic acid in methylene chloride.

Yield: 28.0% of theory,
Melting point: 236°–238° C.
$C_{35}H_{40}N_4O_2$ (548.73)
$R_f$ value: 0.61 (silica gel; methylene chloride/methanol= 9:1)
Mass spectrum: m/e=548

EXAMPLE 117

4'-[(2-Ethoxy-4-methyl-6-(1-cyclopropylmethyl-imidazol-4-yl)-benzimidazol-1-yl)-methyl]-biphenyl-2-carboxylic acid Prepared analogously to Example 88 from tert.butyl 4'-[(2-ethoxy-4-methyl-6-(1-cyclopropylmethyl-imidazol-4-yl)-benzimidazol-1-yl)-methyl]-biphenyl-2-carboxylate and trifluoroacetic acid in methylene chloride.

Yield: 52.0% of theory,
Melting point: 172°–173° C.
$C_{31}H_{30}N_4O_3$ (506.61) Calculated: C 73.50 H 5.97 N 11.06 Found: 73.36 5.94 11.30
$R_f$ value: 0.52 (silica gel; methylene chloride/methanol= 9:1)
Mass spectrum: m/e=506

EXAMPLE 118

4'-[(2-Ethoxy-4-methyl-6-(1-cyclopropylmethyl-imidazol-4-yl)-benzimidazol-1-yl)-methyl]-2-(1H-tetrazol-5-yl)-biphenyl Prepared analogously to Example 103 from 4'-[(2-ethoxy-4-methyl-6-(1-cyclopropylmethyl-imidazol-4-yl)-benzimidazol-1-yl)-methyl]-2-(2-triphenylmethyl-tetrazol-5-yl)-biphenyl.

Yield: 42.0% of theory,
Melting point: amorphous
$C_{31}H_{30}N_8O$ (530.64)
$R_f$ value: 0.50 (silica gel; methylene chloride/methanol= 9:1)
Mass spectrum: m/e=530

EXAMPLE 119

4'-[(2-n-Propyl-4-methyl-6-(1-(1-n-propyl-n-butyl)-imidazol-4-yl)-benzimidazol-1-yl)-methyl]-2-(1H-tetrazol-5-yl)-biphenyl Prepared analogously to Example 103 from 4'-[(2-n-propyl-4-methyl-6-(1-(1-n-propyl-n-butyl)-imidazol-4-yl)-benzimidazol-1-yl)-methyl]-2-(2-triphenylmethyl-tetrazol-5-yl)-biphenyl.

Yield: 12.0% of theory,
Melting point: from 150° C. (sintering)
$C_{35}H_{40}N_8$ (572,76)
$R_f$ value: 0.34 (silica gel; methylene chloride/methanol= 9:1)
Mass spectrum: m/e=572

EXAMPLE 120

4'-[(2-n-Propyl-4-methyl-6-(1,2-dimethyl-imidazol-4-yl)-benzimidazol-1-yl)-methyl]-biphenyl-2-carboxylic acid hydrate a) tert. Butyl 4'-[(2-n-propyl-4-methyl-6-(2-methyl-oxazol-4-yl)-benzimidazol-1-yl)-methyl]-biphenyl-2-carboxylate A solution of 2.8 g (11 mMol) of 2-n-propyl-4-methyl-6-(2-methyl-oxazol-4-yl)-benzimidazole and 1.7 g (15 mMol) of potassium tert.butoxide in 60 ml of dimethylsulphoxide is stirred for 15 minutes at ambient temperature. Then 5.2 g (15 mMol) of tert.butyl 4'-bromomethyl-biphenyl-2-carboxylate are added and the mixture is stirred for a further 14 hours at ambient temperature. Then the solution is stirred into about 150 ml of saturated sodium chloride solution, the crude product precipitated is suction filtered and purified by column chromatography (400 g of silica gel; eluant: methylene chloride with 1 to 2% ethanol).

Yield: 3.5 g (61.4% of theory),
Melting point: amorphous
$R_f$ value: 0.90 (silica gel; methylene chloride/ethanol= 4:1)

4'-[(2-n-Propyl-4-methyl-6-(1,2-dimethyl-imidazol-4-yl)-benzimidazol-1-yl)-methyl]-biphenyl-2-carboxylic acid hydrate A mixture of 1.5 g (3 mMol) of tert.butyl 4'-[(2-n-propyl-4-methyl-6-(2-methyl-oxazol-4-yl)-benzimidazol-1-yl)-methyl]-biphenyl-2-carboxylate, 10 ml of 40% N-methylamine solution and 15 ml of N-methylformamide is heated for 10 hours to 200° C. in an autoclave. After cooling, the contents of the autoclave are stirred with about 40 ml of water, this suspension is adjusted to pH 6.5 with glacial acetic acid, then the crude product precipitated is suction filtered and dissolved in 1N sodium hydroxide solution. This solution is washed successively with 25 ml of acetic acid and diethylether, then adjusted to pH 6 with 20% citric acid. The product precipitated is suction filtered, washed with about 30 ml of water and dried, then triturated with diethylether and dried in a high vacuum.

Yield: 950 mg (68% of theory),
Melting point: 239°–240° C.
$C_{30}H_{30}N_4O_2 \times H_2O$ (496.62) Calculated: C 72.55 H 6.49 N 11.28 Found: 72.62 6.62 11.54
$R_f$ value: 0.70 (silica gel; methylene chloride/ethanol=4:1)

EXAMPLE 121

4'-[(2-n-Propyl-4-methyl-6-(1,2-dimethyl-imidazol-4-yl)-benzimidazol-1-yl)-methyl]-2-(1H-tetrazol-5-yl)-biphenyl-hydrate a) 4'-[(2-n-Propyl-4-methyl-6-(2-methyl-oxazol-4-yl)-benzimidazol-1-yl)-methyl]-2-(2-triphenylmethyl-tetrazol-5-yl)-biphenyl A solution of 2.8 g (11 mMol) of 2-n-propyl-4-methyl-6-(2-methyl-oxazol-4-yl)-benzimidazole and 1.7 g (15 mMol) of potassium tert.butoxide in 60 ml of dimethylsulphoxide is stirred for 15 minutes at ambient temperature. Then 6.0 g of (11 mMol) of 4'-bromomethyl-2-(2-triphenylmethyl-tetrazol-5-yl)-biphenyl are added and the mixture is stirred for a further 3 hours at ambient temperature. Then the solution is stirred into about 150 ml of saturated sodium chloride solution, the crude product precipitated is suction filtered and purified by column chromatography (500 g of silica gel; eluant: petroleum ether/ethyl acetate=1:1)

Yield: 3.6 g (45% of theory)

b) 4'-[(2-n-Propyl-4-methyl-6-(1,2-dimethyl-imidazol-4-yl)-benzimidazol-1-yl)-methyl]-2-(1H-tetrazol-5-yl)-biphenyl-hydrate A mixture of 3.6 g (4,9 mMol) of 4'[(2-n-propyl-4-methyl-6-(2-methyl-oxazol-4-yl)-benzimidazol-1-yl)-methyl]-2-(2-triphenyl-methyl-tetrazol-5-yl)-biphenyl, 20 ml of 40% N-methylamine solution and 30 ml of N-methylformamide is heated to 200° C. for 10 hours in an autoclave. After cooling, the contents of the autoclave are stirred with about 50 ml of water, this suspension is adjusted to pH 6.5 with 20% citric acid, then the crude product precipitated is suction filtered and purified by column chromatography (200 g silica gel; eluant: methylene chloride with 5 to 20% ethanol).

Yield: 1.0 g (41% of theory),
Melting point: from 195° C. sintering
$C_{30}H_{30}N_8 \times H_2O$ (520.6) Calculated: C 69.21 H 6.19 N 21.52 Found: 68.99 6.26 21.37
Mass spectrum: m/e=502

EXAMPLE 122

4'-[(2-Ethyl-4-methyl-6-(1-(2-methoxyethyl)-imidazol-4-yl)-benzimidazol-1-yl)-methyl]-biphenyl-2-carboxylic acid Prepared analogously to Example 88 from tert.butyl 4'-[(2-ethyl-4-methyl-6-(1-(2-methoxyethyl)-imidazol-4-yl)-benzimidazol- 1-yl)-methyl]-biphenyl-2-carboxylate and trifluoroacetic acid in methylene chloride.

Yield: 49% of theory,
Melting point: 165°–167° C.
$C_{30}H_{30}N_4O_3$ (494.60) Calculated: C 72.85 H 6.11 N 11.33 Found: 72.62 6.27 11.35
Mass spectrum: m/e=494

EXAMPLE 123

4'-[(2-Cyclopropyl-4-methyl-6-(1-(2-methoxyethyl)-imidazol-4-yl)-benzimidazol-1-yl)-methyl]-biphenyl-2-carboxylic acid Prepared analogously to Example 88 from tert. butyl 4'-[(2-cyclopropyl-4-methyl-6-(1-(2-methoxyethyl)-imidazol-4-yl)-benzimidazol-1-yl)-methyl]-biphenyl-2-carboxylate and trifluoroacetic acid in methylene chloride.

Yield: 78% of theory,
Melting point: 179°–181° C.
$C_{31}H_{30}N_4O_3$ (506.61) Calculated: C 73.50 5.97 N 11.06 Found: 73.37 6.02 11.02
Mass spectrum: m/e=506

EXAMPLE 124

4'-[(2-n-Propyl-4-methyl-6-(1-aminocarbonylmethyl-imidazol-4-yl)-benzimidazol-1-yl)-methyl]-biphenyl-2-carboxylic acid Prepared analogously to Example 88 from tert. butyl 4'-[(2-n-propyl-4-methyl-6-(1-aminocarbonylmethyl-imidazol-4-yl)-benzimidazol-1-yl)-methyl]-biphenyl-2-carboxylate and trifluoroacetic acid in methylene chloride.

Yield: 26% of theory,
Melting point: 190°–192° C.
$C_{30}H_{29}N_5O_3$ (507.60)
$R_f$ value: 0.44 (silica gel; methylene chloride/methanol=8:2)

EXAMPLE 125

4'-[(2-n-Propyl-4-methyl-6-(1-ethoxycarbonylmethyl-imidazol-4-yl)-benzimidazol-1-yl)-methyl]-biphenyl-2-carboxylic acid Prepared analogously to Example 88 from tert.butyl 4'-[(2-n-propyl-4-methyl-6-(1-ethoxycarbonylmethyl-imidazol-4-yl)-benzimidazol-1-yl)-methyl]-biphenyl-2-carboxylate and trifluoroacetic acid in methylene chloride.

Yield: 18% of theory,
Melting point: 223°–224° C.
$C_{32}H_{32}N_4O_4$ (536.63)
$R_f$ value: 0.69 (silica gel; methylene chloride/methanol=8:2)
Mass spectrum: m/e=536

EXAMPLE 126

4'-[(2-Cyclopropyl-4-methyl-6-(1-(2-hydroxyethyl)-imidazol-4-yl)-benzimidazol-1-yl)-methyl]-biphenyl-2-carboxylic acid A solution of 500 mg (1.0 mMol) of 4'-[(2-cyclopropyl-4-methyl-6-(1-(2-methoxyethyl)-imidazol-4-yl)-benzimidazol-1-yl)-methyl]-biphenyl-2-carboxylic acid and 1.5 g (6.0 mMol) of boron tribromide in 50 ml of methylene chloride is stirred for 16 hours at ambient temperature, then mixed with about 30 ml of water and stirred vigorously for another 10 minutes. This mixtures evaporated to dryness and the residue is refluxed in about 40 ml of ethanol for 10 minutes. The mixture is evaporated to dryness once more, the residue is dissolved in about 30 ml of 2N ammonia solution and this solution is adjusted to pH 5–6 with 2N acetic acid. The crude product precipitated is suction filtered and purified by column chromatography (80 g silica gel; eluant: methylene chloride/methanol=4:1).
Yield: 150 mg (30% of theory),
Melting point: 220°–222° C.
$C_{30}H_{28}N_4O_3$ (492.58)
$R_f$ value: 0.20 (silica gel; methylene chloride/methanol= 9:1)
Mass spectrum: m/e=492

EXAMPLE 127

4'-[(2-n-Propyl-4-methyl-6-(1-(2-N-morpholinoethyl)-imidazol-4-yl)-benzimidazol-1-yl)-methyl]-biphenyl-2-carboxylic acid Prepared analogously to Example 88 from tert. butyl 4'-[(2-n-propyl-4-methyl-6-(1-(2-N-morpholinoethyl)-imidazol-4-yl)-benzimidazol-1-yl)-methyl]-biphenyl-2-carboxylate and trifluoroacetic acid in methylene chloride.
Yield: 54% of theory,
Melting point: 259°–261° C.
$C_{34}H_{37}N_5O_3$ (563.70) Calculated: C 72.44 H 6.62 N 12.42 Found: 72.68 6.65 12.53
Mass spectrum: m/e=563

EXAMPLE 128

4'-[(2-n-Propyl-4-methyl-6-(1-(2-methoxyethoxy-2-ethyl)-imidazol-4-yl)-benzimidazol-1-yl)-methyl]-biphenyl-2-carboxylic acid Prepared analogously to Example 88 from tert.butyl 4'-[(2-n-propyl-4-methyl-6-(1-(2-methoxyethoxy-2-ethyl)-imidazol-4-yl)-benzimidazol-1-yl)-methyl]-biphenyl-2-carboxylate and trifluoroacetic acid in methylene chloride.
Yield: 49% of theory,
Melting point: 192°–194° C.
$C_{33}H_{36}N_4O_4$ (552.67) Calculated: C 71.72 H 6.57 N 10.14 Found: 71.52 6.36 10.25
$R_f$ value: 0.36 (silica gel; dichloromethane/methanol=9:1)
Mass spectrum: m/e=552

EXAMPLE 129

4'-[(2-n-Propyl-4-methyl-6-(1-(3-dimethylaminopropyl)-imidazol-4-yl)-benzimidazol-1-yl)-methyl]-biphenyl-2-carboxylic acid dihydrochloride-pentahydrate Prepared analogously to Example 88 from tert.butyl 4'-[(2-n-propyl-4-methyl-6-(1-(3-dimethylaminopropyl)-imidazol-4-yl)-benzimidazol-1-yl)-methyl]-biphenyl-2-carboxylate and trifluoroacetic acid in methylene chloride.
Yield: 12% of theory,
Melting point: from 128° C. (decomp.)
$C_{33}H_{37}N_5O_2 \times 2$ HCl$\times 5$ H$_2$O (535.70)
$R_f$ value: 0.20 (silica gel; dichloromethane/methanol=9:1)
Mass spectrum: m/e=535

EXAMPLE 130

4'-[(2-n-Propyl-4-methyl-6-(2-methyl-thiazol-4-yl)-benzimidazol-1-yl)-methyl]-biphenyl-2-carboxylic acid Prepared analogously to Example 88 from tert.butyl 4'-[(2-n-propyl-4-methyl-6-(2-methyl-thiazol-4-yl)-benzimidazol-1-yl)-methyl]-biphenyl-2-carboxylate and trifluoroacetic acid in methylene chloride.
Yield: 32% of theory,
Melting point: 248°–250° C.
$C_{29}H_{27}N_3O_2S$ (481.62) Calculated: C 72.32 H 5.65 N 8.72 Found: 72.21 5.83 8.67

$R_f$ value: 0.26 (silica gel; dichloromethane/methanol=9:1)
Mass spectrum: m/e=481

EXAMPLE 131

4'-[(2-n-Propyl-4-methyl-6-(2-methyl-thiazol-4-yl)-benzimidazol-1-yl)-methyl]-2-(1H-tetrazol-5-yl)-biphenyl-dihydrochloride Prepared analogously to Example 103 from 4'-[(2-n-propyl-4-methyl-6-(2-methyl-thiazol-4-yl)-benzimidazol-1-yl)-methyl]-2-(2-triphenylmethyl-tetrazol-5-yl)-biphenyl.
Yield: 91% of theory,
Melting point: from 219° C. (decomp.)
$C_{29}H_{29}$
$C_{12}N_7S$ (578.58) Calculated: C 60.20 H 5.05 N 16.95 Cl 12.25 Found: 59.96 5.19 16.63 12.42
$R_f$ value: 0.32 (silica gel; dichloromethane/methanol=9:1)
Mass spectrum: m/e=505

EXAMPLE 132

4'-[(2-Ethyl-4-methyl-6-(1-(2-N-morpholinoethyl)-imidazol-4-yl)-benzimidazol-1-yl)-methyl]-biphenyl-2-carboxylic acid Prepared analogously to Example 88 from tert.butyl 4'-[(2-ethyl-4-methyl-6-(1-(2-N-morpholinoethyl)-imidazol-4-yl)-benzimidazol-1-yl)-methyl]-biphenyl-2-carboxylate and trifluoroacetic acid in methylene chloride.
Yield: 27% of theory,
Melting point: 201°–202° C.
$C_{33}H_{35}N_5O_3$ (549.65) Calculated: C 72.11 H 6.42 N 12.74 Found: 72.00 6.48 12.62
$R_f$ value: 0.36 (silica gel; methylene chloride/methanol=9:1)
mass spectrum: m/e=549

EXAMPLE 133

4'-[(2-Ethyl-4-methyl-6-(1-(2-N-morpholinoethyl)-imidazol-4-yl)-benzimidazol-1-yl)-methyl]-2-(1H-tetrazol-5-yl)-biphenyl-hydrate Prepared analogously to Example 103 from 4'-[(2-ethyl-4-methyl-6-(1-(2-N-morpholinoethyl)-imidazol-4-yl)-benzimidazol-1-yl)-methyl]-2-(2-triphenylmethyl-tetrazol-5-yl)-biphenyl.
Yield: 14% of theory,
Melting point: above 180° C. (decomp.)
$C_{33}H_{35}N_9O \times H_2O$ (573.68) Calculated: C 66.98 H 6.30 N 21.31 Found: 66.87 6.36 21.22
$R_f$ value: 0.31 (silica gel; methylene chloride/methanol=9:1)
mass spectrum: m/e=573

EXAMPLE 134

4'-[(2-Ethyl-4-methyl-6-(1-(2-aminocarbonylethyl)-imidazol-4-yl)-benzimidazol-1-yl)-methyl]-biphenyl-2-carboxylic acid Prepared analogously to Example 88 from tert.butyl 4'-[(2-ethyl-4-methyl-6-(1-(2-aminocarbonylethyl)-imidazol-4-yl)-benzimidazol-1-yl)-methyl]-biphenyl-2-carboxylate and trifluoroacetic acid in methylene chloride.
Yield: 66% of theory,
Melting point: above 185° C. (decomp.)
$C_{30}H_{29}N_5O_3$ (507.59) Calculated: C 70.99 H 5.76 N 13.80 Found: 70.73 5.72 13.66
mass spectrum: m/e=507

EXAMPLE 135

4'-[(2-Ethyl-4-methyl-6-(1-(2-aminocarbonylethyl)-imidazol-4-yl)-benzimidazol-1-yl)-methyl]-2-(1H-tetrazol-5-yl)-biphenyl Prepared analogously to Example 103 from 4'-[(2-ethyl-4-methyl-6-(1-(2-aminocarbonylethyl)-imidazol-4-yl)-benzimidazol-1-yl)-methyl]-2-(2-triphenylmethyl-tetrazol-5-yl)-biphenyl.

Yield: 42% of theory,
Melting point: above 119° C. (decomp.)
$C_{30}H_{29}N_9O$ (531.63) Calculated: C 67.78 H 5.50 N 23.71 Found: 67.79 5.40 23.66
$R_f$ value: 0.20 (silica gel; methylene chloride/methanol= 8:2)
mass spectrum: m/e=531

EXAMPLE 136

4'-[(2-Ethyl-4-methyl-6-(1-(2-N-pyrrolidinoethyl)-imidazol-4-yl)-benzimidazol-1-yl)-methyl]-biphenyl-2-carboxylic acid Prepared analogously to Example 88 from tert.butyl 4'-[(2-ethyl-4-methyl-6-(1-(2-N-pyrrolidinoethyl)-imidazol-4-yl)-benzimidazol-1-yl)-methyl]-biphenyl-2-carboxylate and trifluoroacetic acid in methylene chloride.

Yield: 60% of theory,
Melting point: 215°–217° C.
$C_{33}H_{35}N_5O_2$ (533.67) Calculated: C 74.27 H 6.61 N 13.12 Found: 74.03 6.85 13.11
$R_f$ value: 0.30 (silica gel; methylene chloride/methanol= 8:2)
mass spectrum: m/e=533

EXAMPLE 137

4'-[(2-Ethyl-4-methyl-6-(1-(2-N-pyrrolidinoethyl)-imidazol-4-yl)-benzimidazol-1-yl)-methyl]-2-(1H-tetrazol-5-yl)-biphenyl Prepared analogously to Example 103 from 4'-[(2-ethyl-4-methyl-6-(1-(2-N-pyrrolidinoethyl)-imidazol-4-yl)-benzimidazol-1-yl)-methyl]-2-(2-triphenylmethyl-tetrazol-5-yl)-biphenyl.

Yield 38% of theory,
Melting point: above 128° C. (sintering)
$C_{33}H_{35}N_9$ (551.71) Calculated: C 71.84 H 6.39 N 22.85 Found: 71.63 6.20 22.49
$R_f$ value: 0.23 (silica gel; methylene chloride/methanol= 8:2)

EXAMPLE 138

4'-[(2-Ethyl-4-methyl-6-(1-(2-diethylaminoethyl)-imidazol-4-yl)-benzimidazol-1-yl)-methyl]-biphenyl-2-carboxylic acid-dihydrochloride Prepared analogously to Example 88 from tert.butyl 4'-[(2-ethyl-4-methyl-6-(1-(2-diethylaminoethyl)-imidazol-4-yl)-benzimidazol-1-yl)-methyl]-biphenyl-2-carboxylate and trifluoroacetic acid in methylene chloride.

Yield: 32% of theory,
Melting point: 255°–257° C. (decomp.)
$C_{33}H_{37}N_5O_2 \times 2$ HCL (608.60)
$R_f$ value: 0,24 (silica gel; methylene chloride/methanol= 9:1)

EXAMPLE 139

4'-[(2-Ethyl-4-methyl-6-(1-(2-diethylaminoethyl)-imidazol-4-yl)-benzimidazol-1-yl)-methyl]-2-(1H-tetrazol-5-yl)-biphenyl Prepared analogously to Example 103 from 4'-[(2-ethyl-4-methyl-6-(1-(2-diethylaminoethyl)-imidazol-4-yl)-benzimidazol-1-yl)-methyl]-2-(2-triphenylmethyl-tetrazol-5-yl)-biphenyl.

Yield: 51% of theory
Melting point: 191°–193° C.
$C_{33}H_{37}N_9$ (559.70) Calculated C 70.81 H 6.66 N 22.52 Found: 70.59 6.66 22.58
$R_f$ value: 0,30 (silica gel; methylene chloride/methanol= 8:2)

EXAMPLE 140

4'-[(2-Ethyl-4-methyl-6-(1-(3-N-piperidinopropyl)-imidazol-4-yl)-benzimidazol-1-yl)-methyl]-biphenyl-2-carboxylic acid Prepared analogously to Example 88 from tert.butyl 4'-[(2-ethyl-4-methyl-6-(1-(3-N-piperidinopropyl)-imidazol-4-yl)-benzimidazol-1-yl)-methyl]-biphenyl-2-carboxylate and trifluoroacetic acid in methylene chloride.

Yield: 19% of theory,
Melting point: amorphous
$C_{35}H_{39}N_5O_2$ (561.73) Calculated: C 74.84 H 7.00 N 12.47 Found: 74.61 6.92 12.31
$R_f$ value: 0.34 (silica gel; methylene chloride/methanol= 8:2)

EXAMPLE 141

4'-[(2-Ethyl-4-methyl-6-(1-(3-N-piperidinopropyl)-imidazol-4-yl)-benzimidazol-1-yl)-methyl]-2-(1H-tetrazol-5-yl)-biphenyl Prepared analogously to Example 103 from 4'-[(2-ethyl-4-methyl-6-(1-(3-N-piperidinopropyl)-imidazol-4-yl)-benzimidazol-1-yl)-methyl]-2-(2-triphenylmethyl-tetrazol-5-yl)-biphenyl.

Yield: 71% of theory,
Melting point: above 140° C. (decomp.)
$C_{35}H_{39}N_9$ (585.76) Calculated: C 71.77 H 6.71 N 21.52 Found: 71.58 6.68 21.44
$R_f$ value: 0.22 (silica gel; methylene chloride/methanol= 8:2)

EXAMPLE 142

Methyl 4'-[[2-n-propyl-4-methyl-6-(5,6,7,8-tetrahydro-benzimidazol-2-yl)-1H-benzimidazol-1-yl]-methyl]-biphenyl-2-carboxylate a) Methyl 4'-[(2-n-propyl-4-methyl-6-amidino-1H-benzimidazol-1-yl)-methyl]-biphenyl-2-carboxylate Hydrogen chloride gas is piped into a solution of 6.2 g (14.6 mMol) of methyl 4'-[[2-n-propyl-4-methyl-6-cyano-1H-benzimidazol-1-yl]-methyl]-biphenyl-2-carboxylate in 750 ml of absolute methanol for 3 hours at ambient temperature and the mixture is stirred for a further 2 hours at ambient temperature. After removal of the solvent the mixture is evaporated down in vacuo, the residue is taken up twice with 50 ml of methanol and 50 ml of ether and evaporated down once more. Then the residue is dissolved in 750 ml of absolute methanol and mixed with 30 g of ammonium carbonate. After 12 hours at ambient temperature, 50 g of silica gel (particle size: 0.06–0.3 mm) are added. After filtration and evaporation of the filtrate the residue is chromatographed on silica gel (particle size 0.032–0.063 mm) using as eluant mixtures of methylene chloride and methanol of increasing polarity (9:1, 4:1, 3:1 and 1:1). The uniform fractions are combined and evaporated down.

Yield: 4.3 g (57% of theory),

Foam, $R_f$ value: 0.14 (silica gel; methylene chloride/ethanol=9:1)

b) Methyl 4'-[(2-n-propyl-4-methyl-6-(5,6,7,8-tetrahydrobenzimidazol-2-yl)-1H-benzimidazol-1-yl]-methyl]-biphenyl-2-carboxylate 0.5 g (1.0 mMol) of methyl 4'-[(2-n-propyl-4-methyl-6-amidino-1H-benzimidazol-1-yl]-methyl]-biphenyl-2-carboxylate, 0.13 g (1.0 mMol) of 2-chloro-cyclohexanone and 10 ml of liquid ammonia are heated to 60° C. in a bomb for 15 hours. After cooling and evaporation of the ammonia the residue is dissolved in methanol/methylene chloride (2:1) and chromatographed on silica gel (particle size: 0.032–0.063 mm), using as eluant mixtures of methylene chloride and ethanol of increasing polarity (19:1 and 9:1). The uniform fractions are combined and evaporated down.

Yield: 0.1 g (19% of theory),

Foam, $R_f$ value: 0.50 (silica gel; methylene chloride/ethanol=9:1)

EXAMPLE 143

4'-[[2-n-Propyl-4-methyl-6-(5,6,7,8-tetrahydro-benzimidazol-2-yl)-1H-benzimidazol-1-yl]-methyl]-biphenyl-2-carboxylic acid 0.1 g (0.2 mMol) of methyl 4'-[[2-n-propyl-4-methyl-6-(5,6,7,8-tetrahydrobenzimidazol-2-yl)-1H-benzimidazol-1-yl]-methyl]-biphenyl-2-carboxylate and 10 mg (0.02 mMol) of hexadecyl-tributylphosphonium bromide are taken up in 10 ml of (48%) hydrobromic acid and heated to 110° C. for 15 minutes. After cooling, 20 ml of ether are poured over and the mixture is diluted with 10 ml of water. After extraction the organic phase is separated off. The aqueous phase is adjusted to pH 7 with ammonia, the precipitate thus formed is suction filtered, washed with water and taken up in methylene chloride/ethanol (4:1). The solvent is evaporated off, the residue is triturated with ether and dried. The crude product is chromatographed on silica gel (particle size: 0.032–0.063 mm), using as eluant methylene chloride/ethanol (9:1). The uniform fractions are combined and evaporated down. The residue is triturated with ether and dried.

Yield: 64 mg (64% of theory),

Melting point: 231°–235° C. (decomp.)

$C_{32}H_{32}N_4O_2$ (504.64)

Mass spectrum: $(M+H)^+=505$

EXAMPLE 144

4'-[[2-n-Propyl-4-methyl-6-(5,5-spiro-cyclopentano)-dihydroimidazol-4-on-2-yl)-1H-benzimidazol-1-yl]-methyl]-biphenyl-2-carboxylic acid-semihydrate 0.05 g (0.1 mMol) of methyl 4'-[[2-n-propyl-4-methyl-6-(5,6,7,8-tetrahydrobenzimidazol-2-yl)-1H-benzimidazol-1-yl]-methyl]-biphenyl-2-carboxylate are dissolved in 4 ml of ethanol, mixed with 2 ml of 1N sodium hydroxide solution and stirred for 4 days at ambient temperature. After the addition of 4 ml of water the pH is adjusted to 6 using glacial acetic acid, the precipitate formed is suction filtered, washed with water and dried over potassium hydroxide. The crude product is chromatographed on silica gel (particle size: 0.032–0.063 mm), using as eluant methylene chloride/ethanol/glacial acetic acid (50:1:0.1 and 30:1:0.1). The uniform fractions are combined and evaporated down. The residue is triturated with ether and dried.

Yield: 30 mg (59% of theory),

Melting point: 310°–311° C. (decomp.)

$C_{32}H_{32}N_4O_3$ (520.64)

Mass spectrum: $(M+H)^+=521$

EXAMPLE 145

Tert.butyl 4'-[[2-n-propyl-4-methyl-6-(5,6,7,8-tetrahydrobenzoxazol-2-yl)-1H-benzimidazol-1-yl]-methyl]-biphenyl-2-carboxylate a) 2-n-Propyl-4-methyl-6-(5,6,7,8-tetrahydro-benzoxazol-2-yl)-1H-benzimidazole 2.17 g (10 mMol) of 2-n-propyl-4-methyl-6-aminocarbonyl-1H-benzimidazole and 10.25 g (77 mMol) of 2-chlorocyclohexanone are heated to 190° C. for one hour. After cooling to ambient temperature the reaction mixture is triturated with ether and suction filtered. The residue is taken up in water and mixed with concentrated ammonia. Then it is extracted with methylene chloride, the organic phase is washed with water, dried over magnesium sulphate and evaporated down. The residue is chromatographed on silica gel (particle size: 0.032–0.063 mm) using as eluant mixtures of methylene chloride and ethanol of increasing polarity (50:1, 25:1 and 20:1). The uniform fractions are combined and evaporated down.

Yield: 1.9 g (64% of theory),

Foam, $R_f$ value: 0.20 (silica gel; ethyl acetate)

b) Tert.butyl 4'-[[2-n-propyl-4-methyl-6-(5,6,7,8-tetrahydro-benzoxazol-2-yl)-1H-benzimidazol-1-yl]-methyl]-biphenyl-2-carboxylate 3.3 g (11 mMol) of 2-n-propyl-4-methyl-6-(5,6,7,8-tetrahydro-benzoxazol-2-yl)-1H-benzimidazole are dissolved in 15 ml of dimethylformamide and at 5°–0° C. 1.5 g (13.2 mMol) of potassium tert.butoxide are added in batches. After 15 minutes at 5° C. 4.6 g (13.2 mMol) of tert.butyl 4'-bromomethyl-biphenyl-2-carboxylate are added. After a further 45 minutes at 5° C. the reaction mixture is stirred into 200 ml of water. The precipitate formed is suction filtered, washed with water and taken up in 200 ml of ethyl acetate. The solution is washed with water and with saturated sodium chloride solution, dried over magnesium sulphate and evaporated down. The residue is chromatographed on silica gel (particle size: 0.032–0.063 mm) using as eluant methylene chloride/ethanol (50:1). The uniform fractions are combined and evaporated down.

Yield: 4.8 g (78% of theory),

Foam, $R_f$ value: 0.23 (silica gel; methylene chloride/ethanol=49:1)

EXAMPLE 146

4'-[[2-n-Propyl-4-methyl-6-(5,6,7,8-tetrahydro-benzimidazol-2-yl)-1H-benzimidazol-1-yl]-methyl]-biphenyl-2-carboxylate 2.0 g (3.56 mMol) of tert.butyl 4'-[[2-n-propyl-4-methyl-6-(5,6,7,8-tetrahydrobenzoxazol-2-yl)-1H-benzimidazol-1-yl]methyl]-methyl-biphenyl-2-carboxylate, 16 ml (40 mMol) of formamide and 40 ml of ammonia (liquid) are heated to 200° C. in the bomb for 14 hours. After cooling, the reaction mixture is diluted with water, the precipitate thus formed is suction filtered. The filtrate is adjusted to pH 6 with glacial acetic acid, the precipitate formed is removed by centrifuging and washed with water. The residue is taken up in 50 ml of 2N hydrochloric acid. By the addition of concentrated ammonia the pH is adjusted to 6 and the precipitate thus formed is suction filtered, washed with water and dried.

Yield: 1.3 g (72% of theory),

Melting point: from 235° C. (decomp.)

EXAMPLE 147

4'-[[2-n-Propyl-4-methyl-6-(1,3-dimethyl-5,6,7,8-tetrahydrobenzimidazolium iodide-2-yl)-1H-benzimidazol-1-yl]- methyl]-biphenyl-2-carboxylic acid 0.85 g (1.7 mMol) of 4'-[[2-n-propyl-4-methyl-6-(5,6,7, 8-tetrahydrobenzimidazol-2-yl)-1H-benzimidazol-1-yl]-methyl]-biphenyl-2-carboxylic acid are dissolved in 9 ml of dimethylsulphoxide, mixed with 420 mg (3.7 mMol) of potassium tert.-butoxide at 5° C. and stirred for 10 minutes. After the addition of 570 mg (4.0 mMol) of methyliodide the reaction mixture is heated to 70° C. for 25 minutes. After cooling, it is poured onto ice, the precipitate formed is suction filtered and washed with water. The residue is taken up in 50 ml of ethanol, combined with 12 ml of 1N sodium hydroxide solution and stirred for 5 days at ambient temperature. The solvent is evaporated off in vacuo, the residue is mixed with ice and acidified with aqueous citric acid (5%). The precipitate thus formed is suction filtered, washed with water and dried.

Yield: 470 mg (42% of theory),
Melting point: 240°–242° C. (decomp.)
$C_{34}H_{37}N_4O_2I$ (660.61) Calculated: C 61.82 H 5.65 N 8.48 Found: 61.69 5.88 8.72

EXAMPLE 148

4'-[[2-n-Propyl-4-methyl-6-(1-methyl-5,6,7,8-tetrahydrobenzimidazol-2-yl)-1H-benzimidazol-1-yl]-methyl]-biphenyl -2-carboxylic acid-hydrate Prepared analogously to Example 146 from tert.butyl 4'-[[2-n-propyl-4-methyl-6-(5,6,7,8-tetrahydrobenzoxazol-2-yl)-1H-benzimidazol-1-yl]-methyl]-biphenyl-2-carboxylate and N-methylformamide/methylamine.

Yield: 27% of theory,
Melting point: 183°–186° C.
$C_{33}H_{34}N_4O_2 \times H_2O$ (536.68) Calculated: C 73.85 H 6.76 N 10.44 Found: 74.22 6.97 10.48

EXAMPLE 149

4'-[[2-n-Propyl-4-methyl-6-(5,6,7,8-tetrahydro-benzimidazol-2-yl)-1H-benzimidazol-1-yl]-methyl]-2-(1H-tetrazol-5-yl)biphenyl-semihydrate a) 4'-[[2-n-propyl-4-methyl-6-(5,6,7,8-tetrahydrobenzoxazol-2-yl)-1H-benzimidazol-1-yl]-methyl]-2-(1-triphenylmethyltetrazol-5-yl)biphenyl Prepared analogously to Example 145b from 2-n-propyl-4-methyl-6-(5,6,7,8-tetrahydrobenzoxazol-2-yl)-1H-benzimidazole and 4'-bromomethyl-2-(1-triphenylmethyl-tetrazol-5-yl)biphenyl.

Oil, $R_f$ value: 0.67 (silica gel; ethyl acetate)

b) 4'-[[2-n-propyl-4-methyl-6-(5,6,7,8-tetrahydro-benzimidazol-2-yl)-1H-benzimidazol-1-yl]-methyl]-2-(1H-tetrazol-5-yl)biphenyl-semihydrate Prepared analogously to Example 146 from 2-n-propyl-4-methyl-6-(5,6,7,8-tetrahydrobenzoxazol-2-yl)-1H-benzimidazol-1-yl]-methyl]-2-(1-triphenylmethyl-tetrazol-5-yl)biphenyl and formamide/ammonia.

Yield: 70% of theory,
Melting point: from 230° C. (decomp.)
$C_{32}H_{32}N_8 \times 0.5 H_2O$ (537.68) Calculated: C 71.48 H 6.19 N 20.84 Found: 71.43 6.46 21.20

EXAMPLE 150

4'-[[2-n-Propyl -4-methyl-6-(1-methyl-5,6,7,8-tetrahydrobenzimidazol-2-yl)-1H-benzimidazol-1-yl]-methyl]-2-(1H-tetrazol-5-yl)biphenyl-semihydrate Prepared analogously to Example 146 from 4'-[[2-n-propyl-4-methyl-6-(5,6,7,8-tetrahydrobenzoxazol-2-yl)-1H-benzimidazol-1-yl]-methyl]-2-(1-triphenylmethyl-tetrazol-5-yl)biphenyl and N-methyl-formamide/methylamine.

Yield: 63% of theory,
Melting point: from 240° C. (decomp.)
$C_{33}H_{34}N_8 \times 0.5 H_2O$ (551.71) Calculated: C 71.84 H 6.40 N 20.31 Found: 71.63 6.45 20.64

EXAMPLE 151

4'-[[2-n-Propyl-4-methyl-6-(5,6,7,8-tetrahydro-benzoxazol-2-yl)-1H-benzimidazol-1-yl]-methyl]-biphenyl-2-carboxylic acid 1.2 g (24 mMol) of tert.butyl 2-n-propyl-4-methyl-6-(5, 6,7,8-tetrahydrobenzoxazol-2-yl)-1H-benzimidazol-1-yl]-methyl]-biphenyl-2-carboxylate are dissolved in 25 ml of methylene chloride, mixed with 8.5 ml of trifluoroacetic acid and stirred for 3 hours at ambient temperature. Then the solvent is evaporated off in vacuo, the residue is mixed with ice and made alkaline with conc. ammonia. After one hour the pH is adjusted to 5 by the addition of citric acid. The precipitate thus formed is suction filtered, washed with water and dried. The crude product is purified on silica gel (particle size: 0.032–0.063 nm) using ethyl acetate as eluant. The uniform fractions are combined and evaporated down.

Yield: 33% of theory,
Melting point: 229°–232° C. (decomp.)
$C_{32}H_{31}N_3O_3$ (505.62)
Mass spectrum: $M^+=505$

EXAMPLE 152

4'-[[2-Ethyl-4-methyl-6-(1-methyl-5,6,7,8-tetrahydrobenzimidazol-2-yl)-1H-benzimidazol-1-yl]-methyl]-2-(1H-tetrazol-5-yl)-biphenyl-hydrate a) 2-ethyl-4-methyl-6-(5,6,7,8-tetrahydrobenzoxazol-2-yl)-1H-benzimidazole Prepared analogously to Example 145a from 2-ethyl-4-methyl-6-aminocarbonyl-1H-benzimidazole and 2-chlorocyclohexanone.

Yield: 60% of theory,
Oil, $R_f$ value: 0.17 (silica gel; ethyl acetate)

b) 4'-[[2-Ethyl-4-methyl-6-(5,6,7,8-tetrahydro-benzoxazol-2-yl)-1H-benzimidazol-1-yl]-methyl]-2-(1-triphenylmethyltetrazol-5-yl)-biphenyl Prepared analogously to Example 145b from 2-ethyl-4-methyl-6-(5,6,7,8-tetrahydrobenzoxazol-2-yl)-1H-benzimidazole and 4'-bromomethyl-2-(1-triphenylmethyl-tetrazol-5-yl)-biphenyl.

Yield: 63% of theory,
Oil, $R_f$ value: 0.69 (silica gel; ethyl acetate)

c) 4'-[[2-Ethyl-4-methyl-6-(1-methyl-5,6,7,8-tetrahydrobenzimidazol-2-yl)-1H-benzimidazol-1-yl]-methyl]-2-(1H-tetrazol-5-yl)-biphenyl-hydrate Prepared analogously to Example 146 from 4'-[[2-ethyl-4-methyl-6-(5,6,7,8-tetrahydrobenzoxazol-2-yl)-1H-benzimidazol-1-yl]-methyl]-2-(2-triphenylmethyl-tetrazol-5-yl)-biphenyl and N-methyl-formamide/methylamine.

Yield: 51% of theory,
Melting point: from 180° C. (decomp.)
$C_{32}H_{32}N_8 \times H_2O$ (546.69)
Calculated×$H_2O$: C 70.31 H 6.27 N 20.50 Found: 70.07 6.55 20.60
Mass spectrum: $M^+=528$

EXAMPLE 153

4'-[[2-Ethyl-4-methyl-6-(1-methyl-5,6,7,8-tetrahydrobenzimidazol-2-yl)-1H-benzimidazol-1-yl]-methyl]-biphenyl-2-carboxylic acid-hydrate a) tert.butyl 4'-[[2-ethyl-4-methyl-6-(5,6,7,8-tetrahydrobenzoxazol-2-yl)-1H-benzimidazol-1-yl]-methyl]-biphenyl-2-carboxylate Prepared analogously to Example 145b from 2-ethyl-4-methyl-6-(5,6,7,8-tetrahydrobenzoxazol-2-yl)-1H-benzimidazole and tert.butyl 4'-bromomethyl-biphenyl-2-carboxylate.

Yield: 77% of theory,
Melting point: 160°–162° C.

b) 4'-[[2-ethyl-4-methyl-6-(1-methyl-5,6,7,8-tetrahydrobenzimidazol-2-yl)-1H-benzimidazol-1-yl]-methyl]-biphenyl-2-carboxylic acid-hydrate Prepared analogously to Example 146 from tert.butyl 4'-[[2-ethyl-4-methyl-6-(5,6,7,8-tetrahydrobenzoxazol-2-yl)-1H-benzimidaimidazol-1-yl]-methyl]-biphenyl-2-carboxylate and N-methylformamide/methylamine.

Yield: 34% of theory,
Melting point: 292°–300° C. (decomp.)
$C_{32}H_{32}N_4O_2 \times H_2O$ (522.66) Calculated×$H_2O$: C 73.54 H 6.56 N 10.72 Found: 73.38 6.76 10.67
Mass spectrum: $M^+$=504

EXAMPLE 154

4'-[[2-Ethyl-4-methyl-6-(1-phenyl-5,6,7,8-tetrahydrobenzimidazol-2-yl)-1H-benzimidazol-1-yl]-methyl]-biphenyl-2-carboxylic acid-hydrate Prepared analogously to Example 146 from tert.butyl 4'-[[2-ethyl-4-methyl-6-(5,6,7,8-tetrahydrobenzoxazol-2-yl)-1H-benzimidazol-1-yl]-methyl]-biphenyl-2-carboxylate and N-formylanilide/aniline.

Yield: 13% of theory,
Melting point: 255°–257° C. (decomp.)
$C_{37}H_{34}N_4O_2 \times H_2O$ (584.73) Calculated×$H_2O$: C 76.00 H 6.20 N 9.58 Found: 76.36 6.18 9.59
Mass spectrum: $M^+$=566

EXAMPLE 155

4'-[[2-n-Propyl-4-methyl-6-(1-phenyl-5,6,7,8-tetrahydrobenzimidazol-2-yl)-1H-benzimidazol-1-yl]-methyl]-biphenyl-2-carboxylic acid-semihydrate Prepared analogously to Example 146 from tert.butyl 4'-[[2-n-propyl-4-methyl-6-(5,6,7,8-tetrahydrobenzoxazol-2-yl)-1 H-benzimidazol-1-yl]-methyl]-biphenyl-2-carboxylate and N-formylanilide/aniline.

Yield: 23% of theory,
Melting point: 258°–260° C. (decomp.)
$C_{38}H_{36}N_4O_2 \times \frac{1}{2} H_2O$ (589.75)
Calculated×½ $H_2O$: C 77.39 H 6.32 N 9.50 Found: 77.03 6.30 9.39
Mass spectrum: $M^+$=580

EXAMPLE 156

4'-[[2-n-Propyl-4-methyl-6-(1-benzyl-5,6,7,8-tetrahydrobenzimidazol--2-yl)-1H-benzimidazol-1-yl]-methyl]-biphenyl-2-carboxylic acid Prepared analogously to Example 146 from tert.butyl 4'-[[2-n-propyl-4-methyl-6-(5,6,7,8-tetrahydrobenzoxazol-2-yl)-1H-benzimidazol-1-yl]-methyl]-biphenyl-2-carboxylate and N-benzylformamide/benzylamine.

Yield: 54% of theory,
Melting point: 256°–258° C. (decomp.)
$C_{39}H_{38}N_4O_2$ (594.77) Calculated: C 78.76 H 6.44 N 9.42 Found: 78.50 6.49 9.35
Mass spectrum: $M^+$=594

EXAMPLE 157

4'-[[2-n-Propyl-4-methyl-6-(1-ethyl-5,6,7,8-tetrahydrobenzimidazol-2-yl)-1H-benzimidazol-1-yl]-methyl]-biphenyl-2-carboxylic acid-semihydrate Prepared analogously to Example 146 from tert.butyl 4'-[[2-n-propyl-4-methyl-6-(5,6,7,8-tetrahydrobenzoxazol-2-yl)-1H-benzimidazol-1-yl]-methyl]-biphenyl-2-carboxylate and N-ethylformamide/ethylamine.

Yield: 17% of theory,
Melting point: from 228° C. (decomp.)
$C_{34}H_{36}N_4O_2 \times 1.5 H_2O$ (559.71) Calc.×1.5 $H_2O$ : C 72.96 H 7.02 N 10.01 Found: 73.04 6.90 9.77
Mass spectrum: $M^+$=532

EXAMPLE 158

4'-[[2-Ethyl-4-methyl-6-(1-isopropyl-5,6,7,8-tetrahydrobenzimidazol-2-yl)-1H-benzimidazol-1-yl]-methyl]-biphenyl-2-carboxylic acid Prepared analogously to Example 146 from tert.butyl 4'-[[2-ethyl-4-methyl-6-(5,6,7,8-tetrahydrobenzoxazol-2-yl)-1H-benzimidazol-1-yl]-methyl]-biphenyl-2-carboxylate and N-isopropylformamide/isopropylamine.

Yield: 2% of theory,
Melting point: 197° C.
$C_{34}H_{36}N_4O_2$ (532.69)
Mass spectrum: $M^+$=532

EXAMPLE 159

4'-[[2-n-Propyl-4-methyl-6-(1-isobutyl-5,6,7,8-tetrahydrobenzimidazol-2-yl)-1H-benzimidazol-1-yl]-methyl]-biphenyl-2-carboxylic acid Prepared analogously to Example 146 from tert.butyl 4'-[[2-n-propyl-4-methyl-6-(5,6,7,8-tetrahydrobenzoxazol-2-yl)-1H-benzimidazol-1-yl]-methyl]-biphenyl-2-carboxylate and isobutylamine/water.

Yield: 5% of theory,
$C_{36}H_{40}N_4O_2$ (560.75)
Mass spectrum: $(M+H)^+$=561

EXAMPLE 160

4'-[[2-n-Propyl-4-methyl-6-(1,3-dibenzyl-5,6,7,8-tetrahydrobenzimidazolium acetate-2-yl)-1H-benzimidazol-1-yl]-methyl]-biphenyl-2-carboxylic acid-semihydrate Prepared analogously to Example 147 from tert.butyl 4'-[[2-n-propyl-4-methyl-6-(5,6,7,8-tetrahydrobenzimidazol-2-yl)-1H-benzimidazol-1-yl]-methyl]-biphenyl-2-carboxylate and benzylbromide/sodium hydroxide solution/ glacial acetic acid.

Yield: 76% of theory,
Melting point: sintering from 80° C.
$C_{46}H_{44}N_4O_2 \times CH_3COOH \times \frac{1}{2} H_2O$ (753.95) Calc.×$CH_3COOH$×½ $H_2O$ : C 76.47 H 6.55 N 7.43 Found: 76.46 6.65 7.76
Mass spectrum: $M^+$=684

EXAMPLE 161

4,-[[2-n-propyl-4-methyl-6-(1-carboxymethyl-5,6,7,8-tetrahydrobenzimidazol-2-yl)-1H-benzimidazol-1-yl]-methyl]-biphenyl-2-carboxylic acid-semihydrate Prepared analogously to Example 147 from 4'-[[2-n-propyl-4-methyl-6-(5,6,7,8-tetrahydrobenzimidazol-2-yl)-1H-benzimidazol-1-yl]-methyl]-biphenyl-2-carboxylic acid and ethyl bromoacetate/sodium hydroxide solution.

Yield: 34% of theory,

Melting point: 239°–242° C.

$C_{34}H_{34}N_4O_4 \times ½ H_2O$ (571.69) Calc.׽ $H_2O$: C 71.43 H 6.17 N 9.80 Found: 71.39 6.19 9.81

Mass spectrum: $M^+=562$

EXAMPLE 162

4'-[[2-Cyclopropyl-4-methyl-6-(1-methyl-5,6,7,8-tetrahydro-benzimidazol-2-yl)-1H-benzimidazol-1-yl]-methyl]-biphenyl-2-carboxylic acid-semihydrate Prepared analogously to Example 146 from tert.butyl 4'-[[2-cyclopropyl-4-methyl-6-(5,6,7,8-tetrahydrobenzoxazol-2-yl)-1H-benzimidazol-1-yl]-methyl]-biphenyl-2-carboxylate and N-methyl-formamide/methylamine.

Yield: 50% of theory,

Melting point: 285°–289° C.

$C_{33}H_{32}N_4O_2 \times ½ H_2O$ (525.66) Calculated: C 75.40 H 6.33 N 10.66 Found: 75.24 6.44 10.42

Mass spectrum: $M^+=516$

The following compounds may be obtained analogously to the preceding Examples:

(1) 4'-[[2-cyclopropyl-4-methyl-6-(1-methyl-5,6,7,8-tetrahydrobenzimidazol-2-yl)-1H-benzimidazol-1-yl]-methyl]-2-(1H-tetrazol-5-yl)biphenyl (2) 4-[[2-ethoxy-4-methyl-6-(1-methyl-5,6,7,8-tetrahydrobenzimidazol-2-yl)-1H-benzimidazol-1-yl]-methyl]-biphenyl-2-carboxylic acid (3) 4-[[2-ethoxy-4-methyl-6-(1-methyl-5,6,7,8-tetrahydrobenzimidazol-2-yl)-1H-benzimidazol-1-yl]-methyl]-2-(1H-tetrazol-5-yl)biphenyl (4) 4-[[2-ethyl-4-methyl-6-(1-isopropyl-5,6,7,8-tetrahydrobenzimidazol-2-yl)-1H-benzimidazol-1-yl]-methyl]-2-(1H-tetrazol-5-yl)biphenyl (5) 4-[[2-n-propyl-4-methyl-6-(1-isopropyl-5,6,7,8-tetrahydrobenzimidazol-2-yl)-1H-benzimidazol-1-yl]-methyl]-biphenyl-2-carboxylic acid (6) 4-[[2-n-propyl-4-methyl-6-(1-isopropyl-5,6,7,8-tetrahydrobenzimidazol-2-yl)-1H-benzimidazol-1-yl]-methyl]-2-(1H-tetrazol-5-yl)biphenyl (7) 4-[[2-ethyl-4-methyl-6-(1-isobutyl-5,6,7,8-tetrahydrobenzimidazol-2-yl)-1H-benzimidazol-1-yl]-methyl]-biphenyl-2-carboxylic acid (8) 4-[[2-ethyl-4-methyl-6-(1-isobutyl-5,6,7,8-tetrahydrobenzimidazol-2-yl)-1H-benzimidazol-1-yl]-methyl]-2-(1H-tetrazol-5-yl)biphenyl (9) 4-[[2-n-propyl-4-methyl-6-(1-isobutyl-5,6,7,8-tetrahydrobenzimidazol-2-yl)-1H-benzimidazol-1-yl]-methyl]-2-(1H-tetrazol-5-yl)biphenyl

(10) 4'-[[2-n-propyl-4-methyl-6-(1-carboxymethyl-5,6,7,8-tetrahydrobenzimidazol-2-yl)-1H-benzimidazol-1-yl]-methyl]-2-(1H-tetrazol-5-yl)biphenyl

(11) 4'-[[2-n-propyl-4-methyl-6-(1-methyl-4,5-trimethyleneimidazol-2-yl)-1H-benzimidazol-1-yl]-methyl]-biphenyl-2-carboxylic acid

(12) 4'-[[2-n-propyl-4-methyl-6-(1-methyl-4,5-trimethyleneimidazol-2-yl)-1H-benzimidazol-1-yl]-methyl]-2-(1H-tetrazol-5-yl)biphenyl

EXAMPLE 163

4'-[[2-Ethyl-4-methyl-6-(5,6,7,8-tetrahydrobenzoxazol-2-yl)-1H-benzimidazol-1-yl]-methyl]-2-(1H-tetrazol-5-yl)-biphenyl Prepared analogously to Example 151 from 4'-[[2-ethyl-4-methyl-6-(5,6,7,8-tetrahydrobenzoxazol-2-yl)-1H-benzimidazol-1-yl]-methyl]-2-(1-triphenylmethyl-tetrazol-5-yl)-biphenyl and hydrochloric acid in methanol.

Yield: 15% of theory,

Melting point: 140°–142° C. (decomp.)

$C_{31}H_{29}N_7O$ (515.63)

Mass spectrum: $(M+H)^+=516$

EXAMPLE 164

4'-[[2-Ethyl-4-methyl-6-(1-ethyl-5,6,7,8-tetrahydro-benzimidazol-2-yl)-1H-benzimidazol-1-yl]-methyl]-2-(1H-tetrazol-5-yl)-biphenyl-hydrate Prepared analogously to Example 146 from 4'-[[2-ethyl-4-methyl-6-(5,6,7,8-tetrahydrobenzoxazol-2-yl)-1H-benzimidazol-1-yl]-methyl]-2-(1-triphenylmethyl-tetrazol-5-yl)-biphenyl and N-ethyl-formamide/ethylamine.

Yield: 25% of theory,

Melting point: from 180° C. (decomp.)

$C_{33}H_{34}N_8 \times H_2O$ (560.72) Calculated: C 70.68 H 6.47 N 19.99 Found: 70.46 6.44 19.56

Mass spectrum: $M^+=542$

EXAMPLE 165

4'-[[2-n-Propyl-4-methyl-6-(4,4-dimethyl-oxazolin-2-yl)-1H-benzimidazol-1-yl]-methyl]-biphenyl-2-carboxylic acid ditrifluoroacetate Prepared analogously to Example 151 from tert.butyl 4'-[[2-n-propyl-4-methyl-6-(4,4-dimethyl-oxazolin-2-yl)-1H-benzimidazol-1-yl]-methyl]-biphenyl-2-carboxylate and trifluoroacetic acid.

Yield: 60% of theory,

Melting point: 158°–159° C.

$C_{30}H_{31}N_3O_3 \times 2$ $CF_3COOH$ (709.64) Calculated: C 57.55 H 4.69 N 5.92 Found: 57.76 4.72 6.02

Mass spectrum: $M^+=481$

EXAMPLE 166

4'-[[2-n-Propyl-4-methyl-6-(1,5-dimethyl-4-phenyl-imidazol-2-yl)-1H-benzimidazol-1-yl]-methyl]-biphenyl-2-carboxylic acid-hydrate a) Tert.butyl 4'-[[2-n-propyl-4-methyl-6-[N-(1-benzoyl-ethyl)-methylaminocarbonyl]-1H-benzimidazol-1-yl]-methyl]-biphenyl-2-carboxylate To a solution of 1.0 g (2.0 mMol) of tert.butyl 4'-[[2-n-propyl-4-methyl-6-chlorocarbonyl-1H-benzimidazol-1-yl]-methyl]-biphenyl-carboxylate in 20 ml of methylene chloride are added 20 ml of toluene and 0.44 g (2.2 mMol) of 2-methylamino-propiophenone. The reaction mixture is heated to 85° C. and 10 ml of pyridine are added dropwise within 4 hours. Then the reaction mixture is evaporated down, the residue is mixed with ice water and extracted twice with methylene chloride. The combined organic phases are dried over magnesium sulphate and evaporated down. The crude product is chromatographed on silica gel (particle size: 0.032–0.063 mm) using as eluant methylene chloride to start with and later methylene chloride/ethanol/ammonia (50:1:0.25 and 25:1:0.01). The uniform fractions are combined and evaporated down.

Yield: 1.0 g (79% of theory),

Foam, $R_f$ value: 0.50 (silica gel; methylene chloride/ethanol=9:1)

b) Tert.butyl 4'-[[2-n-propyl-4-methyl-6-(1,5-dimethyl-4-phenyl-imidazol-2-yl)-1H-benzimidazol-1-yl]-methyl]-biphenyl-2-carboxylate A solution of 1.0 g (1.5 mMol) of tert.butyl 4'-[[2-n-propyl-4-methyl-6-[N-(1-benzoyl-ethyl)-methylaminocarbonyl]-1H-benzimidazol-1-yl]-methyl]-biphenyl-2-carboxylate and 15 g of ammonium acetate in 80 ml of glacial acetic acid is refluxed for 2.5 hours. Then the reaction mixture is evaporated down to half, the residue is mixed with ice water and extracted twice with ethyl acetate. The combined organic phases are washed with water, dried over magnesium sulphate and evaporated down. The crude product is chromatographed on silica gel (particle size: 0.032–0.063 mm) using as eluant methylene chloride with increasing amounts of ethanol (3%, 10% and 20%). The uniform fractions are combined and evaporated down.

Yield: 0.68 g (74% of theory),
Foam, $R_f$ value: 0.40 (silica gel; methylene chloride/ethanol=19:1)

c) 4'-[[2-n-Propyl-4-methyl-6-(1,5-dimethyl-4-phenyl-imidazol-2-yl)-1H-benzimidazol-1-yl]-methyl]-biphenyl-2-carboxylic acid-hydrate Prepared analogously to Example 151 from tert.butyl 4'-[[2-n-propyl-4-methyl-6-(1,5-dimethyl-4-phenyl-imidazol-2-yl)-1H-benzimidazol-1-yl]-methyl]-biphenyl-2-carboxylate and trifluoroacetic acid.

Yield: 90% of theory,
Melting point: from 152° C. (decomp.)
$C_{36}H_{33}N_4O_2 \times H_2O$ (572.72) Calculated: C 75.50 H 6.34 N 9.78 Found: 75.95 6.48 9.92
Mass spectrum: $M^+=554$

EXAMPLE 167

4'-[[2-n-Propyl-4-methyl-6-(1-methyl-4,5-diphenyl-imidazol-2-yl)-1H-benzimidazol-1-yl]-methyl]-biphenyl-2-carboxylic acid-sesquihydrate a) Tert.butyl 4'-[[2-n-propyl-4-methyl-6-(1-methyl-4,5-diphenyl-imidazol-2-yl)-1H-benzimidazol-1-yl]-methyl]-biphenyl-2-carboxylate Prepared analogously to Example 166b from tert.butyl 4'-[[2-n-propyl-4-methyl-6-[N-(1-benzoyl-benzyl)-methylaminocarbonyl]-1H-benzimidazol-1-yl]-methyl]-biphenyl-2-carboxylate and ammonium acetate in glacial acetic acid.

Yield: 27% of theory,
Oil, $R_f$ value: 0.40 (silica gel; methylene chloride/ethanol=19:1)

b) 4'-[[2-n-Propyl-4-methyl-6-(1-methyl-4,5-diphenyl-imidazol-2-yl)-1H-benzimidazol-1-yl]-methyl]-biphenyl-2-carboxylic acid-sesquihydrate Prepared analogously to Example 151 from tert.butyl 4'-[[2-n-propyl-4-methyl-6-(1-methyl-4,5-diphenyl-imidazol-2-yl)-1H-benzimidazol-1-yl]-methyl]-biphenyl-2-carboxylate and trifluoroacetic acid.

Yield: 60% of theory,
Melting point: 325°–328° C. (decomp.)
$C_{41}H_{36}N_4O_2 \times 1.5\ H_2O$ (643.79) Calculated: C 76.49 H 6.11 N 8.70 Found: 76.53 6.15 8.75
Mass spectrum: $M^+=616$

EXAMPLE 168

4'-[[2-n-Propyl-4-methyl-6-(5-methyl-4-isopropyl-imidazol-2-yl)-1H-benzimidazol-1-yl]-methyl]-biphenyl-2-carboxylic acid-dihydrate-acetate a) Tert.butyl 4'-[[2-n-propyl-4-methyl-6-(5-methyl-4-isopropyl-imidazol-2-yl)-1H-benzimidazol-1-yl]-methyl]-biphenyl-2-carboxylate Prepared analogously to Example 166b from tert.butyl 4'-[[2-n-propyl-4-methyl-6-[N-(1-acetyl-2-methyl-n-propyl)-methylaminocarbonyl]-1H-benzimidazol-1-yl]-methyl]-biphenyl-2-carboxylate and ammonium acetate in glacial acetic acid.

Yield: 45% of theory,
Oil, $R_f$ value: 0.10 (silica gel; ethyl acetate/petroleum ether=2:1)

b) 4'-[[2-n-Propyl-4-methyl-6-(5-methyl-4-isopropyl-imidazol-2-yl)-1H-benzimidazol-1-yl]-methyl]-biphenyl-2-carboxylic acid-dihydrate-acetate Prepared analogously to Example 151 from tert.butyl 4'-[[2-n-propyl-4-methyl-6-(5-methyl-4-isopropyl-imidazol-2-yl)-1H-benzimidazol-1-yl]-methyl]-biphenyl-2-carboxylate and trifluoroacetic acid.

Yield: 75% of theory,
Melting point: from 155° C. (decomp.)
$C_{32}H_{34}N_4O_2 \times CH_3COOH \times 2\ H_2O$ (602.74) Calculated: C 67.75 H 7.02 N 9.30 Found: 67.69 7.02 9.53
Mass spectrum: $M^+=506$

EXAMPLE 169

4'-[[2-n-Propyl-4-methyl-6-(4-methyl-imidazolin-2-yl)-1H-benzimidazol-1-yl]-methyl]-biphenyl-2-carboxylic acid-ditrifluoroacetate a) Tert.butyl 4'-[[2-n-propyl-4-methyl-6-(4-methyl-imidazolin-2-yl)-1H-benzimidazol-1-yl]-methyl]-biphenyl-2-carboxylate A mixture of 0.43 g (0.8 mMol) of tert.butyl 4'-[[2-n-propyl-4-methyl-6-(4,4-dimethyl-oxazolin-2-yl)-1H-benzimidazol-1-yl]methyl]-biphenyl-2-carboxylate and 0.67 ml (5.8 mMol) of 1,2-diaminopropane is heated to 120° C. for 48 hours. The yellow solid obtained after cooling to ambient temperature is stirred with water for 1 hour, suction filtered and dried. The crude product is chromatographed on silica gel (particle size: 0.032–0.063 mm) using as eluant methylene chloride/ethanol/ammonia (50:1:0.05, 20:1:0.02 and 7:1:0.07). The uniform fractions are combined and evaporated down.

Yield: 0.26 g (62% of theory),
Foam, $R_f$ value: 0.20 (silica gel; methylene chloride/ethanol=9:1+ammonia)

b) 4'-[[2-n-Propyl-4-methyl-6-(4-methyl-imidazolin-2-yl)-1H-benzimidazol-1-yl]-methyl]-biphenyl-2-carboxylic acid-ditrifluoroacetate Prepared analogously to Example 151 from tert.butyl 4'-[[2-n-propyl-4-methyl-6-(4-methyl-imidazolin-2-yl)-1H-benzimidazol-1-yl]-methyl]-biphenyl-2-carboxylate and trifluoroacetic acid.

Yield: 72% of theory,
Melting point: 115°–118° C. (decomp., sinters from 100° C.)
$C_{29}H_{30}N_4O_2 \times 2\ CF_3COOH$ (694.63) Calculated: C 57.06 H 4.64 N 8.07 Found: 57.02 5.02 8.13
Mass spectrum: $M^+=466$

EXAMPLE 170

4'-[[2-n-Propyl-4-methyl-6-(4-isopropyl-5-methyl-oxazol-2-yl)-1H-benzimidazol-1-yl]-methyl]-biphenyl-2-carboxylic acid 3.9 g (6.7 mMol) of tert.butyl 4'-[[2-n-propyl-4-methyl-6-[N-(1-acetyl-2-methyl-n-propyl)-aminocarbonyl]-1H-benzimidazol-1-yl]-methyl]-biphenyl-2-carboxylate are dissolved in 50 ml of phosphorusoxychloride and stirred for 2.5 hours at 105° C. Then the phosphorusoxychloride is removed, the residue is decomposed with water at 80° C. and, after cooling, mixed with conc. ammonia. The pH is adjusted to 5 by the addition of glacial acetic acid, the precipitate thus formed is suction filtered, washed with water, taken up in methylene chloride/methanol (9:1) and dried over magnesium sulphate. The crude product is chromatographed on silica gel (particle size: 0.032–0.063 mm)

using as eluant petroleum ether/ethyl acetate/glacial acetic acid (1:1:0.002) and methylene chloride/ethanol/glacial acetic acid (20:1:0.002). The uniform fractions are combined, evaporated down, triturated with ether and suction filtered.

Yield: 2.4 g (71% of theory),
Melting point: 222°–223° C.
$C_{32}H_{33}N_3O_3$ (507.64) Calculated: C 75.71 H 6.55 N 8.28 Found: 75.61 6.59 8.36
Mass spectrum: $M^+=507$

EXAMPLE 171

4'-[[2-n-Propyl-4-methyl-6-(4-isopropyl-1,5-dimethyl-imidazol-2-yl)-1H-benzimidazol-1-yl]-methyl]-biphenyl-2-carboxylic acid ×1.25 water Prepared analogously to Example 146 from tert.butyl 4'-[[2-n-propyl-4-methyl-6-(4-isopropyl-5-methyl-oxazol-2-yl)-1H-benzimidazol-1-yl]-methyl]-biphenyl-2-carboxylate and N-methyl-formamide/methylamine.

Yield: 38% of theory,
Melting point: from 150° C. (decomp.)
$C_{33}H_{36}N_4O_2 \times 1.25\ H_2O$ (543.20) Calculated: C 72.97 H 7.14 N 10.32 Found: 72.95 7.02 9.94
Mass spectrum: $M^+=520$

EXAMPLE 172

4'-[[2-n-Propyl-4-methyl-6-(1-ethyl-4-isopropyl-5-methyl-imidazol-2-yl)-1H-benzimidazol-1-yl]-methyl]-biphenyl-2-carboxylic acid Prepared analogously to Example 146 from tert.butyl 4'-[[2-n-propyl-4-methyl-6-(4-isopropyl-5-methyl-oxazol-2-yl)-1 H-benzimidazol-1-yl]-methyl]-biphenyl-2-carboxylate and N-ethyl-formamide/ethylamine.

EXAMPLE 173

4'-[[2-n-Propyl-4-methyl-6-(1-isopropyl-4-isopropyl-5-methyl-imidazol-2-yl)-1H-benzimidazol-1-yl]-methyl]-biphenyl -2-carboxylic acid Prepared analogously to Example 146 from tert.butyl 4'-[[2-n-propyl-4-methyl-6-(4-isopropyl-5-methyl-oxazol-2-yl)-1H-benzimidazol- 1-yl]-methyl]-biphenyl-2-carboxylate and N-isopropyl-formamide/isopropylamine.

EXAMPLE 174

4'-[[2-n-Propyl-4-methyl-6-(1-cyclohexyl-4-isopropyl-5-methyl-imidazol-2-yl)-1H-benzimidazol-1-yl]-methyl]-biphenyl-2-carboxylic acid Prepared analogously to Example 146 from tert.butyl 4'-[[2-n-propyl-4-methyl-6-(4-isopropyl-5-methyl-oxazol-2-yl)-1H-benzimidazol-1-yl]-methyl]-biphenyl-2-carboxylate and N-cyclohexyl-formamide/cyclohexylamine.

Yield: 10% of theory,
$C_{38}H_{44}N_4O_2$ (588.80)
$R_f$ value: 0.24 (silica gel; methylene chloride/ethanol/acetic acid=9:1:0.01)
Mass spectrum: $(M+H)^+=589$

EXAMPLE 175

4'-[[2-n-Propyl-4-methyl-6-[1-(2-dimethylamino-ethyl)-4-isopropyl-5-methyl-imidazol-2-yl]-1H-benzimidazol-1-yl]-methyl]-biphenyl-2-carboxylic acid-semihydrate Prepared analogously to Example 146 from tert.butyl 4'-[[2-n-propyl-4-methyl-6-(4-isopropyl-5-methyl-oxazol-2-yl)-1H-benzimidazol-1-yl]-methyl]-biphenyl-2-carboxylate and N-(2-dimethylamino-ethyl)-formamide/2-dimethylamino-ethylamine.

Yield: 48% of theory,
Melting point: 192°–195° C. (decomp.)
$C_{36}H_{43}N_5O_2 \times 0.5\ H_2O$ (586.79) Calculated: C 73.69 H 7.56 N 11.93 Found: 73.53 7.55 11.94
Mass spectrum: $M^+=577$

EXAMPLE 176

4'-[[2-n-Propyl-4-methyl-6-(1,5-dimethyl-4-isobutyl-imidazol-2-yl)-1H-benzimidazol-1-yl]-methyl]-biphenyl-2-carboxylic acid Prepared analogously to Example 146 from tert.butyl 4'-[[2-n-propyl-4-methyl-6-(4-isobutyl-5-methyl-oxazol-2-yl)-1H-benzimidazol-1-yl]-methyl]-biphenyl-2-carboxylate and N-methylformamide/methylamine.

Yield: 64% of theory,
Melting point: 155–157 C. (decomp.)
$C_{34}H_{38}N_4O_2 \times 0.75\ H_2O$ (548.22) Calculated: C 74.49 H 7.28 10.22 Found: 74.45 7.29 10.35
Mass spectrum: $M^+=534$

EXAMPLE 177

4'-[[2-n-Propyl-4-methyl-6-(1-ethyl-4-isobutyl-5-methyl-imidazol-2-yl)-1H-benzimidazol-1-yl]-methyl]-biphenyl-2-carboxylic acid×0.25 water Prepared analogously to Example 146 from tert.butyl 4'-[[2-n-propyl-4-methyl-6-(4-isobutyl-5-methyl-oxazol-2-yl)-1H-benzimidazol-1-yl]-methyl]-biphenyl-2-carboxylate and N-ethyl-formamide/ethylamine.

Yield: 62% of theory,
Melting point: 239°–241° C.
$C_{33}H_{35}N_3O_3 \times 0.25\ H_2O$ (526.17) Calc.×0.25 $H_2O$: C 75.33 H 6.80 N 7.99 Found: 75.35 6.75 7.96
Mass spectrum: $M^+=527$

EXAMPLE 178

4'-[[2-n-Propyl-4-methyl-6-(1-tert.butyl-4-isobutyl-5-methyl-imidazol-2-yl)-1H-benzimidazol-1-yl]-methyl]-biphenyl-2-carboxylic acid Prepared analogously to Example 146 from tert.butyl 4'-[[2-n-propyl-4-methyl-6-(4-isobutyl-5-methyl-oxazol-2-yl)-1H-benzimidazol-1-yl]-methyl]-biphenyl-2-carboxylate and N-tert.butyl-formamide/tert.butylamine.

EXAMPLE 179

4'-[[2-n-Propyl-4-methyl-6-(1-benzyl-4-isobutyl-5-methyl-imidazol-2-yl)-1H-benzimidazol-1-yl]-methyl]-biphenyl-2-carboxylic acid Prepared analogously to Example 146 from tert.butyl 4'-[[2-n-propyl-4-methyl-6-(4-isobutyl -5-methyl-oxazol-2-yl)-1H-benzimidazol-1-yl]-methyl]-biphenyl-2-carboxylate and N-benzyl-formamide/benzylamine.

EXAMPLE 180

4'-[[2-n-Propyl-4-methyl-6-[1-(2-morpholino-ethyl)-4-isobutyl-5-methyl-imidazol-2-yl)-1H-benzimidazol-1-yl]-methyl]-biphenyl-2-carboxylic acid Prepared analogously to Example 146 from tert.butyl 4'-[[2-n-propyl-4-methyl-6-(4-isobutyl-5-methyl-oxazol-2-yl)-1H-benzimidazol-1-yl]-methyl]-biphenyl-2-carboxylate and N-(2-morpholino-ethyl)-formamide/2-morpholino-ethylamine.

Yield: 30% of theory,

Melting point: 201°–203° C. (decomp.)
$C_{39}H_{47}N_5O_3$ (633.85) Calculated: C 73.90 H 7.47 N 11.05 Found: 73.65 7.45 11.07
Mass spectrum: $M^+$=633

EXAMPLE 181

4'-[[2-n-Propyl-4-methyl-6-[1-(2-methoxy-ethyl)-4-isobutyl-5-methyl-imidazol-2-yl]-1H-benzimidazol-1-yl]-methyl]-biphenyl-2-carboxylic acid-hydrate Prepared analogously to Example 146 from tert.butyl 4'-[[2-n-propyl-4-methyl-6-(4-isobutyl-5-methyl-oxazol-2-yl)-1H-benzimidazol-1-yl]-methyl]-biphenyl-2-carboxylate and N-(2-methoxy-ethyl)-formamide/2-methoxy-ethylamine.

Yield: 29% of theory,
Melting point: 135–137 C. (decomp., sintering from 110 C.)
$C_{36}H_{42}N_4O_3 \times H_2O$ (596.78) Calculated: C 72.46 H 7.43 N 9.39 Found: 72.50 7.45 9.77
Mass spectrum: $M^+$=578

EXAMPLE 182

4'-[[2-n-Propyl-4-methyl-6-[1-(2-hydroxy-ethyl)-4-isobutyl-5-methyl-imidazol-2-yl]-1H-benzimidazol-1-yl]-methyl]-biphenyl-2-carboxylic acid Prepared analogously to Example 146 from tert.butyl 4'-[[2-n-propyl-4-methyl-6-(4-isobutyl-5-methyl-oxazol-2-yl)-1H-benzimidazol-1-yl]-methyl]-biphenyl-2-carboxylate and N-(2-hydroxy-ethyl)-formamide/2-hydroxy-ethylamine.

EXAMPLE 183

4'-[[2-n-Propyl-4-methyl-6-[1-(3-dimethylamino-propyl)-4-isobutyl-5-methyl-imidazol-2-yl]-1H-benzimidazol-1-yl]-methyl]-biphenyl-2-carboxylic acid Prepared analogously to Example 146 from tert.butyl 4'-[[2-n-propyl-4-methyl-6-(4-isobutyl-5-methyl-oxazol-2-yl)-1H-benzimidazol-1-yl]-methyl]-biphenyl-2-carboxylate and N-(3-dimethylamino-propyl)-formamide/3-dimethylamino-propylamine.

EXAMPLE 184

4'-[[2-n-Propyl-4-methyl-6-(1-carboxymethyl-4-isobutyl-5-methyl-imidazol-2-yl)-1H-benzimidazol-1-yl]-methyl]-biphenyl-2-carboxylic acid Prepared analogously to Example 146 from tert.butyl 4'-[[2-n-propyl-4-methyl-6-(4-isobutyl -5-methyl-oxazol-2-yl)-1H-benzimidazol-1-yl]-methyl]-biphenyl-2-carboxylate and N-formylglycineethylester/glycineethylester.

EXAMPLE 185

4'-[[2-n-Propyl-4-methyl-6-(1-aminocarbonylmethyl-4-isobutyl-5-methyl-imidazol-2-yl)-1H-benzimidazol-1-yl]-methyl]-biphenyl-2-carboxylate Prepared analogously to Example 146 from tert.butyl 4'-[[2-n-propyl-4-methyl-6-(4-isobutyl -5-methyl-oxazol-2-yl)-1H-benzimidazol-1-yl]-methyl]-biphenyl-2-carboxylate and N-formylglycinamide/glycinamide.

EXAMPLE 186

4'-[[2-n-Propyl-4-methyl-6-[1-(2-carboxy-ethyl)-4-isobutyl-5-methyl-imidazol-2-yl)-1H-benzimidazol-1-yl]-methyl]-biphenyl-2-carboxylic acid Prepared analogously to Example 146 from tert.butyl 4'-[[2-n-propyl-4-methyl-6-(4-isobutyl-5-methyl-oxazol-2-yl)-1H-benzimidazol-1-yl]-methyl]-biphenyl-2-carboxylate and ethyl 3-formylamino-propionate/ethyl 3-aminopropionate.

The following compounds may be obtained analogously:

4'-[[2-n-propyl-4-methyl-6-(1,5-dimethyl-4-isobutyl-imidazol-2-yl)-1H-benzimidazol-1-yl]-methyl]-(1H-tetrazol-5-yl)biphenyl 4'-[[2-n-propyl-4-methyl-6-(1-n-propyl-4-isobutyl-5-methyl-imidazol-2-yl)-1H-benzimidazol-1-yl]-methyl]-(1H-tetrazol-5-yl)biphenyl 4'-[[2-n-propyl-4-methyl-6-[1-(2-dimethylamino-ethyl)-4-isobutyl-5-methyl-imidazol-2-yl]-1H-benzimidazol-1-yl] methyl]-(1H-tetrazol-5-yl)biphenyl

EXAMPLE 187

Methyl 4'-[[2-n-propyl-4-methyl-6-(4-methyl-imidazol-2-yl)-1H-benzimidazol-1-yl]-methyl]-biphenyl-2-carboxylate A solution of 0.35 g (0.7 mMol) of methyl 4'-[[2-n-propyl-4-methyl-6-(4-methyl-imidazolin-2-yl)-1H-benzimidazol-1-yl]methyl]-biphenyl-2-carboxylate in 10 ml of toluene is mixed with 0.16 g palladium (10% on activated charcoal) under nitrogen and the mixture is refluxed for 66 hours. Then the toluene is evaporated off, the residue is taken up in methylene chloride, filtered and evaporated down. The crude product is chromatographed on silica gel (particle size: 0.032–0.063 mm) using as eluant methylene chloride to start with, later followed by methylene chloride/ethanol/ammonia (50:1:0.05, 20:1:0.02, 10:1:0.01 and 5:1:0.005). The uniform fractions are combined and evaporated down.

Yield: 0.30 g (9% of theory),
Mass spectrum: $M^+$=478

EXAMPLE 188

4'-[[2-n-Propyl-4-methyl-6-(1,4,5-trimethyl-imidazol-2-yl)-1H-benzimidazol-1-yl]-methyl]-biphenyl-2-carboxylic acid Prepared analogously to Example 146 from tert.butyl 4'-[[2-n-propyl-4-methyl-6-(4,5-dimethyl-oxazol-2-yl)-1H-benzimidazol-1-yl]-methyl]-biphenyl-2-carboxylate and N-methyl-formamide/methylamine.

Yield: 61% of theory,
Melting point: 217–219 C. (decomp.)
$C_{31}H_{32}N_4O_2 \times 0.25\ H_2O$ (497.13) Calculated: C 74.90 H 6.59 11.27 Found: 74.84 6.58 11.26
Mass spectrum: $M^+$=492

EXAMPLE 189

4'-[[2-n-Propyl-4-methyl-6-(1-ethyl-4,5-dimethyl-imidazol-2-yl)-1H-benzimidazol-1-yl]-methyl]-biphenyl-2-carboxylic acid Prepared analogously to Example 146 from tert.butyl 4'-[[2-n-propyl-4-methyl-6-(4,5-dimethyl-oxazol-2-yl)-1H-benzimidazol-1-yl]-methyl]-biphenyl-2-carboxylate and N-ethylformamide/ethylamine.

EXAMPLE 190

4'-[[2-n-Propyl-4-methyl-6-(1-methyl-4,5-diethyl-imidazol-2-yl)-1H-benzimidazol-1-yl]-methyl]-2-(1H-tetrazol-5-yl)-biphenyl Prepared analogously to Example 146 from 4'-[[2-n-propyl-4-methyl-6-(4,5-diethyl-oxazol-2-yl)-1H-benzimidazol-1-yl]-methyl]-2-(2-triphenylmethyl-tetrazol-5-yl)-biphenyl and N-methyl-formamide/methylamine.

EXAMPLE 191

4'-[[2-n-Propyl-4-methyl-6-(1-ethyl-4,5-dimethyl-imidazol-2-yl)-1H-benzimidazol-1-yl]-methyl]-2-(1H-tetrazol-5-yl)-biphenyl Prepared analogously to Example 146 from 4'-[[2-n-propyl-4-methyl-6-(4,5-dimethyl-oxazol-2-yl)-1H-benzimidazol-1-yl]-methyl]-2-(2-triphenylmethyl-tetrazol-5-yl)-biphenyl and N-ethyl-formamide/ethylamine.

EXAMPLE 192

4'-[[2-n-Propyl-4-methyl-6-(1-isopropyl-4,5-dimethyl-imidazol-2-yl)-1H-benzimidazol-1-yl]-methyl]-biphenyl-2-carboxylic acid Prepared analogously to Example 146 from tert.butyl 4'-[[2-n-propyl-4-methyl-6-(4,5-dimethyl-oxazol-2-yl)-1H-benzimidazol-1-yl]-methyl]-biphenyl-2-carboxylate and N-isopropyl-formamide/isopropylamine.

EXAMPLE 193

4'-[[2-n-Propyl-4-methyl-6-[1-(2-dimethylamino-ethyl)-4,5-dimethyl-imidazol-2-yl]-1H-benzimidazol-1-yl]-methyl]-biphenyl-2-carboxylic acid Prepared analogously to Example 146 from tert.butyl 4'-[[2-n-propyl-4-methyl-6-(4,5-dimethyl-oxazol-2-yl)-1H-benzimidazol-1-yl]-methyl]-biphenyl-2-carboxylate and N-(2-dimethylaminoethyl)formamide/2-dimethylaminoethylamine.

EXAMPLE 194

4'-[[2-n-Propyl-4-methyl-6-[1-(2-morpholino-ethyl)-4,5-dimethyl-imidazol-2-yl]-1H-benzimidazol-1-yl]-methyl]-biphenyl-2-carboxylic acid Prepared analogously to Example 146 from tert.butyl 4'-[[2-n-propyl-4-methyl-6-(4,5-dimethyl-oxazol-2-yl)-1H-benzimidazol-1-yl]-methyl]-biphenyl-2-carboxylate and N-(2-morpholinoethyl)-formamide/2-morpholino-ethylamine.

EXAMPLE 195

4'-[[2-n-Propyl-4-methyl-6-[1-(2-morpholino-ethyl)-4,5-diethyl-imidazol-2-yl]-1H-benzimidazol-1-yl]-methyl]-2-(1H-tetrazol-5-yl)-biphenyl Prepared analogously to Example 146 from 4'-[[2-n-propyl-4-methyl-6-(4,-5-diethyl-oxazol-2-yl)-1H-benzimidazol-1-yl]-methyl]-2-(2-triphenylmethyl-tetrazol-5-yl)-biphenyl and N-(2-morpholino-ethyl)-formamide/2-morpholino-ethylamine.

EXAMPLE 196

4'-[[2-n-Propyl-4-methyl-6-[1-(2-methoxy-ethyl)-4,5-dimethyl-imidazol-2-yl]-1H-benzimidazol-1-yl]-methyl]-biphenyl-2-carboxylic acid Prepared analogously to Example 146 from tert.butyl 4'-[[2-n-propyl-4-methyl-6-(4,5-dimethyl-oxazol-2-yl)-1H-benzimidazol-1-yl]-methyl]-biphenyl-2-carboxylate and N-(2-methoxy-ethyl)formamide/2-methoxy-ethylamine.

EXAMPLE 197

4'-[[2-n-Propyl-4-methyl-6-[1-(2-methoxy-ethyl)-4,5-dimethyl-imidazol-2-yl]-1H-benzimidazol-1-yl]-methyl]-2-(1H-tetrazol-5-yl)-biphenyl Prepared analogously to Example 146 from 4'-[[2-n-propyl-4-methyl-6-(4,5-dimethyl-oxazol-2-yl)-1H-benzimidazol-1-yl]-methyl]-2-(2-triphenylmethyl-tetrazol-5-yl)-biphenyl and N-(2-methoxy-ethyl)-formamide/2-methoxy-ethylamine.

EXAMPLE 198

4'-[[2-n-Propyl-4-methyl-6-[1-(2-carboxy-ethyl)-4,5-dimethyl-imidazol-2-yl]-1H-benzimidazol-1-yl]-methyl]-2-biphenyl-carboxylic acid Prepared analogously to Example 146 from tert.butyl 4'-[[2-n-propyl-4-methyl-6-(4,5-dimethyl-oxazol-2-yl)-1H-benzimidazol-1-yl]-methyl]-biphenyl-2-carboxylate and ethyl N-formyl-3-aminopropionate/ethyl 3-aminopropionate.

EXAMPLE 199

4'-[[2-n-Propyl-4-methyl-6-(1-methyl-4,5-diethyl-imidazol-2-yl)-1H-benzimidazol-1-yl]-methyl]-biphenyl-2-carboxylic acid×0.25 H$_2$O Prepared analogously to Example 146 from tert.butyl 4'-[[2-n-propyl-4-methyl-6-(4,5-diethyl-oxazol-2-yl)-1H-benzimidazol-1-yl]-methyl]-biphenyl-2-carboxylate and N-methyl-formamide/methylamine.

Yield: 65% of theory,
Melting point: 247–249 C. (decomp.)
C$_{33}$H$_{36}$N$_4$O$_2$×0.25 H$_2$O (525.18) Calculated: C 75.47 H 7.01 10.67 Found: 75.43 7.11 10.68
Mass spectrum: M$^+$=520

EXAMPLE 200

4'-[[2-n-Propyl-4-methyl-6-(1-methyl-imidazolin-2-yl)-1H-benzimidazol-1-yl]-methyl]-biphenyl-2-carboxylic acid Prepared by heating of tert.butyl 4'-[[2-n-propyl-4-methyl-6-[2-(N-methylamino)-ethylaminocarbonyl]-1H-benzimidazol-1-yl]-methyl]-biphenyl-2-carboxylate in phosphorus oxychloride and isolating analogously to Example 151.

Yield : 30% of theory,
C$_{29}$H$_{30}$N$_4$O$_2$ (466.59)
R$_f$ value: 0.50 (methylene chloride/methanol/acetic acid= 2:1:0.02)
Mass spectrum: (M+H)$^+$=467

EXAMPLE 201

4'-[[2-n-Propyl-4-methyl-6-[1-(2-dimethylamino-ethyl)-4,5-diethyl-imidazol-2-yl]-1H-benzimidazol-1-yl]-methyl]-biphenyl-2-carboxylic acid-dihydrate-trihydrochloride Prepared analogously to Example 146 from tert.butyl 4'-[[2-n-propyl-4-methyl-6-(4,5-diethyl-oxazol-2-yl)-1H-benzimidazol-1-yl]-methyl]-biphenyl-2-carboxylate and N-(2-dimethylamino-ethyl)-formamide/2-dimethylaminoethylamine.

Yield: 14% of theory,
Melting point: from 210° C. (decomp.)
C$_{36}$H$_{43}$N$_5$O$_2$×3 HCl×2 H$_2$O (723.21) Calculated: C 59.79 H 6.97 N 9.69 C$_1$ $_{14.71}$ Found: 59.28 6.92 9.75 14.26
Mass spectrum: M$^+$=

EXAMPLE 202

4'-[[2-n-Propyl-4-methyl-6-[1-(2-morpholino-ethyl)-4,5-diethyl-imidazol-2-yl]-1H-benzimidazol-1-yl]-methyl]-biphenyl-2-carboxylic acid Prepared analogously to Example 146 from tert.butyl 4'-[[2-n-propyl-4-methyl-6-(4,5-diethyl-oxazol-2-yl)-1H-benzimidazol-1yl]-methyl]-biphenyl-2-carboxylate and N-(2-morpholino-ethyl)formamide/2-morpholino-ethylamine.

Yield: 41% of theory,
Melting point: from 196° C. (decomp.)
$C_{38}H_{45}N_5O_3$ (6 19.82)
Mass spectrum: $M^+=619$

EXAMPLE 203

4'-[[2-n-Propyl-4-methyl-6-[1-(2-methoxy-ethyl)-4,5-diethyl-imidazol-2-yl]-1H-benzimidazol-1-yl]-methyl]-biphenyl-2-carboxylic acid hydrate Prepared analogously to Example 146 from tert.butyl 4'-[[2-n-propyl-4-methyl-6-(4,5-diethyl-oxazol-2-yl)-1H-benzimidazol-1-yl]-methyl]-biphenyl-2-carboxylate and N-(2-methoxy-ethyl)formamide/2-methoxy-ethylamine.

$C_{35}H_{40}N_4O_3 \times H_2O$ (582.76)
Calculated×$H_2O$: C 72.14 H 7.27 N 9.61 Found: 71.99 7.19 9.84
Mass spectrum: $(M–H)^-=563$

EXAMPLE 204

4'-[[2-n-Propyl-4-methyl-6-(4,5-diethyl-oxazol-2-yl)-1H-benzimidazol-1-yl]-methyl]-biphenyl-2-carboxylic acid Prepared analogously to Example 170 from tert.butyl 4'-[[2-n-propyl-4-methyl-6-[N-(1-propionyl-n-propyl)-aminocarbonyl]-1H-benzimidazol-1-yl]-methyl]-biphenyl-2-carboxylate and phosphorusoxychloride.

Yield: 97% of theory,
Melting point: 250°–255° C.
$C_{32}H_{33}N_3O_3$ (507.64) Calculated: C 75.71 H 6.55 N 8.28 Found: 75.77 6.59 8.46
Mass spectrum: $M^+=507$

EXAMPLE 205

4'-[[2-n-Propyl-4-methyl-6-(4,5-diethyl-1H-imidazol-2-yl)-1H-benzimidazol-1-yl]-methyl]-2-(1H-tetrazol-5-yl)-biphenyl Prepared analogously to Example 166b from 4'-[[2-n-propyl-4-methyl-6-[N-(1-propionyl-n-propyl)-aminocarbonyl]-1H-benzimidazol-1-yl]-methyl]-2-(2-triphenylmethyl-tetrazol-5-yl)-biphenyl and ammonium acetate/glacial acetic acid.

Yield: 27% of theory,
Melting point: 221°–223° C.
$C_{32}H_{34}N_8 \times H_2O$ (530.69) Calculated: C 70.05 H 6.61 N 20.42 Found: 70.79 6.98 18.83
Mass spectrum: $M^+=530$

EXAMPLE 206

4'-[[2-n-Propyl-4-methyl-6-(4,5-dimethyl-oxazol-2-yl)-1H-benzimidazol-1-yl]-methyl]-biphenyl-2-carboxylic acid Prepared analogously to Example 170 from tert.butyl 4'-[[2-n-propyl-4-methyl-6-[N-(1-acetyl-ethyl)-aminocarbonyl]-1H-benzimidazol-1-yl]-methyl]-biphenyl-2-carboxylate and phosphorusoxychloride.

Yield: 88% of theory,
Melting point: 259°–260° C. (decomp.)

$C_{30}H_{29}N_3O_3 \times 0.25\ H_2O$ (484.09) Calculated: C 74.44 H 6.14 N 8.68 Found: 74.33 6.14 8.69
Mass spectrum: $M^+=479$

EXAMPLE 207

4'-[[2-n-Propyl-4-methyl-6-(1-methyl-5,6,7,8-tetrahydrobenzimidazol-2-yl)-1H-benzimidazol-1-yl]-methyl]-2'-(2,5-dihydro-5-oxo-1,2,4-oxadiazol-3-yl)-biphenyl a) 4'-[[2-n-Propyl-4-methyl-6-(1-methyl-5,6,7,8-tetrahydro-benzimidazol-2-yl)-1H-benzimidazol-1-yl]-methyl]-2'-(hydroxycarbamimidoyl)-biphenyl To a solution of 8.4 g (0.12 Mol) of hydroxylaminelhydrochloride in 30 ml of dimethylsulfoxide are added 30 ml of a sodium methoxide solution of 30 percent in methanol at room temperature. After 10 minutes 4.5 g (10 mMol) of 4'-[[2-n-propyl-4-methyl-6-(1-methyl-5,6,7,8-tetrahydrobenzimidazol-2-yl)-1H-benzimidazol-1-yl]-methyl]-2'-cyano-biphenyl are added to this solution and the obtained suspension is heated up to 9° C. for 12 hours. After cooling to room temperature the reaction mixture is poured into 200 ml of ice water. The obtained precipitate is suction filtered, washed with water, dissolved in methylene chloride and chromatographed on silica gel (particle size: 0.023–0.063 mm) using as eluant mixtures from ethyl acetate, ethanol and concentrated ammonia (19:1:0.06, 19:1:0.08, 19:1:0.1 and 9:1:0.2). The uniform fractions are combined, evaporated, triturated with ether and dried.

Yield: 1.2 g (25% of theory),
Melting point: 221°–224° C. (decomp.)

b) 4'-[[2-n-Propyl-4-methyl-6-(1-methyl-5,6,7,8-tetrahydro-benzimidazol-2-yl)-1H-benzimidazol-1-yl]-methyl]-2'-(2,5-dihydro-5-oxo-1,2,4-oxadiazol-3-yl)-biphenyl To a solution of 0.5 g (1 mMol) of 4'-[[2-n-propyl-4-methyl-6-(1-methyl-5,6,7,8-tetrahydrobenzimidazol-2-yl)-1H-benzimidazol-1-yl]-methyl]-2'-(hydroxycarbamimidoyl)-biphenyl and 0.14 ml (1 mMol) of triethylamine in 40 ml of tetrahydrofuran are added a solution of 0.1 ml (1 mMol) of ethyl chloroformate in 1 ml of methylene chloride at 5° C. After 2 hours at room temperature, the formed precipitate is suction filtered. After evaporation of the filtrate the obtained residue is dissolved in 5 ml of xylene and refluxed for 90 minutes. After cooling to room temperature, the reaction mixture was mixed with 20 ml of ethyl acetate, washed with water and dried over magnesium sulfate. After evaporating of the organic phase, the obtained residue is chromatographed on silica gel (particle size: 0.032–0.063 mm) using as eluant methylene chloride with increasing amounts of ethanol (0 to 10%). The uniform fractions are combined, evaporated, triturated with ether and dried.

Yield: 80 mg (14% of theory),
Melting point: amorphous
$R_f$-value: 0.33 (silica gel; ethyl acetate/methanol=3:1)
Mass spectrum:

The following compound may be obtained analogeously to Example 207:

4'-[[2-n-Propyl-4-methyl -6-(1,4,5-trimethyl-imidazol-2-yl)-1H-benzimidazol-1-yl]-methyl]-2'-(2,5-dihydro-5-oxo-1,2,4-oxadiazol-3-yl)-biphenyl.

EXAMPLE 208

4'-[(2-Ethyl-4-methyl-6-(1-methyl-5-fluoro-benzimidazol-2-yl)-benzimidazol-1-yl)-methyl]-biphenyl-2-carboxylic acid a) 2-Ethyl-4-methyl-6-(1-methyl-5-fluoro-benzimidazol-2-yl)-benzimidazole A mixture of 4.5 g (21 mMol) of 1-methylamino-2-amino-4-fluoro-benzene-dihydrochloride and 4.3 g (21 mMol) of 2-ethyl-4-methyl-benzimidazol-6-yl -carboxylic acid is stirred for four hours at 140° C. in 100 g of polyphosphoric acid, then stirred into about 300 g of ice water and made alkaline with concentrated ammonia solution. The crude product precipitated is suction filtered, dried and then purified by column chromatography (300 g of silica gel; methylene chloride/ethanol=95:5).

Yield: 3.1 g (48% of theory), $R_f$ value: 0.24 (silica gel; methylene chloride/ethanol= 19:1)

b) Tert.butyl 4'-[(2-ethyl-4-methyl-6-(1-methyl-5-fluoro-benzimidazol-2-yl)-benzimidazol-1-yl)-methyl]-biphenyl-2-carboxylate 616 mg (5.5 mMol) of potassium tert.butoxide are added to a solution of 1.55 g (5 mMol) of 2-ethyl-4-methyl-6-(1-methyl-5-fluoro-benzimidazol-2-yl)-benzimidazole in 30 ml of dimethylsulphoxide and the resulting mixture is stirred for 15 minutes at ambient temperature. Then 1.9 g (5.5 mMol) of tert.butyl 4'-bromomethyl-biphenyl-2-carboxylate are added and stirring is continued for a further 20 hours at ambient temperature. The mixture is then stirred into about 80 ml of saturated sodium chloride solution, the crude product precipitated is suction filtered and purified by column chromatography (150 g silica gel; eluant: methylene chloride/ethanol=98:2).

Yield: 1.4 g (50% of theory), $R_f$ value: 0.47 (silica gel; methylene chloride/ethanol= 19:1)

c) 4'-[(2-Ethyl-4-methyl-6-(1-methyl-5-fluoro-benzimidazol-2-yl)-benzimidazol-1-yl)-methyl]-biphenyl-2-carboxylic acid A solution of 1.4 g (2.4 mMol) of tert.butyl 4'-[(2-ethyl-4-methyl -6-(1-methyl-5-fluoro-benzimidazol-2-yl)-benzimidazol-1-yl)-methyl]-biphenyl-2-carboxylate and 15 ml of trifluoroacetic acid in 30 ml of methylene chloride is stirred for 14 hours at ambient temperature, then concentrated by evaporation, the residue is mixed with about 30 ml of water and made alkaline with 2N sodium hydroxide solution. After extracting twice with 30 ml of diethyl ether, the aqueous phase is acidified with 20% citric acid. The crude product precipitated is suction filtered and purified by column chromatography (100 g silica gel; eluant: methylene chloride/ethanol=96:4).

Yield: 850 mg (69% of theory),

Melting point: 246°–248° C.

$C_{32}H_{27}FN_4O_2$ (518.60) Calculated: C 74.11 H 5.25 N 10.80 Found: 73.95 5.34 10.80

Mass spectrum: m/e=518

EXAMPLE 209

4'-[(2-n-Propyl-4-methyl-6-(butanesultam-1-yl)-benzimidazol-1-yl)-methyl]-biphenyl-2-carboxylic acid Prepared analogously to Example 208 from tert.butyl 4'-[(2-n-propyl-4-methyl-6-(butanesultam-1-yl)-benzimidazol-1-yl)-methyl]-biphenyl-2-carboxylate and trifluoroacetic acid.

Yield: 87% of theory,

Melting point: 269°–271° C.

$C_{29}H_{31}N_3O_4S$ (517.65) Calculated: C 67.29 H 6.04 N 8.12 Found: 67.56 6.12 8.28

$R_f$ value: 0.39 (silica gel; methylene chloride/ethanol= 9:1)

Mass spectrum: m/e=517

EXAMPLE 210

4'-[(2-Cyclopropyl-4-methyl-6-(imidazo[1,2-a]pyridin-2-yl)-benzimidazol-1-yl)-methyl]-biphenyl-2-carboxylic acid Prepared analogously to Example 208 from tert.butyl 4'-[(2-cyclopropyl-4-methyl-6-(imidazo[1,2-a]pyridin-2-yl)-benzimidazol-1-yl)-methyl]-biphenyl-2-carboxylate and trifluoroacetic acid.

Yield: 50% of theory,

Melting point: 245°–248° C.

$C_{32}H_{26}N_4O_2$ (498.59) Calculated: C 77.09 H 5.26 N 11.24 Found: 76.88 5.37 11.30

$R_f$ value: 0.63 (silica gel; methylene chloride/ethanol= 9:1)

Mass spectrum: m/e=498

EXAMPLE 211

4'-[(2-Cyclopropyl-4-methyl-6-(5,6,7,8-tetrahydro-imidazo[1,2-a]pyridin-2-yl)-benzimidazol-1-yl)-methyl]-biphenyl-2-carboxylic acid Prepared analogously to Example 208 from tert.butyl 4'-[(2-cyclopropyl-4-methyl-6-(5,6,7,8-tetrahydro-imidazo[1,2-a]-pyridin-2-yl)-benzimidazol-1-yl)-methyl]-biphenyl-2-carboxylate and trifluoroacetic acid.

Yield: 53% of theory,

Melting point: 310°–312° C.

$C_{32}H_{30}N_4O_2$ (502.62)

Calculated: C 76.47 H 6.02 N 11.15 Found: 76.23 5.97 10.85

$R_f$ value: 0.17 (silica gel; methylene chloride/ethanol= 9:1)

Mass spectrum: m/e=502

EXAMPLE 212

4'-[(2-Ethyl-4-methyl-6-(1-methyl-5-fluoro-benzimidazol-2-yl)-benzimidazol-1-yl)-methyl]-2-(1H-tetrazol-5-yl)-biphenyl a) 4'-[(2-Ethyl-4-methyl-6-(1-methyl-5-fluoro-benzimidazol-2-yl)-benzimidazol-1-yl)-methyl]-2-cyano-biphenyl 616 mg (5.5 mMol) of potassium tert.butoxide are added to a solution of 1.55 g (5 mMol) of 2-ethyl-4-methyl-6-(1-methyl-5-fluoro-benzimidazol-2-yl)-benzimidazole in 30 ml of dimethylsulphoxide and the mixture is stirred for 15 minutes at ambient temperature. Then 1.5 g (5.5 mMol) of 4'-bromomethyl-2-cyano-biphenyl are added and the resulting mixture is stirred for a further 20 hours at ambient temperature. Then the mixture is stirred into approximately 80 ml of saturated sodium chloride solution, the crude product precipitated is suction filtered and purified by column chromatography (150 g of silica gel; eluant: methylene chloride/ethanol=97:3).

Yield: 1.9 g (76% of theory), $R_f$ value: 0.43 (silica gel; methylene chloride/ethanol= 19:1)

b) 4'[(2-Ethyl-4-methyl-6-(1-methyl-5-fluoro-benzimidazol-2-yl)-benzimidazol-1-yl)-methyl]-2-(1H-tetrazol-5-yl)-biphenyl A solution of 1.9 g (3.8 mMol) of 4'-[(2-ethyl-4-methyl-6-(1-methyl-5-fluoro-benzimidazol-2-yl)-benzimidazol-1-yl)-methyl]-2-cyano-biphenyl, 4.1 g (76 mMol) of ammonium chloride and 4.9 g (76 mMol) of sodium azide in 30 ml of dimethylformamide is heated to 140° C. for 15 hours, then a further 2.0 g of ammonium chloride and 2.4 g of sodium azide are added and the mixture is heated for another 4 hours to 140° C. Then the solution is stirred into about 80 ml of saturated sodium chloride solution, the crude product precipitated is suction filtered and purified by column chromatography (150 g of silica gel; eluant: methylene chloride/ethanol=19:1).

Yield: 1.25 g (61% of theory),

Melting point: 267°–269° C.

$C_{32}H_{27}FN_8$ (542.60) Calculated: C 70.84 H 5.02 N 20.65 Found: 70.52 5.04 20.82

$R_f$ value: 0.60 (silica gel; methylene chloride/ethanol=9:1)

Mass spectrum: m/e=542

EXAMPLE 213

4'-[(2-Ethoxy-4-methyl-6-(1-methyl-benzimidazol-2-yl)-benzimidazol-1-yl)-methyl]-2-(1H-tetrazol-5-yl)-biphenyl a) 4'-[(2-Ethoxy-4-methyl-6-(1-methyl-benzimidazol-2-yl)-benzimidazol-1-yl)-methyl]-2-(2-triphenylmethyl-tetrazol-5-yl)-biphenyl To a solution of 570 mg (1.86 mMol) of 2-ethoxy-4-methyl-6-(1-methyl-benzimidazol-2-yl)-benzimidazole in 20 ml of dimethylsulphoxide are added 224 mg (2.0 mMol) of potassium tert.butoxide and the mixture is stirred for 15 minutes at ambient temperature. Then 1.11 g (2.0 mMol) of 4'-bromomethyl-2-(2-triphenylmethyl-tetrazol-5-yl)-biphenyl are added and the mixture is stirred for a further 3 hours at ambient temperature. Then the mixture is stirred into about 50 ml of saturated sodium chloride solution, the crude product precipitated is suction filtered and purified by column chromatography (100 g silica gel; eluant: ethyl acetate/petroleum ether=4:1).

Yield: 860 mg (59% of theory), $R_f$ value: 0.56 (silica gel; ethyl acetate/petroleum ether=4:1)

b) 4'-[(2-Ethoxy-4-methyl-6-(1-methyl-benzimidazol-2-yl)-benzimidazol-1-yl)-methyl]-2-(1H-tetrazol-5-yl)-biphenyl A mixture of 830 mg (1.06 mMol) of 4'-[(2-ethoxy-4-methyl-6-(1-methyl-benzimidazol-2-yl)-benzimidazol-1-yl)-methyl]-2-(2-triphenylmethyl-tetrazol-5-yl)-biphenyl, 2.5 ml of 1N sodium hydroxide solution and 20 ml of ethanol is stirred for 2 hours at 80° C. The solution is then evaporated down, the residue is mixed with about 30 ml of water and made slightly acidic with glacial acetic acid. It is then extracted three times with about 20 ml of methylene chloride, the combined organic extracts are washed with 20 ml of water and concentrated by evaporation. The crude product thus obtained is purified by column chromatography (50 g silica gel; methylene chloride/ethanol=97:3).

Yield: 430 mg (75% of theory),

Melting point: 194°–197° C.

$C_{32}H_{28}N_8O$ (540.60) Calculated: C 71.10 H 5.22 N 20.73 Found: 69.99 5.36 20.54

Mass spectrum: m/e=540

EXAMPLE 214

4'-[(2-Ethoxy-4-methyl-6-(imidazo[1,2-a]pyridin-2-yl)-benzimidazol-1-yl)-methyl]-biphenyl-2-carboxylic acid-hydrate Prepared analogously to Example 208 from tert.butyl 4'-[(2-ethoxy-4-methyl-6-(imidazo[1,2-a]pyridin-2-yl)-benzimidazol-1-yl)-methyl]-biphenyl-2-carboxylate and trifluoroacetic acid in methylene chloride.

Yield: 72% of theory,

Melting point: 207°–209° C.

$C_{31}H_{26}N_4O_3 \times H_2O$ (520.60) Calculated: C 71.52 H 5.42 N 10.76 Found: 71.22 5.37 10.76

$R_f$ value: 0.36 (silica gel; methylene chloride/ethanol=19:1)

EXAMPLE 214

Mixture of
4'-[(2-n-Propyl-4-methyl-6-(butanesultam-1-yl)-benzimidazol-1-yl)-methyl]-2-[1-(pivaloyloxymethyl)-tetrazol-5-yl]-biphenyl and
4'-[(2-n-Propyl-4-methyl-6-(butanesultam-1-yl)-benzimidazol-1-yl)-methyl]-2-[2-(pivaloyloxymethyl)-tetrazol-5-yl]-biphenyl A solution of 400 mg (0.74 mMol) of 4'-[(2-n-propyl-4-methyl-6-(butanesultam-1-yl)-benzimidazol-1-yl)-methyl]-2-(1H-tetrazol-5-yl)-biphenyl, 0.16 ml (1.1 mMol) of chloromethyl pivalate and 194 mg (1.1 mMol) of potassium carbonate-dihydrate in 10 ml of dimethyl formamide is stirred for 14 hours at ambient temperature, then stirred into about 50 ml of saturated sodium chloride solution and extracted three times with about 20 ml of methylene chloride. The combined organic extracts are washed with water and evaporated down. The crude product thus obtained is purified by column chromatography (50 g silica gel; eluant: methylene chloride/ethanol=98:2).

Yield: 400 mg (82% of theory),

Melting point: amorphous $C_{35}H_{41}N_7O_4S$ (655.80) Calculated: C 64.10 H 6.30 N 14.95 S 4.88 Found: 63.99 6.22 14.80 5.03

$R_f$ value: 0.46 (silica gel; methylene chloride/ethanol=19:1)

EXAMPLE 216

Mixture of
4'-[(2-n-Propyl-4-methyl-6-(5,6,7,8-tetrahydro-imidazo[1,2-a]-pyridin-2-yl)-benzimidazol-1-yl)-methyl]-2-[1-(pivaloyloxymethyl)-tetrazol-5-yl]-biphenyl and
4'-[(2-n-Propyl-4-methyl-6-(5,6,7,8-tetrahydro-imidazo[1,2-a]-pyridin-2-yl)-benzimidazol-1-yl)-methyl]-2-[2-(pivaloyloxymethyl)-tetrazol-5-yl]-biphenyl Prepared analogously to Example 215 from 4'-[(2-n-propyl-4-methyl-6-(5,6,7,8-tetrahydro-imidazo[1,2-a]-pyridin-2-yl)-benzimidazol-1-yl)-methyl]-2-(1H-tetrazol-5-yl)-biphenyl and chloromethylpivalate.

Yield: 75% of theory,

Melting point: 203°–205° C.

$C_{38}H_{42}N_8O_2$ (642.80) Calculated: C 71.00 H 6.59 N 17.43 Found: 70.85 6.63 17.43

$R_f$ value: 0.43 (silica gel; methylene chloride/ethanol=19:1)

Mass spectrum: m/e=642

EXAMPLE 217

4'-[(2-n-Propyl-4-methyl-6-(5,6,7,8-tetrahydro-imidazo[1,2-a]-pyridin-2-yl)-benzimidazol-1-yl)-methyl]-2-[1-(cyclohexyloxy-carbonyloxy)-ethyloxycarbonyl]-biphenyl A solution of 504 mg (1.0 mMol) of 4'-[(2-n-propyl-4-methyl-6-(5,6,7,8-tetrahydro-imidazo[1,2-a]pyridin-2-yl)-benzimidazol-1-yl)-methyl]-biphenyl-2-carboxylic acid, 600 mg of 1-(cyclohexyloxycarbonyloxy)-ethyliodide and 350 mg of potassium carbonate in 25 ml of dimethylsulphoxide is stirred for 14 hours at ambient temperature, then stirred into about 70 ml of saturated sodium chloride solution and extracted three times with 30 ml of ethyl acetate. The combined organic extracts are washed with water and evaporated down. The crude product thus obtained is purified by column chromatography (100 g silica gel; eluant: methylene chloride/ethanol=98:2).

Yield: 325 mg (48% of theory),

Melting point: 162°–164° C.

$C_{41}H_{46}N_4O_5$ (674.85) Calculated: C 72.97 H 6.87 N 8.30 Found: 72.63 6.77 8.17

$R_f$ value: 0.52 (silica gel; methylene chloride/ethanol= 19:1)

Mass spectrum: m/e=674

EXAMPLE 218

4'-[(2-n-Propyl-4-methyl-6-(5,6,7,8-tetrahydro-imidazo[1,2-a]-pyridin-2-yl)-benzimidazol-1-yl)-methyl]-2-(pivaloyloxymethyloxycarbonyl)-biphenyl Prepared analogously to Example 215 from 4'-[(2-n-propyl-4-methyl-6-(5,6,7,8-tetrahydro-imidazo[1,2-a]pyridin-2-yl)-benzimidazol-1-yl)-methyl]-biphenyl-2-carboxylic acid and chloromethylpivalate in dimethylformamide.

Yield: 76% of theory,

Melting point: 142°–144° C.

$C_{38}H_{42}N_4O_4$ (618.79) Calculated: C 73.76 H 6.84 N 9.09 Found: 73.60 6.92 9.17

$R_f$ value: 0.40 (silica gel; methylene chloride/ethanol= 19:1)

Mass spectrum: m/e=618

EXAMPLE 219

4'-[(2-n-Propyl-4-methyl-6-(butanesultam-1-yl)-benzimidazol-1-yl)-methyl]-2-(pivaloyloxymethyloxy-carbonyl)-biphenyl Prepared analogously to Example 215 from 4'-[(2-n-propyl-4-methyl-6-(butanesultam-1-yl)-benzimidazol-1-yl)-methyl]-biphenyl-2-carboxylic acid and chloromethylpivalate in dimethylformamide.

Yield: 70% of theory,

Melting point: Oil $C_{35}H_{41}N_3O_6S$ (631.80) Calculated: C 66.54 H 6.54 N 6.65 S 5.08 Found: 66.21 6.67 6.54 5.34

$R_f$ value: 0.49 (silica gel; methylene chloride/ethanol= 19:1)

Mass spectrum: m/e=631

EXAMPLE 220

4'-[(2-n-Propyl-4-methyl-6-(5,6,7,8-tetrahydro-imidazo[1,2-a]-pyridin-2-yl)-benzimidazol-1-yl)-methyl]-2-[1-(ethoxycarbonyl-oxymethyloxy)-carbonyl]-biphenyl Prepared analogously to Example 215 from 4'-[(2-n-propyl-4-methyl-6-(5,6,7,8-tetrahydro-imidazo[1,2-a]-pyridin-2-yl)-benzimidazol-1-yl)-methyl]-biphenyl-2-carboxylic acid and 1-(ethoxycarbonyloxy)-methylchloride in dimethylformamide.

Yield: 38.5% of theory,

Melting point: 123°–125° C.

$C_{37}H_{40}N_4O_5$ (620.76) Calculated: C 71.59 H 6.50 N 9.03 Found: 71.57 6.58 9.03

$R_f$ value: 0.33 (silica gel; methylene chloride/ethanol= 19:1)

Mass spectrum: m/e=620

EXAMPLE 221

4'-[(2-Ethoxy-4-methyl-6-(imidazo[1,2-a]pyridin-2-yl)-benzimidazol-1-yl)-methyl]-2-(1H-tetrazol-5-yl)-biphenyl Prepared analogously to Example 213 from 4'-[(2-ethoxy-4-methyl-6-(imidazo[1,2-a]-pyridin-2-yl)-benzimidazol-1-yl)-methyl]-2-(2-triphenylmethyl-tetrazol-5-yl)-biphenyl and sodium hydroxide solution in ethanol.

EXAMPLE 222

4'-[(2-Ethoxy-4-methyl-6-(5,6,7,8-tetrahydro-imidazo[1,2-a]-pyridin-2-yl)-benzimidazol-1-yl)-methyl]-2-(1H-tetrazol-5-yl)-biphenyl Prepared analogously to Example 213 from 4'-[(2-ethoxy-4-methyl-6-(5,6,7,8-tetrahydro-imidazo[1,2-a]pyridin-2-yl)-benzimidazol-1-yl)-methyl]-2-(2-triphenylmethyl-tetrazol-5-yl)-biphenyl and sodium hydroxide solution in ethanol.

EXAMPLE 223

4'-[(2-Ethoxy-4-methyl-6-(5,6,7,8-tetrahydro-imidazo[1,2-a]-pyridin-2-yl)-benzimidazol-1-yl)-methyl]-biphenyl-2-carboxylic acid Prepared analogously to Example 208 from tert.butyl 4'-[(2-ethoxy-4-methyl-6-(5,6,7,8-tetrahydro-imidazo[1,2-a]pyridin-2-yl)-benzimidazol-1-yl)-methyl]-biphenyl-2-carboxylate and trifluoroacetic acid in methylene chloride.

Yield: 63% of theory,

Melting point: 238°–240° C.

$R_f$ value: 0.62 (silica gel; methylene chloride/ethanol= 9:1)

EXAMPLE 224

4'-[(2-Ethyl-4-methyl-6-(butanesultam-1-yl)-benzimidazol-1-yl)-methyl]-biphenyl-2-carboxylic acid Prepared analogously to Example 208 from tert.butyl 4'-[(2-ethyl-4-methyl-6-(butanesultam-2-yl)-benzimidazol-1-yl)-methyl]-biphenyl-2-carboxylate and trifluoroacetic acid in methylene chloride.

Yield: 68% of theory,

Melting point: >240° C.

$C_{28}H_{29}N_3O_4S$ (503.60) Calculated: C 66.77 H 5.80 N 8.34 Found: 66.57 5.69 8.30

$R_f$ value: 0.36 (silica gel; methylene chloride/ethanol= 9:1)

EXAMPLE 225

4'-[(2-Ethyl-4-methyl-6-(3-chloro-5,6,7,8-tetrahydro-imidazo-[1,2-a]pyridin-2-yl)-benzimidazol-1-yl)-methyl]-biphenyl-2-carboxylic acid Prepared analogously to Example 208 from tert.butyl 4'-[(2-ethyl-4-methyl-6-(3-chloro-5,6,7,8-tetrahydro-imidazo[1,2-a]-pyridin-2-yl)-benzimidazol-1-yl)-methyl]-biphenyl-2-carboxylate and trifluoroacetic acid in methylene chloride.

Yield: 43% of theory,

Melting point: 295–297 C.

$C_{31}H_{29}ClN_4O_2$ (525.06) Calculated: C 70.91 H 5.57 N 10.67 $C_{1\ 6.75}$ Found: 70.81 5.54 10.55 6.83

$R_f$ value: 0.36 (silica gel; methylene chloride/ethanol= 9:1)

In the Examples of Pharmaceutical Formulations which follow, any suitable compound of formula I, particularly those compounds wherein $R_4$ represents a carboxy- or 1H-tetrazolyl group or a group which can be metabolised into a carboxy- or 1H-tetrazolyl group o, may be used as the active substance:

EXAMPLE 226

| Ampoules containing 50 mg of active substance per 5 ml | |
|---|---|
| Active substance | 50 mg |
| $KH_2PO_4$ | 2 mg |
| $Na_2HPO_4 \times 2H_2O$ | 50 mg |
| NaCl | 12 mg |
| Water for injections ad | 5 ml |

Preparation:

The buffer substances and isotonic substance are dissolved in some of the water. The active substance is added and, once it has been completely dissolved, water is added to make up the required volume.

EXAMPLE 227

| Ampoules containing 100 mg of active substance per 5 ml | |
|---|---|
| Active substance | 100 mg |
| Methyl glucamine | 35 mg |
| Glycofurol | 1000 mg |
| Polyethyleneglycol-polypropylene-glycol block polymer | 250 mg |
| Water for injections ad | 5 ml |

Preparation:

Methyl glucamine is dissolved in some of the water and the active substance is dissolved with stirring and heating. After the addition of solvents, water is added to make up the desired volume.

EXAMPLE 228

| Tablets containing 50 mg of active substance | |
|---|---|
| Active substance | 50.0 mg |
| Calcium phosphate | 70.0 mg |
| Lactose | 40.0 mg |
| Corn starch | 35.0 mg |
| Polyvinylpyrrolidone | 3.5 mg |
| Magnesium stearate | 1.5 mg |
| | 200.0 mg |

Preparation:

The active substance, $CaHPO_4$, lactose and corn starch are uniformly moistened with an aqueous PVP solution. The mass is passed through a 2 mm screen, dried at 50° C. in a circulating air dryer and screened again.

After the lubricant has been added, the granules are compressed in a tablet making machine.

EXAMPLE 229

| Coated tablets containing 50 mg of active substance | |
|---|---|
| Active substance | 50.0 mg |
| Lysine | 25.0 mg |
| Lactose | 60.0 mg |
| Corn starch | 34.0 g |
| Gelatin | 10.0 mg |
| Magnesium stearate | 1.0 mg |
| | 180.0 mg |

Preparation:

The active substance is mixed with the excipients and moistened with an aqueous gelatin solution. After screening and drying the granules are mixed with magnesium stearate and compressed to form tablet cores, The cores thus produced are covered with a coating by known methods. A colouring may be added to the coating suspension or solution,

EXAMPLE 230

| Coated tablets containing 100 mg of active substance | |
|---|---|
| Active substance | 100.0 mg |
| Lysine | 50.0 mg |
| Lactose | 86.0 mg |
| Corn starch | 50.0 mg |
| Polyvinylpyrrolidone | 2.8 mg |
| Microcrystalline cellulose | 60.0 mg |
| Magnesium stearate | 1.2 mg |
| | 350.0 mg |

Preparation:

The active substance is mixed with the excipients and moistened with an aqueous PVP solution. The moist mass is passed through a 1.5 mm screen and dried at 45° C. After drying, it is screened again and the magnesium stearate is added. This mixture is compressed into cores.

The cores thus produced are covered with a coating by known methods. Colouring may be added to the coating suspension or solution.

EXAMPLE 231

| Capsules containing 250 mg of active substance | |
|---|---|
| Active substance | 250.0 mg |
| Corn starch | 68.5 mg |
| Magnesium stearate | 1.5 mg |
| | 320.0 mg |

Preparation:

The active substance and corn starch are mixed together and moistened with water. The moist mass is screened and dried. The dry granules are screened and mixed with magnesium stearate. The final mixture is packed into size 1 hard gelatine capsules.

EXAMPLE 232

| Oral suspension containing 50 mg of active substance per 5 ml | |
|---|---|
| Active substance | 50.0 mg |
| Hydroxyethylcellulose | 50.0 mg |
| Sorbic acid | 5.0 mg |
| 70% sorbitol | 600.0 mg |
| Glycerol | 200.0 mg |
| Flavouring | 15.0 mg |
| Water ad | 5.0 ml |

Preparation:

Distilled water is heated to 70° C. Hydroxyethyl-cellulose is dissolved therein with stirring. With the addition of sorbitol solution and glycerol the mixture is cooled to ambient temperature. At ambient temperature, sorbic acid, flavouring and active substance are added. The suspension is evacuated with stirring to remove any air. One dose of 50 mg is contained in 5.0 ml.

EXAMPLE 233

| Suppositories containing 100 mg of active substance | |
|---|---|
| Active substance | 100.0 mg |
| Solid fat | 1600.0 mg |
| | 1700.0 mg |

Preparation:

The hard fat is melted. At 40° C. the ground active substance is homogeneously dispersed in the melt. It is cooled to 38° C. and poured into slightly chilled suppository moulds.

What is claimed is:

1. A compound of the formula I

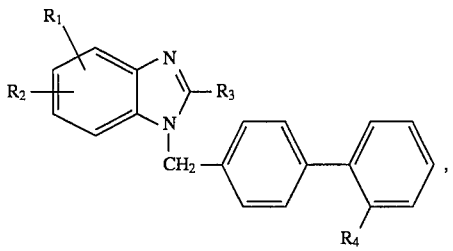

wherein $R_1$ is in the 4-position and represents a $C_{1-4}$-alkyl, $C_{3-7}$-cycloalkyl or trifluoromethyl group, $R_2$ represents a 5,6,7,8-tetrahydro-imidazo[1,2-a]pyridin-2-yl group, $R_3$ represents a $C_{1-5}$-alkyl group or cyclopropyl, and $R_4$ denotes a 1H-tetrazolyl group or an $R_aO$—CO— group, wherein $R_a$ denotes a hydrogen atom or a straight-chained or branched $C_{1-4}$-alkyl group, or a pharmaceutically acceptable salt thereof.

2. In accordance with claim 1, a compound of the formula I, wherein $R_2$ is in the 6-position, or a pharmaceutically acceptable salt thereof.

3. In accordance with claim 2, a compound of the formula I, wherein $R_1$ represents a methyl group, $R_2$ is in the 6-position and represents a 5,6,7,8-tetrahydro-imidazo[1,2-a]pyridin-2-yl group, $R_3$ represents a $C_{1-5}$-alkyl group, and $R_4$ represents a carboxy or 1H-tetrazolyl group, or a pharmaceutically acceptable salt thereof.

4. 4'-[(2-Ethyl-4-methyl-6-(5,6,7,8-tetrahydro-imidazo[1,2-a]pyridin-2-yl)-benzimidazol-1-yl)-methyl]-biphenyl-2-carboxylic acid or a pharmaceutically acceptable salt thereof.

5. A pharmaceutical composition comprising a compound as in any one of claims 1, 2, 3 or 4.

6. A method for treating hypertension which comprises administering to a mammalian host suffering from the same an antihypertensive amount of a compound as in any one of claims 1, 2, 3 or 4.

* * * * *